United States Patent
Wagner et al.

(10) Patent No.: US 10,137,122 B2
(45) Date of Patent: *Nov. 27, 2018

(54) KINASE INHIBITORS AND METHODS OF USE THEREOF

(71) Applicants: The Broad Institute, Inc., Cambridge, MA (US); Dana-Farber Cancer Institute, Inc., Boston, MA (US); The General Hospital Corporation, Boston, MA (US)

(72) Inventors: Florence Fevrier Wagner, Ashland, MA (US); Jennifer Q. Pan, Acton, MA (US); Sivaraman Dandapani, Wakefield, MA (US); Andrew Germain, Somerville, MA (US); Edward Holson, Newton, MA (US); Benito Munoz, Newtonville, MA (US); Partha P. Nag, Somerville, MA (US); Michael C. Lewis, Dedham, MA (US); Stephen J. Haggarty, Gloucester, MA (US); Joshua A. Bishop, Southborough, MA (US); Kimberly Stegmaier, Jamaica Plain, MA (US); Michel Weiwer, Cambridge, MA (US); Versha Banerji, Winnipeg (CA)

(73) Assignees: The Broad Institute, Inc., Cambridge, MA (US); Dana-Farber Cancer Institute, Inc., Boston, MA (US); The General Hospital Corporation, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/799,281

(22) Filed: Jul. 14, 2015

(65) Prior Publication Data
US 2015/0313890 A1    Nov. 5, 2015

Related U.S. Application Data

(63) Continuation of application No. 14/052,661, filed on Oct. 11, 2013, now Pat. No. 9,096,594.

(60) Provisional application No. 61/779,394, filed on Mar. 13, 2013, provisional application No. 61/713,314, filed on Oct. 12, 2012.

(51) Int. Cl.
*A61K 31/4745* (2006.01)
*C07D 471/04* (2006.01)
*A61K 31/4747* (2006.01)
*C07D 471/10* (2006.01)

(52) U.S. Cl.
CPC ...... *A61K 31/4745* (2013.01); *A61K 31/4747* (2013.01); *C07D 471/04* (2013.01); *C07D 471/10* (2013.01)

(58) Field of Classification Search
CPC ... C07D 471/10; C07D 471/04; A61K 31/437

USPC .......................................... 514/293; 546/82
See application file for complete search history.

(56) References Cited

U.S. PATENT DOCUMENTS

| | | | |
|---|---|---|---|
| 4,270,537 A | 6/1981 | Romaine |
| 4,596,556 A | 6/1986 | Morrow et al. |
| 4,790,824 A | 12/1988 | Morrow et al. |
| 4,886,499 A | 12/1989 | Cirelli et al. |
| 4,940,460 A | 7/1990 | Casey et al. |
| 4,941,880 A | 7/1990 | Burns |
| 5,015,235 A | 5/1991 | Crossman |
| 5,064,413 A | 11/1991 | McKinnon et al. |
| 5,141,496 A | 8/1992 | Dalto et al. |
| 5,190,521 A | 3/1993 | Hubbard et al. |
| 5,312,335 A | 5/1994 | McKinnon et al. |
| 5,328,483 A | 7/1994 | Jacoby |
| 5,334,114 A | 8/1994 | Ando et al. |
| 5,339,163 A | 8/1994 | Homma et al. |

(Continued)

FOREIGN PATENT DOCUMENTS

| | | |
|---|---|---|
| DE | 2722416 A1 | 11/1978 |
| WO | WO 94/24131 A1 | 10/1994 |

(Continued)

OTHER PUBLICATIONS

Samantha Portis et al , Role of Glycogen Synthase kinase-3 in neurodevelopment and fragile X syndrome. Sep. 2012.*

(Continued)

*Primary Examiner* — Rita J Desai
(74) *Attorney, Agent, or Firm* — Wolf, Greenfield & Sacks, P.C.

(57) ABSTRACT

The present invention provides compounds of formula I, pharmaceutically acceptable salts thereof, and pharmaceutical compositions thereof. Compounds of the present invention are useful for inhibiting kinase (e.g., GSK3 (e.g., GSK3α or GSK3β) or CK1) activity. The present invention further provides methods of using the compounds described herein for treating kinase-mediated disorders, such as neurological diseases, psychiatric disorders, metabolic disorders, and cancer.

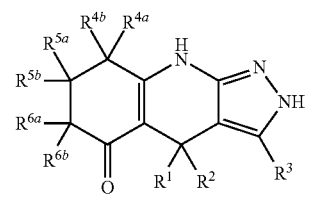

66 Claims, 15 Drawing Sheets
Specification includes a Sequence Listing.

(56) References Cited

U.S. PATENT DOCUMENTS

| | | | |
|---|---|---|---|
| 5,383,851 A | 1/1995 | McKinnon et al. |
| 5,417,662 A | 5/1995 | Hjertman et al. |
| 5,466,220 A | 11/1995 | Brenneman |
| 5,480,381 A | 1/1996 | Weston |
| 5,503,627 A | 4/1996 | McKinnon et al. |
| 5,520,639 A | 5/1996 | Peterson et al. |
| 5,527,288 A | 6/1996 | Gross et al. |
| 5,569,189 A | 10/1996 | Parsons |
| 5,599,302 A | 2/1997 | Lilley et al. |
| 5,649,912 A | 7/1997 | Peterson |
| 5,704,911 A | 1/1998 | Parsons |
| 5,750,528 A | 5/1998 | Brown et al. |
| 5,893,397 A | 4/1999 | Peterson et al. |
| 5,993,412 A | 11/1999 | Deily et al. |
| 6,977,262 B2 | 12/2005 | Kohara et al. |
| 8,778,986 B1 | 7/2014 | Tan et al. |
| 9,096,594 B2 | 8/2015 | Wagner et al. |
| 2009/0181986 A1 | 7/2009 | Abelman et al. |
| 2011/0008468 A1 | 1/2011 | Haggarty et al. |
| 2014/0107141 A1 | 4/2014 | Wagner et al. |
| 2016/0375006 A1 | 12/2016 | Scolnick et al. |

FOREIGN PATENT DOCUMENTS

| | | |
|---|---|---|
| WO | WO 97/13537 A1 | 4/1997 |
| WO | WO 97/37705 A1 | 10/1997 |
| WO | WO 99/34850 A1 | 7/1999 |
| WO | WO 00/32606 A1 | 6/2000 |
| WO | WO 02/062795 A2 | 8/2002 |
| WO | 2007012972 * | 2/2007 |
| WO | WO 2007/012972 A2 | 2/2007 |
| WO | WO 2008/016123 | 2/2008 |
| WO | WO 2010/133794 A1 | 11/2010 |
| WO | WO 2013/007663 A1 | 1/2013 |
| WO | WO 2015/087996 A1 | 6/2015 |

OTHER PUBLICATIONS

International Search Report and Written Opinion for PCT/US2013/064716, dated Nov. 19, 2013.
International Preliminary Report on Patentability for PCT/US2013/064716, dated Apr. 23, 2015.
Banerji et al., The intersection of genetic and chemical genomic screens identifies GSK-3α as a target in human acute myeloid leukemia. J Clin Invest. Mar. 1, 2012;122(3):935-47. doi: 10.1172/JCI46465. Epub Feb. 13, 2012.
Bang et al., GSK-3α promotes oncogenic KRAS function in pancreatic cancer via TAK1-TAB stabilization and regulation of noncanonical NF-κB. Cancer Discov. Jun. 2013;3(6):690-703. doi: 10.1158/2159-8290.CD-12-0541. Epub Apr. 1, 2013.
Beaulieu et al., The Akt-GSK-3 signaling cascade in the actions of dopamine. Trends Pharmacol Sci. Apr. 2007;28(4):166-72. Epub Mar. 8, 2007. Review.
Berge et al., Pharmaceutical salts. J Pharm Sci. Jan. 1977; 66(1):1-19.
Beurel et al., Inhibition of glycogen synthase kinase-3 is necessary for the rapid antidepressant effect of ketamine in mice. Mol Psychiatry. Nov. 2011;16(11):1068-70. doi: 10.1038/mp.2011.47. Epub Apr. 19, 2011.
Biechele et al., Assaying beta-catenin/TCF transcription with beta-catenin/TCF transcription-based reporter constructs. Methods Mol Biol. 2008;468:99-110. doi: 10.1007/978-1-59745-249-6_8.
Chalecka-Franaszek et al., Lithium activates the serine/threonine kinase Akt-1 and suppresses glutamate-induced inhibition of Akt-1 activity in neurons. Proc Natl Acad Sci U S A. Jul. 20, 1999;96(15):8745-50.
Chang et al., Synthesis and application of functionally diverse 2,6,9-trisubstituted purine libraries as CDK inhibitors. Chem Biol. Jun. 1999;6(6):361-75.
Cheong et al., Phosphatase and tensin homologue phosphorylation in the C-terminal regulatory domain is frequently observed in acute myeloid leukaemia and associated with poor clinical outcome. Br J Haematol. Aug. 2003;122(3):454-6.
Cozza et al., Identification of novel protein kinase CK1 delta (CK1delta) inhibitors through structure-based virtual screening. *Bioorg Med Chem Lett*. Oct. 15, 2008;18(20):5672-5. doi: 10.1016/j.bmcl.2008.08.072. Epub Aug. 26, 2008.
De Sarno et al., Regulation of Akt and glycogen synthase kinase-3 beta phosphorylation by sodium valproate and lithium. Neuropharmacology. Dec. 2002;43(7):1158-64.
Dirzin et al., Structure-Activity studies for a novel series of tricyclic dihydropyrimidines as K(ATP) channel openers (KCOs). Bioorg Med Chem Lett. Jun. 3, 2002;12(11):1481-4.
Emamian, AKT/GSK3 signaling pathway and schizophrenia. Front Mol Neurosci. Mar. 15, 2012;5:33. doi: 10.3389/fnmol.2012.00033. eCollection 2012.
Emamian et al., Convergent evidence for impaired AKT1-GSK3beta signaling in schizophrenia. Nat Genet. Feb. 2004;36(2):131-7. Epub Jan. 25, 2004.
Forde et al., Glycogen synthase kinase 3: a key regulator of cellular fate. Cell Mol Life Sci. Aug. 2007;64(15):1930-44. Review.
Franklin et al., Glycogen synthase kinase-3 inhibitors reverse deficits in long-term potentiation and cognition in fragile X mice. Biol Psychiatry. Feb. 1, 2014;75(3):198-206. doi: 10.1016/j.biopsych.2013.08.003. Epub Sep. 13, 2013.
Gould et al., Targeting glycogen synthase kinase-3 in the CNS: implications for the development of new treatments for mood disorders. Curr Drug Targets. Nov. 2006;7(11):1399-409. Review.
Hahn et al., Proteomic and genetic approaches identify Syk as an AML target. Cancer Cell. Oct. 6, 2009;16(4):281-94. doi: 10.1016/j.ccr.2009.08.018.
Hooper et al., The GSK3 hypothesis of Alzheimer's disease. J Neurochem. Mar. 2008;104(6):1433-9. Epub Dec. 18, 2007. Review.
Jones et al., Animal models of schizophrenia. *Br J Pharmacol*. Oct. 2011;164(4):1162-94. doi: 10.1111/j.1476-5381.2011.01386.x. Review.
Kaidanovich-Beilin et al., Abnormalities in brain structure and behavior in GSK-3alpha mutant mice. Mol Brain. Nov. 19, 2009;2:35. doi: 10.1186/1756-6606-2-35.
Kozlovsky et al., Reduced GSK-3beta mRNA levels in postmortem dorsolateral prefrontal cortex of schizophrenic patients. J Neural Transm. Dec. 2004;111(12):1583-92. Epub Jun. 30, 2004.
Leclerc et al., Indirubins inhibit glycogen synthase kinase-3 beta and CDK5/p25, two protein kinases involved in abnormal tau phosphorylation in Alzheimer's disease. A property common to most cyclin-dependent kinase inhibitors? J Biol Chem. Jan. 5, 2001;276(1):251-60.
Lee et al., Developing therapeutic approaches to tau, selected kinases, and related neuronal protein targets. Cold Spring Harb Perspect Med. Sep. 2011;1(1):a006437. doi:10.1101/cshperspect.a006437. Review.
Leost et al., Paullones are potent inhibitors of glycogen synthase kinase-3beta and cyclin-dependent kinase 5/p25. Eur J Biochem. Oct. 2000;267(19):5983-94.
Lo Monte et al., Identification of glycogen synthase kinase-3 inhibitors with a selective sting for glycogen synthase kinase-3α. J Med Chem. May 10, 2012;55(9):4407-24. doi: 10.1021/jm300309a. Epub May 1, 2012.
Macaulay et al., Glycogen synthase kinase 3alpha-specific regulation of murine hepatic glycogen metabolism. Cell Metab. Oct. 2007;6(4):329-37.
Manisastry et al., Early temporal-specific responses and differential sensitivity to lithium and Wnt-3A exposure during heart development. Dev Dyn. Aug. 2006;235(8):2160-74.
Manoukian et al., Role of glycogen synthase kinase-3 in cancer: regulation by Wnts and other signaling pathways. Adv Cancer Res. 2002;84:203-29. Review.
Mao et al., Disrupted in schizophrenia 1 regulates neuronal progenitor proliferation via modulation of GSK3beta/beta-catenin signaling. Cell. Mar. 20, 2009;136(6):1017-31. doi:10.1016/j.cell.2008.12.044.
Matsuda et al., Distinct roles of GSK-3alpha and GSK-3beta phosphorylation in the heart under pressure overload. Proc Natl Acad Sci U S A. Dec. 30, 2005;105(52):20900-5. doi: 10.1073/pnas.0808315106. Epub Dec. 23, 2008.

(56) References Cited

OTHER PUBLICATIONS

Meijer et al., GSK-3-selective inhibitors derived from Tyrian purple indirubins. Chem Biol. Dec. 2003;10(12):1255-66.
Meijer et al., Inhibition of cyclin-dependent kinases, GSK-3beta and CK1 by hymenialdisine, a marine sponge constituent. Chem Biol. Jan. 2000;7(1):51-63.
Norton et al. Association analysis of AKT1 and schizophrenia in a UK case control sample. Schizophr Res. Jul. 2007;93(1-3):58-65. Epub Mar. 26, 2007.
Pan et al., AKT kinase activity is required for lithium to modulate mood-related behaviors in mice. Neuropsychopharmacology. Jun. 2011;36(7):1397-411. doi: 10.1038/npp.2011.24. Epub Mar. 9, 2011.
Phiel et al., GSK-3alpha regulates production of Alzheimer's disease amyloid-beta peptides. Nature. May 22, 2003;423(6938):435-9.
Piazza et al., Glycogen Synthase Kinase-3 regulates multiple myeloma cell growth and bortezomib-induced cell death. BMC Cancer. Oct. 4, 2010;10:526. doi: 10.1186/1471-2407-10-526.
Polychronopoulos et al., Structural basis for the synthesis of indirubins as potent and selective inhibitors of glycogen synthase kinase-3 and cyclin-dependent kinases. J Med Chem. Feb. 12, 2004;47(4):935-46.
Polter et al., Deficiency in the inhibitory serine-phosphorylation of glycogen synthase kinase-3 increases sensitivity to mood disturbances. Neuropsychopharmacology. Jul. 2010;35(8):1761-74. doi: 10.1038/npp.2010.43. Epub Mar. 31, 2010.
Quiroga et al., Regioselective synthesis of 4,7,8,9-tetrahydro-2H-pyrazolo[3,4-b]quinolin-5(6H)-ones. Mechanism and structural analysis. Tetrahedron. 2001;57(32):6947-53.
Ryves et al., Lithium inhibits glycogen synthase kinase-3 by competition for magnesium. Biochem Biophys Res Commun. Jan. 26, 2001;280(3):720-5.
Song et al., Central role of glycogen synthase kinase-3beta in endoplasmic reticulum stress-induced caspase-3 activation. J Biol Chem. Nov. 22, 2002;277(47):44701-8. Epub Sep. 12, 2002.
Stegmaier et al., Gene expression-based high-throughput screening(GE-HTS) and application to leukemia differentiation. Nat Genet. Mar. 2004;36(3):257-63. Epub Feb. 8, 2004.
Thiselton et al., AKT1 is associated with schizophrenia across multiple symptom dimensions in the Irish study of high density schizophrenia families. Biol Psychiatry. Mar. 1, 2008;63(5):449-57. Epub Sep. 6, 2007.
Wagman et al., Discovery and development of GSK3 inhibitors for the treatment of type 2 diabetes. Curr Pharm Des. 2004;10(10):1105-37. Review.
Wang et al., Downregulation of Mcl-1 through GSK-3β activation contributes to arsenic trioxide-induced apoptosis in acute myeloid leukemia cells. Leukemia. Feb. 2013;27(2):315-24. doi: 10.1038/leu.2012.180. Epub Jul. 3, 2012.
Wang et al., Glycogen synthase kinase 3 in MLL leukaemia maintenance and targeted therapy. Nature. Oct. 30, 2008;455(7217):1205-9. doi: 10.1038/nature07284. Epub Sep. 17, 2008.
Wang et al., GSK-3 promotes conditional association of CREB and its coactivators with MEIS1 to facilitate HOX-mediated transcription and oncogenesis. Cancer Cell. Jun. 15, 2010;17(6):597-608. doi: 10.1016/j.ccr.2010.04.024.
Wang et al., The Wnt/beta-catenin pathway is required for the development of leukemia stem cells in AML. Science. Mar. 26, 2010;327(5973):1650-3. doi: 10.1126/science.1186624.
Wexler et al., Lithium regulates adult hippocampal progenitor development through canonical Wnt pathway activation. Mol Psychiatry. Mar. 2008;13(3):285-92. Epub Oct. 30, 2007.
Woodgett, Physiological roles of glycogen synthase kinase-3: potential as a therapeutic target for diabetes and other disorders. Curr Drug Targets Immune Endocr Metabol Disord. Dec. 2003;3(4):281-90. Review.
Zhao et al., A high-throughput screen for Wnt/β-catenin signaling pathway modulators in human iPSC-derived neural progenitors. J Biomol Screen. Oct. 2012;17(9):1252-63. Epub Aug. 24, 2012.

Zhou et al., Forebrain overexpression of CK1delta leads to down-regulation of dopamine receptors and altered locomotor activity reminiscent of ADHD. Proc Natl Acad Sci U S A. Mar. 2, 2010;107(9):4401-6. doi: 10.1073/pnas.0915173107. Epub Feb. 9, 2010.
An et al., Discovery of Potent and Highly Selective Inhibitors of GSK3b. Released in excerpt form on May 7, 2013. [Last Update: May 13, 2014]. Full report published on Jul. 17, 2014. In: Probe Reports from the NIH Molecular Libraries Program [Internet]. Bethesda (MD): National Center for Biotechnology Information (US); 2010-. Available from: https://www.ncbi.nlm.nih.gov/books/NBK133436/.
Wagner et al., Inhibitors of Glycogen Synthase Kinase 3 with Exquisite Kinome-Wide Selectivity and Their Functional Effects. ACS Chem Biol. Jul. 15, 2016;11(7):1952-63. doi: 10.1021/acschembio.6b00306. Epub May 13, 2016.
Doble et al., Functional redundancy of GSK-3alpha and GSK-3beta in Wnt/beta-catenin signaling shown by using an allelic series of embryonic stem cell lines. Dev Cell. Jun. 2007;12(6):957-71.
Koh et al., Inhibition of glycogen synthase kinase-3 suppresses the onset of symptoms and disease progression of G93A-SOD1 mouse model of ALS. Exp Neurol. Jun. 2007;205(2):336-46. Epub Mar. 12, 2007.
Lei et al., GSK-3 in Neurodegenerative Diseases. Int J Alzheimers Dis. 2011;2011:189246, 9 pages. doi: 10.4061/2011/189246. Epub May 4, 2011.
Mines et al., GSK3 influences social preference and anxiety-related behaviors during social interaction in a mouse model of fragile X syndrome and autism. PLoS One. Mar. 16, 2010;5(3):e9706, 12 pages. doi: 10.1371/journal.pone.0009706.
Wang et al., Changes of tau profiles in brains of the hamsters infected with scrapie strains 263 K or 139 A possibly associated with the alteration of phosphate kinases. BMC Infect Dis. Apr. 1, 2010;10:86, 10 pages. doi: 10.1186/1471-2334-10-86.
U.S. Appl. No. 14/052,661, filed Oct. 11, 2013, Wagner et al.
PCT/US2013/064716, Nov. 19, 2013, International Search Report and Written Opinion.
PCT/US2013/064716, Apr. 23, 2015, International Preliminary Report on Patentability.
Barnes et al., Convergence of Hippocampal Pathophysiology in Syngap+/− and Fmr1 −/y Mice. J Neurosci. Nov. 11, 2015;35(45):15073-81. doi: 10.1523/JNEUROSCI.1087-15.2015.
Dahlhoff et al., AKT/GSK-3beta/beta-catenin signalling within hippocampus and amygdala reflects genetically determined differences in posttraumatic stress disorder like symptoms. Neuroscience. Sep. 1, 2010;169(3):1216-26. doi: 10.1016/j.neuroscience.2010.05.066.
Georgievska et al., AZD1080, a novel GSK3 inhibitor, rescues synaptic plasticity deficits in rodent brain and exhibits peripheral target engagement in humans. J Neurochem. May 2013;125(3):446-. doi: 10.1111/jnc.12203.
Kelleher et al., The autistic neuron: troubled translation? Cell. Oct. 31, 2008;135(3):401-6. doi: 10.1016/j.cell.2008.10.017.
Mukai et al., Molecular substrates of altered axonal growth and brain connectivity in a mouse model of schizophrenia. Neuron. May 6, 2015;86(3):680-95. doi: 10.1016/j.neuron.2015.04.003.
Neumann et al., Evaluation of Improved Glycogen Synthase Kinase-3α Inhibitors in Models of Acute Myeloid Leukemia. J Med Chem. Nov. 25, 2015;58(22):8907-19. doi: 10.1021/acs.jmedchem.5b01200.
Rowe et al., GSK-3 is a viable potential target for therapeutic intervention in bipolar disorder. Neurosci Biobehav Rev. 2007;31(6):920-31. Epub Mar. 15, 2007.
U.S. Appl. No. 15/260,262, filed Sep. 8, 2016, Scolnick et al.
Achab et al., A short route to functionalized imidazo[4,5-c]carbazoles. Synthesis of the first example of the imidazo[4,5-c]β-carboline ring system. Tetrahedron Letters. Dec. 10, 2001;42(50):8825-28.
Quiroga et al., An efficient synthesis of pyrazolo [3,4-b]pyridine-4-spiroindolinones by a three-component reaction of 5-aminopyrazoles, isatin, and cyclic β-diketones. Tetrahedron Letters. 2011;52(21):2664-6.

(56) References Cited

OTHER PUBLICATIONS

Wada, GSK-3 inhibitors and insulin receptor signaling in health, disease, and therapeutics. Front Biosci (Landmark Ed). Jan. 1, 2009;14:1558-70. Review.

* cited by examiner

CHIR 99021

AR A014418

SB216763

SB415286

GW8510

| | | Brain | | | Brain/Plasma | Brain/Plasma |
|---|---|---|---|---|---|---|
| | | AUC Brain µmol/L.hr | T₁/₂ Brain hr | Cmax Brain µmol/L | Cmax | AUC |
| 70 | 30 mg/kg | 16.52 | 2.32 | 4.48 | 0.25 | 0.16 |
| CHIR99021 | 12.5 mg/kg | 0.15 | 0.46 | 0.16 | 0.01 | 0.01 |

Compound 70

SEQUENCE LISTING

```
<160> NUMBER OF SEQ ID NOS: 1

<210> SEQ ID NO 1
<211> LENGTH: 26
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (21)..(21)
<223> OTHER INFORMATION: Modified by PO3H2

<400> SEQUENCE: 1

Tyr Arg Arg Ala Ala Val Pro Pro Ser Pro Ser Leu Ser Arg His Ser
1               5                   10                  15

Ser Pro His Gln Ser Glu Asp Glu Glu Glu
            20                  25
```

KINASE INHIBITORS AND METHODS OF USE THEREOF

RELATED APPLICATIONS

The present application is a continuation of and claims priority under 35 U.S.C. § 120 to U.S. Application, U.S. Ser. No. 14/052,661, filed Oct. 11, 2013, which claims priority under 35 U.S.C. § 119(e) to U.S. provisional patent applications, U.S. Ser. No. 61/713,314, filed Oct. 12, 2012, and U.S. Ser. No. 61/779,394, filed Mar. 13, 2013, each of which is incorporated herein by reference.

GOVERNMENT SUPPORT

This invention was made with government support under Grant Nos. MH087442 and CA140292 awarded by the National Institutes of Health. The government has certain rights in the invention.

BACKGROUND OF THE INVENTION

The search for new therapeutic agents has been greatly aided in recent years by a better understanding of the structure of enzymes and other biomolecules associated with diseases. One important class of enzymes that has been the subject of extensive study is protein kinases.

Protein kinases constitute a large family of structurally related enzymes that are responsible for the control of a variety of signal transduction processes within the cell. Protein kinases are thought to have evolved from a common ancestral gene due to the conservation of their structure and catalytic function. Almost all kinases contain a similar 250-300 amino acid catalytic domain. The kinases may be categorized into families by the substrates they phosphorylate (e.g., protein-tyrosine, protein-serine/threonine, lipids, etc.).

In general, protein kinases mediate intracellular signaling by effecting a phosphoryl transfer from a nucleoside triphosphate to a protein acceptor that is involved in a signaling pathway. These phosphorylation events act as molecular on/off switches that can modulate or regulate the target protein biological function. These phosphorylation events are ultimately triggered in response to a variety of extracellular and other stimuli. Examples of such stimuli include environmental and chemical stress signals (e.g., osmotic shock, heat shock, ultraviolet radiation, bacterial endotoxin, and $H_2O_2$), cytokines (e.g., interleukin-1 (IL-I) and tumor necrosis factor α (TNF-α)), and growth factors (e.g., granulocyte macrophage-colony-stimulating factor (GM-CSF), and fibroblast growth factor (FGF)). An extracellular stimulus may affect one or more cellular responses related to cell growth, migration, differentiation, secretion of hormones, activation of transcription factors, muscle contraction, glucose metabolism, control of protein synthesis, and regulation of the cell cycle.

Many diseases are associated with abnormal cellular responses triggered by protein kinase-mediated events as described above. These diseases include, but are not limited to, autoimmune diseases, inflammatory diseases, bone diseases, metabolic diseases, neurological and neurodegenerative diseases, cancer, cardiovascular diseases, allergies and asthma, Alzheimer's disease, metabolic disorders (e.g., diabetes), and hormone-related diseases. Accordingly, there remains a need to find protein kinase inhibitors, particularly GSK3 inhibitors, useful as therapeutic agents.

SUMMARY OF THE INVENTION

It is important to identify selective kinase inhibitors in order to reduce or eliminate off-target effects. In certain embodiments, compounds of described herein are selective kinase inhibitors.

In one some embodiments, the present disclosure provides a compound of formula I:

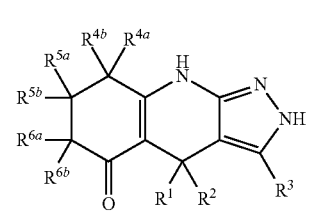

or a pharmaceutically acceptable salt thereof, wherein $R^1$, $R^2$, $R^3$, $R^{4a}$, $R^{4b}$, $R^{5a}$, $R^{5b}$, $R^{6a}$, and $R^{6b}$ are as defined herein. In certain embodiments, the present disclosure provides a compound of formula II:

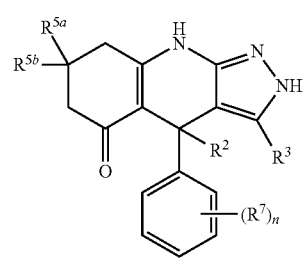

or a pharmaceutically acceptable salt thereof, wherein $R^2$, $R^3$, $R^{5a}$, $R^{5b}$, $R^7$, and n are as defined herein. In certain embodiments, the present disclosure provides a compound of formula III:

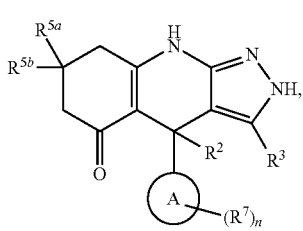

or a pharmaceutically acceptable salt thereof, wherein Ring A, $R^2$, $R^3$, $R^{5a}$, $R^{5b}$, $R^7$, and n are as defined herein.

In some embodiments, a compound described herein is enantiomerically enriched. For example, in certain embodiments, a provided compound is of formula II-a-i, II-a-ii, II-b-i, or II-b-ii:

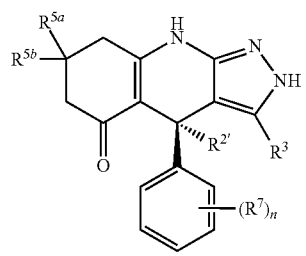

II-a-i

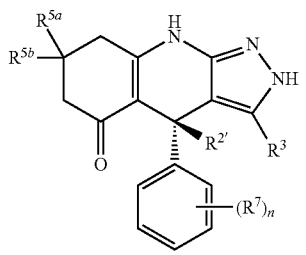

II-a-ii

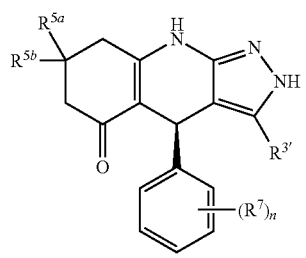

II-b-i

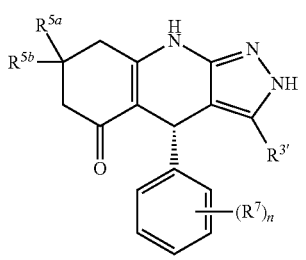

II-b-ii or a pharmaceutically acceptable salt thereof.

In some embodiments, pharmaceutical compositions are provided which comprise a compound described herein (e.g., a compound of formula I, II, or III), or a pharmaceutically acceptable salt thereof, and a pharmaceutically acceptable excipient.

In certain embodiments, compounds described herein inhibit activity of one or more kinases (e.g., glycogen synthase kinase 3 (GSK3), casein kinase 1 (CK1)). In certain embodiments, methods of inhibiting a kinase are provided which comprise contacting a kinase, or mutant or variant thereof, with an effective amount of a compound of formula I, II, or III, or a pharmaceutically acceptable salt thereof. The kinase may be purified or crude, and may be present in a cell, tissue, or a subject. Thus, such methods encompass both inhibition of in vitro and in vivo kinase activity. In certain embodiments, methods of inhibiting GSK3 are provided which comprise contacting GSK3, or a mutant or variant thereof, with an effective amount of a compound described herein (e.g., a compound of formula I, II, or III), or a pharmaceutically acceptable salt thereof. In certain embodiments, the GSK3 is wild-type GSK3. In certain embodiments, the GSK3 is GSK3β. In certain embodiments, the GSK3 is GSK3α. In certain embodiments, the GSK3 is in a cell. In certain embodiments, methods of inhibiting CK1 are provided which comprise contacting CK1, or a mutant or variant thereof, with an effective amount of a compound described herein (e.g., a compound of formula I, II, or III), or a pharmaceutically acceptable salt thereof. In certain embodiments, the CK1 is in a cell. In certain embodiments, the CK1 is wild-type CK1. In certain embodiments, the CK1 is CK1δ. In certain embodiments, the CK1δ is wild-type CK1δ. In certain embodiments, the CK1δ is in a cell. In some embodiments, a provided compound is selective for GSK3 over CK1.

In some embodiments, methods of treating a kinase-mediated disorder are provided which comprise administering to a subject suffering from a kinase-mediated disorder an effective amount of a compound described herein (e.g., a compound of formula I, II, or III), or a pharmaceutically acceptable salt thereof. In certain embodiments, methods of treating a GSK3-mediated disorder are provided which comprise administering to a subject suffering from a GSK3-mediated disorder an effective amount of a compound described herein (e.g., a compound of formula I, II, or III), or a pharmaceutically acceptable salt thereof. In certain embodiments, the GSK3-mediated disorder is a GSK3β-mediated disorder, such as neurological disease, psychiatric disorder, cancer (e.g., glioma, pancreatic cancer), or a metabolic disorder (e.g., diabetes (e.g., Type II diabetes)). In certain embodiments, the GSK3-mediated disorder is a neurodegenerative disorder, such as Alzheimer's disease, frontotemporal dementia (including progressive supranuclear palsy, corticobasal degeneration), or amyotrophic lateral sclerosis (ALS). In certain embodiments, the GSK3-mediated disorder is a psychiatric disorder, such as bipolar disorder, schizophrenia, autism, Fragile X syndrome, or depression (e.g., lithium-resistant depression). In certain embodiments, the GSK3-mediated disorder is a GSK3α-mediated disorder. In certain embodiments, the GSK3α-mediated disorder is cancer. In certain embodiments, the GSK3α-mediated disorder is leukemia, such as acute myeloid leukemia. In certain embodiments, the GSK3α-mediated disorder is a metabolic disorder (e.g., diabetes (e.g., Type II diabetes)). In certain embodiments, methods of treating a CK1-mediated disorder are provided which comprise administering to a subject suffering from a CK1-mediated disorder an effective amount of a compound described herein (e.g., a compound of formula I, II, or III), or a pharmaceutically acceptable salt thereof. In certain embodiments, methods of treating a CK1δ-mediated disorder are provided which comprise administering to a subject suffering from a CK1δ-mediated disorder an effective amount of a compound described herein (e.g., a compound of formula I, II, or III), or a pharmaceutically acceptable salt thereof. In certain embodiments, the CK1δ-mediated disorder is a neuropsychiatric disorder, such as attention deficit hyperactivity disorder (ADHD). In certain embodiments, a provided compound stimulates neurogenesis (e.g., of human neurons).

In some embodiments, compounds described herein show improved potency, selectivity, and/or stability over previously disclosed kinase (e.g., GSK3, CK1δ) inhibitors. In certain embodiments, a provided compound is potent for GSK (e.g., <1 µM). In certain embodiments, a provided compound is selective for GSK versus other kinases selectivity (e.g., >10-fold $IC_{50}$). In certain embodiments, a provided compound inhibits Tau phosphorylation (e.g., $IC_{50}$<10 µM). In certain embodiments, a provided compound activates Wnt signaling (e.g., $EC_{50}$<10 µM). In certain embodiments, a provided compound is potent for CK1δ (e.g., <1 µM). In certain embodiments, a provided compound is selective for CK1δ versus other kinases selectivity (e.g., >10-fold $IC_{50}$). In certain embodiments, compounds described herein show an improved pharmacokinetic profile, such as enhanced brain penetration.

In some embodiments, compounds described herein are useful as probe compounds for investigating the role of kinase signaling, e.g., GSK3 signaling, in the pathophysiology of various disorders, e.g., bipolar disorder and other psychiatric disorders. In certain embodiments, provided compounds are useful as probe compounds for modulating human neurogenesis.

This application refers to various issued patent, published patent applications, journal articles, and other publications, all of which are incorporated herein by reference.

Definitions

Chemical Definitions

Definitions of specific functional groups and chemical terms are described in more detail below. The chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in Thomas Sorrell, *Organic Chemistry*, University Science Books, Sausalito, 1999; Smith and March, *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987.

Compounds described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGraw-Hill, NY, 1962); and Wilen, *Tables of Resolving Agents and Optical Resolutions* p. 268 (E. L. Eliel, Ed., Univ. of Notre Dame Press, Notre Dame, Ind. 1972). The present disclosure additionally encompasses compounds described herein as individual isomers substantially free of other isomers, and alternatively, as mixtures of various isomers.

Unless otherwise stated, structures depicted herein are also meant to include compounds that differ only in the presence of one or more isotopically enriched atoms. For example, compounds described herein where the compounds are enriched with deuterium, tritium, $^{18}F$, $^{13}C$, and/or $^{14}C$ are within the scope of the disclosure. Such compounds are useful, for example, as analytical tools or probes in biological assays.

The term "aliphatic" includes both saturated and unsaturated, nonaromatic, straight chain (i.e., unbranched), branched, acyclic, and cyclic (i.e., carbocyclic) hydrocarbons. In some embodiments, an aliphatic group is optionally substituted with one or more functional groups (e.g., halo, such as fluorine). As will be appreciated by one of ordinary skill in the art, "aliphatic" is intended herein to include alkyl, alkenyl, alkynyl, cycloalkyl, cycloalkenyl, and cycloalkynyl moieties.

When a range of values is listed, it is intended to encompass each value and sub-range within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

"Alkyl" refers to a radical of a straight-chain or branched saturated hydrocarbon group having from 1 to 20 carbon atoms ("$C_{1-20}$ alkyl"). In some embodiments, an alkyl group has 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), n-propyl ($C_3$), isopropyl ($C_3$), n-butyl ($C_4$), tert-butyl ($C_4$), sec-butyl ($C_4$), isobutyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Additional examples of alkyl groups include n-heptyl ($C_7$), n-octyl ($C_8$) and the like. Unless otherwise specified, each instance of an alkyl group is independently optionally substituted, e.g., unsubstituted (an "unsubstituted alkyl") or substituted (a "substituted alkyl") with one or more substituents. In certain embodiments, the alkyl group is unsubstituted $C_{1-10}$ alkyl (e.g., —$CH_3$). In certain embodiments, the alkyl group is substituted $C_{1-10}$ alkyl.

In some embodiments, an alkyl group is substituted with one or more halogens. "Perhaloalkyl" is a substituted alkyl group as defined herein wherein all of the hydrogen atoms are independently replaced by a halogen, e.g., fluoro, bromo, chloro, or iodo. In some embodiments, the alkyl moiety has 1 to 8 carbon atoms ("$C_{1-8}$ perhaloalkyl"). In some embodiments, the alkyl moiety has 1 to 6 carbon atoms ("$C_{1-4}$ perhaloalkyl"). In some embodiments, the alkyl moiety has 1 to 4 carbon atoms ("$C_{1-4}$ perhaloalkyl"). In some embodiments, the alkyl moiety has 1 to 3 carbon atoms ("$C_{1-3}$ perhaloalkyl"). In some embodiments, the alkyl moiety has 1 to 2 carbon atoms ("$C_{1-2}$ perhaloalkyl"). In some embodiments, all of the hydrogen atoms are replaced with fluoro. In some embodiments, all of the hydrogen atoms are replaced with chloro. Examples of perhaloalkyl groups include —$CF_3$, —$CF_2CF_3$, —$CF_2CF_2CF_3$, —$CCl_3$, —$CFCl_2$, —$CF_2Cl$, and the like.

"Alkenyl" refers to a radical of a straight-chain or branched hydrocarbon group having from 2 to 20 carbon atoms, one or more carbon-carbon double bonds, and no triple bonds ("$C_{2-20}$ alkenyl"). In some embodiments, an alkenyl group has 2 to 10 carbon atoms ("$C_{2-10}$ alkenyl"). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-6}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently optionally substituted, e.g., unsubstituted (an "unsubstituted alkenyl") or substituted (a "substituted alkenyl") with one or more substituents. In certain embodiments, the alkenyl group is unsubstituted $C_{2-10}$ alkenyl. In certain embodiments, the alkenyl group is substituted $C_{2-10}$ alkenyl.

"Alkynyl" refers to a radical of a straight-chain or branched hydrocarbon group having from 2 to 20 carbon atoms, one or more carbon-carbon triple bonds, and optionally one or more double bonds ("$C_{2-20}$ alkynyl"). In some embodiments, an alkynyl group has 2 to 10 carbon atoms ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-8}$ alkynyl"). In some embodiments, an alkynyl group has 2 to 7 carbon atoms ("$C_{2-7}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$ alkenyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like. Unless otherwise specified, each instance of an alkynyl group is independently optionally substituted, e.g., unsubstituted (an "unsubstituted alkynyl") or substituted (a "substituted alkynyl") with one or more substituents. In certain embodiments, the alkynyl group is unsubstituted $C_{2-10}$ alkynyl. In certain embodiments, the alkynyl group is substituted $C_{2-10}$ alkynyl.

"Carbocyclyl" or "carbocyclic" refers to a radical of a non-aromatic cyclic hydrocarbon group having from 3 to 10 ring carbon atoms ("$C_{3-10}$ carbocyclyl") and zero heteroatoms in the non-aromatic ring system. In some embodiments, a carbocyclyl group has 3 to 8 ring carbon atoms ("$C_{3-8}$ carbocyclyl"). In some embodiments, a carbocyclyl group has 3 to 6 ring carbon atoms ("$C_{3-6}$ carbocyclyl"). In some embodiments, a carbocyclyl group has 3 to 6 ring carbon atoms ("$C_{3-6}$ carbocyclyl"). In some embodiments, a carbocyclyl group has 5 to 10 ring carbon atoms ("$C_{5-10}$ carbocyclyl"). Exemplary $C_{3-6}$ carbocyclyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ carbocyclyl groups include, without limitation, the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), and the like. Exemplary $C_{3-10}$ carbocyclyl groups include, without limitation, the aforementioned $C_{3-8}$ carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the carbocyclyl group is either monocyclic ("monocyclic carbocyclyl") or contain a fused, bridged or spiro ring system such as a bicyclic system ("bicyclic carbocyclyl"). Carbocyclyl can be saturated, and saturated carbocyclyl is referred to as "cycloalkyl." In some embodiments, carbocyclyl is a monocyclic, saturated carbocyclyl group having from 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Examples of $C_{5-6}$ cycloalkyl groups include cyclopentyl ($C_5$) and cyclohexyl ($C_5$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is unsubstituted $C_{3-10}$ cycloalkyl. In certain embodiments, the cycloalkyl group is substituted $C_{3-10}$ cycloalkyl. Carbocyclyl can be partially unsaturated. Carbocyclyl including one or more C=C double bonds in the carbocyclic ring is referred to as "cycloalkenyl." Carbocyclyl including one or more C≡C triple bonds in the carbocyclic ring is referred to as "cycloalkynyl." Carbocyclyl includes aryl. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently optionally substituted, e.g., unsubstituted (an "unsubstituted carbocyclyl") or substituted (a "substituted carbocyclyl") with one or more substituents. In certain embodiments, the carbocyclyl group is unsubstituted $C_{3-10}$ carbocyclyl. In certain embodiments, the carbocyclyl group is a substituted $C_{3-10}$ carbocyclyl.

In some embodiments, "carbocyclyl" is a monocyclic, saturated carbocyclyl group having from 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Examples of $C_{5-6}$ cycloalkyl groups include cyclopentyl ($C_5$) and cyclohexyl ($C_5$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is unsubstituted $C_{3-10}$ cycloalkyl. In certain embodiments, the cycloalkyl group is substituted $C_{3-10}$ cycloalkyl.

"Heterocyclyl" or "heterocyclic" refers to a radical of a 3- to 10-membered non-aromatic ring system having ring carbon atoms and 1 to 4 ring heteroatoms, wherein each heteroatom is independently selected from nitrogen, oxygen, and sulfur ("3-10 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or a fused, bridged or spiro ring system such as a bicyclic system ("bicyclic heterocyclyl"), and can be saturated or can be partially unsaturated. Partially unsaturated heterocyclyl groups includes heteroaryl. Heterocyclyl bicyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of heterocyclyl is independently optionally substituted, e.g., unsubstituted (an "unsubstituted heterocyclyl") or substituted (a "substituted heterocyclyl") with one or more substituents. In certain embodiments, the heterocyclyl group is unsubstituted 3-10 membered heterocyclyl. In certain embodiments, the heterocyclyl group is substituted 3-10 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, and sulfur ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has one ring heteroatom selected from nitrogen, oxygen, and sulfur.

Exemplary 3-membered heterocyclyl groups containing one heteroatom include, without limitation, azirdinyl, oxiranyl, thiorenyl. Exemplary 4-membered heterocyclyl groups containing one heteroatom include, without limitation, azetidinyl, oxetanyl and thietanyl. Exemplary 5-membered heterocyclyl groups containing one heteroatom include, without limitation, tetrahydrofuranyl, dihydrofuranyl, tetrahydrothiophenyl, dihydrothiophenyl, pyrrolidinyl, dihydropyrrolyl and pyrrolyl-2,5-dione. Exemplary 5-membered heterocyclyl groups containing two heteroatoms include, without limitation, dioxolanyl, oxasulfuranyl, disulfuranyl, and oxazolidin-2-one. Exemplary 5-membered heterocyclyl groups containing three heteroatoms include, without limitation, triazolinyl, oxadiazolinyl, and thiadiazolinyl. Exemplary 6-membered heterocyclyl groups containing one heteroatom include, without limitation, piperidinyl, tetrahydropyranyl, dihydropyridinyl, and thianyl. Exemplary 6-membered heterocyclyl groups containing two heteroatoms include, without limitation, piperazinyl, morpholinyl, dithianyl, and dioxanyl. Exemplary 6-membered heterocyclyl groups containing two heteroatoms include, without limitation, triazinanyl. Exemplary 7-membered heterocyclyl groups containing one heteroatom include, without limitation, azepanyl, oxepanyl and thiepanyl. Exemplary 8-membered heterocyclyl groups containing one heteroatom include, without limitation, azocanyl, oxecanyl, and thiocanyl. Exemplary 5-membered heterocyclyl groups fused to a $C_6$ aryl ring (also referred to herein as a 5,6-bicyclic heterocyclic ring) include, without limitation, indolinyl, isoindolinyl, dihydrobenzofuranyl, dihydrobenzothienyl, benzoxazolinonyl, and the like. Exemplary 6-membered heterocyclyl groups fused to an aryl ring (also referred to herein as a 6,6-bicyclic heterocyclic ring) include, without limitation, tetrahydroquinolinyl, tetrahydroisoquinolinyl, and the like.

"Aryl" refers to a radical of a monocyclic or polycyclic (e.g., bicyclic or tricyclic) 4n+2 aromatic ring system (e.g., having 6, 10, or 14π electrons shared in a cyclic array) having 6-14 ring carbon atoms and zero heteroatoms provided in the aromatic ring system ("$C_{6-14}$ aryl"). In some embodiments, an aryl group has six ring carbon atoms ("$C_6$ aryl"; e.g., phenyl). In some embodiments, an aryl group has ten ring carbon atoms ("$C_{10}$ aryl"; e.g., naphthyl such as 1-naphthyl and 2-naphthyl). In some embodiments, an aryl group has fourteen ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently optionally substituted, e.g., unsubstituted (an "unsubstituted aryl") or substituted (a "substituted aryl") with one or more substituents. In certain embodiments, the aryl group is unsubstituted $C_{6-14}$ aryl. In certain embodiments, the aryl group is substituted $C_{6-14}$ aryl.

"Heteroaryl" refers to a radical of a 5-10 membered monocyclic or bicyclic 4n+2 aromatic ring system (e.g., having 6 or 10π electrons shared in a cyclic array) having ring carbon atoms and 1-4 ring heteroatoms provided in the aromatic ring system, wherein each heteroatom is independently selected from nitrogen, oxygen and sulfur ("5-10 membered heteroaryl"). In heteroaryl groups that contain one or more nitrogen atoms, the point of attachment can be a carbon or nitrogen atom, as valency permits. Heteroaryl bicyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused (aryl/heteroaryl) ring system. Bicyclic heteroaryl groups wherein one ring does not contain a heteroatom (e.g., indolyl, quinolinyl, carbazolyl, and the like) the point of attachment can be on either ring, e.g., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently optionally substituted, e.g., unsubstituted ("unsubstituted heteroaryl") or substituted ("substituted heteroaryl") with one or more substituents. In certain embodiments, the heteroaryl group is unsubstituted 5-14 membered heteroaryl. In certain embodiments, the heteroaryl group is substituted 5-14 membered heteroaryl.

Exemplary 5-membered heteroaryl groups containing one heteroatom include, without limitation, pyrrolyl, furanyl and thiophenyl. Exemplary 5-membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl. Exemplary 5-membered heteroaryl groups containing four heteroatoms include, without limitation, tetrazolyl. Exemplary 6-membered heteroaryl groups containing one heteroatom include, without limitation, pyridinyl. Exemplary 6-membered heteroaryl groups containing two heteroatoms include, without limitation, pyridazinyl, pyrimidinyl, and pyrazinyl. Exemplary 6-membered heteroaryl groups containing three or four heteroatoms include, without limitation, triazinyl and tetrazinyl, respectively. Exemplary 7-membered heteroaryl groups containing one heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl.

"Partially unsaturated" refers to a group that includes at least one double or triple bond. The term "partially unsaturated" is intended to encompass rings having multiple sites of unsaturation, but is not intended to include aromatic groups (e.g., aryl or heteroaryl groups) as herein defined. Likewise, "saturated" refers to a group that does not contain a double or triple bond, i.e., contains all single bonds.

In some embodiments, aliphatic, alkyl, alkenyl, alkynyl, carbocyclyl, heterocyclyl, aryl, and heteroaryl groups, as defined herein, are optionally substituted (e.g., "substituted" or "unsubstituted" alkyl, "substituted" or "unsubstituted" alkenyl, "substituted" or "unsubstituted" alkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. The present disclosure contemplates any and all such combinations in order to arrive at a stable compound. For purposes of this disclosure, heteroatoms such as nitrogen may have hydrogen substituents and/or any suitable substituent as described herein which satisfy the valencies of the heteroatoms and results in the formation of a stable moiety.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3$$^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$—C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)$_2$R$^{aa}$, —OP(=O)$_2$R$^{aa}$, —P(=O)(R$^{aa}$)$_2$, —OP(=O)(R$^{aa}$)$_2$, —OP(=O)(OR$^{cc}$)$_2$, —P(=O)$_2$N(R$^{bb}$)$_2$, —OP(=O)$_2$N(R$^{bb}$)$_2$, —P(=O)(NR$^{bb}$)$_2$, —OP(=O)(NR$^{bb}$)$_2$, —NR$^{bb}$P(=O)(OR$^{cc}$)$_2$, —NR$^{bb}$P(=O)(NR$^{bb}$)$_2$, —P(R$^{cc}$)$_2$, —P(R$^{cc}$)$_3$, —OP(R$^{cc}$)$_2$, —OP(R$^{cc}$)$_3$, —B(R$^{aa}$)$_2$, —B(OR$^{cc}$)$_2$, —BR$^{aa}$(OR$^{cc}$), C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, carbocyclyl, heterocyclyl, aryl, and heteroaryl is independently substituted with 0, 1, 2, 3, 4, or 5 R$^{dd}$ groups;

or two geminal hydrogens on a carbon atom are replaced with the group =O, =S, =NN($R^{bb}$)$_2$, =NN$R^{bb}$C(=O)$R^{aa}$, =NN$R^{bb}$C(=O)O$R^{aa}$, =NN$R^{bb}$S(=O)$_2$$R^{aa}$, =N$R^{bb}$, or =NO$R^{cc}$;

each instance of $R^{aa}$ is, independently, selected from $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two $R^{aa}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups;

each instance of $R^{bb}$ is, independently, selected from hydrogen, —OH, —O$R^{aa}$, —N($R^{cc}$)$_2$, —CN, —C(=O)$R^{aa}$, —C(=O)N($R^{cc}$)$_2$, —CO$_2$$R^{aa}$, —SO$_2$$R^{aa}$, —C(=N$R^{cc}$)O$R^{aa}$, —C(=N$R^{cc}$)N($R^{cc}$)$_2$, —SO$_2$N($R^{cc}$)$_2$, —SO$_2$$R^{cc}$, —SO$_2$O$R^{cc}$, —SO$R^{aa}$, —C(=S)N($R^{cc}$)$_2$, —C(=O)S$R^{cc}$, —C(=S)S$R^{cc}$, —P(=O)$_2$$R^{aa}$, —P(=O)($R^{aa}$)$_2$, —P(=O)$_2$N($R^{cc}$)$_2$, —P(=O)(N$R^{cc}$)$_2$, $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two $R^{bb}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups;

each instance of $R^{cc}$ is, independently, selected from hydrogen, $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two $R^{cc}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups;

each instance of $R^{dd}$ is, independently, selected from halogen, —CN, —NO$_2$, —N$_3$, —SO$_2$H, —SO$_3$H, —OH, —O$R^{ee}$, —ON($R^{ff}$)$_2$, —N($R^{ff}$)$_2$, —N($R^{ff}$)$_3$$^+$X$^-$, —N(O$R^{ee}$)$R^{ff}$, —SH, —S$R^{ee}$, —SS$R^{ee}$, —C(=O)$R^{ee}$, —CO$_2$H, —CO$_2$$R^{ee}$, —OC(=O)$R^{ee}$, —OCO$_2$$R^{ee}$, —C(=O)N($R^{ff}$)$_2$, —OC(=O)N($R^{ff}$)$_2$, —N$R^{ff}$C(=O)$R^{ee}$, —N$R^{ff}$CO$_2$$R^{ee}$, —N$R^{ff}$C(=O)N($R^{ff}$)$_2$, —C(=N$R^{ff}$)O$R^{ee}$, —OC(=N$R^{ff}$)$R^{ee}$, —OC(=N$R^{ff}$)O$R^{ee}$, —C(=N$R^{ff}$)N($R^{ff}$)$_2$, —N$R^{ff}$C(=N$R^{ff}$)N($R^{ff}$)$_2$, —N$R^{ff}$SO$_2$$R^{ee}$, —SO$_2$N($R^{ff}$)$_2$, —SO$_2$$R^{ee}$, —SO$_2$O$R^{ee}$, —OSO$_2$$R^{ee}$, —S(=O)$R^{ee}$, —Si($R^{ee}$)$_3$, —OSi($R^{ee}$)$_3$, —C(=S)N($R^{ff}$)$_2$, —C(=O)S$R^{ee}$, —C(=S)S$R^{ee}$, —SC(=S)S$R^{ee}$, —P(=O)$_2$$R^{ee}$, —P(=O)($R^{ee}$)$_2$, —OP(=O)($R^{ee}$)$_2$, —OP(=O)(O$R^{ee}$)$_2$, $C_{1-6}$ alkyl, $C_{1-6}$ perhaloalkyl, $C_{2-6}$ alkenyl, $C_{2-6}$ alkynyl, $C_{3-10}$ carbocyclyl, 3-10 membered heterocyclyl, $C_{6-10}$ aryl, 5-10 membered heteroaryl, wherein each alkyl, alkenyl, alkynyl, carbocyclyl, heterocyclyl, aryl, and heteroaryl is independently substituted with 0, 1, 2, 3, 4, or 5 $R^{gg}$ groups, or two geminal $R^{dd}$ substituents can be joined to form =O or =S;

each instance of $R^{ee}$ is, independently, selected from $C_{1-6}$ alkyl, $C_{1-6}$ perhaloalkyl, $C_{2-6}$ alkenyl, $C_{2-6}$ alkynyl, $C_{3-10}$ carbocyclyl, $C_{6-10}$ aryl, 3-10 membered heterocyclyl, and 3-10 membered heteroaryl, wherein each alkyl, alkenyl, alkynyl, carbocyclyl, heterocyclyl, aryl, and heteroaryl is independently substituted with 0, 1, 2, 3, 4, or 5 $R^{gg}$ groups;

each instance of $R^{ff}$ is, independently, selected from hydrogen, $C_{1-6}$ alkyl, $C_{1-6}$ perhaloalkyl, $C_{2-6}$ alkenyl, $C_{2-6}$ alkynyl, $C_{3-10}$ carbocyclyl, 3-10 membered heterocyclyl, $C_{6-10}$ aryl and 5-10 membered heteroaryl, or two $R^{ff}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{gg}$ groups; and each instance of $R^{gg}$ is, independently, halogen, —CN, —NO$_2$, —N$_3$, —SO$_2$H, —SO$_3$H, —OH, —O$C_{1-6}$ alkyl, —ON($C_{1-6}$ alkyl)$_2$, —N($C_{1-6}$ alkyl)$_2$, —N($C_{1-6}$ alkyl)$_3$$^+$X$^-$, —NH($C_{1-6}$ alkyl)$_2$$^+$X$^-$, —NH$_2$($C_{1-6}$ alkyl)$^+$X$^-$, —NH$_3$$^+$X$^-$, —N(O$C_{1-6}$ alkyl)($C_{1-6}$ alkyl), —N(OH)($C_{1-6}$ alkyl), —NH(OH), —SH, —S$C_{1-6}$ alkyl, —SS($C_{1-6}$ alkyl), —C(=O)($C_{1-6}$ alkyl), —CO$_2$H, —CO$_2$($C_{1-6}$ alkyl), —OC(=O)($C_{1-6}$ alkyl), —OCO$_2$($C_{1-6}$ alkyl), —C(=O)NH$_2$, —C(=O)N($C_{1-4}$ alkyl)$_2$, —OC(=O)NH($C_{1-6}$ alkyl), —NHC(=O)($C_{1-6}$ alkyl), —N($C_{1-6}$ alkyl)C(=O)($C_{1-6}$ alkyl), —NHCO$_2$($C_{1-6}$ alkyl), —NHC(=O)N($C_{1-6}$ alkyl)$_2$, —NHC(=O)NH($C_{1-6}$ alkyl), —NHC(=O)NH$_2$, —C(=NH)O($C_{1-6}$ alkyl), —OC(=NH)($C_{1-6}$ alkyl), —OC(=NH)O$C_{1-6}$ alkyl, —C(=NH)N($C_{1-6}$ alkyl)$_2$, —C(=NH)NH($C_{1-6}$ alkyl), —C(=NH)NH$_2$, —OC(=NH)N($C_{1-6}$ alkyl)$_2$, —OC(NH)NH($C_{1-6}$ alkyl), —OC(NH)NH$_2$, —NHC(NH)N($C_{1-6}$ alkyl)$_2$, —NHC(=NH)NH$_2$, —NHSO$_2$($C_{1-6}$ alkyl), —SO$_2$N($C_{1-6}$ alkyl)$_2$, —SO$_2$NH($C_{1-6}$ alkyl), —SO$_2$NH$_2$, —SO$_2$$C_{1-6}$ alkyl, —SO$_2$O$C_{1-6}$ alkyl, —OSO$_2$$C_{1-6}$ alkyl, —SO$C_{1-6}$ alkyl, —Si($C_{1-6}$ alkyl)$_3$, —OSi($C_{1-6}$ alkyl)$_3$-C(=S)N($C_{1-6}$ alkyl)$_2$, C(=S)NH($C_{1-6}$ alkyl), C(=S)NH$_2$, —C(=O)S($C_{1-6}$ alkyl), —C(=S)S$C_{1-6}$ alkyl, —SC(=S)S$C_{1-6}$ alkyl, —P(=O)$_2$($C_{1-6}$ alkyl), —P(=O)($C_{1-6}$ alkyl)$_2$, —OP(=O)($C_{1-6}$ alkyl)$_2$, —OP(=O)(O$C_{1-6}$ alkyl)$_2$, $C_{1-6}$ alkyl, $C_{1-6}$ perhaloalkyl, $C_{2-6}$ alkenyl, $C_{2-6}$ alkynyl, $C_{3-10}$ carbocyclyl, $C_{6-10}$ aryl, 3-10 membered heterocyclyl, 5-10 membered heteroaryl; or two geminal $R^{gg}$ substituents can be joined to form =O or =S; wherein X$^-$ is a counterion.

A "counterion" or "anionic counterion" is a negatively charged group associated with a cationic quaternary amino group in order to maintain electronic neutrality. Exemplary counterions include halide ions (e.g., F$^-$, Cl$^+$, Br$^+$, I$^+$), NO$_3$$^-$, ClO$_4$$^-$, OH$^-$, H$_2$PO$_4$$^-$, HSO$_4$$^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), and carboxylate ions (e.g., acetate, ethanoate, propanoate, benzoate, glycerate, lactate, tartrate, glycolate, and the like).

"Halo" or "halogen" refers to fluorine (fluoro, —F), chlorine (chloro, —Cl), bromine (bromo, —Br), or iodine (iodo, —I).

Nitrogen atoms can be substituted or unsubstituted as valency permits, and include primary, secondary, tertiary, and quarternary nitrogen atoms. Exemplary nitrogen atom substitutents include, but are not limited to, hydrogen, —OH, —O$R^{aa}$, —N($R^{cc}$)$_2$, —CN, —C(=O)$R^{aa}$, —C(=O)N($R^{cc}$)$_2$, —CO$_2$$R^{aa}$, —SO$_2$$R^{aa}$, —C(=N$R^{bb}$)$R^{aa}$, —C(=N$R^{cc}$)O$R^{aa}$, —C(=N$R^{cc}$)N($R^{cc}$)$_2$, —SO$_2$N($R^{cc}$)$_2$, —SO$_2$$R^{cc}$, —SO$_2$O$R^{cc}$, —SO$R^{aa}$, —C(=S)N($R^{cc}$)$_2$, —C(=O)S$R^{cc}$, —C(=S)S$R^{cc}$, —P(=O)$_2$$R^{aa}$, —P(=O)($R^{aa}$)$_2$, —P(=O)$_2$N($R^{cc}$)$_2$, —P(=O)(N$R^{cc}$)$_2$, $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two $R^{cc}$ groups attached to a nitrogen atom are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined above.

In certain embodiments, the substituent present on a nitrogen atom is a nitrogen protecting group (also referred to as an amino protecting group). Nitrogen protecting groups include, but are not limited to, —OH, —OR$^{aa}$, —N(R$^{cc}$)$_2$, —C(=O)R$^{aa}$, —C(=O)N(R$^{cc}$)$_2$, —CO$_2$R$^{aa}$, —SO$_2$R$^{aa}$, —C(=NR$^{cc}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, C$_{1-10}$ alkyl (e.g., aralkyl, heteroaralkyl), C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl groups, wherein each alkyl, alkenyl, alkynyl, carbocyclyl, heterocyclyl, aralkyl, aryl, and heteroaryl is independently substituted with 0, 1, 2, 3, 4, or 5 R$^{dd}$ groups, and wherein R$^{aa}$, R$^{bb}$, R$^{cc}$, and R$^{dd}$ are as defined herein. Nitrogen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

Amide nitrogen protecting groups (e.g., —C(=O)R$^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy) propanamide, 4-chlorobutanamide, 3-methyl-3-nitrobutanamide, o-nitrocinnamide, N-acetylmethionine, o-nitrobenzamide, and o-(benzoyloxymethyl)benzamide.

Carbamate nitrogen protecting groups (e.g., —C(=O) OR$^{aa}$) include, but are not limited to, methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10, 10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N, N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium) benzyl carbamate, and 2,4,6-trimethylbenzyl carbamate.

Sulfonamide nitrogen protecting groups (e.g., —S(=O)$_2$R$^{aa}$) include, but are not limited to, p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene) amine, N,N'-isopropylidenediamine, N-p-nitrobenzylideneamine, N-salicylideneamine, N-5-chlorosalicylideneamine, N-(5-chloro-2-hydroxyphenyl) phenylmethyleneamine, N-cyclohexylideneamine, N-(5,5-dimethyl-3-oxo-1-cyclohexenyl)amine, N-borane derivative, N-diphenylborinic acid derivative, N-[phenyl (pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

In certain embodiments, the substituent present on an oxygen atom is an oxygen protecting group (also referred to as a hydroxyl protecting group). Oxygen protecting groups include, but are not limited to, —$R^{aa}$, —$N(R^{bb})_2$, —$C(=O)SR^{aa}$, —$C(=O)R^{aa}$, —$CO_2R^{aa}$, —$C(=O)N(R^{bb})_2$, —$C(=NR^{bb})R^{aa}$, —$C(=NR^{bb})OR^{aa}$, —$C(=NR^{bb})N(R^{bb})_2$, —$S(=O)R^{aa}$, —$SO_2R^{aa}$, —$Si(R^{aa})_3$, —$P(R^{cc})_2$, —$P(R^{cc})_3$, —$P(=O)_2R^{aa}$, —$P(=O)(R^{aa})_2$, —$P(=O)(OR^{cc})_2$, —$P(=O)_2N(R^{bb})_2$, and —$P(=O)(NR^{bb})_2$, wherein $R^{aa}$, $R^{bb}$, and $R^{cc}$ are as defined herein. Oxygen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

Exemplary oxygen protecting groups include, but are not limited to, methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxyl)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodisulfuran-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

In certain embodiments, the substituent present on a sulfur atom is a sulfur protecting group (also referred to as a thiol protecting group). Sulfur protecting groups include, but are not limited to, —$R^{aa}$, —$N(R^{bb})_2$, —$C(=O)SR^{aa}$, —$C(=O)R^{aa}$, —$CO_2R^{aa}$, —$C(=O)N(R^{bb})_2$, —$C(=NR^{bb})R^{aa}$, —$C(=NR^{bb})OR^{aa}$, —$C(=NR^{bb})N(R^{bb})_2$, —$S(=O)R^{aa}$, —$SO_2R^{aa}$, —$Si(R^{aa})_3$, —$P(R^{cc})_2$, —$P(R^{cc})_3$, —$P(=O)_2R^{aa}$, —$P(=O)(R^{aa})_2$, —$P(=O)(OR^{cc})_2$, —$P(=O)_2N(R^{bb})_2$, and —$P(=O)(NR^{bb})_2$, wherein $R^{aa}$, $R^{bb}$, and $R^{cc}$ are as defined herein. Sulfur protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

These and other exemplary substituents are described in more detail in the Detailed Description, Examples, and claims. The present disclosure is not intended to be limited in any manner by the above exemplary listing of substituents.

Other Definitions

"Pharmaceutically acceptable salt" refers to those salts which are, within the scope of sound medical judgment, suitable for use in contact with the tissues of humans and other animals without undue toxicity, irritation, allergic response, and the like, and are commensurate with a reasonable benefit/risk ratio. Pharmaceutically acceptable salts are well known in the art. For example, Berge et al., describe pharmaceutically acceptable salts in detail in *J. Pharmaceutical Sciences* (1977) 66:1-19. Pharmaceutically acceptable salts of the compounds describe herein include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid, or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, quaternary salts.

A "subject" to which administration is contemplated includes, but is not limited to, humans (e.g., a male or female of any age group, e.g., a pediatric subject (e.g, infant, child, adolescent) or adult subject (e.g., young adult, middle-aged adult or senior adult)) and/or other non-human animals, for example mammals (e.g., primates (e.g., cynomolgus monkeys, rhesus monkeys); commercially relevant mammals such as cattle, pigs, horses, sheep, goats, cats, and/or dogs), birds (e.g., commercially relevant birds such as chickens, ducks, geese, and/or turkeys), reptiles, amphibians, and fish. In certain embodiments, the non-human animal is a mammal. The non-human animal may be a male or female at any stage of development. A non-human animal may be a transgenic animal.

"Condition," "disease," and "disorder" are used interchangeably herein.

"Treat," "treating" and "treatment" encompasses an action that occurs while a subject is suffering from a condition which reduces the severity of the condition or retards or slows the progression of the condition ("therapeutic treatment"). "Treat," "treating" and "treatment" also encompasses an action that occurs before a subject begins to suffer from the condition and which inhibits or reduces the severity of the condition ("prophylactic treatment").

An "effective amount" of a compound refers to an amount sufficient to elicit the desired biological response, e.g., treat the condition. As will be appreciated by those of ordinary skill in this art, the effective amount of a compound described herein may vary depending on such factors as the desired biological endpoint, the pharmacokinetics of the compound, the condition being treated, the mode of administration, and the age and health of the subject. An effective amount encompasses therapeutic and prophylactic treatment.

A "therapeutically effective amount" of a compound is an amount sufficient to provide a therapeutic benefit in the treatment of a condition or to delay or minimize one or more symptoms associated with the condition. A therapeutically effective amount of a compound means an amount of therapeutic agent, alone or in combination with other therapies, which provides a therapeutic benefit in the treatment of the condition. The term "therapeutically effective amount" can encompass an amount that improves overall therapy, reduces or avoids symptoms or causes of the condition, or enhances the therapeutic efficacy of another therapeutic agent.

A "prophylactically effective amount" of a compound is an amount sufficient to prevent a condition, or one or more symptoms associated with the condition or prevent its recurrence. A prophylactically effective amount of a compound means an amount of a therapeutic agent, alone or in combination with other agents, which provides a prophylactic benefit in the prevention of the condition. The term "prophylactically effective amount" can encompass an amount that improves overall prophylaxis or enhances the prophylactic efficacy of another prophylactic agent.

The term "kinase" represents transferase class enzymes that are able to transfer a phosphate group from a donor molecule to an acceptor molecule, e.g., an amino acid residue of a protein or a lipid molecule. Representative, non-limiting examples of kinases include Abl, ACK, Akt1/PKBα, Akt2/PKBβ, Akt3/PKBγ, ALK1, ALK2, Alk4, AMPKα1/β1/γ1, AMPKα1/β1/γ2, AMPKα1/β1/γ3, AMPKα1/β2/γ1, AMPKα2/β1/γ1, AMPKα2/β2/γ2, Abl2, ARK5, Ask1, Aurora A, Aurora B, Aurora C, Axl, BARK1, Blk, Bmx, B-Raf, Brk, BrSK1, BrSK2, Btk, CaMK1α, CaMK1β, CaMK1γ, CaMK1δ, CAMK2α, CaMK2β, CAMK2δ, CAMK2γ, CAMK4, CAMKK1, CAMKK2, CDK1, CDK2, CDK3, CDK4, CDK5, CDK6, CDK7, CDK9, CDK1/cyclin B, CDK2/cyclin A, CDK2/cyclin E, CDK3/cyclin E, CDK5/p25, CDK5/p35, CDK6/cyclinD3, CDK7/cyclin H/MAT1, CDK9/cyclin T1, CHK1, CHK2, CK1α, CK1γ, CK1δ, CK1ε, CK1β1, CK1γ1, CK1γ2, CK1γ3, CK2α1, CK2α2, cKit, c-RAF, CLK1, CLK2, CLK3, COT, Csk, DAPK1, DAPK2, DAPK3, DCAMLK2, DDR2, DMPK, DRAK1, DYRK1A, DYRK2, DYRK3, eEF2K, EGFR, EPHA1, EPHA2, EPHA3, EPHA4, EPHA5, EPHA6, EPHA7, EPHA8, EphB1, EphB2, EphB3, EphB4, ErbB4, Erk1, Erk2, FAK, Fer, Fes, FGFR1, Flt2, Flt4, FLT3 D835Y, FGFR2, FGFR3, FGFR4, Fgr, Flt1, Flt3, Fms, FRK, FynA, GCK, GPRK5, GRK2, GRK4, GRK6, GRK7, GSK3α, GSK3β, Hck, HER2, HER4, HIPK1, HIPK2, HIPK3, HIPK4, IGF1R, IKKβ, IKKα, IKKε, IR, InsR, IRR, IRAK1, IRAK2, IRAK4, Itk, JAK2, JAK3, JNK1, JNK2, JNK3, KDR, KHS1, Kit, Lck, LIMK1, LKB1, LOK, LRRK2, Lyn A, Lyn B, MAPK1, MAPK2, MAPK12, MAP-KAP-K2, MAPKAP-K3, MAPKAPK2, MAPKAPK3, MAPKAPK5, MARK1, MARK2, MARK3, MARK4, MELK, MEK1, MEK2, MEKK2, MEKK3, Mer, Met, MET M1250T, MINK, MKK4, MKK6, MKK7β, MLCK, MLK1, MLK3, MNK1, MNK2, MRCKα, MRCKβ, MSK1, MSK2, MSSK1, STK23, STK4, STK3, STK24, MST1, MST2, MST3, MST4, MUSK, mTOR, MYO33, MYT1, NDR1, NEK11, NEK2, NEK3, NEK6, NEK7, NEK9, NLK, NUAK2, p38α, p38β, p38δ, p38γ, p70S6K, S6K, SRK, PAK1/CDC42, PAK2, PAK3, PAK4, PAK5, PAK6, PAR-1B, PASK, PBK, PDGFRα, PDGFRPβ, PDK1, PEK, PHKG2, PI3Kα, PI3Kβ, PI3Kγ, PI3Kδ, Pim1, Pim2, PKAcα, PKAcβ, PKAcγ, PKA(b), PKA, PKBα, PKBβ, PKBγ, PKCα, PKCβ1, PKCβ2, PKCβ11, PKCδ, PKCε, PKCγ, PKCμ, PKCη, PKCι, PKCθ, PKCζ, PKD1, PKD2, PKD3, PKG1α, PKG1B, PKN1, PKN2, PKR, PLK1, PLK2, PLK3, PLK4, Polo, PRAK, PRK2, PrKX, PTK5, PYK2, QIK, Raf1, Ret, RIPK2, RIPK5, ROCK1, ROCK2, RON, ROS, Rse, RSK1, RSK2, RSK3, RSK4, SAPK2a, SAPK2b, SAPK3, SAPK4, SGK1, SGK2, SGK3, SIK, MLCK, SLK, Snk, Src, SRPK1, SRPK2, STK33, SYK, TAK1-TAB1, TAK1, TBK1, TAO1, TAO2, TAO3, TBK1, TEC, TESK1, TGFβR1, TGFβR2, Tie2, TLK2, TrkA, TrkB, TrkC, TSSK1, TSSK2, TTK, TXK, TYK2, TYRO3, ULK1, ULK2, WEE1, WNK2, WNK3, Yes1, YSK1, ZAK, ZAP70, ZC3, and ZIPK.

The term "mutant" refers to a sequence (e.g., a protein sequence or a nucleic acid sequence) having at least one mutation. The term "mutation," as used herein, refers to a substitution of a residue within a sequence, e.g., a nucleic acid or amino acid sequence, with another residue, or a deletion or insertion of one or more residues within a sequence.

The term "variant" refers to variations of the nucleic acid or amino acid sequences of the biomolecule of interest. Encompassed within the term "variant" are nucleotide and amino acid substitutions, additions, or deletions. Also, encompassed within the term "variant" are chemically modified natural and synthetic biomolecules. For example, variant may refer to polypeptides that differ from a reference polypeptide. Generally, the differences between the polypeptide that differs in amino acid sequence from reference polypeptide, and the reference polypeptide are limited so that the amino acid sequences of the reference and the variant are closely similar overall and, in some regions, identical. A variant and reference polypeptide may differ in amino acid sequence by one or more substitutions, deletions, additions, fusions and truncations that may be conservative or non-conservative and may be present in any combination. For example, variants may be those in which several, for instance from 50 to 30, from 30 to 20, from 20 to 10, from 10 to 5, from 5 to 3, from 3 to 2, from 2 to 1 or 1 amino acids are inserted, substituted, or deleted, in any combination. Additionally, a variant may be a fragment of a polypeptide that differs from a reference polypeptide sequence by being shorter than the reference sequence, such as by a terminal or internal deletion. A variant of a polypeptide also includes a polypeptide which retains essentially the same biological function or activity as such polypeptide, e.g., precursor proteins which can be activated by cleavage of the precursor portion to produce an active mature polypeptide. These variants may be allelic variations characterized by differences in the nucleotide sequences of the structural gene coding for the protein, or may involve differential splicing or post-translational modification. Variants also include a related protein having substantially the same biological activity, but obtained from a different species. The skilled artisan can produce variants having single or multiple amino acid substitutions, deletions, additions, or replacements. These variants may include, inter alia: (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more amino acids are deleted from the peptide or protein, or (iii) one in which one or more amino acids are added to the polypeptide or protein, or (iv) one in which one or more of the amino acid residues include a substituent group, or (v) one in which the mature polypeptide is fused with another compound, such as a compound to increase the half-life of the polypeptide (for example, polyethylene glycol), or (vi) one in which the additional amino acids are fused to the mature polypeptide such as a leader or secretory sequence or a sequence which is employed for purification of the mature polypeptide or a precursor protein sequence. A variant of the polypeptide may also be a naturally occurring variant such as a naturally occurring allelic variant, or it may be a variant that is not known to occur naturally.

The term "cancer" refers to a class of diseases characterized by the development of abnormal cells that proliferate uncontrollably and have the ability to infiltrate and destroy normal body tissues. See, e.g., *Stedman's Medical Dictionary*, 25th ed.; Hensyl ed.; Williams & Wilkins: Philadelphia, 1990. Exemplary cancers include, but are not limited to, acoustic neuroma; adenocarcinoma; adrenal gland cancer; anal cancer; angiosarcoma (e.g., lymphangiosarcoma, lymphangioendotheliosarcoma, hemangiosarcoma); appendix cancer; benign monoclonal gammopathy; biliary cancer (e.g., cholangiocarcinoma); bladder cancer; breast cancer (e.g., adenocarcinoma of the breast, papillary carcinoma of the breast, mammary cancer, medullary carcinoma of the breast); brain cancer (e.g., meningioma, glioblastomas, glioma (e.g., astrocytoma, oligodendroglioma), medulloblastoma); bronchus cancer; carcinoid tumor; cervical cancer (e.g., cervical adenocarcinoma); choriocarcinoma; chordoma; craniopharyngioma; colorectal cancer (e.g., colon cancer, rectal cancer, colorectal adenocarcinoma); connective tissue cancer; epithelial carcinoma; ependymoma; endotheliosarcoma (e.g., Kaposi's sarcoma, multiple idiopathic hemorrhagic sarcoma); endometrial cancer (e.g., uterine cancer, uterine sarcoma); esophageal cancer (e.g., adenocarcinoma of the esophagus, Barrett's adenocarinoma); Ewing's sarcoma; ocular cancer (e.g., intraocular melanoma, retinoblastoma); familiar hypereosinophilia; gall bladder cancer; gastric cancer (e.g., stomach adenocarcinoma); gastrointestinal stromal tumor (GIST); germ cell cancer; head and neck cancer (e.g., head and neck squamous cell carcinoma, oral cancer (e.g., oral squamous cell carcinoma), throat cancer (e.g., laryngeal cancer, pharyngeal cancer, nasopharyngeal cancer, oropharyngeal cancer)); hematopoietic cancers (e.g., leukemia such as acute lymphocytic leukemia (ALL) (e.g., B-cell ALL, T-cell ALL), acute myelocytic leukemia (AML) (e.g., B-cell AML, T-cell AML), chronic myelocytic leukemia (CML) (e.g., B-cell CML, T-cell CML), and chronic lymphocytic leukemia (CLL) (e.g., B-cell CLL, T-cell CLL)); lymphoma such as Hodgkin lymphoma (HL) (e.g., B-cell HL, T-cell HL) and non-Hodgkin lymphoma (NHL) (e.g., B-cell NHL such as diffuse large cell lymphoma (DLCL) (e.g., diffuse large B-cell lymphoma), follicular lymphoma, chronic lymphocytic leukemia/small lymphocytic lymphoma (CLL/SLL), mantle cell lymphoma (MCL), marginal zone B-cell lymphomas (e.g., mucosa-associated lymphoid tissue (MALT) lymphomas, nodal marginal zone B-cell lymphoma, splenic marginal zone B-cell lymphoma), primary mediastinal B-cell lymphoma, Burkitt lymphoma, lymphoplasmacytic lymphoma (i.e., Waldenström's macroglobulinemia), hairy cell leukemia (HCL), immunoblastic large cell lymphoma, precursor B-lymphoblastic lymphoma and primary central nervous system (CNS) lymphoma; and T-cell NHL such as precursor T-lymphoblastic lymphoma/leukemia, peripheral T-cell lymphoma (PTCL) (e.g., cutaneous T-cell lymphoma (CTCL) (e.g., mycosis fungiodes, Sezary syndrome), angioimmunoblastic T-cell lymphoma, extranodal natural killer T-cell lymphoma, enteropathy type T-cell lymphoma, subcutaneous panniculitis-like T-cell lymphoma, and anaplastic large cell lymphoma); a mixture of one or more leukemia/lymphoma as described above; and multiple myeloma (MM)), heavy chain disease (e.g., alpha chain disease, gamma chain disease, mu chain disease); hemangioblastoma; hypopharynx cancer; inflammatory myofibroblastic tumors; immunocytic amyloidosis; kidney cancer (e.g., nephroblastoma a.k.a. Wilms' tumor, renal cell carcinoma); liver cancer (e.g., hepatocellular cancer (HCC), malignant hepatoma); lung cancer (e.g., bronchogenic carcinoma, small cell lung cancer (SCLC), non-small cell lung cancer (NSCLC), adenocarcinoma of the lung); leiomyosarcoma (LMS); mastocytosis (e.g., systemic mastocytosis); muscle cancer; myelodysplastic syndrome (MDS); mesothelioma; myeloproliferative disorder (MPD) (e.g., polycythemia vera (PV), essential thrombocytosis (ET), agnogenic myeloid metaplasia (AMM) a.k.a. myelofibrosis (MF), chronic idiopathic myelofibrosis, chronic myelocytic leukemia (CML), chronic neutrophilic leukemia (CNL), hypereosinophilic syndrome (HES)); neuroblastoma; neurofibroma (e.g., neurofibromatosis (NF) type 1 or type 2, schwannomatosis); neuroendocrine cancer (e.g., gastroenteropancreatic neuroendoctrine tumor (GEP-NET), carcinoid tumor); osteosarcoma (e.g., bone cancer); ovarian cancer (e.g., cystadenocarcinoma, ovarian embryonal carcinoma, ovarian adenocarcinoma); papillary adenocarcinoma; pancreatic cancer (e.g., pancreatic andenocarcinoma, intraductal papillary mucinous neoplasm (IPMN), Islet cell tumors); penile cancer (e.g., Paget's disease of the penis and scrotum); pinealoma; primitive neuroectodermal tumor (PNT); plasma cell neoplasia; paraneoplastic syndromes; intraepithelial neoplasms; prostate cancer (e.g., prostate adenocarcinoma); rectal cancer; rhabdomyosarcoma; salivary gland cancer; skin cancer (e.g., squamous cell carcinoma (SCC), keratoacanthoma (KA), melanoma, basal cell carcinoma (BCC)); small bowel cancer (e.g., appendix cancer); soft tissue sarcoma (e.g., malignant fibrous histiocytoma (MFH), liposarcoma, malignant peripheral nerve sheath tumor (MPNST), chondrosarcoma, fibrosarcoma, myxosarcoma); sebaceous gland carcinoma; small intestine cancer; sweat gland carcinoma; synovioma; testicular cancer (e.g., seminoma, testicular embryonal carcinoma); thyroid cancer (e.g., papillary carcinoma of the thyroid, papillary thyroid carcinoma (PTC), medullary thyroid cancer); urethral cancer; vaginal cancer; and vulvar cancer (e.g., Paget's disease of the vulva).

The term "metabolic disorder" refers to any disorder that involves an alteration in the normal metabolism of carbohydrates, lipids, proteins, nucleic acids, or a combination thereof. A metabolic disorder is associated with either a deficiency or excess in a metabolic pathway resulting in an imbalance in metabolism of nucleic acids, proteins, lipids, and/or carbohydrates. Factors affecting metabolism include, and are not limited to, the endocrine (hormonal) control system (e.g., the insulin pathway, the enteroendocrine hormones including GLP-1, PYY or the like), the neural control system (e.g., GLP-1 in the brain), or the like. Examples of metabolic disorders include, but are not limited to, diabetes (e.g., type 1 diabetes, type 2 diabetes, gestational diabetes), hyperglycemia, hyperinsulinemia, insulin resistance, and obesity. In certain embodiments, the metabolic disorder is type II diabetes.

DETAILED DESCRIPTION OF CERTAIN EMBODIMENTS

Figure 1:
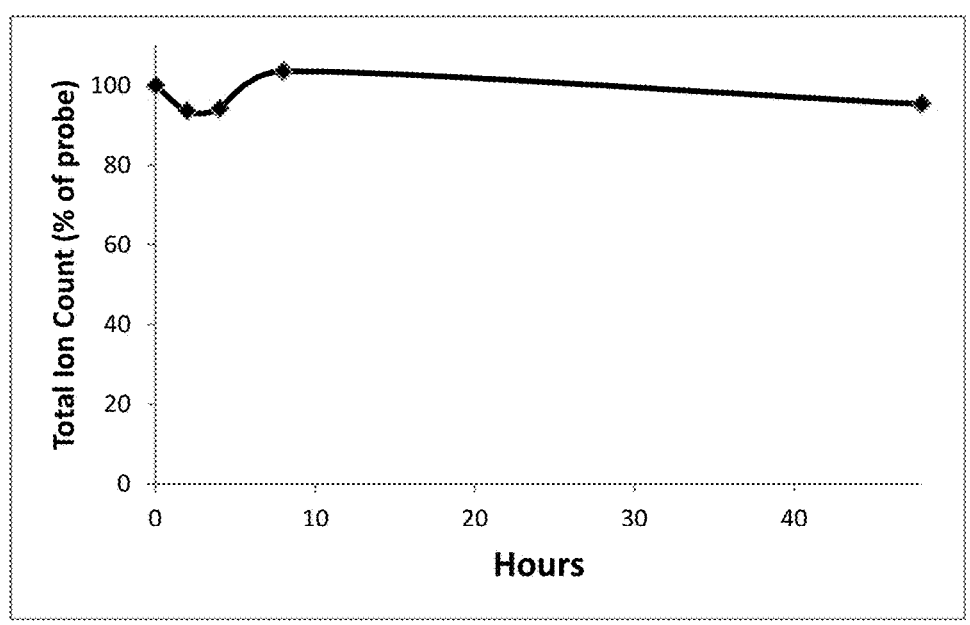
FIG. 1 shows stability data for Compound 54 in PBS buffer (pH 7.4, 23° C.).

The present disclosure provides compounds that are useful for inhibiting kinases, e.g., GSK3 or CK1. The present disclosure further provides pharmaceutical compositions of compounds described herein and methods of using compounds described herein. In certain embodiments, a provided compound is a GSK3 inhibitor (e.g., a GSK3α inhibitor, a GSK3β inhibitor). In certain embodiments, a provided compound is a CK1 inhibitor (e.g., a CK1δ inhibitor). In certain embodiments, a provided compound is used to prevent and/or treat a kinase-mediated disorder (e.g., a GSK-mediated disorder or a CK1-mediated disorder) in a subject.

The serine/threonine kinase glycogen synthase kinase-3 beta (GSK3β) is a known master regulator for several cellular pathways that include insulin signaling and glycogen synthesis, neurotrophic factor signaling, Wnt signaling, neurotransmitter signaling and microtubule dynamics (Forde, et al. Cell Mol Life Sci, 2007, 64(15):1930-44; Phiel, et al. Nature, 2003, 423(6938):435-9; Beaulieu, et al. Trends Pharmacol Sci, 2007, 28(4):166-72). Consequently, this enzyme has a critical role in metabolism, transcription, development, cell survival, and neuronal functions and has been implicated in multiple human disorders including neurological diseases (e.g., Alzheimer's disease), psychiatric disorders (e.g., bipolar disorder), noninsulin-dependent diabetes mellitus, cardiac hypertrophy, and cancer (Gould, T D, et al. Curr Drug Targets, 2006, 7(11):1399-409; Matsuda, et al. Proc Natl Acad Sci USA, 2008, 105(52):20900-5; Biechele, et al. Methods Mol Biol, 2008, 468:99-110; Woodgett, Curr Drug Targets Immune Endocr Metabol Disord, 2003, 3(4):281-90; Manoukian, et al. Adv Cancer Res, 2002, 84:203-29). For example, acute myeloid leukemia (AML) is a cancer characterized by multiple cellular derangements, including a block in myeloid cell differentiation. And while current therapy for the majority of patients with AML utilizes high-dose cytotoxic chemotherapy, the most successfully treated subtype of AML, acute promyelocytic leukemia, combines all-trans-retinoic acid differentiation therapy with low-dose cytotoxic therapy (Ades L, Guerci A, Raffoux E, Sanz M, Chevallier P, Lapusan S, Recher C, Thomas X, Rayon C, Castaigne S, Tournilhac O, de Botton S, Ifrah N, Cahn J Y, Solary E, Gardin C, Fegeux N, Bordessoule D, Ferrant A, Meyer-Monard S, Vey N, Dombret H, Degos L, Chevret S, Fenaux P. Very long-term outcome of acute promyelocytic leukemia after treatment with all-trans retinoic acid and chemotherapy: the European APL Group experience. *Blood*. 115: 1690-1696). To identify new targets of AML differentiation, two independent small-molecule library screens and an shRNA screen were performed. glycogen synthase kinase-3α (GSK3α) emerged as a target at the intersection of these three screens (Banerji V, Frumm S M, Ross K N, Li L S, Schinzel A C, Hahn C K, Kakoza R M, Chow K T, Ross L, Alexe G, Tolliday N, Inguilizian H, Galinsky I, Stone R M, DeAngelo D J, Roti G, Aster J C, Hahn W C, Kung A L, Stegmaier K. The intersection of genetic and chemical genomic screens identifies GSK-3alpha as a target in human acute myeloid leukemia. *J Clin Invest.* 2012; 122:935-947). It was demonstrated that alpha-specific loss of GSK3 induces differentiation in AML by multiple measurements, including morphological changes, expression of cell surface marker consistent with myeloid maturation and induction of a gene expression program consistent with myeloid maturation. GSK3α-specific suppression also leads to impaired growth and proliferation in vitro, induction of apoptosis, loss of colony formation in methylcellulose, and anti-AML activity in vivo. Importantly, selective inhibition of GSK3α in AML does not lead to the stabilization of β-catenin. The stabilization of β-catenin is undesirable in AML therapy because β-catenin promotes the AML stem cell population (Wang Y, Krivtsov A V, Sinha A U, North T E, Goessling W, Feng Z, Zon L I, Armstrong S A. The Wnt/beta-catenin pathway is required for the development of leukemia stem cells in AML. *Science.* 2010; 327:1650-1653). While much of the literature has focused on the role of pan GSK3 inhibition in AML, there have been data that support a role for selective GSK3α inhibitors in this disease (Wang Z, Smith K S, Murphy M, Piloto O, Somervaille T C, Cleary M L. Glycogen synthase kinase 3 in MLL leukaemia maintenance and targeted therapy. *Nature.* 2008; 455:1205-1209; Wang Z, Iwasaki M, Ficara F, Lin C, Matheny C, Wong S H, Smith K S, Cleary M L. GSK-3 promotes conditional association of CREB and its coactivators with MEIS1 to facilitate HOX-mediated transcription and oncogenesis. *Cancer Cell.* 2010; 17:597-608). Moreover, a growing literature suggests a broader role for perturbing GSK3α in cancer (Piazza F, Manni S, Tubi L Q, Montini B, Pavan L, Colpo A, Gnoato M, Cabrelle A, Adami F, Zambello R, Trentin L, Gurrieri C, Semenzato G. Glycogen Synthase Kinase-3 regulates multiple myeloma cell growth and bortezomib-induced cell death. *BMC Cancer.* 2010; 10:526; Bang D, Wilson W, Ryan M, Yeh J J, Baldwin A S. GSK-3alpha promotes oncogenic KRAS function in pancreatic cancer via TAK1-TAB stabilization and regulation of noncanonical NF-kappaB. *Cancer discovery.* 2013; 3:690-703).

Lithium has been shown to inhibit GSK3 kinase activity directly, via competition with magnesium, and indirectly, by increasing inhibitory phosphorylation of GSK3 (Beaulieu et al., 2004, 2008; Chalecka-Franaszek and Chuang, 1999; De Sarno et al., 2002; Klein and Melton, 1996). Furthermore, GSK3α null or GSK3β haploinsufficient mice phenocopy lithium's effect of attenuating aberrant behaviors (Beaulieu et al., 2004; Kaidanovich-Beilin et al., 2009; O'Brien et al., 2004). Conversely, mice overexpressing GSK3β or carrying mutations preventing inhibitory phosphorylation of GSK3α (Ser21) and GSK3β (Ser9) exhibit behaviors modeling psychiatric symptoms, as do mice with targeted disruption of AKT1, which phosphorylates and inactivates GSK3α (Ser21) and GSK3β (Ser9) (Emamian et al., 2004; Lai et al., 2006; Polter et al., 2010; Prickaerts et al., 2006).

Pan et al. showed that GSK3β inhibitors are efficacious in lithium insensitive models (Pan et al., *Neuropsychopharmacology*, 2011, 36(7):1397-411). Therefore, GSK3β inhibitors may be efficacious in lithium resistant bipolar patients.

AKT/GSK3 signaling has been implicated in the pathophysiology of neuropsychiatric disorders through biochemical and genetic association studies of patients (Emamian et al., 2004; Tan et al., 2008; Thiselton et al., 2008). In addition to lithium, antidepressants, antipsychotics, and other mood stabilizers also modulate GSK3 activity (Beaulieu et al., 2009), further supporting its involvement in psychiatric illness. Various pharmacological probes of GSK3 have been used to implicate GSK3 kinase activity in the regulation of behavior in vivo (Beaulieu et al., 2007a; Gould et al., 2004).

In Beurel et al. (*Mol. Psych.*, 2011), removing GSK3β inhibition demonstrated insensitivity to the model of antidepressant treatment by ketamine. In addition, recently inhibiting GSK3β has shown to be effective in models of fragile X syndrome (Franklin et al., *Biol. Psychiatry.* 2013 Sep. 13, Glycogen Synthase Kinase-3 Inhibitors Reverse Deficits in Long-term Potentiation and Cognition in Fragile X Mice). Thus, inhibiting GSK3β may lead to multiple indication of treating mental illnesses and mood disorders.

In certain embodiments, highly selective small molecule modulators are needed to help elucidate GSK3β function and regulation in central nervous system disorders. Currently, no such small molecule exists with the correct combination of selectivity and pharmacokinetic properties to accurately perturb the role of GSK3β in established rodent models of memory and mood.

Significant evidence exists for a critical role for GSK3 signaling in the regulation of neurogenesis, neurodevelopment, and in neuroplasticity. GSK3 function is modulated by both mood stabilizers that treat bipolar disorder patients and antipsychotics for treating schizophrenia. Aberrant GSK3 signaling has further been implicated in the etiology of neuropsychiatric disorders which demonstrates a role for the inhibition of GSK3 by the schizophrenia-associated gene DISC1 (Mao Y, et al. Cell 2009, 136(6):1017-1031). Accordingly, small molecules that inhibit GSK3 signaling are useful as valuable tool compounds for probing the role of Wnt/GSK3 signaling in the pathophysiology of bipolar disorder and other neuropsychiatric disorders and also as therapeutics for modulating human neurogenesis.

In certain embodiments, compounds described herein are useful as probe compounds for investigating the role of kinase signaling, e.g., GSK3 signaling, in the pathophysiology of various disorders, e.g., bipolar disorder and other neuropsychiatric disorders. In certain embodiments, a provided compound is useful as a tool to probe the GSK/Wnt molecular pathways both in in vitro studies with human and rodent neural progenitors, and/or in vivo. Wnt/GSK3 signaling has been shown to play an important role in regulating mammalian neurogenesis and neurodevelopment (Chen, et al. J Neurochem. 2000, 75(4):1729-34; Wexler, et al. Mol Psychiatry. 2008, 13(3):285-92). In certain embodiments, a provided compound is useful as a tool to probe the effect of descreasing Tau phosphorylation. Aberrant Tau phosphorylation, including at GSK3 sites, has been implicated in the pathophysiology of a number of human neurodegenerative disorders, including Alzheimer's disease and the primary tauopathies (e.g., progressive supranuclear palsy and other frontotemporal dementias). (Lee, et al. Cold Spring Harb Perspect Med. 2011, 1(1):a006437; Hooper, et al. J Neurochem. 2008, 104(6):1433-9) Thus decreasing Tau phosphorylation with a selective GSK3 inhibitor can provide insight into the underlying disease mechanisms and may provide a method of reversing disease symptoms.

In certain embodiments, a provided compound is useful as a tool to assess whether there are differences in the response of induced pluripotent stem cell (iPSC)-derived neural progenitor cells (iPSC-NPCs) from patients with neuropsychiatric disorders to GSK3 modulators than those without such disorders. For examples, a panel of iPSC models developed from patients with bipolar disorder, schizophrenia, and/or Fragile X syndrome may be used; evidence exists that such disorders are related to dysregulation of GSK3 signaling.

In certain embodiments, a provided compound is useful as a tool to probe whether selective GSK3 inhibition can rescue deficits caused by genetic variation in human/mouse DISC1, including in assays of in vivo neurogenesis in embryonic and adult mice. The role of DISC1/GSK3 signaling in the pathophysiology of neuropsychiatric disorders (Mao, et al. Cell. 2009, 136(6):1017-1031) is an area of ongoing study.

In certain embodiments, a provided compound modulates post-natal and/or adult neurogenesis, providing a therapeutic avenue for multiple neuropsychiatric and neurodegenerative disorders including bipolar disorder, major depression, traumatic brain injury, Alzheimer's disease, Parkinson's disease, and Huntington's disease.

Compounds

As generally described above, provided herein are compounds useful as kinase inhibitors, e.g., GSK3 inhibitors or CK1 inhibitors. In some embodiments, the present disclosure provides a compound of formula I:

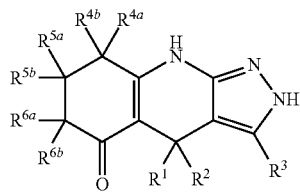

or a pharmaceutically acceptable salt thereof,
wherein
$R^1$ and $R^2$ are independently selected from the group consisting of hydrogen, optionally substituted aliphatic, optionally substituted aryl, and optionally substituted heteroaryl, wherein $R^1$ and $R^2$ are not simultaneously hydrogen; or $R^1$ and $R^2$ are taken together with their intervening atoms to form an optionally substituted 3- to 7-membered saturated carbocyclic or heterocyclic ring, wherein the ring formed by $R^1$ and $R^2$ may be optionally fused to an aryl or heteroaryl ring;

$R^3$ is selected from the group consisting of hydrogen, halo, —CN, —NO$_2$, optionally substituted aliphatic, optionally substituted phenyl, optionally substituted heterocyclyl, optionally substituted heteroaryl, —OR$^A$, —N(R$^B$)$_2$, —SR$^A$, —C(=O)R$^A$, —C(=O)OR$^A$, —C(=O)SR$^A$, —C(=O)N(R$^B$)$_2$, —OC(=O)R$^A$, —NR$^B$C(=O)R$^A$, —NR$^B$C(=O)N(R$^B$)$_2$, —OC(=O)N(R$^B$)$_2$, —NR$^B$C(=O)OR$^A$, —SC(=O)R$^A$, —C(=NR$^B$)R$^A$, —C(=NR$^B$)N(R$^B$)$_2$, —NR$^B$C(=NR$^B$)R$^B$, —C(=S)R$^A$, —C(=S)N(R$^B$)$_2$, —NR$^B$C(=S)R$^A$, —S(=O)R$^A$, —SO$_2$R$^A$, —NR$^B$SO$_2$R$^A$, and —SO$_2$N(R$^B$)$_2$;

each $R^A$ is independently hydrogen, optionally substituted aliphatic, optionally substituted carbocyclyl, optionally substituted heterocyclyl, optionally substituted aryl, or optionally substituted heteroaryl;

each $R^B$ is independently hydrogen, optionally substituted aliphatic, optionally substituted carbocyclyl, optionally substituted heterocyclyl, optionally substituted aryl, optionally substituted heteroaryl, or two $R^B$ groups are taken together with their intervening atoms to form an optionally substituted heterocyclic ring;

$R^{4a}$ and $R^{4b}$ are independently hydrogen, halo, —CN, —OR$^A$, —N(R$^B$)$_2$, or optionally substituted aliphatic, or $R^{4a}$ and $R^{4b}$ are taken together with their intervening atoms to form an optionally substituted 3- to 7-membered saturated carbocyclic or heterocyclic ring;

$R^{5a}$ and $R^{5b}$ are independently hydrogen, halo, —CN, —OR$^A$, —N(R$^B$)$_2$, optionally substituted aliphatic, optionally substituted aryl, or optionally substituted heteroaryl, or $R^{5a}$ and $R^{5b}$ are taken together with their intervening atoms to form an optionally substituted 3- to 7-membered saturated carbocyclic or heterocyclic ring; and $R^{6a}$ and $R^{6b}$ are independently hydrogen, halo, —CN, —OR$^A$, —N(R$^B$)$_2$, or optionally substituted aliphatic, or $R^{6a}$ and $R^{6b}$ are taken together with their intervening atoms to form an optionally substituted 3- to 7-membered saturated carbocyclic or heterocyclic ring.

In certain embodiments, when $R^1$ or $R^2$ is hydrogen, $R^3$ is not hydrogen, —OH, or —CH$_3$.

In certain embodiments, a provided compound is of formula I-a:

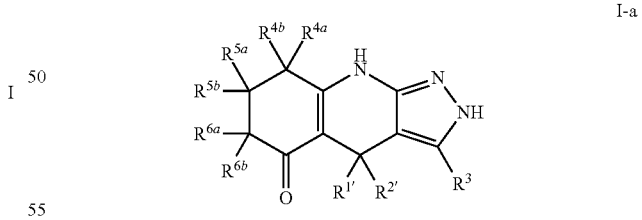

or a pharmaceutically acceptable salt thereof, wherein $R^3$, $R^{4a}$, $R^{4b}$, $R^{5a}$, $R^{5b}$, $R^{6a}$, and $R^{6b}$ are as defined for formula I, and $R^{1'}$ and $R^{2'}$ are independently selected from the group consisting of optionally substituted aliphatic, optionally substituted aryl, and optionally substituted heteroaryl; or $R^{1'}$ and $R^{2'}$ are taken together with their intervening atoms to form an optionally substituted 3- to 7-membered carbocyclic or heterocyclic ring, wherein the ring formed by $R^{1'}$ and $R^{2'}$ may be optionally fused to an aryl or heteroaryl ring.

In certain embodiments, a provided compound is of formula I-b:

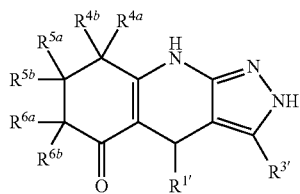

or a pharmaceutically acceptable salt thereof, wherein $R^{4a}$, $R^{4b}$, $R^{5a}$, $R^{5b}$, $R^{6a}$, and $R^{6b}$ are as defined for formula I, $R^{1'}$ is selected from the group consisting of optionally substituted aliphatic, optionally substituted aryl, and optionally substituted heteroaryl;

$R^{3'}$ is selected from the group consisting of halo, —CN, —NO$_2$, substituted C$_1$ alkyl, optionally substituted C$_{2-6}$ alkyl, optionally substituted alkoxy, optionally substituted alkenyl, optionally substituted alkynyl, optionally substituted carbocyclyl, optionally substituted phenyl, optionally substituted heterocyclyl, optionally substituted heteroaryl, —N(R$^B$)$_2$, —SR$^A$, —C(=O)R$^A$, —C(=O)OR$^A$, —C(=O)SR$^A$, —C(=O)N(R$^B$)$_2$, —OC(=O)R$^A$, —NR$^B$C(=O)R$^A$, —NR$^B$C(=O)N(R$^B$)$_2$, —OC(=O)N(R$^B$)$_2$, —NR$^B$C(=O)OR$^A$, —SC(=O)R$^A$, —C(=NR$^B$)R$^A$, —C(=NR$^B$)N(R$^B$)$_2$, —NR$^B$C(=NR$^B$)R$^B$, —C(=S)R$^A$, —C(=S)N(R$^B$)$_2$, —NR$^B$C(=S)R$^A$, —S(=O)R$^A$, —SO$_2$R$^A$, —NR$^B$SO$_2$R$^A$, and —SO$_2$N(R$^B$)$_2$;

each R$^A$ is independently hydrogen, optionally substituted aliphatic, optionally substituted carbocyclyl, optionally substituted heterocyclyl, optionally substituted aryl, or optionally substituted heteroaryl; and each R$^B$ is independently hydrogen, optionally substituted aliphatic, optionally substituted carbocyclyl, optionally substituted heterocyclyl, optionally substituted aryl, optionally substituted heteroaryl, or two R$^B$ groups are taken together with their intervening atoms to form an optionally substituted heterocyclic ring.

In certain embodiments, a provided compound is of formula II:

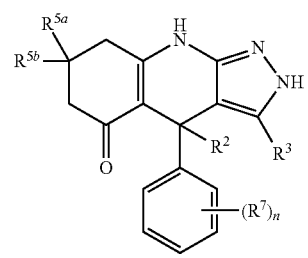

or a pharmaceutically acceptable salt thereof, wherein $R^2$, $R^3$, $R^{5a}$, and $R^{5b}$ are as defined for formula I, each $R^7$ is independently selected from the group consisting of hydrogen, halo, —CN, —NO$_2$, optionally substituted aliphatic, optionally substituted phenyl, optionally substituted heterocyclyl, optionally substituted heteroaryl, —OR$^A$, —N(R$^B$)$_2$, —SR$^A$, —C(=O)R$^A$, —C(=O)OR$^A$, —C(=O)SR$^A$, —C(=O)N(R$^B$)$_2$, —OC(=O)R$^A$, —NR$^B$C(=O)R$^A$, —NR$^B$C(=O)N(R$^B$)$_2$, —OC(=O)N(R$^B$)$_2$, —NR$^B$C(=O)OR$^A$, —SC(=O)R$^A$, —C(=NR$^B$)R$^A$, —C(=NR$^B$)N(R$^B$)$_2$, —NR$^B$C(=NR$^B$)R$^B$, —C(=S)R$^A$, —C(=S)N(R$^B$)$_2$, —NR$^B$C(=S)R$^A$, —S(=O)R$^A$, —SO$_2$R$^A$, —NR$^B$SO$_2$R$^A$, and —SO$_2$N(R$^B$)$_2$; or two adjacent R$^7$ groups are taken together with their intervening atoms to form an optionally substituted carbocyclic or heterocyclic fused ring; or $R^2$ and $R^7$ are taken together with their intervening atoms to form an optionally substituted carbocyclic or heterocyclic fused ring; and n is 0, 1, 2, 3, 4, or 5.

In certain embodiments, when $R^2$ is hydrogen, $R^3$ is not hydrogen, —OH, or —CH$_3$.

In certain embodiments, a provided compound is of formula II-a:

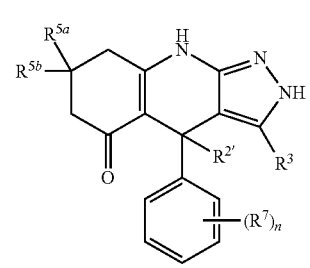

or a pharmaceutically acceptable salt thereof, wherein $R^3$, $R^{5a}$, $R^{5b}$, $R^7$, and n are as defined for formula II, and $R^{2'}$ is selected from the group consisting of optionally substituted aliphatic, optionally substituted aryl, and optionally substituted heteroaryl; or $R^{2'}$ and $R^7$ are taken together with their intervening atoms to form an optionally substituted carbocyclic or heterocyclic fused ring.

In certain embodiments, a provided compound is of formula II-b:

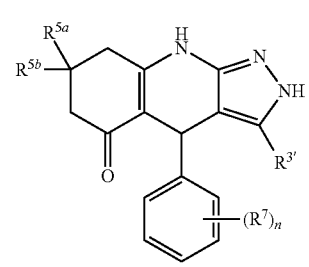

or a pharmaceutically acceptable salt thereof, wherein $R^{5a}$, $R^{5b}$, $R^7$, and n are as defined for formula II, $R^{3'}$ is selected from the group consisting of halo, —CN, —NO$_2$, substituted C$_1$ alkyl, optionally substituted C$_{2-6}$ alkyl, optionally substituted alkoxy, optionally substituted alkenyl, optionally substituted alkynyl, optionally substituted carbocyclyl, optionally substituted phenyl, optionally substituted heterocyclyl, optionally substituted heteroaryl, —N(R$^B$)$_2$, —SR$^A$, —C(=O)R$^A$, —C(=O)OR$^A$, —C(=O)SR$^A$, —C(=O)N(R$^B$)$_2$, —OC(=O)R$^A$, —NR$^B$C(=O)R$^A$, —NR$^B$C(=O)N(R$^B$)$_2$, —OC(=O)N(R$^B$)$_2$, —NR$^B$C(=O)OR$^A$, —SC(=O)R$^A$, —C(=NR$^B$)R$^A$, —C(=NR$^B$)N(R$^B$)$_2$, —NR$^B$C(=NR$^B$)R$^B$, —C(=S)R$^A$, —C(=S)N(R$^B$)$_2$, —NR$^B$C(=S)R$^A$, —S(=O)R$^A$, —SO$_2$R$^A$, —NR$^B$SO$_2$R$^A$, and —SO$_2$N(R$^B$)$_2$;

each R$^A$ is independently hydrogen, optionally substituted aliphatic, optionally substituted carbocyclyl, optionally substituted heterocyclyl, optionally substituted aryl, or optionally substituted heteroaryl; and each R$^B$ is independently hydrogen, optionally substituted aliphatic, optionally substituted carbocyclyl, optionally substituted heterocyclyl, optionally substituted aryl, optionally substituted heteroaryl, or two $R^B$ groups are taken together with their intervening atoms to form an optionally substituted heterocyclic ring.

In certain embodiments, a provided compound is of formula II-a-i, II-a-ii, II-b-i, or II-b-ii:

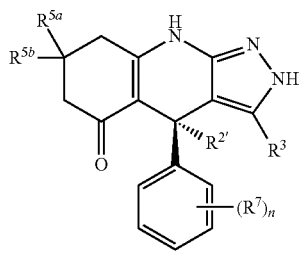

II-a-i

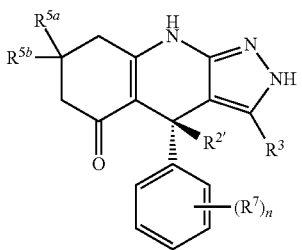

II-a-ii

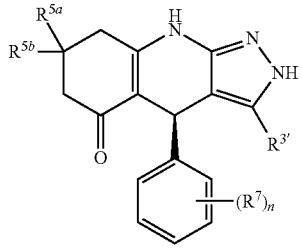

II-b-i

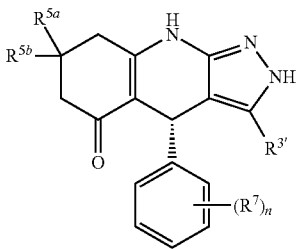

II-b-ii or a pharmaceutically acceptable salt thereof.

In certain embodiments, a provided compound is of formula III:

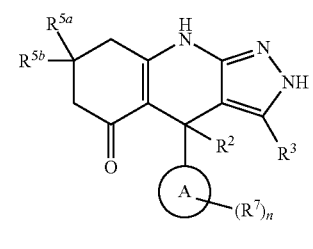

III or a pharmaceutically acceptable salt thereof, wherein $R^2$, $R^3$, $R^{5a}$, and $R^{5b}$ are as defined for formula I, Ring A is a 5- to 6-membered heteroaryl, a 4- to 6-membered carbocyclyl, or a 4- to 6-membered heterocyclyl;

each $R^7$ is independently selected from the group consisting of hydrogen, halo, —CN, —NO$_2$, optionally substituted aliphatic, optionally substituted phenyl, optionally substituted heterocyclyl, optionally substituted heteroaryl, —OR$^A$, —N(R$^B$)$_2$, —SR$^A$, —C(=O)R$^A$, —C(=O)OR$^A$, —C(=O)SR$^A$, —C(=O)N(R$^B$)$_2$, —OC(=O)R$^A$, —NR$^B$C(=O)R$^A$, —NR$^B$C(=O)N(R$^B$)$_2$, —OC(=O)N(R$^B$)$_2$, —NR$^B$C(=O)OR$^A$, —SC(=O)R$^A$, —C(=NR$^B$)R$^A$, —C(=NR$^B$)N(R$^B$)$_2$, —NR$^B$C(=NR$^B$)R$^B$, —C(=S)R$^A$, —C(=S)N(R$^B$)$_2$, —NR$^B$C(=S)R$^A$, —S(=O)R$^A$, —SO$_2$R$^A$, —NR$^B$SO$_2$R$^A$, and —SO$_2$N(R$^B$)$_2$; or two adjacent $R^7$ groups are taken together with their intervening atoms to form an optionally substituted carbocyclic or heterocyclic fused ring; or $R^2$ and $R^7$ are taken together with their intervening atoms to form an optionally substituted carbocyclic or heterocyclic fused ring;

each $R^A$ is independently hydrogen, optionally substituted aliphatic, optionally substituted carbocyclyl, optionally substituted heterocyclyl, optionally substituted aryl, or optionally substituted heteroaryl; and each $R^B$ is independently hydrogen, optionally substituted aliphatic, optionally substituted carbocyclyl, optionally substituted heterocyclyl, optionally substituted aryl, optionally substituted heteroaryl, or two $R^B$ groups are taken together with their intervening atoms to form an optionally substituted heterocyclic ring; and n is 0, 1, 2, 3, or 4, as valency allows.

In certain embodiments, when $R^2$ is hydrogen, $R^3$ is not hydrogen, —OH, or —CH$_3$.

In some embodiments, Ring A is a 5- to 6-membered heteroaryl.

In certain embodiments, a provided compound is of formula III-a:

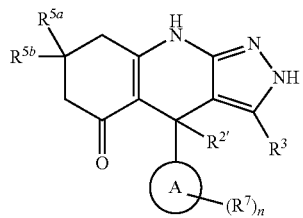

III-a or a pharmaceutically acceptable salt thereof, wherein $R^3$, $R^{5a}$, $R^{5b}$, $R^7$, and n are as defined for formula III, and $R^{2'}$ is selected from the group consisting of optionally substituted aliphatic, optionally substituted aryl, and optionally substituted heteroaryl; or $R^{2'}$ and $R^7$ are taken together with their intervening atoms to form an optionally substituted carbocyclic or heterocyclic fused ring.

In certain embodiments, a provided compound is of formula III-b:

III-b or a pharmaceutically acceptable salt thereof, wherein $R^3$, $R^{5a}$, $R^{5b}$, $R^7$, and n are as defined for formula III. In certain embodiments, for a compound of formula III-b, $R^3$ is $R^{3'}$ and is selected from the group consisting of halo, —CN, —NO$_2$, substituted $C_1$ alkyl, optionally substituted $C_{2-6}$ alkyl, optionally substituted alkoxy, optionally substituted alkenyl, optionally substituted alkynyl, optionally substituted carbocyclyl, optionally substituted phenyl, optionally substituted heterocyclyl, optionally substituted heteroaryl, —N(R$^B$)$_2$, —SR$^A$, —C(=O)R$^A$, —C(=O)OR$^A$, —C(=O)SR$^A$, —C(=O)N(R$^B$)$_2$, —OC(=O)R$^A$, —NR$^B$C(=O)R$^A$, —NR$^B$C(=O)N(R$^B$)$_2$, —OC(=O)N(R$^B$)$_2$, —NR$^B$C(=O)OR$^A$, —SC(=O)R$^A$, —C(=NR$^B$)R$^A$, —C(=NR$^B$)N(R$^B$)$_2$, —NR$^B$C(=NR$^B$)R$^B$, —C(=S)R$^A$, —C(=S)N(R$^B$)$_2$, —NR$^B$C(=S)R$^A$, —S(=O)R$^A$, —SO$_2$R$^A$, —NR$^B$SO$_2$R$^A$, and —SO$_2$N(R$^B$)$_2$, where $R^A$ and $R^B$ are as defined herein.

In certain embodiments, a provided compound is of formula III-a-i, III-a-ii, III-b-i, or III-b-ii:

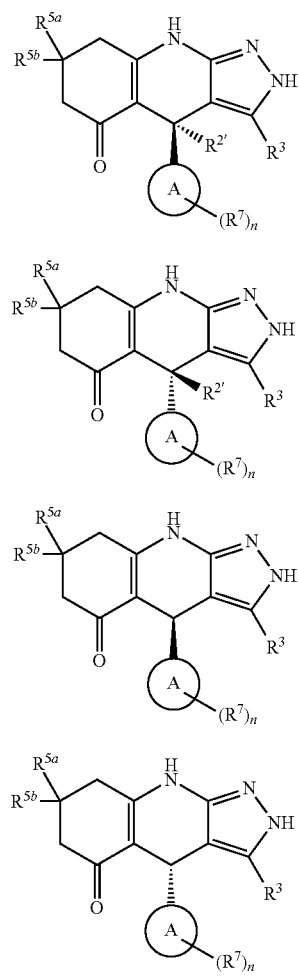

or a pharmaceutically acceptable salt thereof.

In certain embodiments, for a compound of formula III-b-i or III-b-ii, $R^3$ is $R^{3'}$ as defined herein.

As defined generally above, $R^1$ and $R^2$ are independently selected from the group consisting of hydrogen, optionally substituted aliphatic, optionally substituted aryl, and optionally substituted heteroaryl, wherein $R^1$ and $R^2$ are not simultaneously hydrogen; or $R^1$ and $R^2$ are taken together with their intervening atoms to form an optionally substituted 3- to 7-membered saturated carbocyclic or heterocyclic ring, wherein the ring formed by $R^1$ and $R^2$ may be optionally fused to an aryl or heteroaryl ring. As defined generally above, $R^{1'}$ and $R^{2'}$ are independently selected from the group consisting of optionally substituted aliphatic, optionally substituted aryl, and optionally substituted heteroaryl, or $R^{1'}$ and $R^{2'}$ are taken together with their intervening atoms to form an optionally substituted 3- to 7-membered saturated carbocyclic or heterocyclic ring, wherein the ring formed by $R^{1'}$ and $R^{2'}$ may be optionally fused to an aryl or heteroaryl ring.

In certain embodiments, $R^1$ is hydrogen. In certain embodiments, $R^1$ is not hydrogen. In certain embodiments, $R^2$ is hydrogen. In certain embodiments, $R^2$ is not hydrogen. In some embodiments, $R^1$ is deuterium. In some embodiments, $R^2$ is deuterium. One of ordinary skill in the art will appreciate that e.g., "$R^1$ is deuterium" or "$R^2$ is deuterium" indicates that $R^1$ or $R^2$ is isotopically enriched with deuterium beyond naturally occurring levels.

In some embodiments, $R^1$ or $R^{1'}$ is optionally substituted aliphatic. In certain embodiments, $R^1$ or $R^{1'}$ is optionally substituted alkyl. In certain embodiments, $R^1$ or $R^{1'}$ is unsubstituted alkyl. In certain embodiments, $R^1$ or $R^{1'}$ is substituted alkyl. In certain embodiments, $R^1$ or $R^{1'}$ is methyl, ethyl, or propyl. In certain embodiments, $R^1$ or $R^{1'}$ is methyl. In certain embodiments, $R^1$ or $R^{1'}$ is optionally substituted cycloalkyl. In certain embodiments, $R^1$ or $R^{1'}$ is cyclopropyl, cyclobutyl, cyclopentyl, or cyclohexyl. In certain embodiments, $R^1$ or $R^{1'}$ is optionally substituted alkenyl. In certain embodiments, $R^1$ or $R^{1'}$ is unsubstituted alkenyl. In certain embodiments, $R^1$ or $R^{1'}$ is substituted alkenyl. In certain embodiments, $R^1$ or $R^{1'}$ is optionally substituted alkynyl. In certain embodiments, $R^1$ or $R^{1'}$ is unsubstituted alkynyl. In certain embodiments, $R^1$ or $R^{1'}$ is substituted alkynyl. In some embodiments, $R^1$ or $R^{1'}$ is optionally substituted aryl. In certain embodiments, $R^1$ or $R^{1'}$ is optionally substituted phenyl. In certain embodiments, $R^1$ or $R^{1'}$ is unsubstituted phenyl. In certain embodiments, $R^1$ or $R^{1'}$ is substituted phenyl. In some embodiments, $R^1$ or $R^{1'}$ is optionally substituted heteroaryl. In certain embodiments, $R^1$ or $R^{1'}$ is an optionally substituted 5- to 6-membered heteroaryl having 1-3 heteroatoms selected from nitrogen, oxygen, and sulfur. In certain embodiments, $R^1$ or $R^{1'}$ is unsubstituted heteroaryl. In certain embodiments, $R^1$ or $R^{1'}$ is substituted heteroaryl. In certain embodiments, $R^1$ or $R^{1'}$ is optionally substituted thiophenyl. In certain embodiments, $R^1$ or $R^{1'}$ is unsubstituted thiophenyl. In certain embodiments, $R^1$ or $R^{1'}$ is substituted thiophenyl. In certain embodiments, $R^1$ or $R^{1'}$ is optionally substituted 2-thiophenyl. In certain embodiments, $R^1$ or $R^{1'}$ is optionally substituted 3-thiophenyl. In some embodiments, $R^1$ or $R^{1'}$ is optionally substituted pyridyl. In certain embodiments, $R^1$ or $R^{1'}$ is unsubstituted pyridyl. In certain embodiments, $R^1$ or $R^{1'}$ is substituted pyridyl. In certain embodiments, $R^1$ or $R^{1'}$ is optionally substituted 2-pyridyl. In certain embodiments, $R^1$ or $R^{1'}$ is optionally substituted 3-pyridyl. In certain embodiments, $R^1$ or $R^{1'}$ is optionally substituted 4-pyridyl. In certain embodiments, $R^1$ or $R^{1'}$ is optionally substituted 9- to 10-membered heteroaryl having 1-4 heteroatoms selected from nitrogen, oxygen, and sulfur. In certain embodiments, $R^1$ or $R^{1'}$ is optionally substituted benzoxadiazolyl.

In some embodiments, $R^2$ or $R^{2'}$ is optionally substituted aliphatic. In certain embodiments, $R^2$ or $R^{2'}$ is optionally substituted alkyl. In certain embodiments, $R^2$ or $R^{2'}$ is unsubstituted alkyl. In certain embodiments, $R^2$ or $R^{2'}$ is substituted alkyl. In certain embodiments, $R^2$ or $R^{2'}$ is methyl, ethyl, or propyl. In certain embodiments, $R^2$ or $R^{2'}$ is methyl. In certain embodiments, $R^2$ or $R^{2'}$ is ethyl. In certain embodiments, $R^2$ or $R^{2'}$ is propyl. In certain embodiments, $R^2$ or $R^{2'}$ is optionally substituted cycloalkyl. In certain embodiments, $R^2$ or $R^{2'}$ is cyclopropyl, cyclobutyl, cyclopentyl, or cyclohexyl. In certain embodiments, $R^2$ or $R^{2'}$ is optionally substituted alkenyl. In certain embodiments, $R^2$ or $R^{2'}$ is unsubstituted alkenyl. In certain embodiments, $R^2$ or $R^{2'}$ is substituted alkenyl. In certain embodiments, $R^2$ or $R^{2'}$ is optionally substituted alkynyl. In certain embodiments, $R^2$ or $R^{2'}$ is unsubstituted alkynyl. In certain embodiments, $R^2$ or $R^{2'}$ is substituted alkynyl. In some embodiments, $R^2$ or $R^{2'}$ is optionally substituted aryl. In certain embodiments, $R^2$ or $R^{2'}$ is optionally substituted phenyl. In certain embodiments, $R^2$ or $R^{2'}$ is unsubstituted phenyl. In certain embodiments, $R^2$ or $R^{2'}$ is substituted phenyl. In some embodiments, $R^2$ or $R^{2'}$ is optionally substituted heteroaryl. In certain embodiments, $R^2$ or $R^{2'}$ is an optionally substituted 5-6 membered heteroaryl having 1-3 heteroatoms selected from nitrogen, oxygen, and sulfur. In certain embodiments, $R^2$ or $R^{2'}$ is unsubstituted heteroaryl. In certain embodiments, $R^2$ or $R^{2'}$ is substituted heteroaryl. In certain embodiments, $R^2$ or $R^{2'}$ is unsubstituted heteroaryl. In certain embodiments, $R^2$ or $R^{2'}$ is substituted heteroaryl. In certain embodiments, $R^2$ or $R^{2'}$ is optionally substituted thiophenyl. In certain embodiments, $R^2$ or $R^{2'}$ is unsubstituted thiophenyl. In certain embodiments, $R^2$ or $R^{2'}$ is substituted thiophenyl. In certain embodiments, $R^2$ or $R^{2'}$ is optionally substituted 2-thiophenyl. In certain embodiments, $R^2$ or $R^{2'}$ is optionally substituted 3-thiophenyl. In some embodiments, $R^2$ or $R^{2'}$ is optionally substituted pyridyl. In certain embodiments, $R^2$ or $R^{2'}$ is unsubstituted pyridyl. In certain embodiments, $R^2$ or $R^{2'}$ is substituted pyridyl. In certain embodiments, $R^2$ or $R^{2'}$ is optionally substituted 2-pyridyl. In certain embodiments, $R^2$ or $R^{2'}$ is optionally substituted 3-pyridyl. In certain embodiments, $R^2$ or $R^{2'}$ is optionally substituted 4-pyridyl. In certain embodiments, $R^2$ or $R^{2'}$ is optionally substituted 9- to 10-membered heteroaryl having 1-4 heteroatoms selected from nitrogen, oxygen, and sulfur. In certain embodiments, $R^2$ or $R^{2'}$ is optionally substituted benzoxadiazolyl.

In some embodiments, $R^1$ is optionally substituted phenyl, and $R^2$ is hydrogen. In some embodiments, $R^1$ is optionally substituted heteroaryl, and $R^2$ is hydrogen. In some embodiments, $R^1$ is optionally substituted aliphatic, and $R^2$ is hydrogen. In some embodiments, $R^1$ is optionally substituted phenyl, and $R^2$ is deuterium. In some embodiments, $R^1$ is optionally substituted heteroaryl, and $R^2$ is deuterium. In some embodiments, $R^1$ is optionally substituted aliphatic, and $R^2$ is deuterium. In some embodiments, $R^1$ is optionally substituted phenyl, and $R^2$ is optionally substituted aliphatic. In some embodiments, $R^1$ is optionally substituted heteroaryl, and $R^2$ is optionally substituted aliphatic. In some embodiments, $R^1$ is optionally substituted aliphatic, and $R^2$ is optionally substituted aliphatic. In some embodiments, $R^1$ is optionally substituted phenyl, and $R^2$ is methyl. In some embodiments, $R^1$ is optionally substituted heteroaryl, and $R^2$ is methyl. In some embodiments, $R^1$ is optionally substituted aliphatic, and $R^2$ is methyl. In some embodiments, $R^{1'}$ is optionally substituted phenyl, and $R^{2'}$ is optionally substituted aliphatic. In some embodiments, $R^{1'}$ is optionally substituted heteroaryl, and $R^{2'}$ is optionally substituted aliphatic. In some embodiments, $R^{1'}$ is optionally substituted aliphatic, and $R^{2'}$ is optionally substituted aliphatic. In some embodiments, $R^{1'}$ is optionally substituted phenyl, and $R^{2'}$ is methyl. In some embodiments, $R^{1'}$ is optionally substituted heteroaryl, and $R^{2'}$ is methyl. In some embodiments, $R^{1'}$ is optionally substituted aliphatic, and $R^{2'}$ is methyl. In certain embodiments, at least one of $R^1$, $R^{1'}$, $R^2$ and $R^{2'}$ is ethyl. In certain embodiments, at least one of $R^1$ and $R^2$ is ethyl. In certain embodiments, at least one of $R^{1'}$ and $R^{2'}$ is ethyl.

In certain embodiments, $R^1$ and $R^2$ or $R^{1'}$ and $R^{2'}$ are taken together with their intervening atoms to form an optionally substituted 3- to 7-membered saturated carbocyclic or heterocyclic ring. In certain embodiments, $R^1$ and $R^2$ are taken together with their intervening atoms to form an optionally substituted 3- to 7-membered saturated carbocyclic or heterocyclic ring, wherein the ring is fused to an aryl or heteroaryl ring (e.g., to form an indane ring).

As generally defined above, $R^3$ is selected from the group consisting of hydrogen, halo, —CN, —NO$_2$, optionally substituted aliphatic, optionally substituted phenyl, optionally substituted heterocyclyl, optionally substituted heteroaryl, —OR$^A$, —N(R$^B$)$_2$, —SR$^A$, —C(=O)R$^A$, —C(=O)OR$^A$, —C(=O)SR$^A$, —C(=O)N(R$^B$)$_2$, —OC(=O)R$^A$, —NR$^B$C(=O)R$^A$, —NR$^B$C(=O)N(R$^B$)$_2$, —OC(=O)N(R$^B$)$_2$, —NR$^B$C(=O)OR$^A$, —SC(=O)R$^A$, —C(=NR$^B$)R$^A$, —C(=NR$^B$)N(R$^B$)$_2$, —NR$^B$C(=NR$^B$)R$^B$, —C(=S)R$^A$, —C(=S)N(R$^B$)$_2$, —NR$^B$C(=S)R$^A$, —S(=O)R$^A$, —SO$_2$R$^A$, —NR$^B$SO$_2$R$^A$, and —SO$_2$N(R$^B$)$_2$, wherein R$^A$ and R$^B$ are as described herein. In certain embodiments, $R^3$ is hydrogen. In certain embodiments, $R^3$ is not hydrogen. In certain embodiments, $R^3$ is —OH. In certain embodiments, $R^3$ is not —OH. In certain embodiments, $R^3$ is methyl. In certain embodiments, $R^3$ is not methyl. In some embodiments, $R^3$ is optionally substituted aliphatic. In certain embodiments, $R^3$ is optionally substituted alkyl. In certain embodiments, $R^3$ is unsubstituted alkyl. In certain embodiments, $R^3$ is substituted alkyl. In certain embodiments, $R^3$ is methyl, ethyl, n-propyl, isopropyl, or tert-butyl. In certain embodiments, $R^3$ is methyl. In certain embodiments, $R^3$ is isopropyl. In certain embodiments, $R^3$ is tert-butyl. In certain embodiments, $R^3$ is isobutyl. In certain embodiments, $R^3$ is haloalkyl. In certain embodiments, $R^3$ is trifluoromethyl. In certain embodiments, $R^3$ is optionally substituted alkenyl. In certain embodiments, $R^3$ is unsubstituted alkenyl. In certain embodiments, $R^3$ is substituted alkenyl. In certain embodiments, $R^3$ is optionally substituted alkynyl. In certain embodiments, $R^3$ is unsubstituted alkynyl. In certain embodiments, $R^3$ is substituted alkynyl. In some embodiments, $R^3$ is halo. In certain embodiments, $R^3$ is fluoro. In certain embodiments, $R^3$ is chloro. In certain embodiments, $R^3$ is bromo. In certain embodiments, $R^3$ is unsubstituted cycloalkyl. In certain embodiments, $R^3$ is cyclopropyl. In certain embodiments, $R^3$ is cyclobutyl. In certain embodiments, $R^3$ is cyclopentyl. In certain embodiments, $R^3$ is cyclohexyl. In certain embodiments, $R^3$ is substituted cycloalkyl. In certain embodiments, $R^3$ is cycloalkyl substituted with one or more fluoro. In certain embodiments, $R^3$ is cyclopropyl substituted with one or more fluoro. In certain embodiments, $R^3$ is cyclobutyl substituted with one or more fluoro. In certain embodiments, $R^3$ is difluorocyclobutyl. In certain embodiments, $R^3$ is cyclopentyl substituted with one or more fluoro. In certain embodiments, $R^3$ is cyclohexyl substituted with one or more fluoro. In some embodiments, $R^3$ is optionally substituted phenyl, optionally substituted heterocyclyl, or optionally substituted heteroaryl. In certain embodiments, $R^3$ is phenyl. In some embodiments, $R^3$ is —N(R$^B$)$_2$ or —SR$^A$. In certain embodiments, $R^3$ is —OR$^A$. In certain embodiments, $R^3$ is —OR$^A$, wherein R$^A$ is not hydrogen. In some embodiments, $R^3$ is —C(=O)R$^A$, —C(=O)OR$^A$, —C(=O)SR$^A$, —C(=O)N(R$^B$)$_2$, —OC(=O)R$^A$, —NR$^B$C(=O)R$^A$, —NR$^B$C(=O)N(R$^B$)$_2$, —OC (=O)N($R^B$)$_2$, —$NR^B$C(=O)O$R^A$, —SC(=O)$R^A$, —C(=N$R^B$)$R^A$, —C(=N$R^B$)N($R^B$)$_2$, —$NR^B$C(=N$R^B$)$R^B$, —C(=S)$R^A$, —C(=S)N($R^B$)$_2$, —$NR^B$C(=S)$R^A$, —S(=O)$R^A$, —SO$_2$$R^A$, —$NR^B$SO$_2$$R^A$, or —SO$_2$N($R^B$)$_2$.

As generally defined above, $R^{3'}$ is selected from the group consisting of halo, —CN, —NO$_2$, substituted $C_1$ alkyl, optionally substituted $C_{2-6}$ alkyl, optionally substituted alkoxy, optionally substituted alkenyl, optionally substituted alkynyl, optionally substituted carbocyclyl, optionally substituted phenyl, optionally substituted heterocyclyl, optionally substituted heteroaryl, —N($R^B$)$_2$, —S$R^A$, —C(=O)$R^A$, —C(=O)O$R^A$, —C(=O)S$R^A$, —C(=O)N($R^B$)$_2$, —OC(=O)$R^A$, —$NR^B$C(=O)$R^A$, —$NR^B$C(=O)N($R^B$)$_2$, —OC(=O)N($R^B$)$_2$, —$NR^B$C(=O)O$R^A$, —SC(=O)$R^A$, —C(=N$R^B$)$R^A$, —C(=N$R^B$)N($R^B$)$_2$, —$NR^B$C(=N$R^B$)$R^B$, —C(=S)$R^A$, —C(=S)N($R^B$)$_2$, —$NR^B$C(=S)$R^A$, —S(=O)$R^A$, —SO$_2$$R^A$, —$NR^B$SO$_2$$R^A$, and —SO$_2$N($R^B$)$_2$, wherein $R^A$ and $R^B$ are as described herein. In some embodiments, $R^{3'}$ is substituted $C_1$ aliphatic. In certain embodiments, $R^{3'}$ is —CF$_3$. In certain embodiments, $R^{3'}$ is optionally substituted $C_{2-6}$ alkyl. In certain embodiments, $R^{3'}$ is unsubstituted $C_{2-6}$ alkyl. In certain embodiments, $R^{3'}$ is substituted $C_{2-6}$ alkyl. In certain embodiments, $R^{3'}$ is methyl, ethyl, n-propyl, isopropyl, tert-butyl, or isobutyl. In certain embodiments, $R^{3'}$ is haloalkyl. In certain embodiments, $R^{3'}$ is trifluoromethyl. In certain embodiments, $R^{3'}$ is optionally substituted alkenyl. In certain embodiments, $R^{3'}$ is unsubstituted alkenyl. In certain embodiments, $R^{3'}$ is substituted alkenyl. In certain embodiments, $R^{3'}$ is optionally substituted alkynyl. In certain embodiments, $R^{3'}$ is unsubstituted alkynyl. In certain embodiments, $R^{3'}$ is substituted alkynyl. In some embodiments, $R^{3'}$ is optionally substituted alkoxy. In certain embodiments, $R^{3'}$ is methoxy or ethoxy. In some embodiments, $R^{3'}$ is halo. In certain embodiments, $R^{3'}$ is fluoro. In certain embodiments, $R^{3'}$ is chloro. In certain embodiments, $R^{3'}$ is bromo. In certain embodiments, $R^{3'}$ is unsubstituted carbocyclyl. In certain embodiments, $R^{3'}$ is unsubstituted cycloalkyl. In certain embodiments, $R^{3'}$ is cyclopropyl. In certain embodiments, $R^{3'}$ is cyclobutyl. In certain embodiments, $R^{3'}$ is cyclopentyl. In certain embodiments, $R^{3'}$ is cyclohexyl. In certain embodiments, $R^{3'}$ is substituted carbocyclyl. In certain embodiments, $R^{3'}$ is substituted cycloalkyl. In certain embodiments, $R^{3'}$ is carbocyclyl substituted with one or more fluoro. In certain embodiments, $R^{3'}$ is cyclobutyl substituted with one or more fluoro. In certain embodiments, $R^{3'}$ is difluorocyclobutyl. In certain embodiments, $R^{3'}$ is optionally substituted cycloalkenyl. In certain embodiments, $R^{3'}$ is optionally substituted cycloalkynyl. In some embodiments, $R^{3'}$ is optionally substituted phenyl, optionally substituted heterocyclyl, or optionally substituted heteroaryl. In certain embodiments, $R^{3'}$ is phenyl. In some embodiments, $R^{3'}$ is —N($R^B$)$_2$ or —S$R^A$. In some embodiments, $R^{3'}$ is —C(=O)$R^A$, —C(=O)O$R^A$, —C(=O)S$R^A$, —C(=O)N($R^B$)$_2$, —OC(=O)$R^A$, —$NR^B$C(=O)$R^A$, —$NR^B$C(=O)N($R^B$)$_2$, —OC(=O)N($R^B$)$_2$, —$NR^B$C(=O)O$R^A$, —SC(=O)$R^A$, —C(=N$R^B$)$R^A$, —C(=N$R^B$)N($R^B$)$_2$, —$NR^B$C(=N$R^B$)$R^B$, —C(=S)$R^A$, —C(=S)N($R^B$)$_2$, —$NR^B$C(=S)$R^A$, —S(=O)$R^A$, —SO$_2$$R^A$, —$NR^B$SO$_2$$R^A$, or —SO$_2$N($R^B$)$_2$.

In certain embodiments, $R^3$ or $R^{3'}$ is fluoro. In certain embodiments, $R^3$ or $R^{3'}$ is optionally substituted aliphatic. In certain embodiments, $R^3$ or $R^{3'}$ is methyl. In certain embodiments, $R^3$ or $R^{3'}$ is trifluoromethyl. In certain embodiments, $R^3$ or $R^{3'}$ is tert-butyl or isobutyl. In certain embodiments, $R^3$ or $R^{3'}$ is cyclopropyl. In certain embodiments, $R^3$ or $R^{3'}$ is difluorocyclobutyl.

As generally defined above, $R^{4a}$ and $R^{4b}$ are independently selected from the group consisting of hydrogen, halo, —CN, —O$R^A$, —N($R^B$)$_2$, and optionally substituted aliphatic, or $R^{4a}$ and $R^{4b}$ are taken together with their intervening atoms to form an optionally substituted 3- to 7-membered saturated carbocyclic or heterocyclic ring. In certain embodiments, $R^{4a}$ is hydrogen. In certain embodiments, $R^{4a}$ is not hydrogen. In some embodiments, $R^{4b}$ is hydrogen. In some embodiments, $R^{4b}$ is not hydrogen. In some embodiments, $R^{4a}$ and $R^{4b}$ are both hydrogen. In some embodiments, $R^{4a}$ and $R^{4b}$ are both not hydrogen. In certain embodiments, $R^{4a}$ is hydrogen, and $R^{4b}$ is not hydrogen. In certain embodiments, $R^{4a}$ and $R^{4b}$ are both optionally substituted aliphatic. In certain embodiments, $R^{4a}$ and $R^{4b}$ are methyl.

As generally defined above, $R^{5a}$ and $R^{5b}$ are independently selected from the group consisting of hydrogen, halo, —CN, —O$R^A$, —N($R^B$)$_2$, optionally substituted aliphatic, optionally substituted aryl, and optionally substituted heteroaryl, or $R^{5a}$ and $R^{5b}$ are taken together with their intervening atoms to form an optionally substituted 3- to 7-membered saturated carbocyclic or heterocyclic ring. In certain embodiments, $R^{5a}$ is hydrogen. In certain embodiments, $R^{5a}$ is not hydrogen. In some embodiments, $R^{5b}$ is hydrogen. In some embodiments, $R^{5b}$ is not hydrogen. In some embodiments, $R^{5a}$ and $R^{5b}$ are both hydrogen. In some embodiments, $R^{5a}$ and $R^{5b}$ are both not hydrogen. In certain embodiments, $R^{5a}$ is hydrogen, and $R^{5b}$ is not hydrogen. In certain embodiments, $R^{5a}$ and $R^{5b}$ are both optionally substituted aliphatic. In certain embodiments, $R^{5a}$ and $R^{5b}$ are methyl. In certain embodiments, at least one instance of $R^{5a}$ and $R^{5b}$ is optionally substituted aryl. In certain embodiments, at least one instance of $R^{5a}$ and $R^{5b}$ is optionally substituted 6- to 14-membered aryl. In certain embodiments, at least one instance of $R^{5a}$ and $R^{5b}$ is optionally substituted phenyl. In certain embodiments, at least one instance of $R^{5a}$ and $R^{5b}$ is unsubstituted phenyl. In certain embodiments, at least one instance of $R^{5a}$ and $R^{5b}$ is optionally substituted heteroaryl. In certain embodiments, at least one instance of $R^{5a}$ and $R^{5b}$ is optionally substituted, 5- to 6-membered, monocyclic heteroaryl, wherein one, two, three, or four atoms in the heteroaryl ring system are independently selected from the group consisting of oxygen, nitrogen, and sulfur. In certain embodiments, at least one instance of $R^{5a}$ and $R^{5b}$ is optionally substituted, 9- to 10-membered, bicyclic heteroaryl, wherein one, two, three, or four atoms in the heteroaryl ring system are independently selected from the group consisting of oxygen, nitrogen, and sulfur.

As generally defined above, $R^{6a}$ and $R^{6b}$ are independently selected from the group consisting of hydrogen, halo, —CN, —O$R^A$, —N($R^B$)$_2$, and optionally substituted aliphatic, or $R^{6a}$ and $R^{6b}$ are taken together with their intervening atoms to form an optionally substituted 3- to 7-membered saturated carbocyclic or heterocyclic ring. In certain embodiments, $R^{6a}$ is hydrogen. In certain embodiments, $R^{6a}$ is not hydrogen. In some embodiments, $R^{6b}$ is hydrogen. In some embodiments, $R^{6b}$ is not hydrogen. In some embodiments, $R^{6a}$ and $R^{6b}$ are both hydrogen. In some embodiments, $R^{6a}$ and $R^{6b}$ are both not hydrogen. In certain embodiments, $R^{6a}$ is hydrogen, and $R^{6b}$ is not hydrogen. In certain embodiments, $R^{6a}$ and $R^{6b}$ are both optionally substituted aliphatic. In certain embodiments, $R^{6a}$ and $R^{6b}$ are methyl.

In some embodiments, $R^{4a}$, $R^{4b}$, $R^{6a}$, and $R^{6b}$ are hydrogen, and $R^{5a}$ and $R^{5b}$ are independently selected from the group consisting of hydrogen, halo, —CN, —O$R^A$, —N($R^B$)$_2$, and optionally substituted aliphatic, or $R^{5a}$ and $R^{5b}$ are taken together with their intervening atoms to form an optionally substituted 3- to 7-membered saturated carbocyclic or heterocyclic ring. In certain embodiments, $R^{4a}$, $R^{4b}$, $R^{6a}$, and $R^{6b}$ are hydrogen, and $R^{5a}$ and $R^{5b}$ are methyl.

In some embodiments, $R^{4a}$, $R^{4b}$, $R^{5a}$, and $R^{5b}$ are hydrogen, and $R^{6a}$ and $R^{6b}$ are independently selected from the group consisting of hydrogen, halo, —CN, —$OR^A$, —$N(R^B)_2$, and optionally substituted aliphatic, or $R^{6a}$ and $R^{6b}$ are taken together with their intervening atoms to form an optionally substituted 3- to 7-membered saturated carbocyclic or heterocyclic ring. In certain embodiments, $R^{4a}$, $R^{4b}$, $R^{5a}$, and $R^{5b}$ are hydrogen, and $R^{6a}$ and $R^{6b}$ are methyl.

In some embodiments, $R^{5a}$, $R^{5b}$, $R^{6a}$, and $R^{6b}$ are hydrogen, and $R^{4a}$ and $R^{4b}$ are independently selected from the group consisting of hydrogen, halo, —CN, —$OR^A$, —$N(R^B)_2$, and optionally substituted aliphatic, or $R^{4a}$ and $R^{4b}$ are taken together with their intervening atoms to form an optionally substituted 3- to 7-membered saturated carbocyclic or heterocyclic ring. In certain embodiments, $R^{5a}$, $R^{5b}$, $R^{6a}$, and $R^{6b}$ are hydrogen, and $R^{4a}$ and $R^{4b}$ are methyl.

In some embodiments, $R^{4a}$, $R^{4b}$, $R^{5a}$, $R^{5b}$, $R^{6a}$, and $R^{6b}$ are hydrogen.

As generally defined above, each $R^7$ is independently selected from the group consisting of hydrogen, halo, —CN, —$NO_2$, optionally substituted aliphatic, optionally substituted phenyl, optionally substituted heterocyclyl, optionally substituted heteroaryl, —$OR^A$, —$N(R^B)_2$, —$SR^A$, —C(=O)$R^A$, —C(=O)$OR^A$, —C(=O)$SR^A$, —C(=O)$N(R^B)_2$, —OC(=O)$R^A$, —$NR^B$C(=O)$R^A$, —$NR^B$C(=O)$N(R^B)_2$, —OC(=O)$N(R^B)_2$, —$NR^B$C(=O)$OR^A$, —SC(=O)$R^A$, —C(=$NR^B$)$R^A$, —C(=$NR^B$)$N(R^B)_2$, —$NR^B$C(=$NR^B$)$R^B$, —C(=S)$R^A$, —C(=S)$N(R^B)_2$, —$NR^B$C(=S)$R^A$, —S(=O)$R^A$, —$SO_2R^A$, —$NR^B SO_2 R^A$, and —$SO_2N(R^B)_2$; or two adjacent $R^7$ groups are taken together with their intervening atoms to form an optionally substituted carbocyclic or heterocyclic fused ring; or $R^2$ and $R^7$ are taken together with their intervening atoms to form an optionally substituted carbocyclic or heterocyclic fused ring.

In some embodiments, $R^7$ is halo. In certain embodiments, $R^7$ is fluoro. In certain embodiments, $R^7$ is chloro. In certain embodiments, $R^7$ is bromo. In some embodiments, $R^7$ is optionally substituted aliphatic. In certain embodiments, $R^7$ is optionally substituted alkyl. In certain embodiments, $R^7$ is unsubstituted alkyl. In certain embodiments, $R^7$ is methyl. In certain embodiments, $R^7$ is haloalkyl. In certain embodiments, $R^7$ is trifluoromethyl. In some embodiments, $R^7$ is —$OR^A$, —$N(R^B)_2$, —$SR^A$. In certain embodiments, $R^7$ is —$OCH_3$ or —$SCH_3$. In certain embodiments, $R^7$ is —$OCF_3$. In some embodiments, $R^7$ is —CN. In some embodiments, an $R^7$ group is ortho. In some embodiments, an $R^7$ group is meta. In some embodiments, an $R^7$ group is para. In some embodiments, two adjacent $R^7$ groups are taken together with their intervening atoms to form an optionally substituted carbocyclic (e.g., aryl or saturated carbocyclic) or heterocyclic (e.g., heteroaryl or saturated heterocyclic) fused ring. For example, in some embodiments, two $R^7$ groups are taken together to form a fused methylenedioxy group. In some embodiments, $R^2$ and $R^7$ are taken together with their intervening atoms to form an optionally substituted carbocyclic (e.g., aryl or saturated carbocyclic) or heterocyclic (e.g., heteroaryl or saturated heterocyclic) fused ring.

As generally defined above, n is 0, 1, 2, 3, 4, or 5, as valency allows. In some embodiments, n is 0. In some embodiments, n is 1. In some embodiments, n is 2. In some embodiments, n is 3. In some embodiments, n is 4. In some embodiments, n is 5.

In certain embodiments, a provided compound is one of the following:

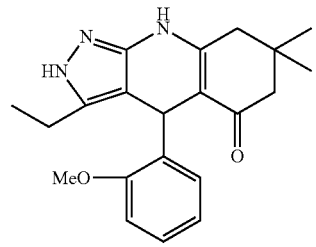

48

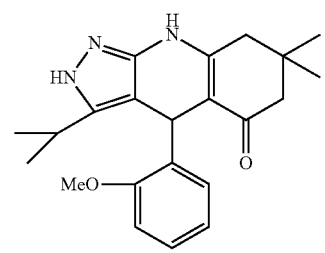

49

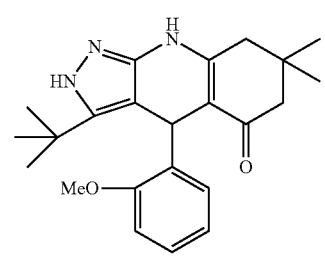

50

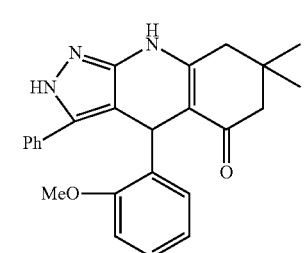

51

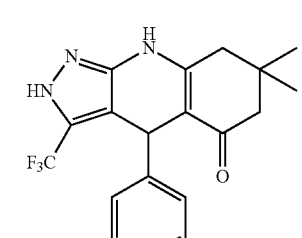

52

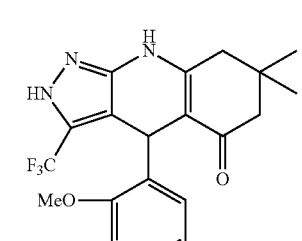

53

54
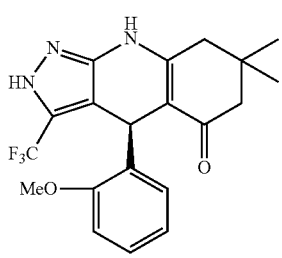
55
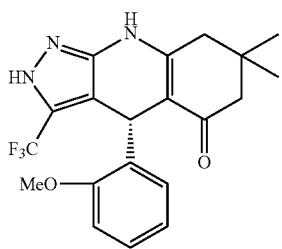
57
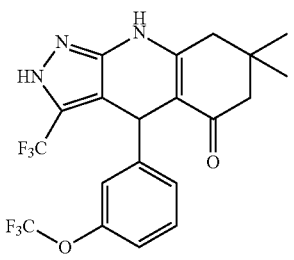
58
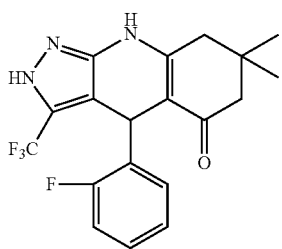
59
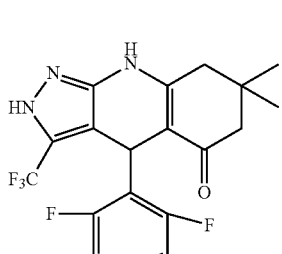
60
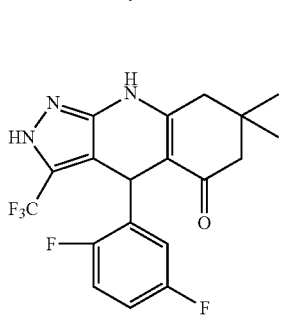
61
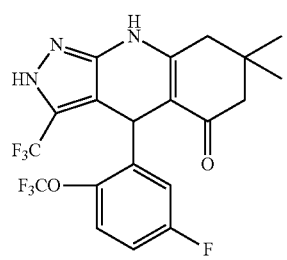
62
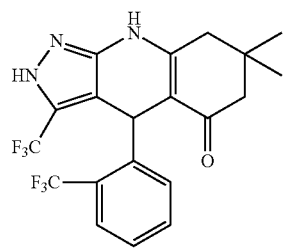
63
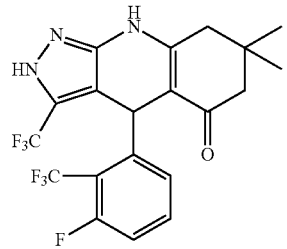
64
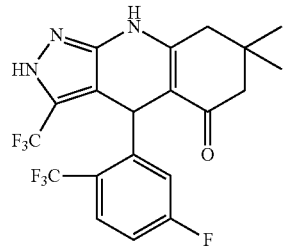
65
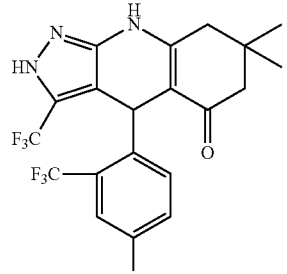
66
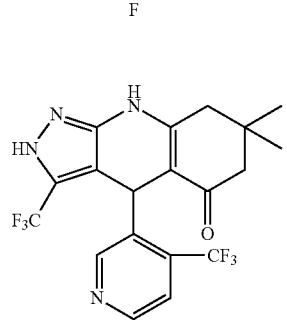

67
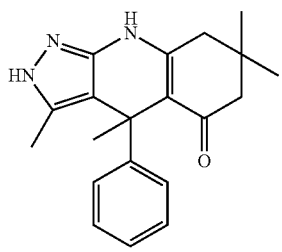
68
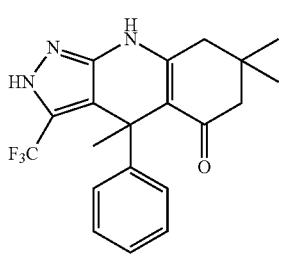
69
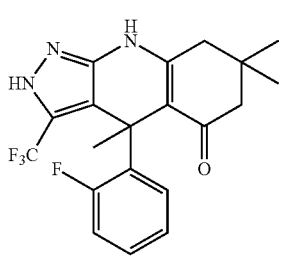
4
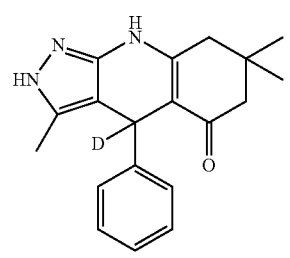
70
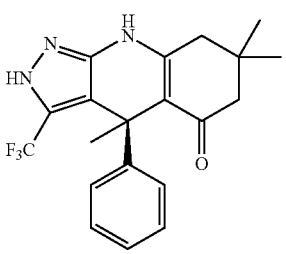
71
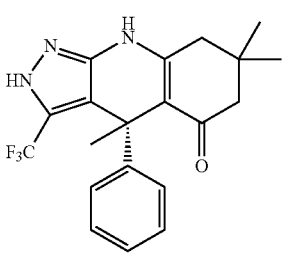
72
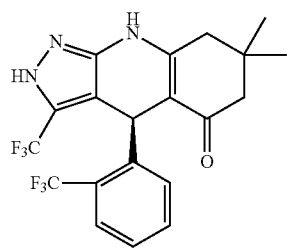
73
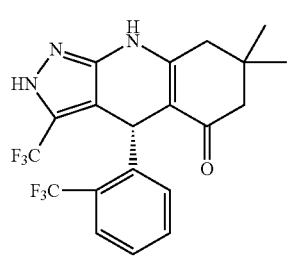
74
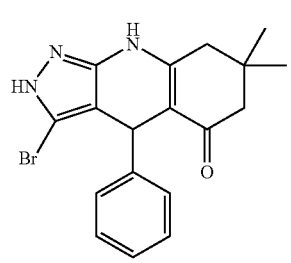
76
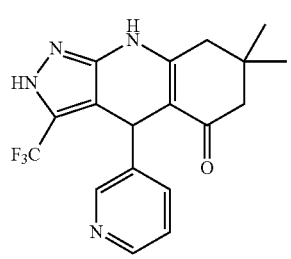
82
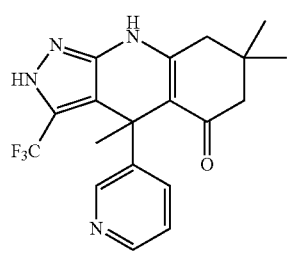
83
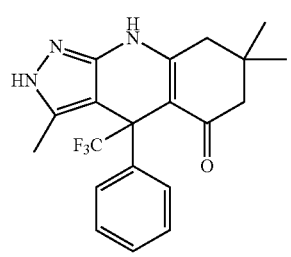

| | |
|---|---|
| 84 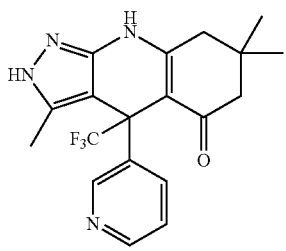 | 90 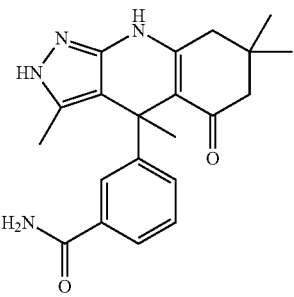 [SMILES: Cc1[nH]nc2c1C(C)(c1cccc(C(N)=O)c1)C1=C(CC(C)(C)CC1=O)N2] |
| 85 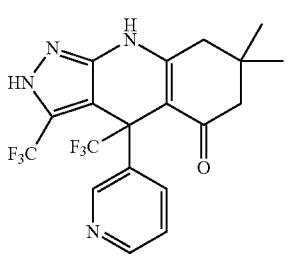 | 91 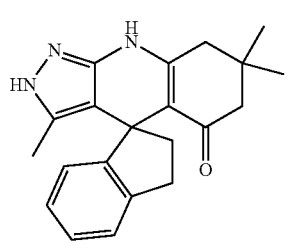 |
| 86 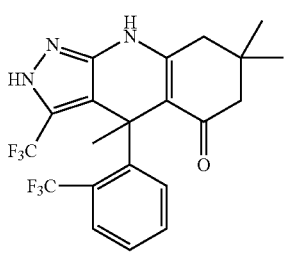 | 92 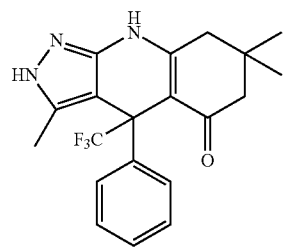 |
| 87 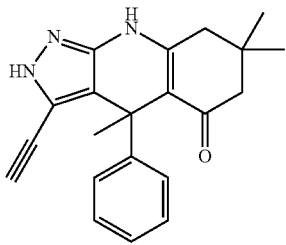 | 93 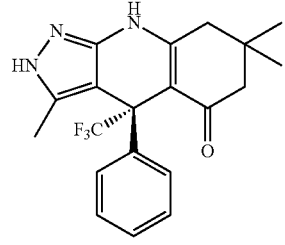 |
| 88 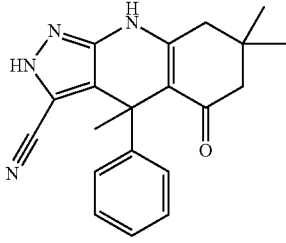 | 94 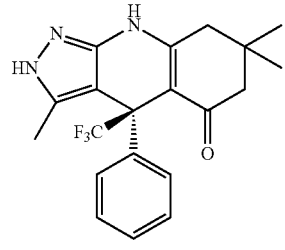 |
| 89 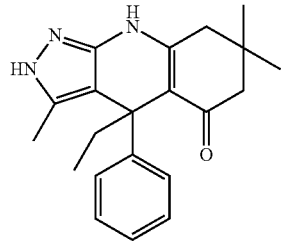 | 95 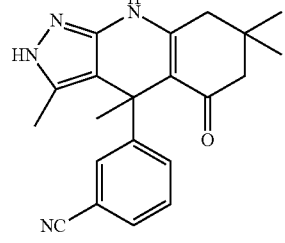 |

96 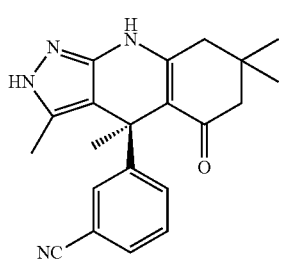
97 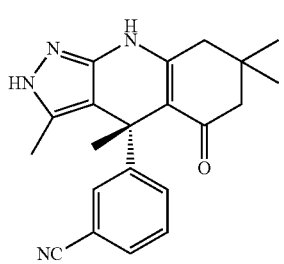
98 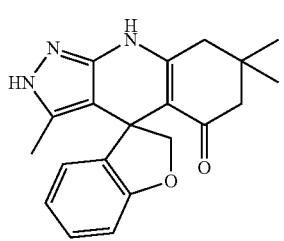 [SMILES: Cc1[nH]nc2c1C1(COc3ccccc31)C1=C(CC(C)(C)CC1=O)N2]
99 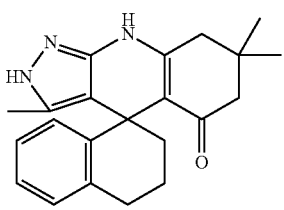
100 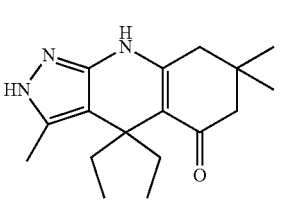
101 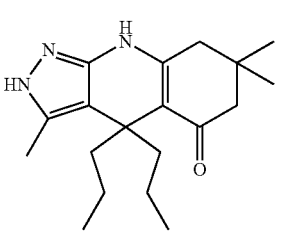
102 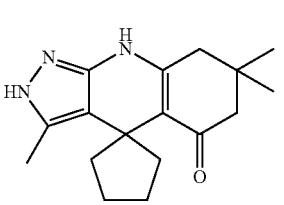
103 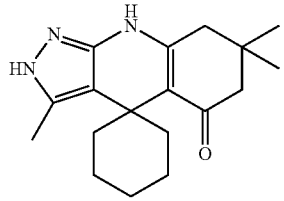
104 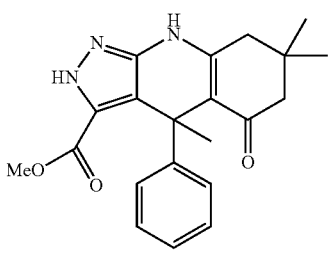
105 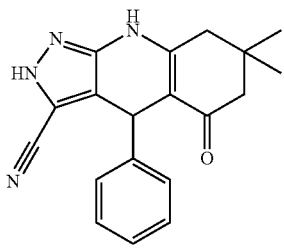
106 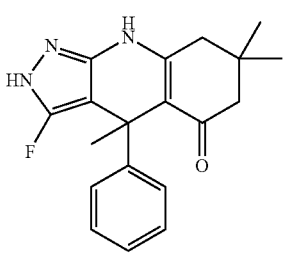
107 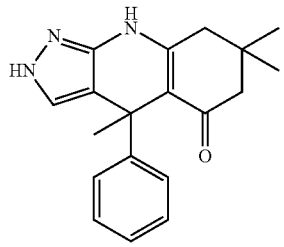
108 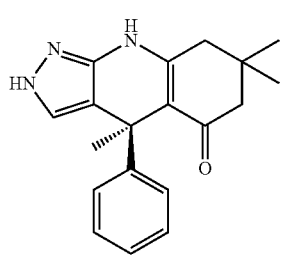

109
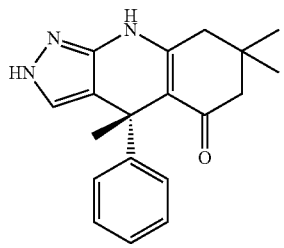
110
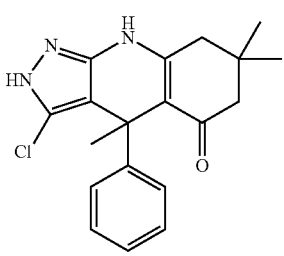
111
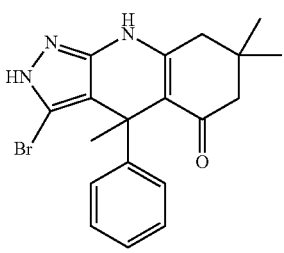
112
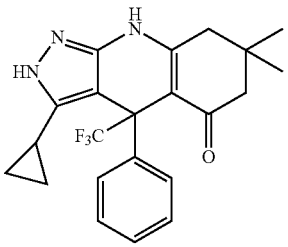
113
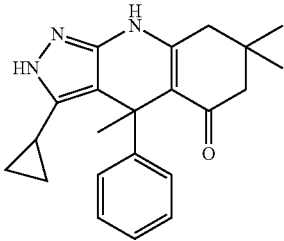
114
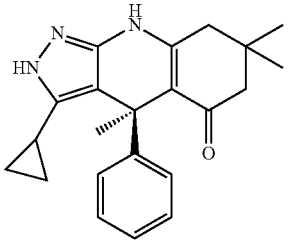
115
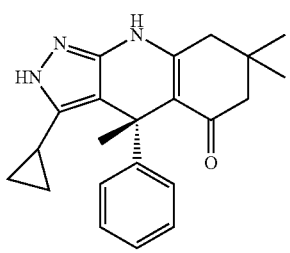
116
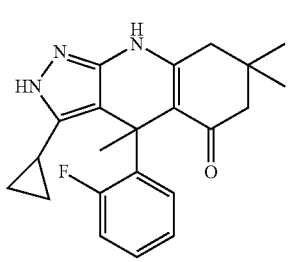
117
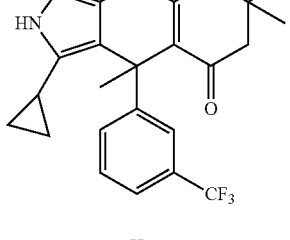
118
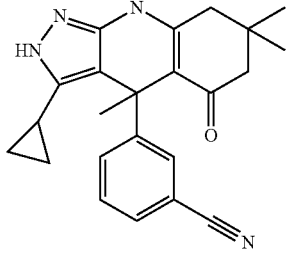
119
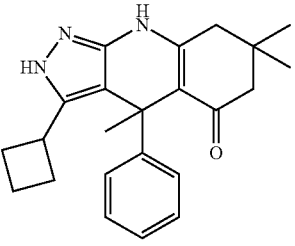
120
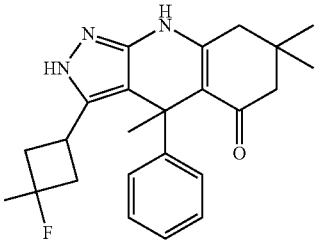

121
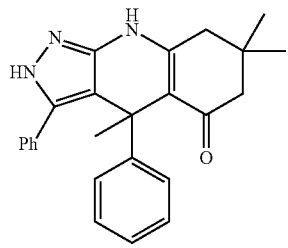
123
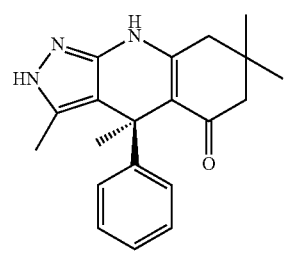
124
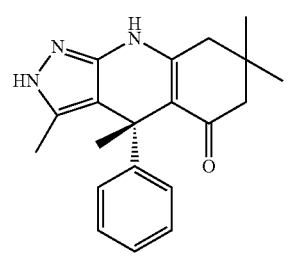
125
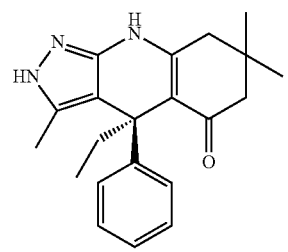
126
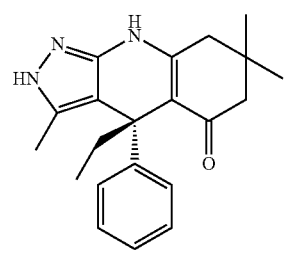
127
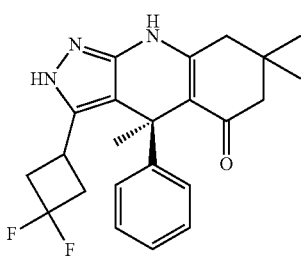
128
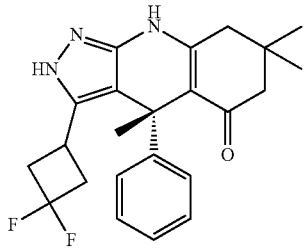
129
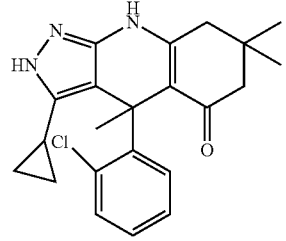
130
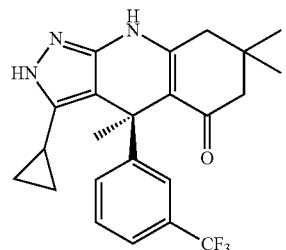
131
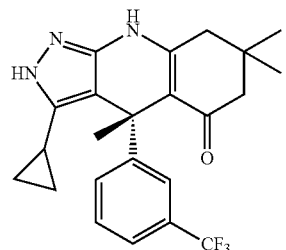
132
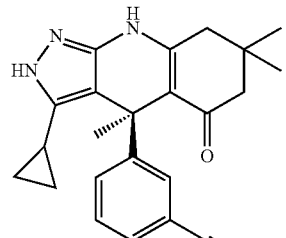
133
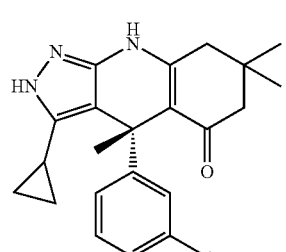

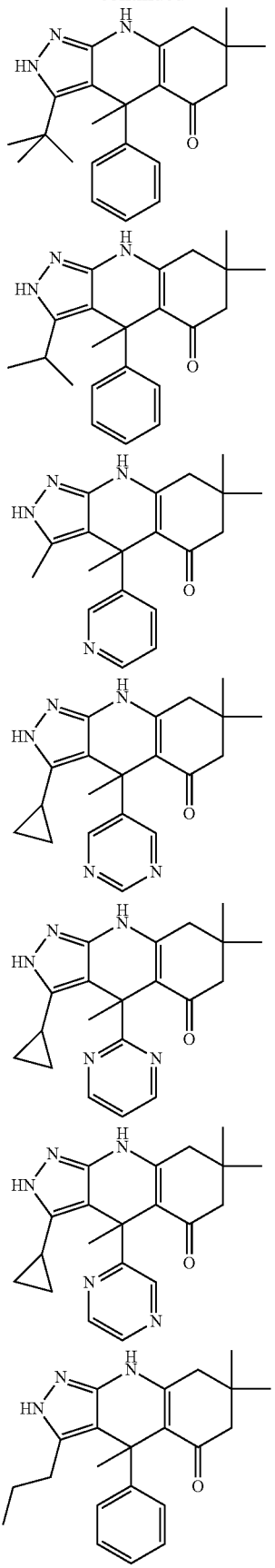
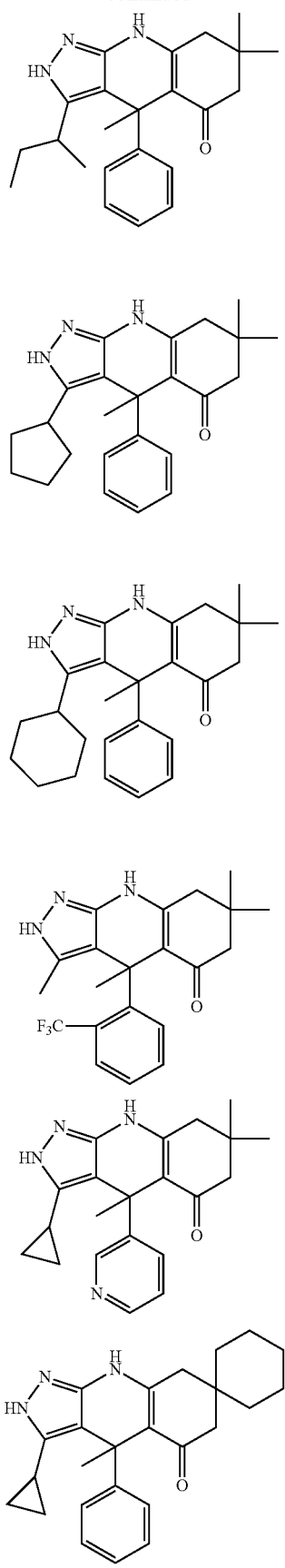

-continued
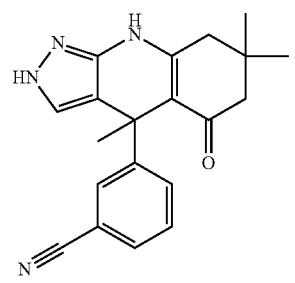
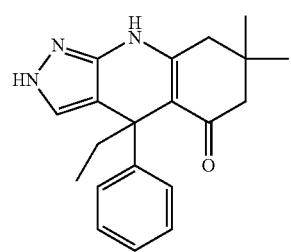
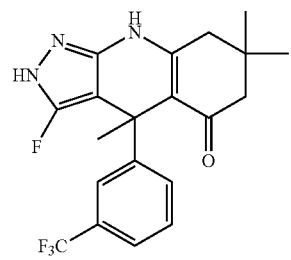
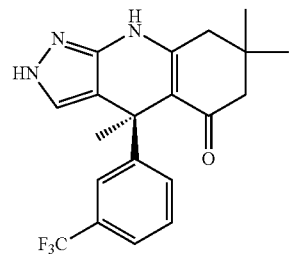
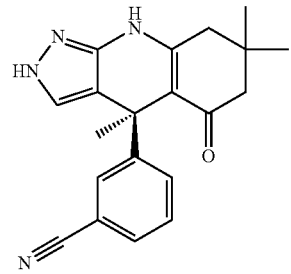
-continued
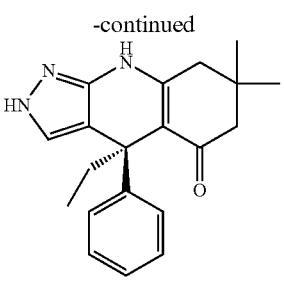
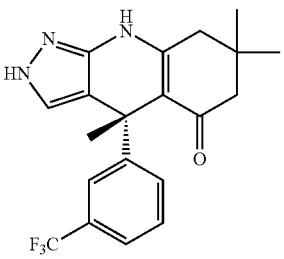
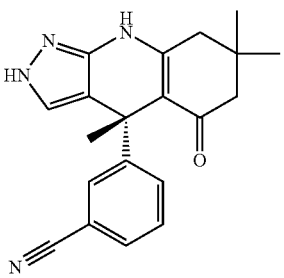
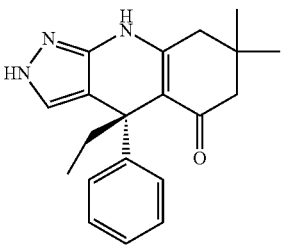
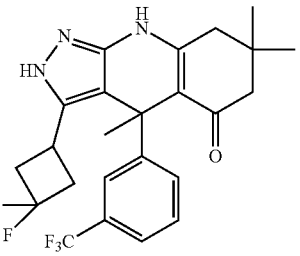
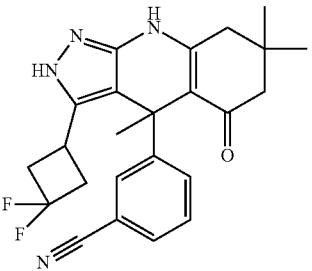

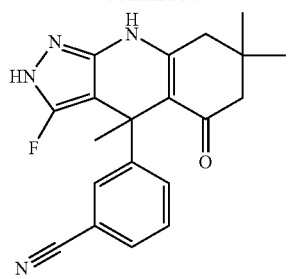
and pharmaceutically acceptable salts thereof.
Other useful compounds include:
5
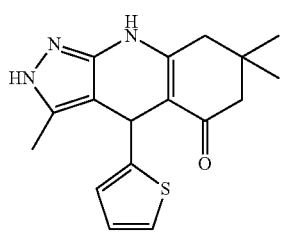
6
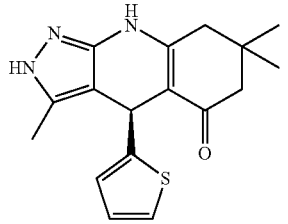
7
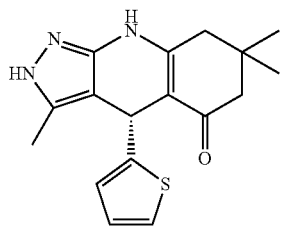
8
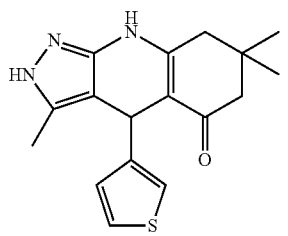
9
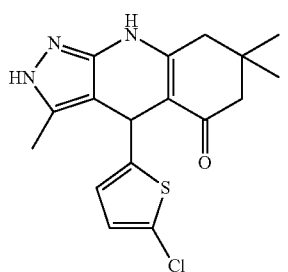
10
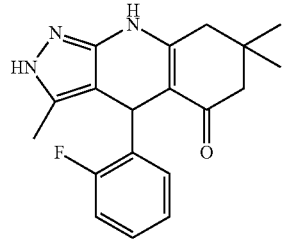
11
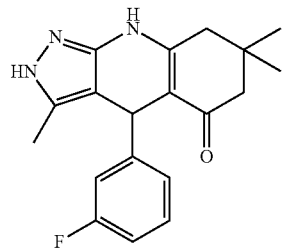
12
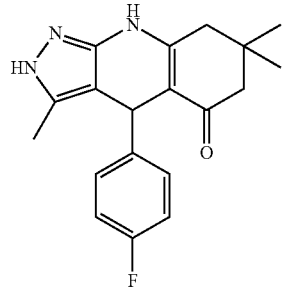
13
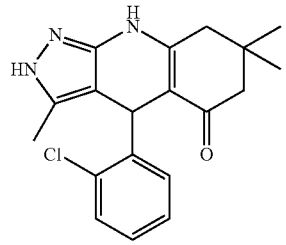
14
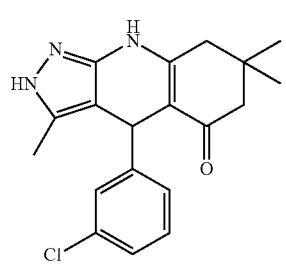
15
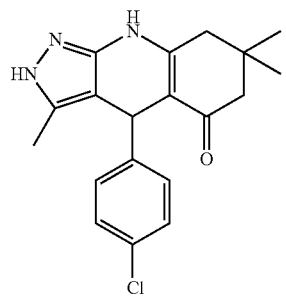

| | |
|---|---|
| 16 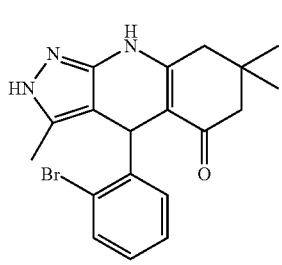 | 22 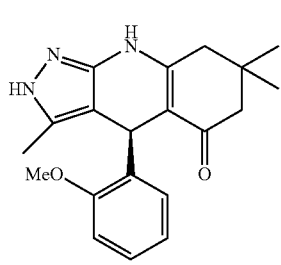 |
| 17 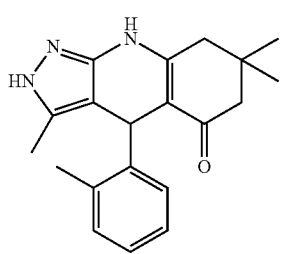 | 23 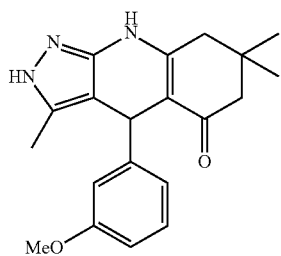 |
| 18 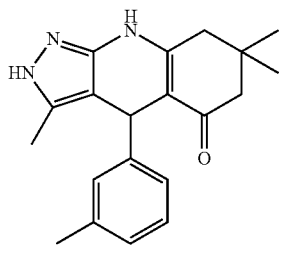 | 24 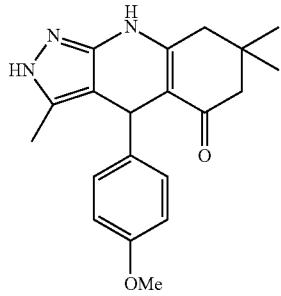 |
| 19 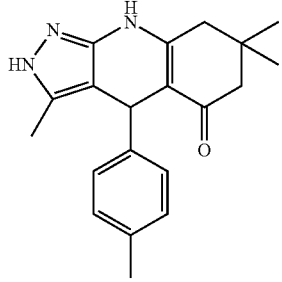 | 25 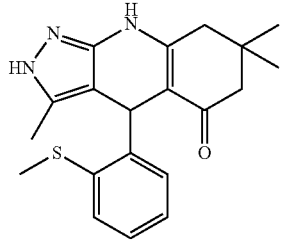 |
| 20 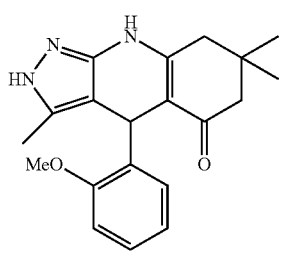 | 26 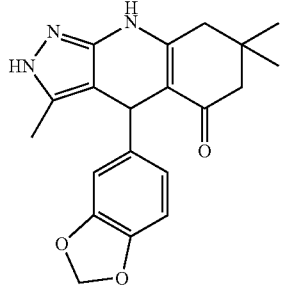 |
| 21 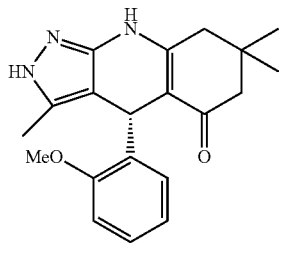 | 27 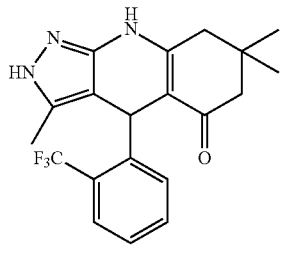 |

28
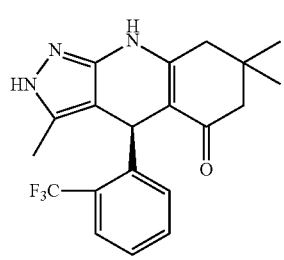
29
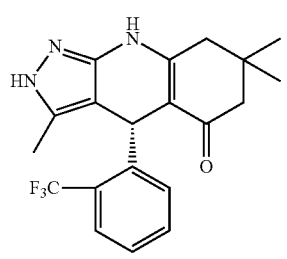
30
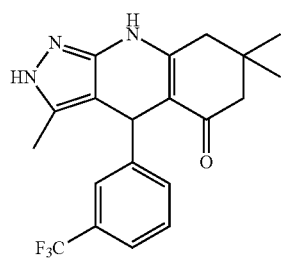
31
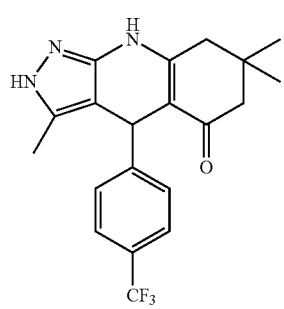
32
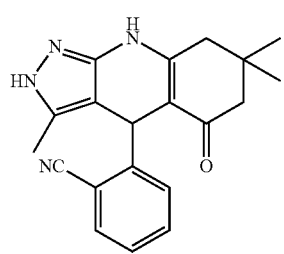
33
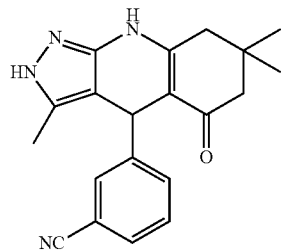
34
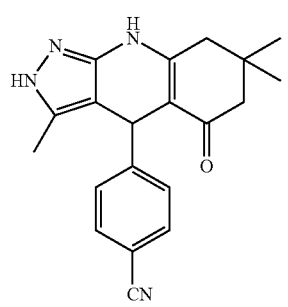
35
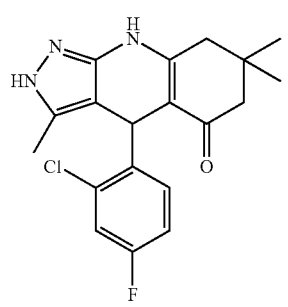
36
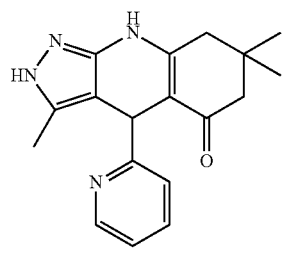
37
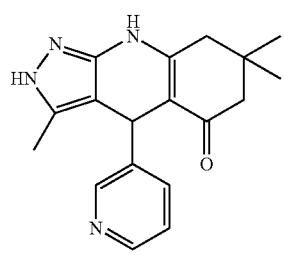
38
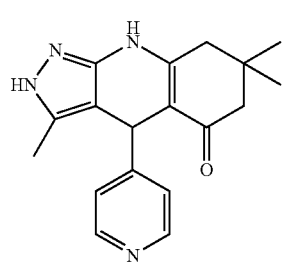

39
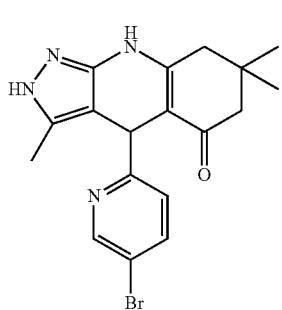
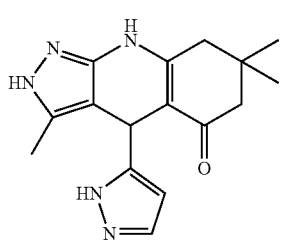
40
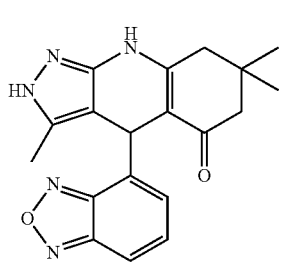
41
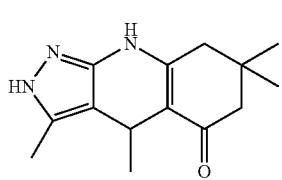
42
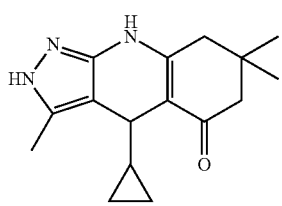
43
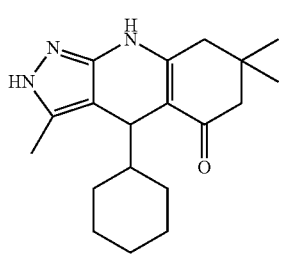
44
45
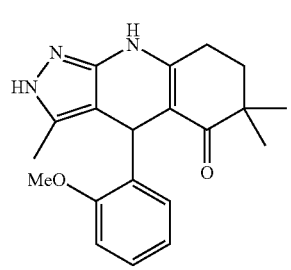
46
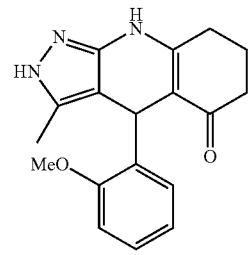
47
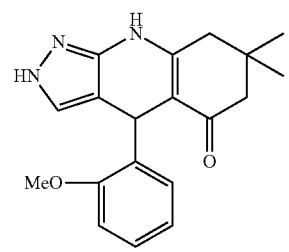
56
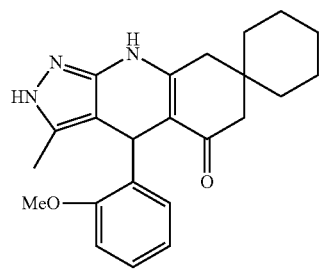
2
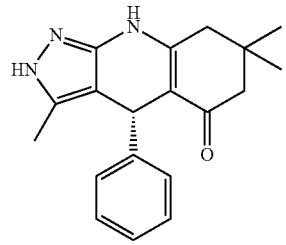
3
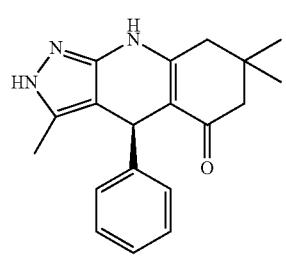

-continued

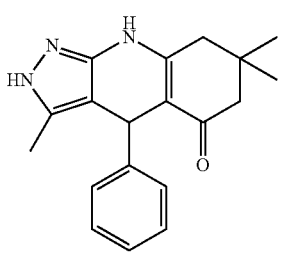

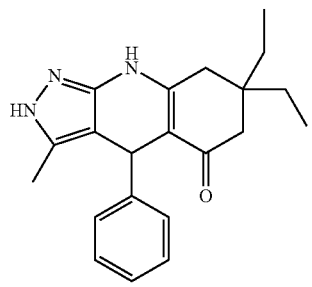

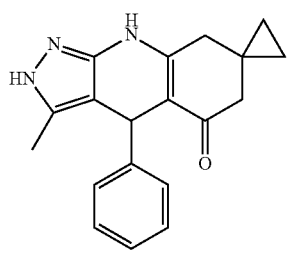

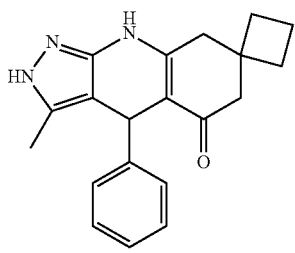

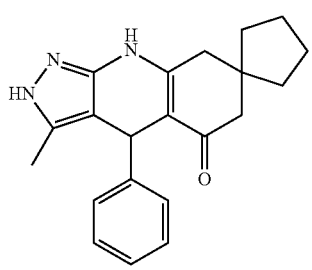

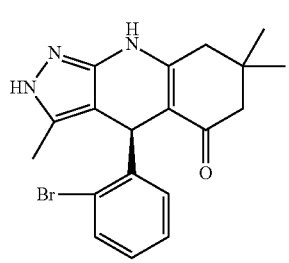

-continued

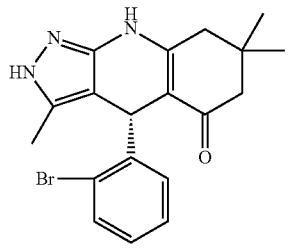

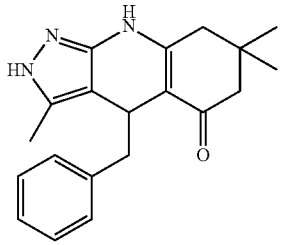

and pharmaceutically acceptable salts thereof.

In some embodiments, the compound is not

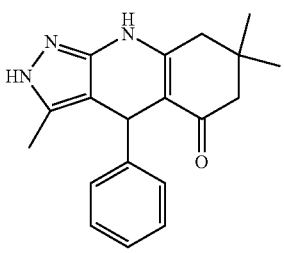

In certain embodiments, the present invention provides compounds of formula I, and pharmaceutically acceptable salts thereof, wherein:

$R^1$ and $R^2$ are independently selected from the group consisting of hydrogen, optionally substituted aliphatic, optionally substituted aryl, and optionally substituted heteroaryl, wherein $R^1$ and $R^2$ are not simultaneously hydrogen; or $R^1$ and $R^2$ are taken together with their intervening atoms to form an optionally substituted 3- to 7-membered saturated carbocyclic or heterocyclic ring, wherein the ring formed by $R^1$ and $R^2$ may be optionally fused to an aryl or heteroaryl ring;

$R^3$ is hydrogen or fluoro;

$R^{4a}$ and $R^{4b}$ are independently selected from the group consisting of hydrogen, halo, —CN, —OR$^A$, —N(R$^B$)$_2$, and optionally substituted aliphatic, or $R^{4a}$ and $R^{4b}$ are taken together with their intervening atoms to form an optionally substituted 3- to 7-membered saturated carbocyclic or heterocyclic ring;

$R^{5a}$ and $R^{5b}$ are independently selected from the group consisting of hydrogen, halo, —CN, —OR$^A$, —N(R$^B$)$_2$, optionally substituted aliphatic, optionally substituted aryl, and optionally substituted heteroaryl, or $R^{5a}$ and $R^{5b}$ are taken together with their intervening atoms to form an optionally substituted 3- to 7-membered saturated carbocyclic or heterocyclic ring; and $R^{6a}$ and $R^{6b}$ are independently selected from the group consisting of hydrogen, halo, —CN, —OR$^A$, —N(R$^B$)$_2$, and optionally substituted aliphatic, or $R^{6a}$ and $R^{6b}$ are taken together with their intervening atoms to form an optionally substituted 3- to 7-membered saturated carbocyclic or heterocyclic ring;

provided that when $R^1$ or $R^2$ is hydrogen, $R^3$ is not hydrogen.

In certain embodiments, the present invention provides compounds of formula I, and pharmaceutically acceptable salts thereof, wherein:

$R^1$ and $R^2$ are independently selected from the group consisting of hydrogen, optionally substituted aliphatic, optionally substituted aryl, and optionally substituted heteroaryl, wherein at least one of $R^1$ and $R^2$ is ethyl;

$R^3$ is selected from the group consisting of hydrogen, halo, —CN, —$NO_2$, optionally substituted aliphatic, optionally substituted phenyl, optionally substituted heterocyclyl, optionally substituted heteroaryl, —$OR^A$, —$N(R^B)_2$, —$SR^A$, —C(=O)$R^A$, —C(=O)$OR^A$, —C(=O)$SR^A$, —C(=O)N($R^B$)$_2$, —OC(=O)$R^A$, —$NR^B$C(=O)$R^A$, —$NR^B$C(=O)N($R^B$)$_2$, —OC(=O)N($R^B$)$_2$, —$NR^B$C(=O)$OR^A$, —SC(=O)$R^A$, —C(=$NR^B$)$R^A$, —C(=$NR^B$)N($R^B$)$_2$, —$NR^B$C(=$NR^B$)$R^B$, —C(=S)$R^A$, —C(=S)N($R^B$)$_2$, —$NR^B$C(=S)$R^A$, —S(=O)$R^A$, —$SO_2R^A$, —$NR^B SO_2R^A$, and —$SO_2$N($R^B$)$_2$;

each $R^A$ is independently selected from the group consisting of hydrogen, optionally substituted aliphatic, optionally substituted carbocyclyl, optionally substituted heterocyclyl, optionally substituted aryl, and optionally substituted heteroaryl;

each $R^B$ is independently selected from the group consisting of hydrogen, optionally substituted aliphatic, optionally substituted carbocyclyl, optionally substituted heterocyclyl, optionally substituted aryl, and optionally substituted heteroaryl, or two $R^B$ groups are taken together with their intervening atoms to form an optionally substituted heterocyclic ring;

$R^{4a}$ and $R^{4b}$ are independently selected from the group consisting of hydrogen, halo, —CN, —$OR^A$, —$N(R^B)_2$, and optionally substituted aliphatic, or $R^{4a}$ and $R^{4b}$ are taken together with their intervening atoms to form an optionally substituted 3- to 7-membered saturated carbocyclic or heterocyclic ring;

$R^{5a}$ and $R^{5b}$ are independently selected from the group consisting of hydrogen, halo, —CN, —$OR^A$, —$N(R^B)_2$, optionally substituted aliphatic, optionally substituted aryl, and optionally substituted heteroaryl, or $R^{5a}$ and $R^{5b}$ are taken together with their intervening atoms to form an optionally substituted 3- to 7-membered saturated carbocyclic or heterocyclic ring; and $R^{6a}$ and $R^{6b}$ are independently selected from the group consisting of hydrogen, halo, —CN, —$OR^A$, —$N(R^B)_2$, and optionally substituted aliphatic, or $R^{6a}$ and $R^{6b}$ are taken together with their intervening atoms to form an optionally substituted 3- to 7-membered saturated carbocyclic or heterocyclic ring;

provided that when $R^1$ or $R^2$ is hydrogen, $R^3$ is not hydrogen, —OH, or —$CH_3$.

In certain embodiments, a provided compound inhibits a kinase, or a mutant or variant thereof. In certain embodiments, a provided compound inhibits GSK3. In certain embodiments, a provided compound inhibits CK1. In certain embodiments, a provided compound inhibits a kinase (e.g., GSK3 or CK1), e.g., as measured in an assay described herein. In certain embodiments, a provided compound inhibits the kinase (e.g., GSK3 or CK1) at an $IC_{50}$ less than or equal to 30 µM. In certain embodiments, a provided compound inhibits the kinase at an $IC_{50}$ less than or equal to 5 µM. In certain embodiments, a provided compound inhibits the kinase at an $IC_{50}$ less than or equal to 1 µM. In certain embodiments, a provided compound inhibits the kinase at an $IC_{50}$ less than or equal to 0.1 µM. In certain embodiments, the compound is selective for GSK3 when compared with other kinases. In certain embodiments, the compound is selective for GSK3α and GSK3β when compared with other kinases. In certain embodiments, the compound is selective for GSK3α when compared with other kinases. In certain embodiments, the compound is selective for GSK3β when compared with other kinases. In certain embodiments, the compound is selective for GSK3 when compared with CDK5. In certain embodiments, the compound is at least 10 times more active against GSK3 than other kinases (e.g., CDK5). In certain embodiments, the compound is at least 5 times more active against GSK3 than other kinases (e.g., CDK5). In certain embodiments, the compound is at least 2 times more active against GSK3 than other kinases (e.g., CDK5). In certain embodiments, the compound is selective for CK1 when compared with other kinases. In certain embodiments, the compound is selective for CK1 when compared with CDK5. In certain embodiments, the compound is at least 10 times more active against CK1 than other kinases (e.g., CDK5). In certain embodiments, the compound is at least 5 times more active against CK1 than other kinases (e.g., CDK5). In certain embodiments, the compound is at least 2 times more active against CK1 than other kinases (e.g., CDK5). In certain embodiments, a GSK3α selective inhibitor is advantageous over a pan GSK3 inhibitor. In certain embodiments, a GSK3β selective inhibitor is advantageous over a pan GSK3 inhibitor.

Methods of Preparing the Compounds

In one aspect, the present invention provides methods of preparing the compounds described herein (e.g., compounds of formula I, and salts thereof). In certain embodiments, the inventive methods include contacting a compound of formula A, or a salt thereof, with a compound of formula B, or a salt thereof, and a compound of formula C, or a salt thereof, under suitable conditions to provide the compound of formula I, or salt thereof:

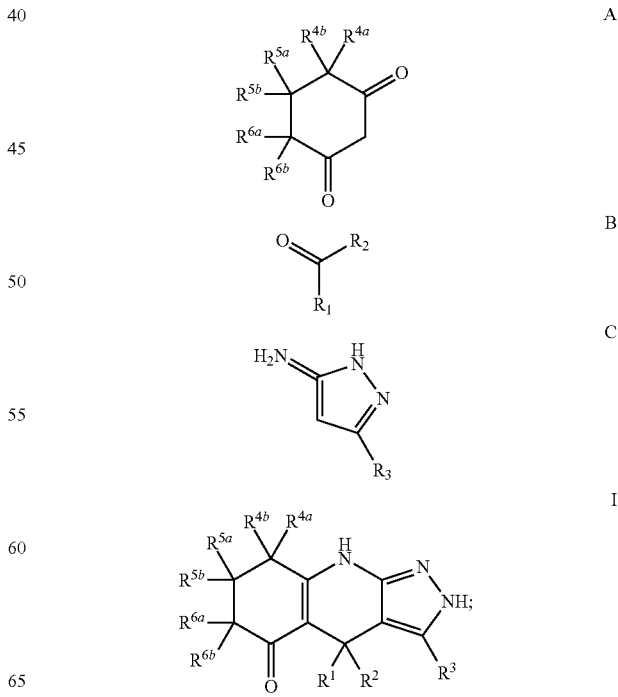

wherein:

R¹ and R² are independently selected from the group consisting of hydrogen, optionally substituted aliphatic, optionally substituted aryl, and optionally substituted heteroaryl, wherein R¹ and R² are not simultaneously hydrogen; or R¹ and R² are taken together with their intervening atoms to form an optionally substituted 3- to 7-membered saturated carbocyclic or heterocyclic ring, wherein the ring formed by R¹ and R² may be optionally fused to an aryl or heteroaryl ring;

R³ is selected from the group consisting of hydrogen, halo, —CN, —NO₂, optionally substituted aliphatic, optionally substituted phenyl, optionally substituted heterocyclyl, optionally substituted heteroaryl, —OR$^A$, —N(R$^B$)₂, —SR$^A$, —C(=O)R$^A$, —C(=O)OR$^A$, —C(=O)SR$^A$, —C(=O)N(R$^B$)₂, —OC(=O)R$^A$, —NR$^B$C(=O)R$^A$, —NR$^B$C(=O)N(R$^B$)₂, —OC(=O)N(R$^B$)₂, —NR$^B$C(=O)OR$^A$, —SC(=O)R$^A$, —C(=NR$^B$)R$^A$, —C(=NR$^B$)N(R$^B$)₂, —NR$^B$C(=NR$^B$)R$^B$, —C(=S)R$^A$, —C(=S)N(R$^B$)₂, —NR$^B$C(=S)R$^A$, —S(=O)R$^A$, —SO₂R$^A$, —NR$^B$SO₂R$^A$, and —SO₂N(R$^B$)₂;

each R$^A$ is independently selected from the group consisting of hydrogen, optionally substituted aliphatic, optionally substituted carbocyclyl, optionally substituted heterocyclyl, optionally substituted aryl, and optionally substituted heteroaryl;

each R$^B$ is independently selected from the group consisting of hydrogen, optionally substituted aliphatic, optionally substituted carbocyclyl, optionally substituted heterocyclyl, optionally substituted aryl, and optionally substituted heteroaryl, or two R$^B$ groups are taken together with their intervening atoms to form an optionally substituted heterocyclic ring;

R$^{4a}$ and R$^{4b}$ are independently selected from the group consisting of hydrogen, halo, —CN, —OR$^A$, —N(R$^B$)₂, and optionally substituted aliphatic, or R$^{4a}$ and R$^{4b}$ are taken together with their intervening atoms to form an optionally substituted 3- to 7-membered saturated carbocyclic or heterocyclic ring;

R$^{5a}$ and R$^{5b}$ are independently selected from the group consisting of hydrogen, halo, —CN, —OR$^A$, —N(R$^B$)₂, optionally substituted aliphatic, optionally substituted aryl, and optionally substituted heteroaryl, or R$^{5a}$ and R$^{5b}$ are taken together with their intervening atoms to form an optionally substituted 3- to 7-membered saturated carbocyclic or heterocyclic ring; and R$^{6a}$ and R$^{6b}$ are independently selected from the group consisting of hydrogen, halo, —CN, —OR$^A$, —N(R$^B$)₂, and optionally substituted aliphatic, or R$^{6a}$ and R$^{6b}$ are taken together with their intervening atoms to form an optionally substituted 3- to 7-membered saturated carbocyclic or heterocyclic ring.

In another aspect, the present invention provides methods of preparing a compound of formula I':

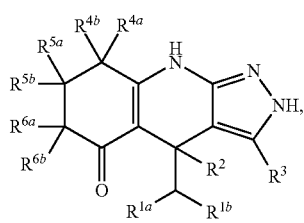

or a salt thereof, the method including:

contacting a compound of formula C, or a salt thereof, with a compound of formula D, or a salt thereof, under suitable conditions to provide a compound of formula E, or a salt thereof:

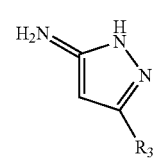

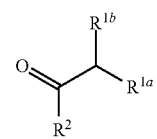

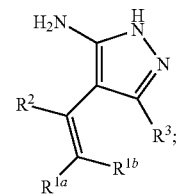

conjugating the compound of formula E, or salt thereof, to a compound of formula A, or a salt thereof, under suitable conditions to provide a compound of formula F, or a salt thereof:

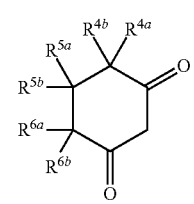

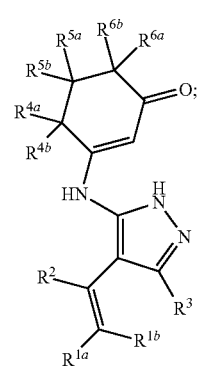

and cyclizing the compound of formula F, or salt thereof, under suitable conditions to provide the compound of formula I', or salt thereof, wherein:

R$^{1a}$ and R$^{1b}$ are independently selected from the group consisting of hydrogen and optionally substituted aliphatic, or R$^{1a}$ and R$^{1b}$ are taken together with their intervening atoms to form an optionally substituted 3- to 7-membered saturated or unsaturated carbocyclic or heterocyclic ring, wherein the ring formed by $R^{1a}$ and $R^{1b}$ may be optionally fused to an aryl or heteroaryl ring;

$R^2$ is selected from the group consisting of optionally substituted aliphatic, optionally substituted aryl, and optionally substituted heteroaryl, or $R^{1a}$ and $R^2$ are taken together with their intervening atoms to form an optionally substituted 3- to 7-membered saturated or unsaturated carbocyclic or heterocyclic ring, wherein the ring formed by $R^{1a}$ and $R^2$ may be optionally fused to an aryl or heteroaryl ring;

$R^3$ is selected from the group consisting of hydrogen, halo, —CN, —NO$_2$, optionally substituted aliphatic, optionally substituted phenyl, optionally substituted heterocyclyl, optionally substituted heteroaryl, —OR$^A$, —N(R$^B$)$_2$, —SR$^A$, —C(=O)R$^A$, —C(=O)OR$^A$, —C(=O)SR$^A$, —C(=O)N(R$^B$)$_2$, —OC(=O)R$^A$, —NR$^B$C(=O)R$^A$, —NR$^B$C(=O)N(R$^B$)$_2$, —OC(=O)N(R$^B$)$_2$, —NR$^B$C(=O)OR$^A$, —SC(=O)R$^A$, —C(=NR$^B$)R$^A$, —C(=NR$^B$)N(R$^B$)$_2$, —NR$^B$C(=NR$^B$)R$^B$, —C(=S)R$^A$, —C(=S)N(R$^B$)$_2$, —NR$^B$C(=S)R$^A$, —S(=O)R$^A$, —SO$_2$R$^A$, —NR$^B$SO$_2$R$^A$, and —SO$_2$N(R$^B$)$_2$;

each $R^A$ is independently selected from the group consisting of hydrogen, optionally substituted aliphatic, optionally substituted carbocyclyl, optionally substituted heterocyclyl, optionally substituted aryl, and optionally substituted heteroaryl;

each $R^B$ is independently selected from the group consisting of hydrogen, optionally substituted aliphatic, optionally substituted carbocyclyl, optionally substituted heterocyclyl, optionally substituted aryl, and optionally substituted heteroaryl, or two $R^B$ groups are taken together with their intervening atoms to form an optionally substituted heterocyclic ring;

$R^{4a}$ and $R^{4b}$ are independently selected from the group consisting of hydrogen, halo, —CN, —OR$^A$, —N(R$^B$)$_2$, and optionally substituted aliphatic, or $R^{4a}$ and $R^{4b}$ are taken together with their intervening atoms to form an optionally substituted 3- to 7-membered saturated carbocyclic or heterocyclic ring;

$R^{5a}$ and $R^{5b}$ are independently selected from the group consisting of hydrogen, halo, —CN, —OR$^A$, —N(R$^B$)$_2$, optionally substituted aliphatic, optionally substituted aryl, and optionally substituted heteroaryl, or $R^{5a}$ and $R^{5b}$ are taken together with their intervening atoms to form an optionally substituted 3- to 7-membered saturated carbocyclic or heterocyclic ring; $R^{6a}$ and $R^{6b}$ are independently selected from the group consisting of hydrogen, halo, —CN, —OR$^A$, —N(R$^B$)$_2$, and optionally substituted aliphatic, or $R^{6a}$ and $R^{6b}$ are taken together with their intervening atoms to form an optionally substituted 3- to 7-membered saturated carbocyclic or heterocyclic ring; and $R^{1a}$ and $R^{1b}$ are independently selected from the group consisting of hydrogen and optionally substituted aliphatic.

Another aspect of the present invention relates to methods of preparing a compound of formula I':

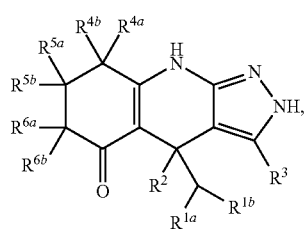

I' or a salt thereof, the method comprising:

protecting the primary amino group of a compound of formula C, or a salt thereof, to provide a compound of formula G, or a salt thereof:

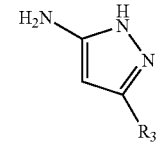

C

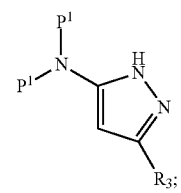

G halogenating the compound of formula G, or salt thereof, to provide a compound of formula H, or a salt thereof:

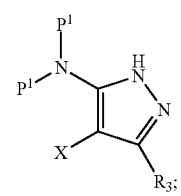

H protecting the secondary amino group of the compound of formula H, or salt thereof, to provide a compound of formula J, or a salt thereof;

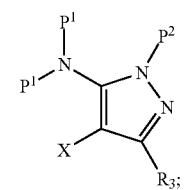

J coupling the compound of formula J, or salt thereof, with a boronic acid or ester of formula K, or a salt thereof, to provide a compound of formula L, or a salt thereof:

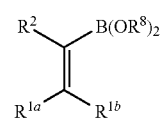

K

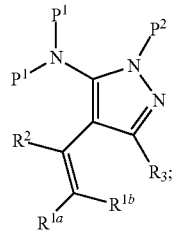

L deprotecting the primary amino group the compound of formula L, or salt thereof, to provide a compound of formula M, or a salt thereof:

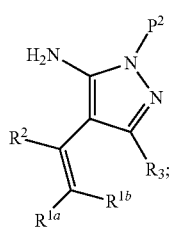

M conjugating the compound of formula M, or salt thereof, to a compound of formula A, or a salt thereof, to provide a compound of formula N, or a salt thereof:

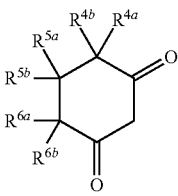

A

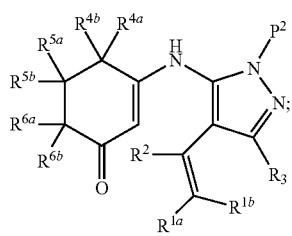

N deprotecting the secondary amino group the compound of formula N, or salt thereof, to provide a compound of formula F, or a salt thereof:

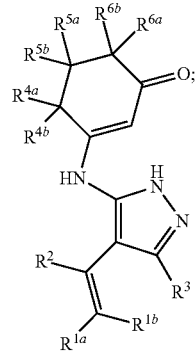

F cyclizing the compound of formula F, or salt thereof, under suitable conditions to provide the compound of formula I', or salt thereof, wherein:

$R^{1a}$ and $R^{1b}$ are independently selected from the group consisting of hydrogen and optionally substituted aliphatic, or $R^{1a}$ and $R^{1b}$ are taken together with their intervening atoms to form an optionally substituted 3- to 7-membered saturated or unsaturated carbocyclic or heterocyclic ring, wherein the ring formed by $R^{1a}$ and $R^{1b}$ may be optionally fused to an aryl or heteroaryl ring;

$R^2$ is selected from the group consisting of hydrogen, optionally substituted aliphatic, optionally substituted aryl, and optionally substituted heteroaryl, or $R^{1a}$ and $R^2$ are taken together with their intervening atoms to form an optionally substituted 3- to 7-membered saturated or unsaturated carbocyclic or heterocyclic ring, wherein the ring formed by $R^{1a}$ and $R^2$ may be optionally fused to an aryl or heteroaryl ring;

$R^3$ is selected from the group consisting of hydrogen, halo, —CN, —NO$_2$, optionally substituted aliphatic, optionally substituted phenyl, optionally substituted heterocyclyl, optionally substituted heteroaryl, —OR$^A$, —N(R$^B$)$_2$, —SR$^A$, —C(=O)R$^A$, —C(=O)OR$^A$, —C(=O)SR$^A$, —C(=O)N(R$^B$)$_2$, —OC(=O)R$^A$, —NR$^B$C(=O)R$^A$, —NR$^B$C(=O)N(R$^B$)$_2$, —OC(=O)N(R$^B$)$_2$, —NR$^B$C(=O)OR$^A$, —SC(=O)R$^A$, —C(=NR$^B$)R$^A$, —C(=NR$^B$)N(R$^B$)$_2$, —NR$^B$C(=NR$^B$)R$^B$, —C(=S)R$^A$, —C(=S)N(R$^B$)$_2$, —NR$^B$C(=S)R$^A$, —S(=O)R$^A$, —SO$_2$R$^A$, —NR$^B$SO$_2$R$^A$, and —SO$_2$N(R$^B$)$_2$;

each $R^A$ is independently selected from the group consisting of hydrogen, optionally substituted aliphatic, optionally substituted carbocyclyl, optionally substituted heterocyclyl, optionally substituted aryl, and optionally substituted heteroaryl;

each $R^B$ is independently selected from the group consisting of hydrogen, optionally substituted aliphatic, optionally substituted carbocyclyl, optionally substituted heterocyclyl, optionally substituted aryl, and optionally substituted heteroaryl, or two $R^B$ groups are taken together with their intervening atoms to form an optionally substituted heterocyclic ring;

$R^{4a}$ and $R^{4b}$ are independently selected from the group consisting of hydrogen, halo, —CN, —OR$^A$, —N(R$^B$)$_2$, and optionally substituted aliphatic, or $R^{4a}$ and $R^{4b}$ are taken together with their intervening atoms to form an optionally substituted 3- to 7-membered saturated carbocyclic or heterocyclic ring;

$R^{5a}$ and $R^{5b}$ are independently selected from the group consisting of hydrogen, halo, —CN, —OR$^A$, —N(R$^B$)$_2$, optionally substituted aliphatic, optionally substituted aryl, and optionally substituted heteroaryl, or $R^{5a}$ and $R^{5b}$ are taken together with their intervening atoms to form an optionally substituted 3- to 7-membered saturated carbocyclic or heterocyclic ring; $R^{6a}$ and $R^{6b}$ are independently selected from the group consisting of hydrogen, halo, —CN, —$OR^A$, —$N(R^B)_2$, and optionally substituted aliphatic, or $R^{6a}$ and $R^{6b}$ are taken together with their intervening atoms to form an optionally substituted 3- to 7-membered saturated carbocyclic or heterocyclic ring;

each instance of $P^1$ is independently a nitrogen protecting group, or two instances of $P^1$ are joined to form an optionally substituted heterocyclic ring;

X is halogen;

$P^2$ is a nitrogen protecting group and is different from any instance of $P^1$;

$R^{2a}$ and $R^{2b}$ are independently selected from the group consisting of hydrogen and optionally substituted aliphatic; and each instance of $R^8$ is independently hydrogen, substituted or unsubstituted acyl, substituted or unsubstituted alkyl, substituted or unsubstituted carbocyclyl, substituted or unsubstituted heterocyclyl, substituted or unsubstituted aryl, or substituted or unsubstituted heteroaryl, or two instances of $R^8$ are joined to form a substituted or unsubstituted heterocyclic ring.

In certain embodiments, two instances of $P^1$ are joined to form phthalimido. In certain embodiments, $P^2$ is EtOCH($CH_3$)—. In certain embodiments, $R^1$ is hydrogen. In certain embodiments, $R^{1a}$ and $R^{1b}$ are each hydrogen. In certain embodiments, $R^3$ is hydrogen, fluorine, chlorine, or methyl. In certain embodiments, $R^{4a}$, $R^{4b}$, $R^{6a}$, and $R^{6b}$ are each hydrogen. In certain embodiments, X is iodine or bromine. In certain embodiments, X is iodine. In certain embodiments, two instances of $R^8$ are each hydrogen, or two instances of $R^8$ are joined to form a heterocyclic ring of the formula:

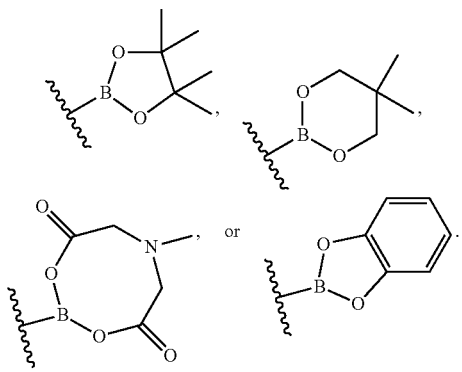

In certain embodiments, two instances of $R^8$ are each hydrogen. In certain embodiments, the suitable conditions comprise the presence of an acid or a temperature of at least about 25° C., or a combination thereof. In certain embodiments, the suitable conditions comprise the presence of an acid (e.g., p-toluenesulfonic acid (PTSA) or trifluoroacetic acid (TFA)). In certain embodiments, the suitable conditions comprise the presence of an alcohol (e.g., ethanol or methanol). In certain embodiments, the suitable conditions comprise a temperature of at least about 25° C. (e.g., at least about 40° C., at least about 70° C., at least about 110° C., or at least about 150° C.). In certain embodiments, the suitable conditions comprise irradiation with microwave. In certain embodiments, the suitable conditions are a combination of suitable conditions described herein.

Pharmaceutical Compositions and Administration

The present disclosure provides pharmaceutical compositions comprising a compound described herein, e.g., a compound of formula I, II, or III, or a pharmaceutically acceptable salt thereof, as described herein, and optionally a pharmaceutically acceptable excipient. It will be understood by one of ordinary skill in the art that the compounds described herein, or salts thereof, may be present in various forms, e.g., amorphous, hydrates, solvates, or polymorphs. In certain embodiments, a compound described herein is provided as a prodrug. In certain embodiments, a compound described herein, or a pharmaceutically acceptable salt thereof, is provided in an effective amount in the pharmaceutical composition. In certain embodiments, the effective amount is a therapeutically effective amount. In certain embodiments, the effective amount is an amount effective for inhibiting a kinase (e.g., GSK3 or CK1). In certain embodiments, the effective amount is an amount effective for treating a kinase-mediated disorder. In certain embodiments, the effective amount is a prophylactically effective amount. In certain embodiments, the effective amount is an amount effective to prevent a kinase-mediated disorder.

Pharmaceutically acceptable excipients include any and all solvents, diluents, or other liquid vehicles, dispersions, suspension aids, surface active agents, isotonic agents, thickening or emulsifying agents, preservatives, solid binders, lubricants, and the like, as suited to the particular dosage form desired. General considerations in formulation and/or manufacture of pharmaceutical compositions agents can be found, for example, in *Remington's Pharmaceutical Sciences*, Sixteenth Edition, E. W. Martin (Mack Publishing Co., Easton, Pa., 1980), and *Remington: The Science and Practice of Pharmacy,* 21st Edition (Lippincott Williams & Wilkins, 2005).

Pharmaceutical compositions described herein can be prepared by any method known in the art of pharmacology. In general, such preparatory methods include the steps of bringing a compound described herein (the "active ingredient") into association with a carrier and/or one or more other accessory ingredients, and then, if necessary and/or desirable, shaping and/or packaging the product into a desired single- or multi-dose unit.

Pharmaceutical compositions can be prepared, packaged, and/or sold in bulk, as a single unit dose, and/or as a plurality of single unit doses. A "unit dose" is discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

Relative amounts of the active ingredient, the pharmaceutically acceptable excipient, and/or any additional ingredients in a pharmaceutical composition of the present disclosure will vary, depending upon the identity, size, and/or condition of the subject treated and further depending upon the route by which the composition is to be administered. By way of example, the composition may comprise between 0.1% and 100% (w/w) active ingredient.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and mixtures thereof.

Exemplary granulating and/or dispersing agents include potato starch, corn starch, tapioca starch, sodium starch glycolate, clays, alginic acid, guar gum, citrus pulp, agar, bentonite, cellulose and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, and mixtures thereof.

Exemplary surface active agents and/or emulsifiers include natural emulsifiers (e.g., acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g., bentonite (aluminum silicate) and Veegum (magnesium aluminum silicate)), long chain amino acid derivatives, high molecular weight alcohols (e.g., stearyl alcohol, cetyl alcohol, oleyl alcohol, triacetin monostearate, ethylene glycol distearate, glyceryl monostearate, and propylene glycol monostearate, polyvinyl alcohol), carbomers (e.g., carboxy polymethylene, polyacrylic acid, acrylic acid polymer, and carboxyvinyl polymer), carrageenan, cellulosic derivatives (e.g., carboxymethylcellulose sodium, powdered cellulose, hydroxymethyl cellulose, hydroxypropyl cellulose, hydroxypropyl methylcellulose, methylcellulose), sorbitan fatty acid esters (e.g., polyoxyethylene sorbitan monolaurate (Tween 20), polyoxyethylene sorbitan (Tween 60), polyoxyethylene sorbitan monooleate (Tween 80), sorbitan monopalmitate (Span 40), sorbitan monostearate (Span 60], sorbitan tristearate (Span 65), glyceryl monooleate, sorbitan monooleate (Span 80)), polyoxyethylene esters (e.g., polyoxyethylene monostearate (Myrj 45), polyoxyethylene hydrogenated castor oil, polyethoxylated castor oil, polyoxymethylene stearate, and Solutol), sucrose fatty acid esters, polyethylene glycol fatty acid esters (e.g., Cremophor™), polyoxyethylene ethers, (e.g., polyoxyethylene lauryl ether (Brij 30)), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic F68, Poloxamer 188, cetrimonium bromide, cetylpyridinium chloride, benzalkonium chloride, docusate sodium, and/or mixtures thereof.

Exemplary binding agents include starch (e.g., cornstarch and starch paste), gelatin, sugars (e.g., sucrose, glucose, dextrose, dextrin, molasses, lactose, lactitol, mannitol, etc.), natural and synthetic gums (e.g., acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum), and larch arabogalactan), alginates, polyethylene oxide, polyethylene glycol, inorganic calcium salts, silicic acid, polymethacrylates, waxes, water, alcohol, and/or mixtures thereof.

Exemplary preservatives include antioxidants, chelating agents, antimicrobial preservatives, antifungal preservatives, alcohol preservatives, acidic preservatives, and other preservatives.

Exemplary antioxidants include alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant Plus, Phenonip, methylparaben, Germall 115, Germaben II, Neolone, Kathon, and Euxyl. In certain embodiments, the preservative is an anti-oxidant. In other embodiments, the preservative is a chelating agent.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and mixtures thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, and mixtures thereof.

Exemplary natural oils include almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macadamia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and mixtures thereof.

Liquid dosage forms for oral and parenteral administration include pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the compounds described herein are mixed with solubilizing agents such as Cremophor™, alcohols, oils, modified oils, glycols, polysorbates, cyclodextrins, polymers, and mixtures thereof.

Injectable preparations, for example, sterile injectable aqueous or oleaginous suspensions can be formulated according to the known art using suitable dispersing or wetting agents and suspending agents. The sterile injectable preparation can be a sterile injectable solution, suspension or emulsion in a nontoxic parenterally acceptable diluent or solvent, for example, as a solution in 1,3-butanediol. Among the acceptable vehicles and solvents that can be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Compositions for rectal or vaginal administration are typically suppositories which can be prepared by mixing the compounds described herein with suitable non-irritating excipients or carriers such as cocoa butter, polyethylene glycol or a suppository wax which are solid at ambient temperature but liquid at body temperature and therefore melt in the rectum or vaginal cavity and release the active ingredient.

Solid dosage forms for oral administration include capsules, tablets, pills, powders, and granules. In such solid dosage forms, the active ingredient is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may comprise buffering agents.

Solid compositions of a similar type can be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes. Solid compositions of a similar type can be employed as fillers in soft and hard-filled gelatin capsules using such excipients as lactose or milk sugar as well as high molecular weight polyethylene glycols and the like.

The active ingredient can be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active ingredient can be admixed with at least one inert diluent such as sucrose, lactose, or starch. Such dosage forms may comprise, as is normal practice, additional substances other than inert diluents, e.g., tableting lubricants and other tableting aids such a magnesium stearate and microcrystalline cellulose. In the case of capsules, tablets, and pills, the dosage forms may comprise buffering agents. They may optionally comprise opacifying agents and can be of a composition that they release the active ingredient(s) only, or preferentially, in a certain part of the intestinal tract, optionally, in a delayed manner.

Examples of embedding compositions which can be used include polymeric substances and waxes.

Dosage forms for topical and/or transdermal administration of a provided compound may include ointments, pastes, creams, lotions, gels, powders, solutions, sprays, inhalants and/or patches. Generally, the active ingredient is admixed under sterile conditions with a pharmaceutically acceptable carrier and/or any desired preservatives and/or buffers as can be required. Additionally, the present disclosure encompasses the use of transdermal patches, which often have the added advantage of providing controlled delivery of an active ingredient to the body. Such dosage forms can be prepared, for example, by dissolving and/or dispensing the active ingredient in the proper medium. Alternatively or additionally, the rate can be controlled by either providing a rate controlling membrane and/or by dispersing the active ingredient in a polymer matrix and/or gel.

Suitable devices for use in delivering intradermal pharmaceutical compositions described herein include short needle devices such as those described in U.S. Pat. Nos. 4,886,499; 5,190,521; 5,328,483; 5,527,288; 4,270,537; 5,015,235; 5,141,496; and 5,417,662. Intradermal compositions can be administered by devices which limit the effective penetration length of a needle into the skin, such as those described in PCT publication WO 99/34850 and functional equivalents thereof. Jet injection devices which deliver liquid vaccines to the dermis via a liquid jet injector and/or via a needle which pierces the stratum corneum and produces a jet which reaches the dermis are suitable. Jet injection devices are described, for example, in U.S. Pat. Nos. 5,480,381; 5,599,302; 5,334,144; 5,993,412; 5,649,912; 5,569,189; 5,704,911; 5,383,851; 5,893,397; 5,466,220; 5,339,163; 5,312,335; 5,503,627; 5,064,413; 5,520,639; 4,596,556; 4,790,824; 4,941,880; 4,940,460; and PCT publications WO 97/37705 and WO 97/13537. Ballistic powder/particle delivery devices which use compressed gas to accelerate vaccine in powder form through the outer layers of the skin to the dermis are suitable. Alternatively or additionally, conventional syringes can be used in the classical mantoux method of intradermal administration.

Formulations suitable for topical administration include, but are not limited to, liquid and/or semi liquid preparations such as liniments, lotions, oil in water and/or water in oil emulsions such as creams, ointments and/or pastes, and/or solutions and/or suspensions. Topically-administrable formulations may, for example, comprise from about 1% to about 10% (w/w) active ingredient, although the concentration of the active ingredient can be as high as the solubility limit of the active ingredient in the solvent. Formulations for topical administration may further comprise one or more of the additional ingredients described herein.

A provided pharmaceutical composition can be prepared, packaged, and/or sold in a formulation suitable for pulmonary administration via the buccal cavity. Such a formulation may comprise dry particles which comprise the active ingredient and which have a diameter in the range from about 0.5 to about 7 nanometers or from about 1 to about 6 nanometers. Such compositions are conveniently in the form of dry powders for administration using a device comprising a dry powder reservoir to which a stream of propellant can be directed to disperse the powder and/or using a self propelling solvent/powder dispensing container such as a device comprising the active ingredient dissolved and/or suspended in a low-boiling propellant in a sealed container. Such powders comprise particles wherein at least 98% of the particles by weight have a diameter greater than 0.5 nanometers and at least 95% of the particles by number have a diameter less than 7 nanometers. Alternatively, at least 95% of the particles by weight have a diameter greater than 1 nanometer and at least 90% of the particles by number have a diameter less than 6 nanometers. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic and/or solid anionic surfactant and/or a solid diluent (which may have a particle size of the same order as particles comprising the active ingredient).

Pharmaceutical compositions formulated for pulmonary delivery may provide the active ingredient in the form of droplets of a solution and/or suspension. Such formulations can be prepared, packaged, and/or sold as aqueous and/or dilute alcoholic solutions and/or suspensions, optionally sterile, comprising the active ingredient, and may conveniently be administered using any nebulization and/or atomization device. Such formulations may further comprise one or more additional ingredients including, but not limited to, a flavoring agent such as saccharin sodium, a volatile oil, a buffering agent, a surface active agent, and/or a preservative such as methylhydroxybenzoate. The droplets provided by this route of administration may have an average diameter in the range from about 0.1 to about 200 nanometers.

Formulations described herein as being useful for pulmonary delivery are useful for intranasal delivery of a pharmaceutical composition. Another formulation suitable for intranasal administration is a coarse powder comprising the active ingredient and having an average particle from about 0.2 to 500 micrometers. Such a formulation is administered by rapid inhalation through the nasal passage from a container of the powder held close to the nares.

Formulations for nasal administration may, for example, comprise from about as little as 0.1% (w/w) and as much as 100% (w/w) of the active ingredient, and may comprise one or more of the additional ingredients described herein. A provided pharmaceutical composition can be prepared, packaged, and/or sold in a formulation for buccal administration. Such formulations may, for example, be in the form of tablets and/or lozenges made using conventional methods, and may contain, for example, 0.1 to 20% (w/w) active ingredient, the balance comprising an orally dissolvable and/or degradable composition and, optionally, one or more of the additional ingredients described herein. Alternately, formulations for buccal administration may comprise a powder and/or an aerosolized and/or atomized solution and/or suspension comprising the active ingredient. Such powdered, aerosolized, and/or aerosolized formulations, when dispersed, may have an average particle and/or droplet size in the range from about 0.1 to about 200 nanometers, and may further comprise one or more of the additional ingredients described herein.

A provided pharmaceutical composition can be prepared, packaged, and/or sold in a formulation for ophthalmic administration. Such formulations may, for example, be in the form of eye drops including, for example, a 0.1/1.0% (w/w) solution and/or suspension of the active ingredient in an aqueous or oily liquid carrier. Such drops may further comprise buffering agents, salts, and/or one or more other of the additional ingredients described herein. Other opthalmically-administrable formulations which are useful include those which comprise the active ingredient in microcrystalline form and/or in a liposomal preparation. Ear drops and/or eye drops are contemplated as being within the scope of this disclosure.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation.

Compounds provided herein are typically formulated in dosage unit form for ease of administration and uniformity of dosage. It will be understood, however, that the total daily usage of provided compositions will be decided by the attending physician within the scope of sound medical judgment. The specific therapeutically effective dose level for any particular subject or organism will depend upon a variety of factors including the disease, disorder, or condition being treated and the severity of the disorder; the activity of the specific active ingredient employed; the specific composition employed; the age, body weight, general health, sex and diet of the subject; the time of administration, route of administration, and rate of excretion of the specific active ingredient employed; the duration of the treatment; drugs used in combination or coincidental with the specific active ingredient employed; and like factors well known in the medical arts.

The compounds and compositions provided herein can be administered by any route, including enteral (e.g., oral), parenteral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, bucal, sublingual; by intratracheal instillation, bronchial instillation, and/or inhalation; and/or as an oral spray, nasal spray, and/or aerosol. Specifically contemplated routes are oral administration, intravenous administration (e.g., systemic intravenous injection), regional administration via blood and/or lymph supply, and/or direct administration to an affected site. In general the most appropriate route of administration will depend upon a variety of factors including the nature of the agent (e.g., its stability in the environment of the gastrointestinal tract), and/or the condition of the subject (e.g., whether the subject is able to tolerate oral administration).

The exact amount of a compound required to achieve an effective amount will vary from subject to subject, depending, for example, on species, age, and general condition of a subject, severity of the side effects or disorder, identity of the particular compound(s), mode of administration, and the like. The desired dosage can be delivered three times a day, two times a day, once a day, every other day, every third day, every week, every two weeks, every three weeks, or every four weeks. In certain embodiments, the desired dosage can be delivered using multiple administrations (e.g., two, three, four, five, six, seven, eight, nine, ten, eleven, twelve, thirteen, fourteen, or more administrations).

In certain embodiments, an effective amount of a compound for administration one or more times a day to a 70 kg adult human may comprise about 0.0001 mg to about 3000 mg, about 0.0001 mg to about 2000 mg, about 0.0001 mg to about 1000 mg, about 0.001 mg to about 1000 mg, about 0.01 mg to about 1000 mg, about 0.1 mg to about 1000 mg, about 1 mg to about 1000 mg, about 1 mg to about 100 mg, about 10 mg to about 1000 mg, or about 100 mg to about 1000 mg, of a compound per unit dosage form.

In certain embodiments, a compound described herein may be administered at dosage levels sufficient to deliver from about 0.001 mg/kg to about 1000 mg/kg, from about 0.01 mg/kg to about mg/kg, from about 0.1 mg/kg to about 40 mg/kg, from about 0.5 mg/kg to about 30 mg/kg, from about 0.01 mg/kg to about 10 mg/kg, from about 0.1 mg/kg to about 10 mg/kg, or from about 1 mg/kg to about 25 mg/kg, of subject body weight per day, one or more times a day, to obtain the desired therapeutic effect.

In some embodiments, a compound described herein is administered one or more times per day, for multiple days. In some embodiments, the dosing regimen is continued for days, weeks, months, or years.

It will be appreciated that dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult.

It will be also appreciated that a compound or composition, as described herein, can be administered in combination with one or more additional therapeutically active agents. The compounds or compositions can be administered in combination with additional therapeutically active agents that improve their efficacy, potency, and/or bioavailability, reduce and/or modify their metabolism, inhibit their excretion, and/or modify their distribution within the body. It will also be appreciated that the therapy employed may achieve a desired effect for the same disorder, and/or it may achieve different effects.

The compound or composition can be administered concurrently with, prior to, or subsequent to, one or more additional therapeutically active agents. In general, each agent will be administered at a dose and/or on a time schedule determined for that agent. In will further be appreciated that the additional therapeutically active agent utilized in this combination can be administered together in a single composition or administered separately in different compositions. The particular combination to employ in a regimen will take into account compatibility of a provided compound with the additional therapeutically active agent and/or the desired therapeutic effect to be achieved. In general, it is expected that additional therapeutically active agents utilized in combination be utilized at levels that do not exceed the levels at which they are utilized individually. In some embodiments, the levels utilized in combination will be lower than those utilized individually.

Exemplary additional therapeutically active agents include, but are not limited to, antimicrobial agents, antifungal agents, antiparasitic agents, anti-inflammatory agents, and a pain-relieving agent. Therapeutically active agents include small organic molecules such as drug compounds (e.g., compounds approved by the U.S. Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins, and cells.

In certain embodiments, a provided compound is combined with an additional therapeutically active agent (e.g., lithium and/or ketamine) for use in treating bipolar disorder and/or depression (e.g., lithium-resistant depression). Lithium has long been the therapy of choice for bipolar disorder and manic syndromes though the exact mechanism of action has been difficult to discern (J. A. Quiroz, T. D. Gould and H. K. Manji, Mol. Interv., 2004, 4, 259). Lithium is known to affect the function of a variety of enzymes, an effect attributed to lithium competing for essential magnesium binding sites (W. J. Ryves and A. J. Harwood, Biochem. Biophys. Res. Commun., 2001, 280, 720). Therapeutically efficacious doses of $Li^+$ (0.6-1.2 mM plasma levels) do approach its GSK3 $IC_{50}$ ($IC_{50}$=2 mM) (Annual Reports in Medicinal Chemistry, 2005, Volume 40, page 137).

In certain embodiments, a provided compound is combined with an additional therapeutically active agent (e.g., all-trans retinoic acid) for use in treating AML. In certain embodiments, a combination of a provided compound and an additional therapeutically active agent shows synergistic effect in treating a neurological disease, psychiatric disorder (e.g., bipolar disorder or depression (e.g., lithium-resistant depression)), metabolic disorder (e.g., diabetes), and/or cancer (e.g., AML).

Also encompassed by the present disclosure are kits (e.g., pharmaceutical packs). The kits provided may comprise a provided pharmaceutical composition or compound and a container (e.g., a vial, ampule, bottle, syringe, and/or dispenser package, or other suitable container). In some embodiments, provided kits may optionally further include a second container comprising a pharmaceutical excipient for dilution or suspension of a provided pharmaceutical composition or compound. In some embodiments, a provided pharmaceutical composition or compound provided in the container and the second container are combined to form one unit dosage form.

Methods of Use and Treatment

Compounds and compositions described herein are generally useful for the inhibition of one or more kinases. In some embodiments, compounds and compositions described herein are useful for inhibiting of the activity of GSK3. In some embodiments, compounds and compositions described herein are useful for inhibiting CK1. In some embodiments, methods of treating kinase-mediated disorder in a subject are provided which comprise administering an effective amount of a compound described herein (e.g., a compound of formula I, II, or III), or a pharmaceutically acceptable salt thereof, to a subject in need of treatment. In certain embodiments, the effective amount is a therapeutically effective amount. In certain embodiments, the effective amount is a prophylactically effective amount. In certain embodiments, the subject is suffering from a kinase-mediated disorder. In certain embodiments, the subject is susceptible to a kinase-mediated disorder. In certain embodiments, the kinase-mediated disorder is a GSK3-mediated disorder (e.g., a GSK3α-mediated disorder, GSK3β-mediated disorder). In certain embodiments, the kinase-mediated disorder is a CK1-mediated disorder (e.g., a CK1δ-mediated disorder).

The term "kinase-mediated disorder" (e.g., GSK3-mediated disorder, CK1-mediated disorder) means any disease, disorder, or other deleterious condition in which one or more kinases (e.g., GSK3 or CK1), or a mutant thereof, are known to play a role. Accordingly, in some embodiments, the present disclosure relates to treating or lessening the severity of one or more diseases in which one or more kinases (e.g., GSK3 or CK1) are known to play a role.

In some embodiments, the present disclosure further provides a method of inhibiting a kinase comprising contacting a kinase with an effective amount of a compound described herein (e.g., a compound of formula I, II, or III), or a pharmaceutically acceptable salt thereof. In some embodiments, the present disclosure provides a method of inhibiting GSK3 comprising contacting GSK3 with an effective amount of a compound described herein (e.g., a compound of formula I, II, or III), or a pharmaceutically acceptable salt thereof. In some embodiments, the present disclosure provides a method of inhibiting CK1 comprising contacting CK1 with an effective amount of a compound described herein (e.g., a compound of formula I, II, or III), or a pharmaceutically acceptable salt thereof. The kinase may be purified or crude, and may be present in a cell, tissue, or subject. Thus, such methods encompass both inhibition of in vitro and in vivo kinase activity. In certain embodiments, the method is an in vitro method, e.g., such as an assay method useful as a research tool.

In some embodiments, provided is a method of inhibiting kinase activity in a subject in need thereof (e.g., having a higher kinase activity than normal) comprising administering to the subject an effective amount of a compound described herein (e.g., a compound of formula I, II, or III), or a pharmaceutically acceptable salt thereof. In some embodiments, provided is a method of inhibiting GSK3 activity in a subject in need thereof comprising administering to the subject an effective amount of a compound described herein (e.g., a compound of formula I, II, or III), or a pharmaceutically acceptable salt thereof. In some embodiments, provided is a method of inhibiting CK1 activity in a subject in need thereof comprising administering to the subject an effective amount of a compound described herein (e.g., a compound of formula I, II, or III), or a pharmaceutically acceptable salt thereof.

In some embodiments, the motivation for administering a compound according to some embodiments is an intention to treat a neurological disease or psychiatric disorder in a subject. In certain embodiments, a provided compound is useful in treating a neurological disease (e.g., a neurological disease described herein). The neurological disease that is treated by a provided compound may be GSK3α- and/or GSK3β-mediated. In certain embodiments, a provided compound is useful in treating a psychiatric disorder (e.g., a psychiatric disorder described herein). The psychiatric disorder that is treated by a provided compound may be GSK3α- and/or GSK3β-mediated.

The term "neurological disease" refers to a condition having as a component a central or peripheral nervous system malfunction. A neurological disease may cause a disturbance in the structure or function of the nervous system resulting from developmental and functional abnormalities, disease, genetic defects, injury or toxin. These disorders may affect the central nervous system (e.g., the brain, brainstem and cerebellum), the peripheral nervous system (e.g., the cranial nerves, spinal nerves, and sympathetic and parasympathetic nervous systems) and/or the autonomic nervous system (e.g., the part of the nervous system that regulates involuntary action and that is divided into the sympathetic and parasympathetic nervous systems). Accordingly, a neurodegenerative disease is an example for a neurological disease.

The term "neurodegenerative disease" refers to a condition characterized by loss of neuronal cells or neuronal cell supporting cells causing cognitive and/or motoric dysfunction and/or disabilities. Accordingly, the term refers to any disease or disorder that might be reversed, deterred, managed, treated, improved, or eliminated with agents that stimulate the generation of new neurons. Examples of neurodegenerative diseases include: (i) chronic neurodegenerative diseases such as familial and sporadic amyotrophic lateral sclerosis (FALS and ALS, respectively), familial and sporadic Parkinson's disease, Huntington's disease, familial and sporadic Alzheimer's disease, Fragile X syndrome, multiple sclerosis, olivopontocerebellar atrophy, multiple system atrophy, progressive supranuclear palsy, diffuse Lewy body disease, corticodentatonigral degeneration, progressive familial myoclonic epilepsy, strionigral degeneration, torsion dystonia, familial tremor, Down's syndrome, Gilles de la Tourette syndrome, Hallervorden-Spatz disease, dementia pugilistica, AIDS dementia, age related dementia, age associated memory impairment, and amyloidosis-related neurodegenerative diseases such as those caused by the prion protein (PrP) which is associated with transmissible spongiform encephalopathy (Creutzfeldt-Jakob disease, Gerstmann-Straussler-Scheinker syndrome, scrapie, and kuru), and those caused by excess cystatin C accumulation (hereditary cystatin C angiopathy); and (ii) acute neurodegenerative disorders such as traumatic brain injury (e.g., surgery-related brain injury), cerebral edema, peripheral nerve damage, spinal cord injury, Leigh's disease, Guillain-Barre syndrome, lysosomal storage disorders such as lipofuscinosis, Alper's disease, vertigo as result of CNS degeneration; pathologies arising with chronic alcohol or drug abuse including, for example, the degeneration of neurons in locus coeruleus and cerebellum; pathologies arising with aging including degeneration of cerebellar neurons and cortical neurons leading to cognitive and motor impairments; and pathologies arising with chronic amphetamine abuse including degeneration of basal ganglia neurons leading to motor impairments; pathological changes resulting from focal trauma such as stroke, focal ischemia, vascular insufficiency, hypoxic-ischemic encephalopathy, hyperglycemia, hypoglycemia or direct trauma; pathologies arising as a negative side-effect of therapeutic drugs and treatments (e.g., degeneration of cingulate and entorhinal cortex neurons in response to anticonvulsant doses of antagonists of the NMDA class of glutamate receptor) and Wernicke-Korsakoff s related dementia. Neurodegenerative diseases affecting sensory neurons include Friedreich's ataxia and retinal neuronal degeneration. Other neurodegenerative diseases include nerve injury or trauma associated with spinal cord injury. Neurodegenerative diseases of limbic and cortical systems include cerebral amyloidosis, Pick's atrophy, and Rett syndrome. The foregoing examples are not meant to be comprehensive but serve merely as an illustration of the term "neurodegenerative disorder".

Alzheimer's disease is a degenerative brain disorder characterized by cognitive and noncognitive psychiatric symptoms. Psychiatric symptoms are common in Alzheimer's disease, with psychosis (hallucinations and delusions) present in approximately fifty percent of affected patients. Similar to schizophrenia, positive psychotic symptoms are common in Alzheimer's disease. Delusions typically occur more frequently than hallucinations. Alzheimer's patients may also exhibit negative symptoms, such as disengagement, apathy, diminished emotional responsiveness, loss of volition, and decreased initiative. Indeed, antipsychotic compounds that are used to relieve psychosis of schizophrenia are also useful in alleviating psychosis in Alzheimer's patients. The term "dementia" refers to the loss of cognitive and intellectual functions without impairment of perception or consciousness. Dementia is typically characterized by disorientation, impaired memory, judgment, and intellect, and a shallow labile affect.

Fragile X Syndrome, or Martin-Bell Syndrome, is a genetic syndrome, which results in a spectrum of characteristic physical, intellectual, emotional and behavioral features which range from severe to mild in manifestation. The syndrome is associated with the expansion of a single trinucleotide gene sequence (CGG) on the X chromosome, and results in a failure to express the FMRP protein that is required for normal neural development. There are four generally accepted forms of Fragile X Syndrome which relate to the length of the repeated CGG sequence in the FMR1 gene; Normal (29-31 CGG repeats), Premutation (55-200 CGG repeats), Full Mutation (more than 200 CGG repeats), and Intermediate or Gray Zone Alleles (40-60 repeats). Normally, the FMR1 gene contains between 6 and 55 repeats of the CGG codon (trinucleotide repeats). In people with the Fragile X Syndrome, the FMR1 allele has over 230 repeats of this codon. Expansion of the CGG repeating codon to such a degree results in a methylation of that portion of the DNA, effectively silencing the expression of the FMR1 protein. This methylation of the FMR1 locus in chromosome band Xq27.3 is believed to result in constriction of the X chromosome which appears 'fragile' under the microscope at that point, a phenomenon that gave the syndrome its name. Mutation of the FMR1 gene leads to the transcriptional silencing of the fragile X-mental retardation protein, FMRP. In normal individuals, FMRP is believed to regulate a substantial population of mRNA: FMRP plays important roles in learning and memory, and also appears to be involved in development of axons, formation of synapses, and the wiring and development of neural circuits.

Amyotrophic lateral sclerosis (ALS), also called Lou Gehrig's disease, is a progressive, fatal neurological disease. ALS occurs when specific nerve cells in the brain and spinal cord that control voluntary movement gradually degenerate and causes the muscles under their control to weaken and waste away, leading to paralysis. Currently, there is no cure for ALS; nor is there a proven therapy that will prevent or reverse the course of the disorder.

Parkinson's disease is a disturbance of voluntary movement in which muscles become stiff and sluggish. Symptoms of the disease include difficult and uncontrollable rhythmic twitching of groups of muscles that produces shaking or tremors. The disease is caused by degeneration of pre-synaptic dopaminergic neurons in the brain and specifically in the brain stem. As a result of the degeneration, an inadequate release of the chemical transmitter dopamine occurs during neuronal activity. Currently, Parkinson's disease is treated with several different compounds and combinations. Levodopa (L-dopa), which is converted into dopamine in the brain, is often given to restore muscle control. Perindopril, an ACE inhibitor that crosses the blood-brain barrier, is used to improve patients motor responses to L-dopa. Carbidopa is administered with L-dopa in order to delay the conversion of L-dopa to dopamine until it reaches the brain, and it also lessens the side effects of L-dopa. Other drugs used in Parkinson's disease treatment include dopamine mimickers Mirapex (pramipexole dihydrochloride) and Requip (ropinirole hydrochloride), and Tasmar (tolcapone), a COMT inhibitor that blocks a key enzyme responsible for breaking down levodopa before it reaches the brain.

The term "psychiatric disorder" refers to a condition or disorder relating to the functioning of the brain and the cognitive processes or behavior. Psychiatric disorders may be further classified based on the type of neurological disturbance affecting the mental faculties. Psychiatric disorders are expressed primarily in abnormalities of thought, feeling, emotion, and/or behavior producing either distress or impairment of function (for example, impairment of mental function such with dementia or senility). The term "psychiatric disorder" is, accordingly, sometimes used interchangeably with the term "mental disorder" or the term "mental illness".

A psychiatric disorder is often characterized by a psychological or behavioral pattern that occurs in an individual and is thought to cause distress or disability that is not expected as part of normal development or culture. Definitions, assessments, and classifications of mental disorders can vary, but guideline criteria listed in the International Classification of Diseases and Related Health Problems (ICD, published by the World Health Organization, WHO), or the Diagnostic and Statistical Manual of Mental Disorders (DSM, published by the American Psychiatric Association, APA) and other manuals are widely accepted by mental health professionals. Individuals may be evaluated for various psychiatric disorders using criteria set forth in these and other publications accepted by medical practitioners in the field and the manifestation and severity of a psychiatric disorder may be determined in an individual using these publications.

Categories of diagnoses in these schemes may include dissociative disorders, mood disorders, anxiety disorders, psychotic disorders, eating disorders, developmental disorders, personality disorders, and other categories. There are different categories of mental disorder, and many different facets of human behavior and personality that can become disordered.

One group of psychiatric disorders includes disorders of thinking and cognition, such as schizophrenia and delirium. A second group of psychiatric disorders includes disorders of mood, such as affective disorders and anxiety. A third group of psychiatric disorders includes disorders of social behavior, such as character defects and personality disorders. And a fourth group of psychiatric disorders includes disorders of learning, memory, and intelligence, such as mental retardation and dementia. Accordingly, psychiatric disorders encompass schizophrenia, delirium, attention deficit disorder (ADD), schizoaffective disorder, depression (e.g., lithium-resistant depression), mania, attention deficit disorders, drug addiction, dementia, agitation, apathy, anxiety, psychoses, personality disorders, bipolar disorders, unipolar affective disorder, obsessive-compulsive disorders, eating disorders, post-traumatic stress disorders, irritability, adolescent conduct disorder and disinhibition.

Some diseases classified as neurodegenerative diseases, for example Alzheimer's disease, also sometimes show aspects of psychiatric disorders as listed herein, for example disorders of memory or dementia. Some neurodegenerative diseases or manifestations thereof can, accordingly, also be referred to as psychiatric disorders. These terms are, therefore, not mutually exclusive.

The state of anxiety or fear can become disordered, so that it is unusually intense or generalized over a prolonged period of time. Commonly recognized categories of anxiety disorders include specific phobia, generalized anxiety disorder, social anxiety disorder, panic disorder, agoraphobia, obsessive-compulsive disorder, post-traumatic stress disorder.

Relatively long lasting affective states can also become disordered. Mood disorder involving unusually intense and sustained sadness, melancholia or despair is known as clinical depression (or major depression), and may more generally be described as emotional dysregulation. Milder but prolonged depression can be diagnosed as dysthymia. Bipolar disorder involves abnormally "high" or pressured mood states, known as mania or hypomania, alternating with normal or depressed mood.

Patterns of belief, language use and perception can become disordered. Psychotic disorders centrally involving this domain include schizophrenia and delusional disorder. schizoaffective disorder is a category used for individuals showing aspects of both schizophrenia and affective disorders. Schizotypy is a category used for individuals showing some of the traits associated with schizophrenia but without meeting cut-off criteria.

The fundamental characteristics of a person that influence his or her cognitions, motivations, and behaviors across situations and time—can be seen as disordered due to being abnormally rigid and maladaptive. Categorical schemes list a number of different personality disorders, such as those classed as eccentric (e.g., paranoid personality disorder, schizoid personality disorder, schizotypal personality disorder), those described as dramatic or emotional (antisocial personality disorder, Borderline personality disorder, histrionic personality disorder, narcissistic personality disorder) or those seen as fear-related (avoidant personality disorder, dependent personality disorder, obsessive-compulsive personality disorder).

Other disorders may involve other attributes of human functioning. Eating practices can be disordered, with either compulsive over-eating or under-eating or binging. Categories of disorder in this area include anorexia nervosa, bulimia nervosa, exercise bulimia or binge eating disorder. Sleep disorders such as Insomnia also exist and can disrupt normal sleep patterns. Sexual and gender identity disorders, such as dyspareunia or gender identity disorder or ego-dystonic homosexuality. People who are abnormally unable to resist urges, or impulses, to perform acts that could be harmful to themselves or others, may be classed as having an impulse control disorder, including various kinds of Tic disorders such as Tourette's Syndrome, and disorders such as kleptomania (stealing) or Pyromania (fire-setting). Substance-use disorders include substance abuse disorder. Addictive gambling may be classed as a disorder. Inability to sufficiently adjust to life circumstances may be classed as an adjustment disorder. The category of adjustment disorder is usually reserved for problems beginning within three months of the event or situation and ending within six months after the stressor stops or is eliminated. People who suffer severe disturbances of their self-identity, memory and general awareness of themselves and their surroundings may be classed as having a dissociative identity disorder, such as depersonalization disorder (which has also been called multiple personality disorder, or "split personality"). Factitious disorders, such as Munchausen syndrome, also exist where symptoms are experienced and/or reported for personal gain.

Disorders appearing to originate in the body, but thought to be mental, are known as somatoform disorders, including somatization disorder. There are also disorders of the perception of the body, including body dysmorphic disorder. Neurasthenia is a category involving somatic complaints as well as fatigue and low spirits/depression, which is officially recognized by the ICD (version 10) but not by the DSM (version IV). Memory or cognitive disorders, such as amnesia or Alzheimer's disease are also sometimes classified as psychiatric disorders.

Other proposed disorders include: self-defeating personality disorder, sadistic personality disorder, passive-aggressive personality disorder, premenstrual dysphoric disorder, video game addiction or internet addiction disorder.

Bipolar disorder is a psychiatric diagnosis that describes a category of mood disorders defined by the presence of one or more episodes of abnormally elevated mood clinically referred to as mania or, if milder, hypomania. Individuals who experience manic episodes also commonly experience depressive episodes or symptoms, or mixed episodes in which features of both mania and Depression are present at the same time. These episodes are usually separated by periods of "normal" mood, but in some individuals, Depression and mania may rapidly alternate, known as rapid cycling. Extreme manic episodes can sometimes lead to psychotic symptoms such as delusions and hallucinations. The disorder has been subdivided into bipolar I, bipolar II, cyclothymia, and other types, based on the nature and severity of mood episodes experienced; the range is often described as the bipolar spectrum.

Autism (also referred to as autism spectrum disorder, or ASD) is a disorder that seriously impairs the functioning of individuals. It is characterized by self-absorption, a reduced ability to communicate with or respond to the outside world, rituals and compulsive phenomena, and mental retardation. Autistic individuals are also at increased risk of developing seizure disorders, such as epilepsy. While the actual cause of Autism is unknown, it appears to include one or more genetic factors, as indicated by the fact that the concordance rate is higher in monozygotic twins than in dizygotic twins, and may also involve immune and environmental factors, such as diet, toxic chemicals and infections.

Schizophrenia is a disorder that affects about one percent of the world population. Three general symptoms of schizophrenia are often referred to as positive symptoms, negative symptoms, and disorganized symptoms. Positive symptoms can include delusions (abnormal beliefs), hallucinations (abnormal perceptions), and disorganized thinking. The hallucinations of schizophrenia can be auditory, visual, olfactory, or tactile. Disorganized thinking can manifest itself in schizophrenic patients by disjointed speech and the inability to maintain logical thought processes. Negative symptoms can represent the absence of normal behavior. Negative symptoms include emotional flatness or lack of expression and can be characterized by social withdrawal, reduced energy, reduced motivation, and reduced activity. Catatonia can also be associated with negative symptoms of schizophrenia. The symptoms of schizophrenia should continuously persist for a duration of about six months in order for the patient to be diagnosed as schizophrenic. Based on the types of symptoms a patient reveals, schizophrenia can be categorized into subtypes including catatonic schizophrenia, paranoid schizophrenia, and disorganized schizophrenia.

Examples of antipsychotic drugs that may be used to treat schizophrenic patients include phenothizines, such as chlorpromazine and trifluopromazine; thioxanthenes, such as chlorprothixene; fluphenazine; butyropenones, such as haloperidol; loxapine; mesoridazine; molindone; quetiapine; thiothixene; trifluoperazine; perphenazine; thioridazine; risperidone; dibenzodiazepines, such as clozapine; and olanzapine. Although these compounds may relieve the symptoms of schizophrenia, their administration can result in undesirable side effects including Parkinson's disease-like symptoms (tremor, muscle rigidity, loss of facial expression); dystonia; restlessness; tardive dyskinesia; weight gain; skin problems; dry mouth; constipation; blurred vision; drowsiness; slurred speech and agranulocytosis.

Mood disorders are typically characterized by pervasive, prolonged, and disabling exaggerations of mood and affect that are associated with behavioral, physiologic, cognitive, neurochemical and psychomotor dysfunctions. The major mood disorders include, but are not limited to major depressive disorder (also known as unipolar disorder), Bipolar Disorder (also known as manic depressive illness or bipolar Depression), dysthymic disorder.

The term "depression", sometimes used interchangeably with "depressive disorder" and refers to mood disorders manifesting in morbid sadness, dejection, or melancholy. Depressive disorders can involve serotonergic and noradrenergic neuronal systems based on current therapeutic regimes that target serotonin and noradrenalin receptors. Mania may result from an imbalance in certain chemical messengers within the brain. Administering phosphotidyl choline has been reported to alleviate the symptoms of mania. In certain embodiments, the depression described herein is lithium-resistant depression.

Mania is a sustained form of euphoria that affects millions of people in the United States who suffer from Depression. Manic episodes can be characterized by an elevated, expansive, or irritable mood lasting several days, and is often accompanied by other symptoms, such as, over-activity, over-talkativeness, social intrusiveness, increased energy, pressure of ideas, grandiosity, distractibility, decreased need for sleep, and recklessness. Manic patients can also experience delusions and hallucinations.

Anxiety disorders are characterized by frequent occurrence of symptoms of fear including arousal, restlessness, heightened responsiveness, sweating, racing heart, increased blood pressure, dry mouth, a desire to run or escape, and avoidance behavior. Generalized anxiety persists for several months, and is associated with motor tension (trembling, twitching, muscle aches, restlessness); autonomic hyperactivity (shortness of breath, palpitations, increased heart rate, sweating, cold hands), and vigilance and scanning (feeling on edge, exaggerated startle response, difficult in concentrating). Benzodiazepines, which enhance the inhibitory effects of the gamma aminobutyric acid (GABA) type A receptor, are frequently used to treat anxiety. Buspirone is another effective anxiety treatment.

Schizo-affective disorder describes a condition where both the symptoms of a mood disorder and schizophrenia are present. A person may manifest impairments in the perception or expression of reality, most commonly in the form of auditory hallucinations, paranoid or bizarre delusions or disorganized speech and thinking, as well as discrete manic and/or depressive episodes in the context of significant social or occupational dysfunction.

In some embodiments, a provided compound is useful in treating attention deficit hyperactivity disorder (ADHD). In some embodiments, treatment of ADHD is effected by inhibiting CK1δ (see, e.g., Zhou, et al. Proc. Natl. Acad. Sci. USA 2010, 107:4401).

In certain embodiments, a provided compound stimulates neurogenesis. Accordingly, in some embodiments, a provided compound is useful in treating diseases that are related to neurogenesis. For example, a provided compound is useful for treating a neurological disorder in a subject comprising administering to the subject an effective amount of a provided compound or pharmaceutically acceptable salt thereof. In some embodiments, the neurological disorder is cognitive decline associated with normal aging, traumatic brain injury, Parkinson's disease, major depression, bipolar disorder, epilepsy, spinocerebellar ataxia, Huntington's disease, ALS, stroke, radiation therapy, post-traumatic stress disorder, Down syndrome, chronic stress, retinal degeneration, spinal cord injury, peripheral nerve injury, physiological weight loss associated with various conditions, abuse of a neuroactive drug, spinal cord injury, or cognitive decline associated with chemotherapy.

In some embodiments, a provided compound is useful in regulating circadian rhythms in a subject in need thereof. In some embodiments, regulation of abnormal circadian rhythms is effected by inhibition of CK1δ.

In some embodiments, a provided compound is useful in treating alopecia.

In some embodiments, a provided compound is useful as an immunopotentiator.

In some embodiments, a provided compound is useful in treating cancer. The cancer that is treated by a provided compound may be GSK3α- and/or GSK3β-mediated. In some embodiments, a provided compound is useful in treating a cancer described herein. For example, in some embodiments, a provided compound is useful in treating leukemia. In certain embodiments, a provided compound is useful in treating acute myeloid leukemia (AML). In certain embodiments, a provided compound is useful in treating acute lymphocytic leukemia (ALL), chronic myelocytic leukemia (CML), and/or chronic lymphocytic leukemia (CLL). In some embodiments, treatment of leukemia (e.g., acute myeloid leukemia) is effected by inhibition of GSK3α. In some embodiments, a provided compound is useful in treating multiple myeloma. In some embodiments, a provided compound is useful in treating glioma or pancreatic cancer. In some embodiments, a provided compound is useful in treating breast cancer, non-small cell lung carcinoma, thyroid cancer, T-cell or B-cell leukemia, or a virus-induced tumor.

GSK3α and GSK3β are also implicated in metabolic disorders, such as diabetes (e.g., type II diabetes) (A. S. Wagman, K. W. Johnson and D. E. Bussiere, Curr. Pharm. Design, 2004, 10, 1105). GSK3 activity is elevated in human and rodent models of diabetes, and various GSK3 inhibitors improve glucose tolerance and insulin sensitivity in rodent models of obesity and diabetes. Unlike GSK3β mutants, which die before birth, GSK3α knockout (GSK3α KO) animals are viable but display enhanced glucose and insulin sensitivity accompanied by reduced fat mass (Katrina et al., *Cell Metabolism* 6, 329-337, October 2007). Fasted and glucose-stimulated hepatic glycogen content was enhanced in GSK3α KO mice, whereas muscle glycogen was unaltered. Insulin-stimulated protein kinase B (PKB/Akt) and GSK3β phosphorylation was higher in GSK3α KO livers compared to wild-type littermates, and IRS-1 expression was markedly increased. It was concluded that GSK3 isoforms exhibit tissue-specific physiological functions and that GSK3α KO mice are insulin sensitive, reinforcing the potential of GSK3 as a therapeutic target for type II diabetes.

In some embodiments, a provided compound is useful in treating a metabolic disorder. In some embodiments, a provided compound is useful in treating diabetes (e.g., type 1 diabetes, type 2 diabetes, or gestational diabetes). In some embodiments, a provided compound is useful in treating type 2 diabetes. In some embodiments, a provided compound is useful in treating obesity.

Exemplary embodiments of the present invention are as follows.

Embodiment 1

A compound of formula I:

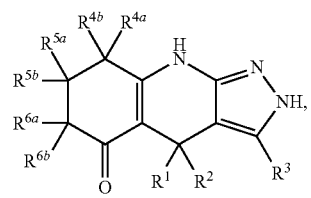

I or a pharmaceutically acceptable salt thereof, wherein:

$R^1$ and $R^2$ are independently selected from the group consisting of hydrogen, optionally substituted aliphatic, optionally substituted aryl, and optionally substituted heteroaryl, wherein $R^1$ and $R^2$ are not simultaneously hydrogen; or $R^1$ and $R^2$ are taken together with their intervening atoms to form an optionally substituted 3- to 7-membered saturated carbocyclic or heterocyclic ring, wherein the ring formed by $R^1$ and $R^2$ may be optionally fused to an aryl or heteroaryl ring;

$R^3$ is selected from the group consisting of hydrogen, halo, —CN, —NO$_2$, optionally substituted aliphatic, optionally substituted phenyl, optionally substituted heterocyclyl, optionally substituted heteroaryl, —OR$^A$, —N(R$^B$)$_2$, —SR$^A$, —C(=O)R$^A$, —C(=O)OR$^A$, —C(=O)SR$^A$, —C(=O)N(R$^B$)$_2$, —OC(=O)R$^A$, —NR$^B$C(=O)R$^A$, —NR$^B$C(=O)N(R$^B$)$_2$, —OC(=O)N(R$^B$)$_2$, —NR$^B$C(=O)OR$^A$, —SC(=O)R$^A$, —C(=NR$^B$)R$^A$, —C(=NR$^B$)N(R$^B$)$_2$, —NR$^B$C(=NR$^B$)R$^B$, —C(=S)R$^A$, —C(=S)N(R$^B$)$_2$, —NR$^B$C(=S)R$^A$, —S(=O)R$^A$, —SO$_2$R$^A$, —NR$^B$SO$_2$R$^A$, and —SO$_2$N(R$^B$)$_2$;

each $R^A$ is independently selected from the group consisting of hydrogen, optionally substituted aliphatic, optionally substituted carbocyclyl, optionally substituted heterocyclyl, optionally substituted aryl, and optionally substituted heteroaryl;

each $R^B$ is independently selected from the group consisting of hydrogen, optionally substituted aliphatic, optionally substituted carbocyclyl, optionally substituted heterocyclyl, optionally substituted aryl, and optionally substituted heteroaryl, or two $R^B$ groups are taken together with their intervening atoms to form an optionally substituted heterocyclic ring;

$R^{4a}$ and $R^{4b}$ are independently selected from the group consisting of hydrogen, halo, —CN, —OR$^A$, —N(R$^B$)$_2$, and optionally substituted aliphatic, or $R^{4a}$ and $R^{4b}$ are taken together with their intervening atoms to form an optionally substituted 3- to 7-membered saturated carbocyclic or heterocyclic ring;

$R^{5a}$ and $R^{5b}$ are independently selected from the group consisting of hydrogen, halo, —CN, —OR$^A$, —N(R$^B$)$_2$, optionally substituted aliphatic, optionally substituted aryl, and optionally substituted heteroaryl, or $R^{5a}$ and $R^{5b}$ are taken together with their intervening atoms to form an optionally substituted 3- to 7-membered saturated carbocyclic or heterocyclic ring; and $R^{6a}$ and $R^{6b}$ are independently selected from the group consisting of hydrogen, halo, —CN, —OR$^A$, —N(R$^B$)$_2$, and optionally substituted aliphatic, or $R^{6a}$ and $R^{6b}$ are taken together with their intervening atoms to form an optionally substituted 3- to 7-membered saturated carbocyclic or heterocyclic ring;

provided that when R¹ or R² is hydrogen, R³ is not hydrogen, —OH, or —CH₃.

Embodiment 2

The compound of embodiment 1, wherein the compound is of formula I-a:

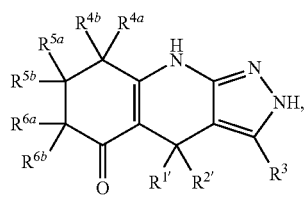

I-a or a pharmaceutically acceptable salt thereof,
wherein:

R¹' and R²' are independently selected from the group consisting of optionally substituted aliphatic, optionally substituted aryl, and optionally substituted heteroaryl; or R¹' and R²' are taken together with their intervening atoms to form an optionally substituted 3- to 7-membered carbocyclic or heterocyclic ring, wherein the ring formed by R¹' and R²' may be optionally fused to an aryl or heteroaryl ring.

Embodiment 3

The compound of embodiment 1, wherein the compound is of formula I-b:

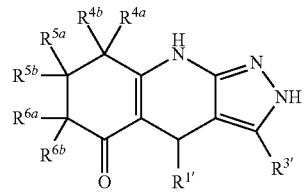

I-b or a pharmaceutically acceptable salt thereof,
wherein:

R¹' is selected from the group consisting of optionally substituted aliphatic, optionally substituted aryl, and optionally substituted heteroaryl;

R³' is selected from the group consisting of halo, —CN, —NO₂, substituted C₁ alkyl, optionally substituted C₂₋₆ alkyl, optionally substituted alkoxy, optionally substituted alkenyl, optionally substituted alkynyl, optionally substituted carbocyclyl, optionally substituted phenyl, optionally substituted heterocyclyl, optionally substituted heteroaryl, —N(R$^B$)₂, —SR$^A$, —C(=O)R$^A$, —C(=O)OR$^A$, —C(=O)SR$^A$, —C(=O)N(R$^B$)₂, —OC(=O)R$^A$, —NR$^B$C(=O)R$^A$, —NR$^B$C(=O)N(R$^B$)₂, —OC(=O)N(R$^B$)₂, —NR$^B$C(=O)OR$^A$, —SC(=O)R$^A$, —C(=NR$^B$)R$^A$, —C(=NR$^B$)N(R$^B$)₂, —NR$^B$C(=NR$^B$)R$^B$, —C(=S)R$^A$, —C(=S)N(R$^B$)₂, —NR$^B$C(=S)R$^A$, —S(=O)R$^A$, —SO₂R$^A$, —NR$^B$SO₂R$^A$, and —SO₂N(R$^B$)₂.

Embodiment 4

The compound of embodiment 1, wherein the compound is of formula II:

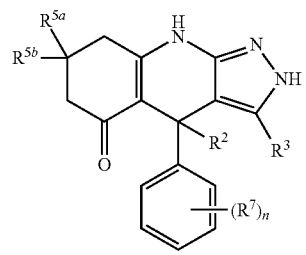

II or a pharmaceutically acceptable salt thereof,
wherein:

each R⁷ is independently selected from the group consisting of hydrogen, halo, —CN, —NO₂, optionally substituted aliphatic, optionally substituted phenyl, optionally substituted heterocyclyl, optionally substituted heteroaryl, —OR$^A$, —N(R$^B$)₂, —SR$^A$, —C(=O)R$^A$, —C(=O)OR$^A$, —C(=O)SR$^A$, —C(=O)N(R$^B$)₂, —OC(=O)R$^A$, —NR$^B$C(=O)R$^A$, —NR$^B$C(=O)N(R$^B$)₂, —OC(=O)N(R$^B$)₂, —NR$^B$C(=O)OR$^A$, —SC(=O)R$^A$, —C(=NR$^B$)R$^A$, —C(=NR$^B$)N(R$^B$)₂, —NR$^B$C(=NR$^B$)R$^B$, —C(=S)R$^A$, —C(=S)N(R$^B$)₂, —NR$^B$C(=S)R$^A$, —S(=O)R$^A$, —SO₂R$^A$, —NR$^B$SO₂R$^A$, and —SO₂N(R$^B$)₂; or two adjacent R⁷ groups are taken together with their intervening atoms to form an optionally substituted carbocyclic or heterocyclic fused ring; or R² and R⁷ are taken together with their intervening atoms to form an optionally substituted carbocyclic or heterocyclic fused ring; and n is 0, 1, 2, 3, 4, or 5.

Embodiment 5

The compound of embodiment 4, wherein the compound is of formula II-a:

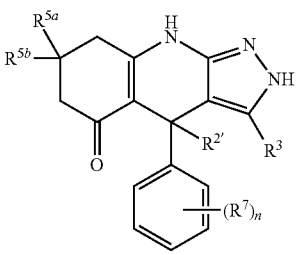

II-a or a pharmaceutically acceptable salt thereof,
wherein:

R²' is selected from the group consisting of optionally substituted aliphatic, optionally substituted aryl, and optionally substituted heteroaryl; or R²' and R⁷ are taken together with their intervening atoms to form an optionally substituted carbocyclic or heterocyclic fused ring.

Embodiment 6

The compound of embodiment 5, wherein the compound is of formula II-a-i or II-a-ii:

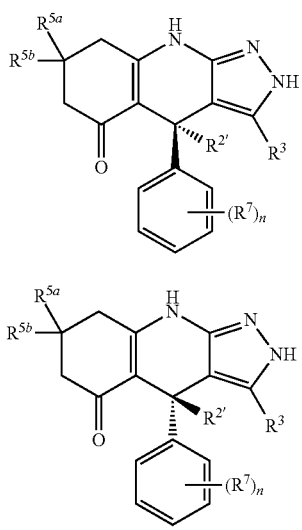

or a pharmaceutically acceptable salt thereof.

Embodiment 7

The compound of embodiment 4, wherein the compound is of formula II-b:

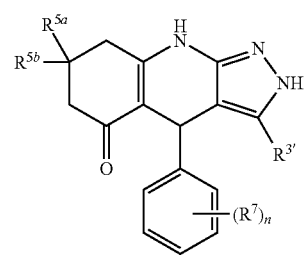

or a pharmaceutically acceptable salt thereof,
wherein:

$R^{3'}$ is selected from the group consisting of halo, —CN, —NO$_2$, substituted C$_1$ alkyl, optionally substituted C$_{2-6}$ alkyl, optionally substituted alkoxy, optionally substituted alkenyl, optionally substituted alkynyl, optionally substituted carbocyclyl, optionally substituted phenyl, optionally substituted heterocyclyl, optionally substituted heteroaryl, —N(R$^B$)$_2$, —SR$^A$, —C(=O)R$^A$, —C(=O)OR$^A$, —C(=O)SR$^A$, —C(=O)N(R$^B$)$_2$, —OC(=O)R$^A$, —NR$^B$C(=O)R$^A$, —NR$^B$C(=O)N(R$^B$)$_2$, —OC(=O)N(R$^B$)$_2$, —NR$^B$C(=O)OR$^A$, —SC(=O)R$^A$, —C(=NR$^B$)R$^A$, —C(=NR$^B$)N(R$^B$)$_2$, —NR$^B$C(=NR$^B$)R$^B$, —C(=S)R$^A$, —C(=S)N(R$^B$)$_2$, —NR$^B$C(=S)R$^A$, —S(=O)R$^A$, —SO$_2$R$^A$, —NR$^B$SO$_2$R$^A$, and —SO$_2$N(R$^B$)$_2$.

Embodiment 8

The compound of embodiment 7, wherein the compound is of formula II-b-i or II-b-ii:

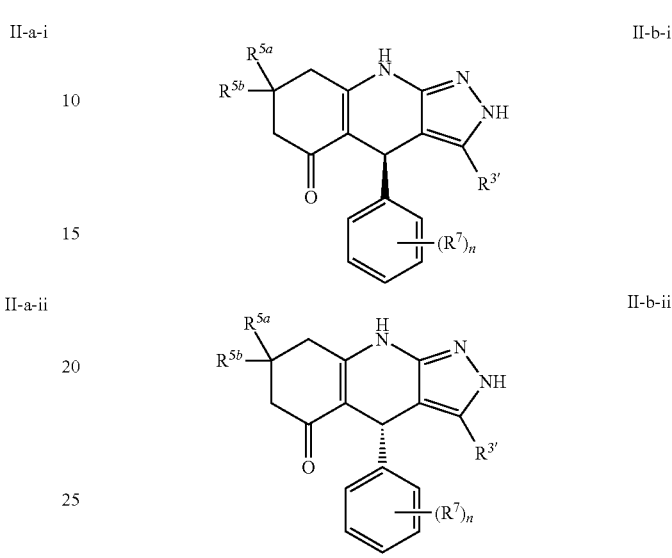

or a pharmaceutically acceptable salt thereof.

Embodiment 9

The compound of embodiment 1, wherein the compound is of formula III:

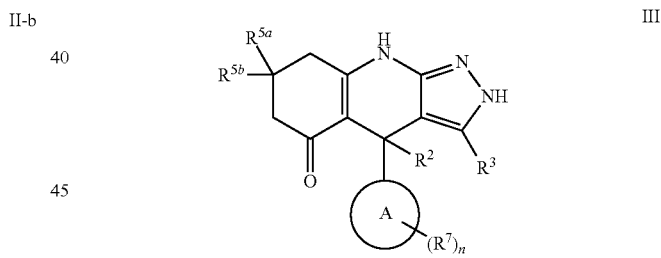

or a pharmaceutically acceptable salt thereof,
wherein:

Ring A is a 5- to 6-membered heteroaryl, 4- to 6-membered carbocyclyl, or 4- to 6-membered heterocyclyl;

each R$^7$ is independently selected from the group consisting of hydrogen, halo, —CN, —NO$_2$, optionally substituted aliphatic, optionally substituted phenyl, optionally substituted heterocyclyl, optionally substituted heteroaryl, —OR$^A$, —N(R$^B$)$_2$, —SR$^A$, —C(=O)R$^A$, —C(=O)OR$^A$, —C(=O)SR$^A$, —C(=O)N(R$^B$)$_2$, —OC(=O)R$^A$, —NR$^B$C(=O)R$^A$, —NR$^B$C(=O)N(R$^B$)$_2$, —OC(=O)N(R$^B$)$_2$, —NR$^B$C(=O)OR$^A$, —SC(=O)R$^A$, —C(=NR$^B$)R$^A$, —C(=NR$^B$)N(R$^B$)$_2$, —NR$^B$C(=NR$^B$)R$^B$, —C(=S)R$^A$, —C(=S)N(R$^B$)$_2$, —NR$^B$C(=S)R$^A$, —S(=O)R$^A$, —SO$_2$R$^A$, —NR$^B$SO$_2$R$^A$, and —SO$_2$N(R$^B$)$_2$; or two adjacent R$^7$ groups are taken together with their intervening atoms to form an optionally substituted carbocyclic or heterocyclic fused ring; or R$^2$ and R⁷ are taken together with their intervening atoms to form an optionally substituted carbocyclic or heterocyclic fused ring; and n is 0, 1, 2, 3, or 4, as valency allows.

Embodiment 10

The compound of embodiment 9, wherein the compound is of formula III-a:

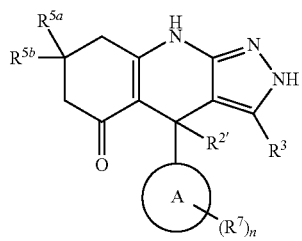

III-a or a pharmaceutically acceptable salt thereof, wherein:

R²' is selected from the group consisting of optionally substituted aliphatic, optionally substituted aryl, and optionally substituted heteroaryl; or R²' and R⁷ are taken together with their intervening atoms to form an optionally substituted carbocyclic or heterocyclic fused ring.

Embodiment 11

The compound of embodiment 10, wherein the compound is of formula III-a-i or III-a-ii:

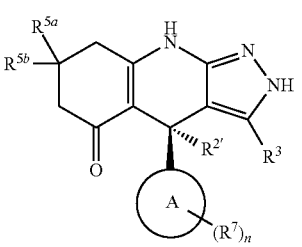

III-a-i

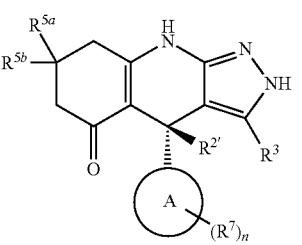

III-a-ii or a pharmaceutically acceptable salt thereof.

Embodiment 12

The compound of embodiment 9, wherein the compound is of formula III-b:

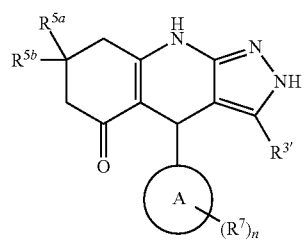

III-b or a pharmaceutically acceptable salt thereof, wherein:

R³' is selected from the group consisting of halo, —CN, —NO₂, substituted C₁ alkyl, optionally substituted C₂₋₆ alkyl, optionally substituted alkoxy, optionally substituted alkenyl, optionally substituted alkynyl, optionally substituted carbocyclyl, optionally substituted phenyl, optionally substituted heterocyclyl, optionally substituted heteroaryl, —N(Rᴮ)₂, —SRᴬ, —C(=O)Rᴬ, —C(=O)ORᴬ, —C(=O)SRᴬ, —C(=O)N(Rᴮ)₂, —OC(=O)Rᴬ, —NRᴮC(=O)Rᴬ, —NRᴮC(=O)N(Rᴮ)₂, —OC(=O)N(Rᴮ)₂, —NRᴮC(=O)ORᴬ, —SC(=O)Rᴬ, —C(=NRᴮ)Rᴬ, —C(=NRᴮ)N(Rᴮ)₂, —NRᴮC(=NRᴮ)Rᴮ, —C(=S)Rᴬ, —C(=S)N(Rᴮ)₂, —NRᴮC(=S)Rᴬ, —S(=O)Rᴬ, —SO₂Rᴬ, —NRᴮSO₂Rᴬ, and —SO₂N(Rᴮ)₂.

Embodiment 13

The compound of embodiment 12, wherein the compound is of formula III-b-i or III-b-ii:

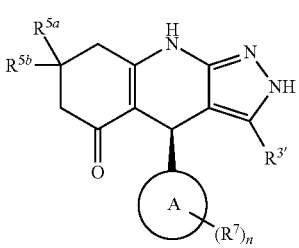

III-b-i

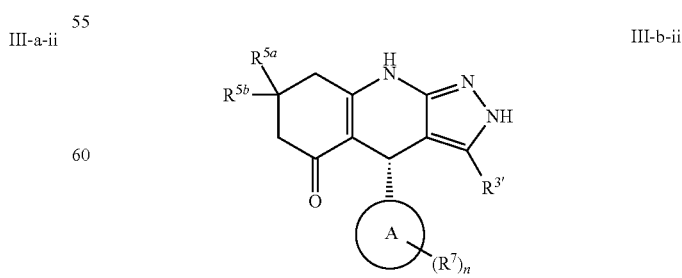

III-b-ii or a pharmaceutically acceptable salt thereof.

Embodiment 14

The compound of any one of embodiments 1, 2, 4-6, and 9-11, wherein R³ is hydrogen.

Embodiment 15

The compound of any one of embodiments 1-13, wherein R³ or R³' is fluoro.

Embodiment 16

The compound of any one of embodiments 1-13, wherein R³ or R³' is optionally substituted aliphatic.

Embodiment 17

The compound of embodiment 16, wherein R³ or R³' is methyl.

Embodiment 18

The compound of embodiment 16, wherein R³ or R³' is trifluoromethyl.

Embodiment 19

The compound of embodiment 16, wherein R³ or R³' is tert-butyl or isobutyl.

Embodiment 20

The compound of embodiment 16, wherein R³ or R³' is cyclopropyl.

Embodiment 21

The compound of embodiment 16, wherein R³ or R³' is difluorocyclobutyl.

Embodiment 22

The compound of any one of embodiments 1-2, 4-6, 9-11, and 14-21, wherein R² or R²' is optionally substituted aliphatic.

Embodiment 23

The compound of embodiment 22, wherein R² or R²' is methyl.

Embodiment 24

The compound of embodiment 22, wherein R² or R²' is ethyl or propyl.

Embodiment 25

The compound of any one of embodiments 1-6, 9-11, and 14-24, wherein at least one of R¹, R¹', R², and R²' is ethyl.

Embodiment 26

The compound of any one of embodiments 1-25, wherein R⁵ᵃ and R⁵ᵇ are methyl.

Embodiment 27

The compound of any one of embodiments 4-26, wherein n is 0.

Embodiment 28

The compound of any one of embodiments 4-26, wherein n is 1.

Embodiment 29

The compound of any one of embodiments 4-26, wherein n is 2.

Embodiment 30

The compound of embodiment 1, wherein the compound is one of the following:

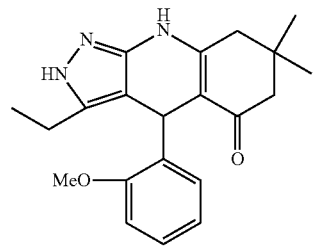

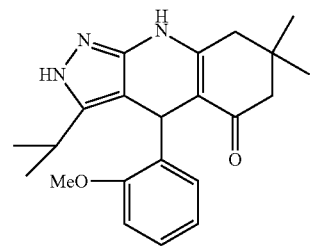

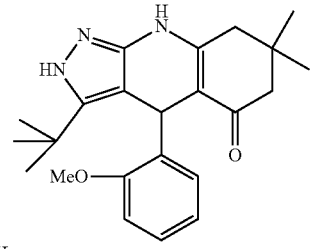

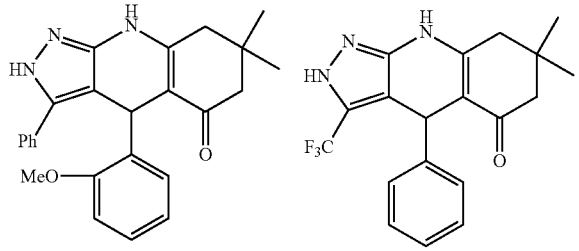

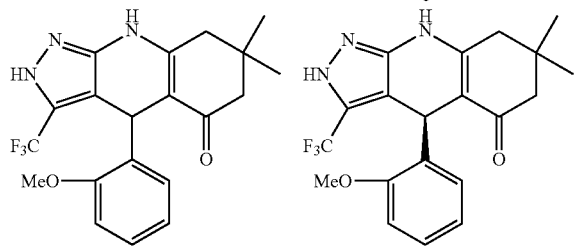

-continued
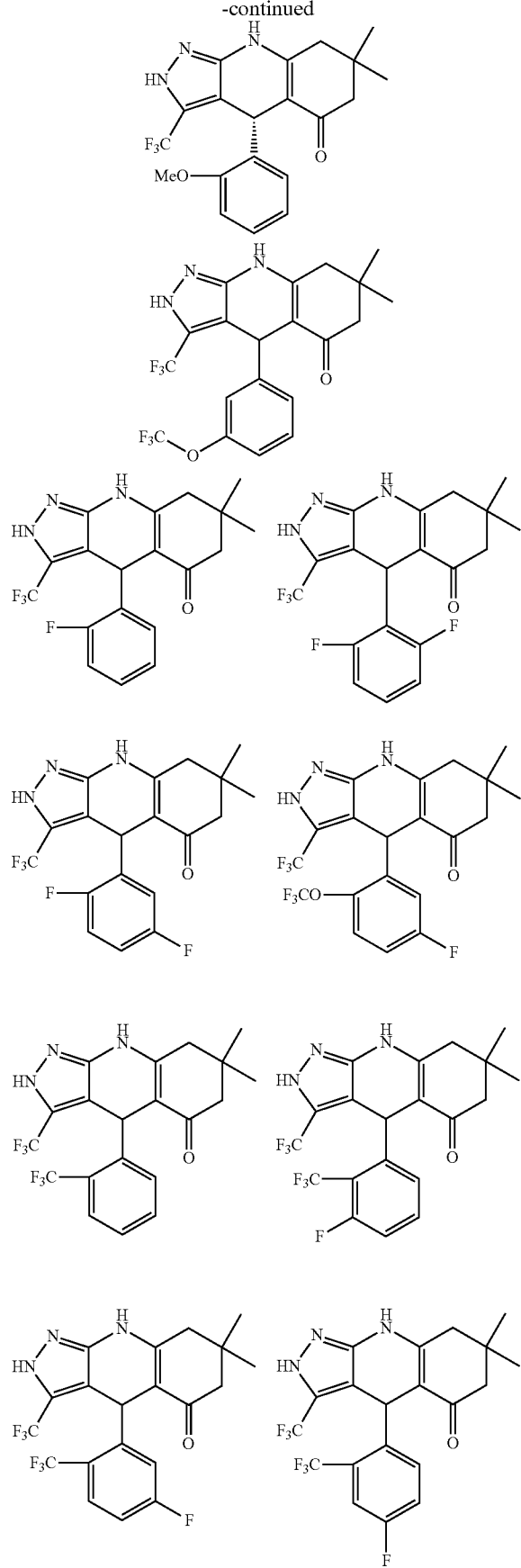
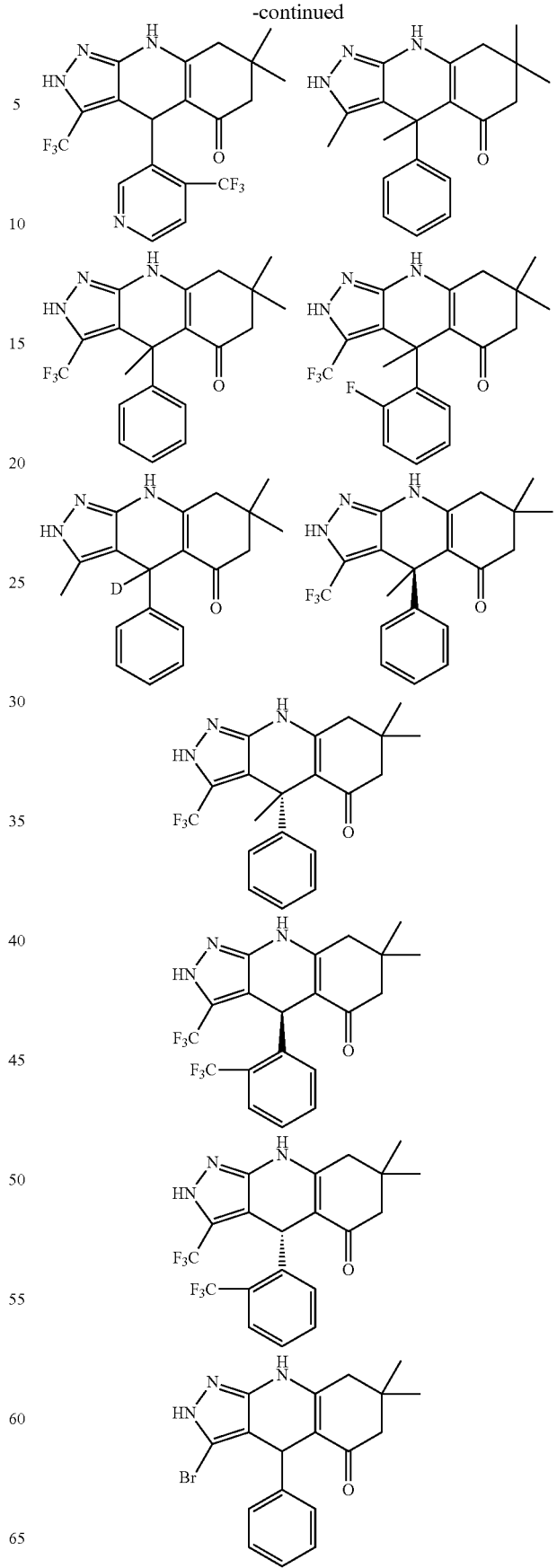

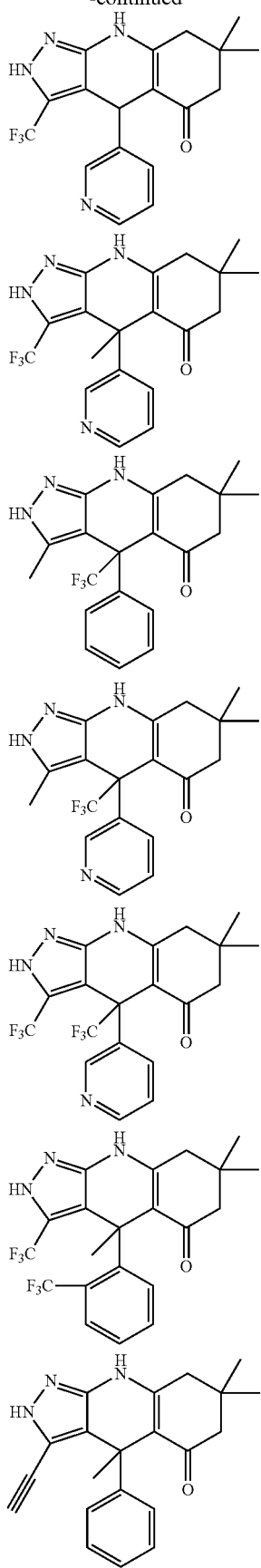
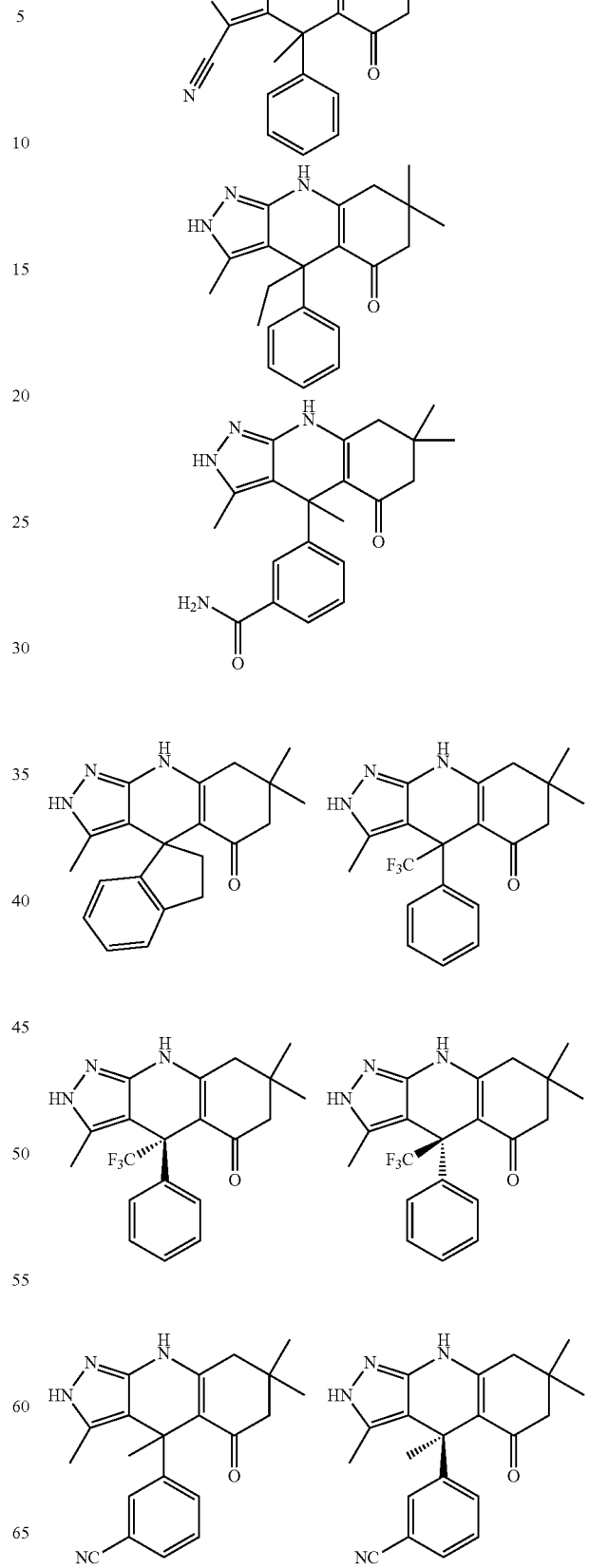

107
-continued
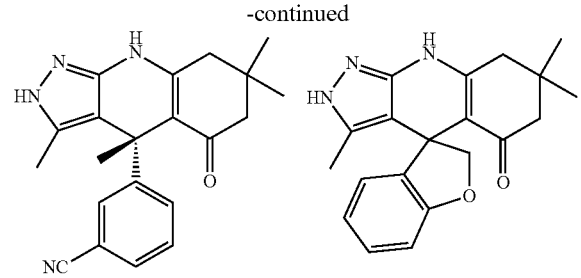
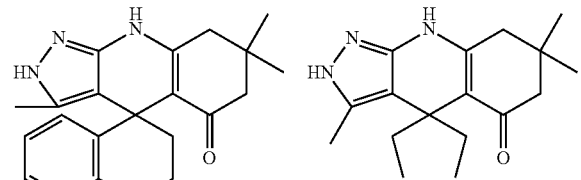
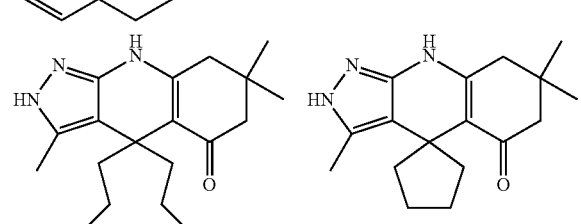
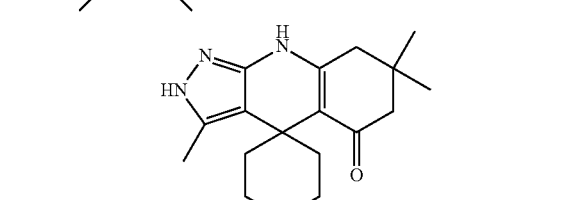
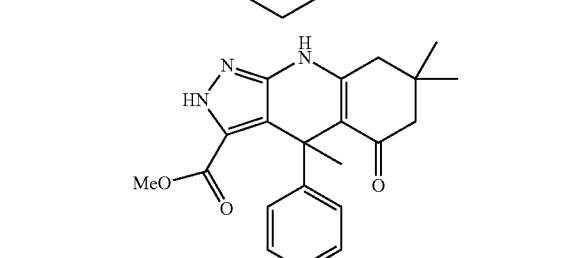
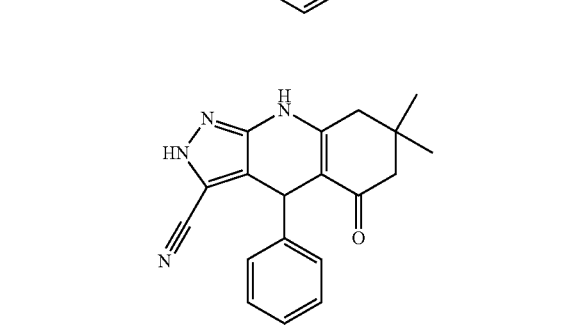
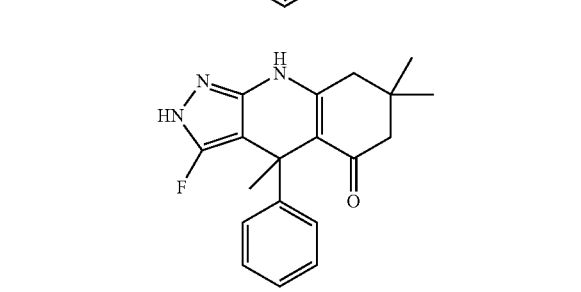
108
-continued
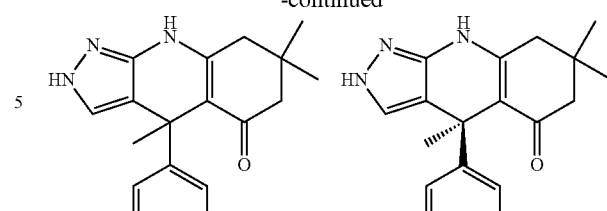
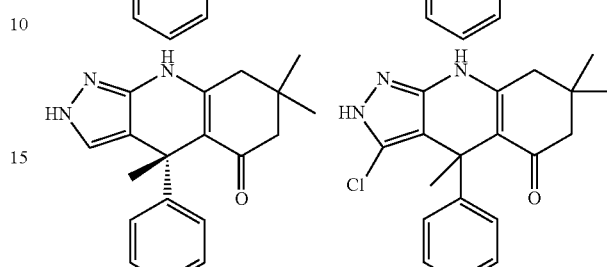
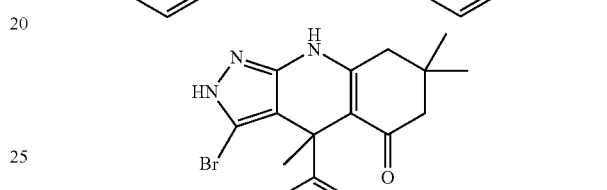
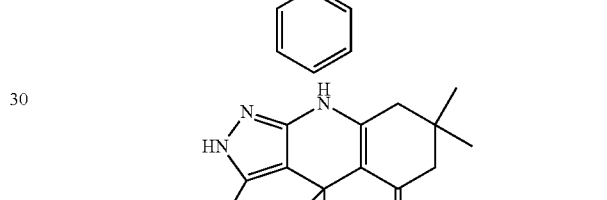
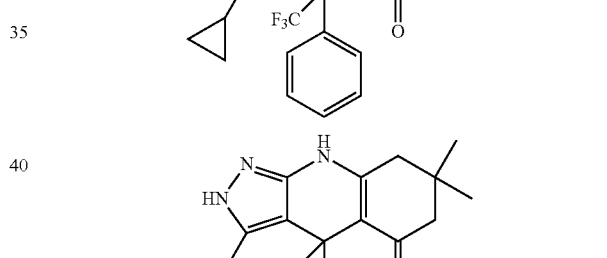
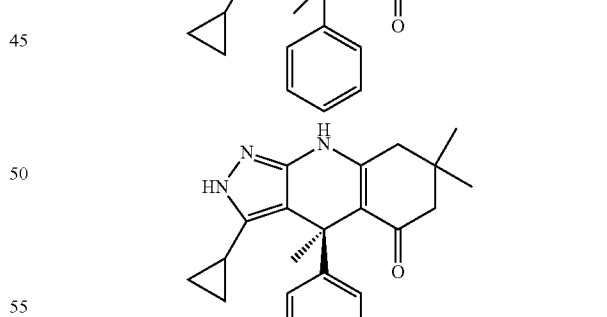
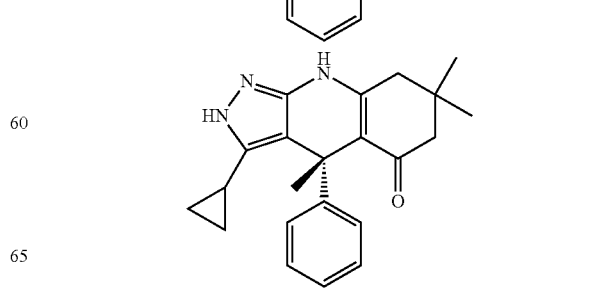

109
-continued
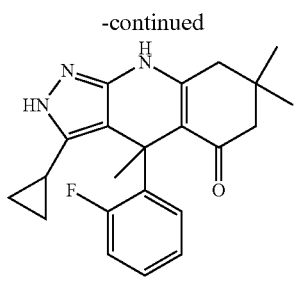
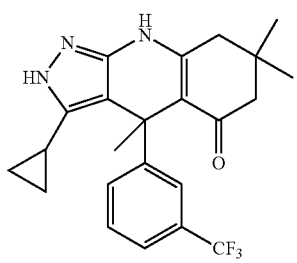
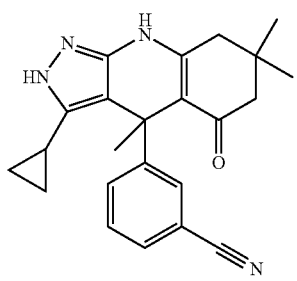
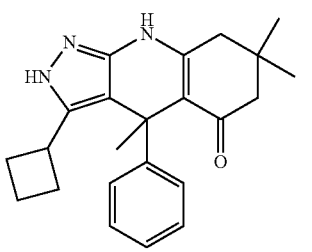
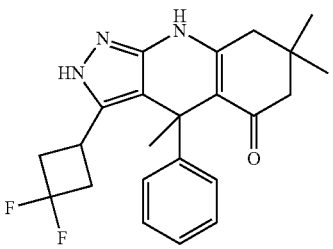
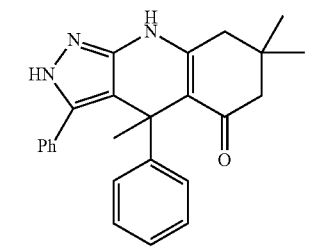
110
-continued
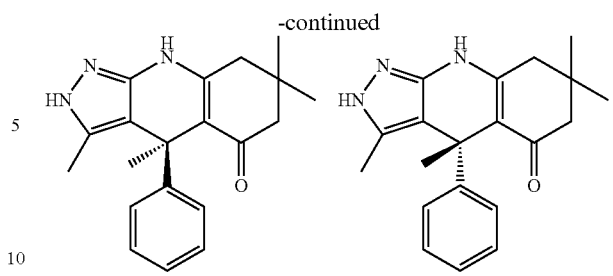
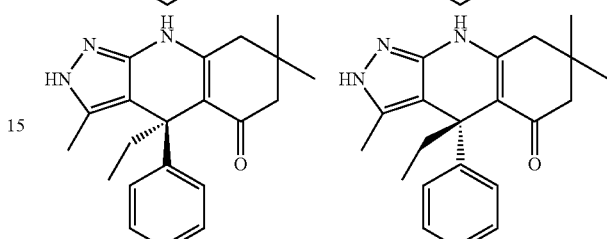
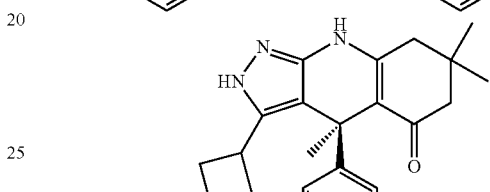
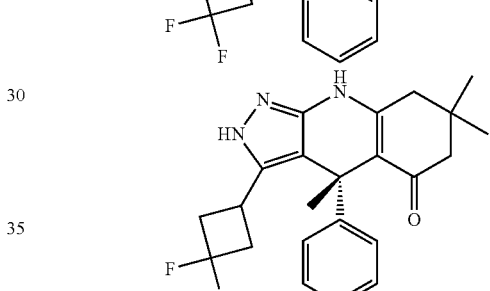
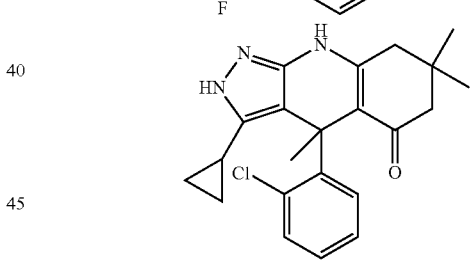
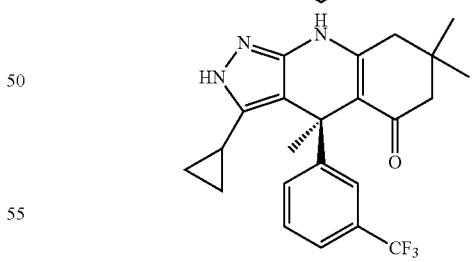
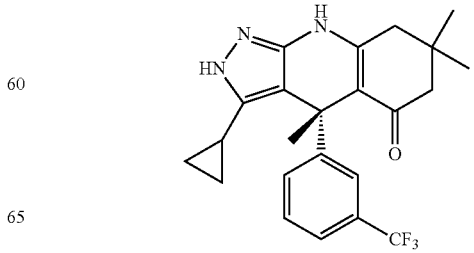

-continued
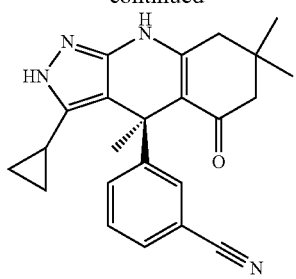
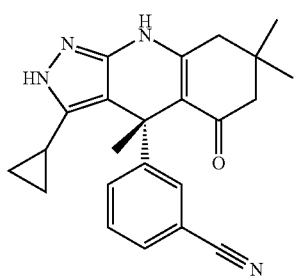
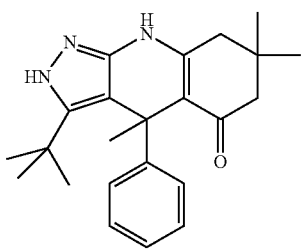
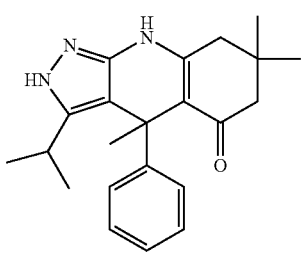
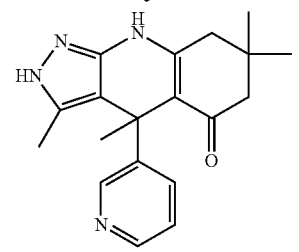
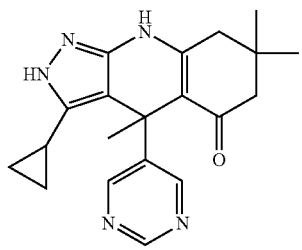
-continued
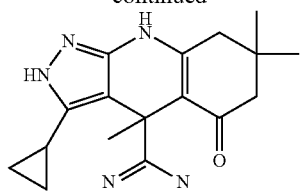
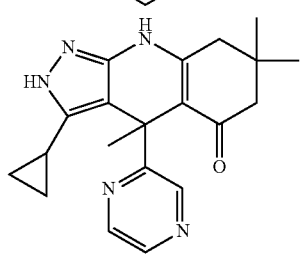
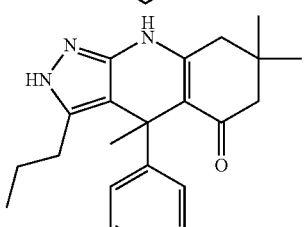
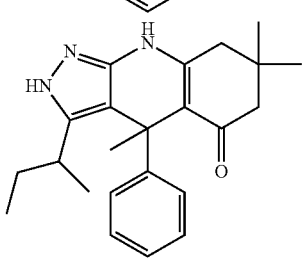
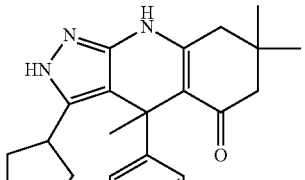
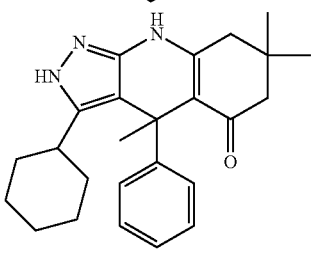
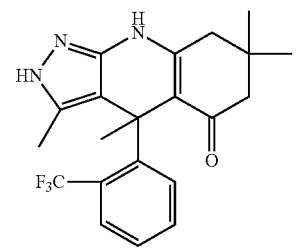

113
-continued
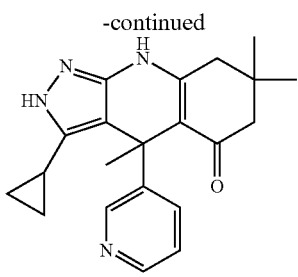
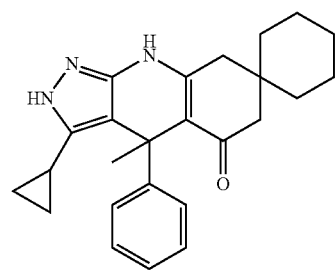
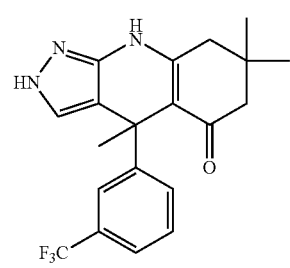
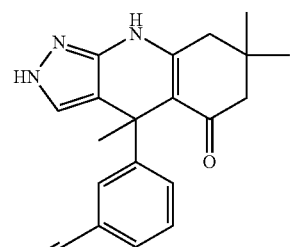
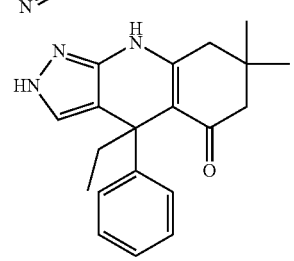
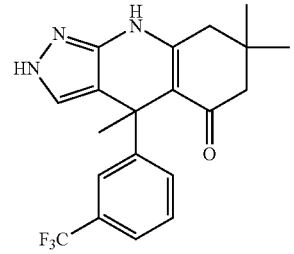
114
-continued
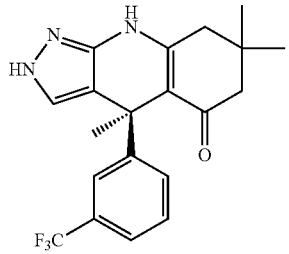
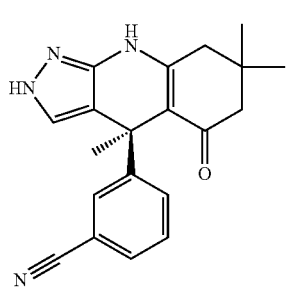
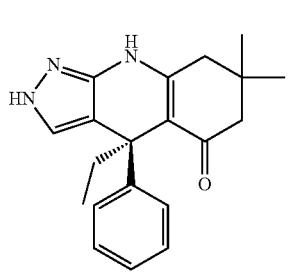
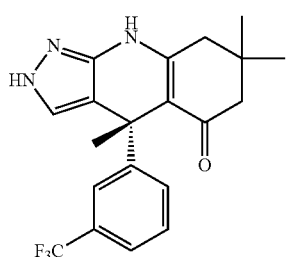
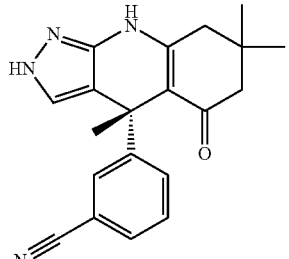
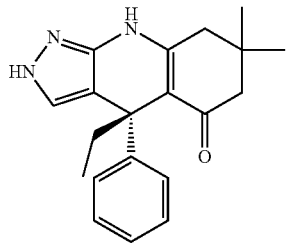

115
-continued

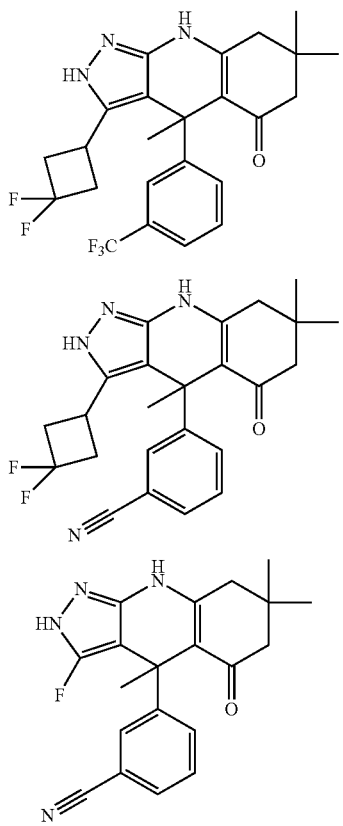

or a pharmaceutically acceptable salt thereof.

Embodiment 31

A composition comprising a compound of any one of embodiments 1-30, or a pharmaceutically acceptable salt thereof, and a pharmaceutically acceptable excipient.

Embodiment 32

The composition of embodiment 31 further comprising lithium.

Embodiment 33

The composition of embodiment 31 further comprising ketamine.

Embodiment 34

The composition of embodiment 31 further comprising all-trans retinoic acid.

Embodiment 35

A method of inhibiting GSK3 comprising contacting GSK3 with an effective amount of a compound of formula I:

116

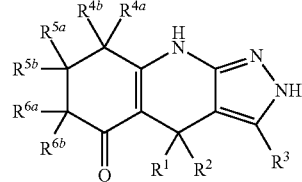

or a pharmaceutically acceptable salt thereof,
wherein:
$R^1$ and $R^2$ are independently selected from the group consisting of hydrogen, optionally substituted aliphatic, optionally substituted aryl, and optionally substituted heteroaryl, wherein $R^1$ and $R^2$ are not simultaneously hydrogen; or $R^1$ and $R^2$ are taken together with their intervening atoms to form an optionally substituted 3- to 7-membered carbocyclic or heterocyclic ring, wherein the ring formed by $R^1$ and $R^2$ may be optionally fused to an aryl or heteroaryl ring;
$R^3$ is selected from the group consisting of hydrogen, halo, —CN, —NO$_2$, optionally substituted aliphatic, optionally substituted phenyl, optionally substituted heterocyclyl, optionally substituted heteroaryl, —OR$^A$, —N(R$^B$)$_2$, —SR$^A$, —C(=O)R$^A$, —C(=O)OR$^A$, —C(=O)SR$^A$, —C(=O)N(R$^B$)$_2$, —OC(=O)R$^A$, —NR$^B$C(=O)R$^A$, —NR$^B$C(=O)N(R$^B$)$_2$, —OC(=O)N(R$^B$)$_2$, —NR$^B$C(=O)OR$^A$, —SC(=O)R$^A$, —C(=NR$^B$)R$^A$, —C(=NR$^B$)N(R$^B$)$_2$, —NR$^B$C(=NR$^B$)R$^B$, —C(=S)R$^A$, —C(=S)N(R$^B$)$_2$, —NR$^B$C(=S)R$^A$, —S(=O)R$^A$, —SO$_2$R$^A$, —NR$^B$SO$_2$R$^A$, and —SO$_2$N(R$^B$)$_2$;
each $R^A$ is independently selected from the group consisting of hydrogen, optionally substituted aliphatic, optionally substituted carbocyclyl, optionally substituted heterocyclyl, optionally substituted aryl, and optionally substituted heteroaryl;
each $R^B$ is independently selected from the group consisting of hydrogen, optionally substituted aliphatic, optionally substituted carbocyclyl, optionally substituted heterocyclyl, optionally substituted aryl, and optionally substituted heteroaryl, or two $R^B$ groups are taken together with their intervening atoms to form an optionally substituted heterocyclic ring;
$R^{4a}$ and $R^{4b}$ are independently selected from the group consisting of hydrogen, halo, —CN, —OR$^A$, —N(R$^B$)$_2$, and optionally substituted aliphatic, or $R^{4a}$ and $R^{4b}$ are taken together with their intervening atoms to form an optionally substituted 3- to 7-membered saturated carbocyclic or heterocyclic ring;
$R^{5a}$ and $R^{5b}$ are independently selected from the group consisting of hydrogen, halo, —CN, —OR$^A$, —N(R$^B$)$_2$, optionally substituted aliphatic, optionally substituted aryl, and optionally substituted heteroaryl, or $R^{5a}$ and $R^{5b}$ are taken together with their intervening atoms to form an optionally substituted 3- to 7-membered saturated carbocyclic or heterocyclic ring; and $R^{6a}$ and $R^{6b}$ are independently selected from the group consisting of hydrogen, halo, —CN, —OR$^A$, —N(R$^B$)$_2$, and optionally substituted aliphatic, or $R^{6a}$ and $R^{6b}$ are taken together with their intervening atoms to form an optionally substituted 3- to 7-membered saturated carbocyclic or heterocyclic ring.

Embodiment 36

The method of embodiment 35, wherein the GSK3 is GSK3β.

Embodiment 37

The method of embodiment 35, wherein the GSK3 is GSK3α.

Embodiment 38

The method of any one of embodiments 35-37, wherein the GSK3 is in a cell.

Embodiment 39

A method of treating a GSK3-mediated disorder comprising administering to a subject suffering from a GSK3-mediated disorder an effective amount of a compound of formula I:

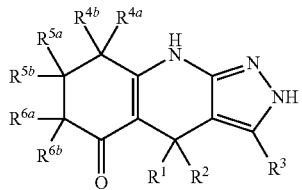

or a pharmaceutically acceptable salt thereof,
wherein:

$R^1$ and $R^2$ are independently selected from the group consisting of hydrogen, optionally substituted aliphatic, optionally substituted aryl, and optionally substituted heteroaryl, wherein $R^1$ and $R^2$ are not simultaneously hydrogen; or $R^1$ and $R^2$ are taken together with their intervening atoms to form an optionally substituted 3- to 7-membered saturated carbocyclic or heterocyclic ring, wherein the ring formed by $R^1$ and $R^2$ may be optionally fused to an aryl or heteroaryl ring;

$R^3$ is selected from the group consisting of hydrogen, halo, —CN, —NO$_2$, optionally substituted aliphatic, optionally substituted phenyl, optionally substituted heterocyclyl, optionally substituted heteroaryl, —OR$^A$, —N(R$^B$)$_2$, —SR$^A$, —C(=O)R$^A$, —C(=O)OR$^A$, —C(=O)SR$^A$, —C(=O)N(R$^B$)$_2$, —OC(=O)R$^A$, —NR$^B$C(=O)R$^A$, —NR$^B$C(=O)N(R$^B$)$_2$, —OC(=O)N(R$^B$)$_2$, —NR$^B$C(=O)OR$^A$, —SC(=O)R$^A$, —C(=NR$^B$)R$^A$, —C(=NR$^B$)N(R$^B$)$_2$, —NR$^B$C(=NR$^B$)R$^B$, —C(=S)R$^A$, —C(=S)N(R$^B$)$_2$, —NR$^B$C(=S)R$^A$, —S(=O)R$^A$, —SO$_2$R$^A$, —NR$^B$SO$_2$R$^A$, and —SO$_2$N(R$^B$)$_2$;

each $R^A$ is independently selected from the group consisting of hydrogen, optionally substituted aliphatic, optionally substituted carbocyclyl, optionally substituted heterocyclyl, optionally substituted aryl, and optionally substituted heteroaryl;

each $R^B$ is independently selected from the group consisting of hydrogen, optionally substituted aliphatic, optionally substituted carbocyclyl, optionally substituted heterocyclyl, optionally substituted aryl, and optionally substituted heteroaryl, or two $R^B$ groups are taken together with their intervening atoms to form an optionally substituted heterocyclic ring;

$R^{4a}$ and $R^{4b}$ are independently selected from the group consisting of hydrogen, halo, —CN, —OR$^A$, —N(R$^B$)$_2$, and optionally substituted aliphatic, or $R^{4a}$ and $R^{4b}$ are taken together with their intervening atoms to form an optionally substituted 3- to 7-membered saturated carbocyclic or heterocyclic ring;

$R^{5a}$ and $R^{5b}$ are independently selected from the group consisting of hydrogen, halo, —CN, —OR$^A$, —N(R$^B$)$_2$, optionally substituted aliphatic, optionally substituted aryl, and optionally substituted heteroaryl, or $R^{5a}$ and $R^{5b}$ are taken together with their intervening atoms to form an optionally substituted 3- to 7-membered saturated carbocyclic or heterocyclic ring; and $R^{6a}$ and $R^{6b}$ are independently selected from the group consisting of hydrogen, halo, —CN, —OR$^A$, —N(R$^B$)$_2$, and optionally substituted aliphatic, or $R^{6a}$ and $R^{6b}$ are taken together with their intervening atoms to form an optionally substituted 3- to 7-membered saturated carbocyclic or heterocyclic ring.

Embodiment 40

The method of embodiment 39, wherein the GSK3-mediated disorder is a GSK3α-mediated disorder.

Embodiment 41

The method of embodiment 39, wherein the GSK3-mediated disorder is a GSK3β-mediated disorder.

Embodiment 42

The method of embodiment 39, wherein the GSK3-mediated disorder is a neurological disease.

Embodiment 43

The method of embodiment 42, wherein the neurological disease is a neurodegenerative disease.

Embodiment 44

The method of embodiment 43, wherein the neurodegenerative disease is Alzheimer's disease, frontotemporal dementia, or amyotrophic lateral sclerosis (ALS).

Embodiment 45

The method of embodiment 43, wherein the neurodegenerative disease is progressive supranuclear palsy or corticobasal degeneration.

Embodiment 46

The method of embodiment 39, wherein the GSK3-mediated disorder is a psychiatric disorder.

Embodiment 47

The method of embodiment 46, wherein the psychiatric disorder is bipolar disorder, schizophrenia, autism, Fragile X syndrome, or depression.

Embodiment 48

The method of embodiment 46, wherein the psychiatric disorder is lithium-resistant depression.

Embodiment 49

The method of embodiment 46, 47, or 48 further comprising administering to the subject an effective amount of lithium.

Embodiment 50

The method of embodiment 46, 47, 48, or 49 further comprising administering to the subject an effective amount of ketamine.

Embodiment 51

The method of embodiment 39, wherein the GSK3-mediated disorder is cancer.

Embodiment 52

The method of embodiment 39, wherein the GSK3-mediated disorder is leukemia.

Embodiment 53

The method of embodiment 39, wherein the GSK3-mediated disorder is acute myeloid leukemia.

Embodiment 54

The method of embodiment 53 further comprising administering to the subject an effective amount of all-trans retinoic acid.

Embodiment 55

The method of embodiment 39, wherein the GSK3-mediated disorder is acute lymphocytic leukemia, chronic myelocytic leukemia, and/or chronic lymphocytic leukemia, multiple myeloma, or pancreatic cancer.

Embodiment 56

The method of embodiment 39, wherein the GSK3-mediated disorder is a metabolic disorder.

Embodiment 57

The method of embodiment 39, wherein the GSK3-mediated disorder is diabetes.

Embodiment 58

A method of inhibiting CK1 comprising contacting CK1 with an effective amount of a compound of formula I:

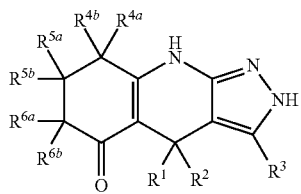

or a pharmaceutically acceptable salt thereof, wherein:
$R^1$ and $R^2$ are independently selected from the group consisting of hydrogen, optionally substituted aliphatic, optionally substituted aryl, and optionally substituted heteroaryl, wherein $R^1$ and $R^2$ are not simultaneously hydrogen; or $R^1$ and $R^2$ are taken together with their intervening atoms to form an optionally substituted 3- to 7-membered carbocyclic or heterocyclic ring, wherein the ring formed by $R^1$ and $R^2$ may be optionally fused to an aryl or heteroaryl ring;

$R^3$ is selected from the group consisting of hydrogen, halo, —CN, —NO$_2$, optionally substituted aliphatic, optionally substituted phenyl, optionally substituted heterocyclyl, optionally substituted heteroaryl, —OR$^A$, —N(R$^B$)$_2$, —SR$^A$, —C(=O)R$^A$, —C(=O)OR$^A$, —C(=O)SR$^A$, —C(=O)N(R$^B$)$_2$, —OC(=O)R$^A$, —NR$^B$C(=O)R$^A$, —NR$^B$C(=O)N(R$^B$)$_2$, —OC(=O)N(R$^B$)$_2$, —NR$^B$C(=O)OR$^A$, —SC(=O)R$^A$, —C(=NR$^B$)R$^A$, —C(=NR$^B$)N(R$^B$)$_2$, —NR$^B$C(=NR$^B$)R$^B$, —C(=S)R$^A$, —C(=S)N(R$^B$)$_2$, —NR$^B$C(=S)R$^A$, —S(=O)R$^A$, —SO$_2$R$^A$, —NR$^B$SO$_2$R$^A$, and —SO$_2$N(R$^B$)$_2$;

each $R^A$ is independently selected from the group consisting of hydrogen, optionally substituted aliphatic, optionally substituted carbocyclyl, optionally substituted heterocyclyl, optionally substituted aryl, and optionally substituted heteroaryl;

each $R^B$ is independently selected from the group consisting of hydrogen, optionally substituted aliphatic, optionally substituted carbocyclyl, optionally substituted heterocyclyl, optionally substituted aryl, and optionally substituted heteroaryl, or two $R^B$ groups are taken together with their intervening atoms to form an optionally substituted heterocyclic ring;

$R^{4a}$ and $R^{4b}$ are independently selected from the group consisting of hydrogen, halo, —CN, —OR$^A$, —N(R$^B$)$_2$, and optionally substituted aliphatic, or $R^{4a}$ and $R^{4b}$ are taken together with their intervening atoms to form an optionally substituted 3- to 7-membered saturated carbocyclic or heterocyclic ring;

$R^{5a}$ and $R^{5b}$ are independently selected from the group consisting of hydrogen, halo, —CN, —OR$^A$, —N(R$^B$)$_2$, optionally substituted aliphatic, optionally substituted aryl, and optionally substituted heteroaryl, or $R^{5a}$ and $R^{5b}$ are taken together with their intervening atoms to form an optionally substituted 3- to 7-membered saturated carbocyclic or heterocyclic ring; and $R^{6a}$ and $R^{6b}$ are independently selected from the group consisting of hydrogen, halo, —CN, —OR$^A$, —N(R$^B$)$_2$, and optionally substituted aliphatic, or $R^{6a}$ and $R^{6b}$ are taken together with their intervening atoms to form an optionally substituted 3- to 7-membered saturated carbocyclic or heterocyclic ring.

Embodiment 59

The method of embodiment 58, wherein the CK1 is in a cell.

Embodiment 60

The method of embodiment 58 or 59, wherein the CK1 is CK1δ.

Embodiment 61

A method of treating a CK1-mediated disorder comprising administering to a subject suffering from a CK1-mediated disorder an effective amount of a compound of formula I:

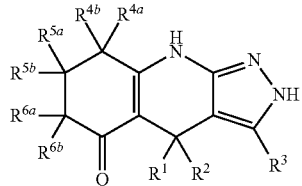

or a pharmaceutically acceptable salt thereof,
wherein:

$R^1$ and $R^2$ are independently selected from the group consisting of hydrogen, optionally substituted aliphatic, optionally substituted aryl, and optionally substituted heteroaryl, wherein $R^1$ and $R^2$ are not simultaneously hydrogen; or $R^1$ and $R^2$ are taken together with their intervening atoms to form an optionally substituted 3- to 7-membered saturated carbocyclic or heterocyclic ring, wherein the ring formed by $R^1$ and $R^2$ may be optionally fused to an aryl or heteroaryl ring;

$R^3$ is selected from the group consisting of hydrogen, halo, —CN, —NO$_2$, optionally substituted aliphatic, optionally substituted phenyl, optionally substituted heterocyclyl, optionally substituted heteroaryl, —OR$^A$, —N(R$^B$)$_2$, —SR$^A$, —C(=O)R$^A$, —C(=O)OR$^A$, —C(=O)SR$^A$, —C(=O)N(R$^B$)$_2$, —OC(=O)R$^A$, —NR$^B$C(=O)R$^A$, —NR$^B$C(=O)N(R$^B$)$_2$, —OC(=O)N(R$^B$)$_2$, —NR$^B$C(=O)OR$^A$, —SC(=O)R$^A$, —C(=NR$^B$)R$^A$, —C(=NR$^B$)N(R$^B$)$_2$, —NR$^B$C(=NR$^B$)R$^B$, —C(=S)R$^A$, —C(=S)N(R$^B$)$_2$, —NR$^B$C(=S)R$^A$, —S(=O)R$^A$, —SO$_2$R$^A$, —NR$^B$SO$_2$R$^A$, and —SO$_2$N(R$^B$)$_2$;

each $R^A$ is independently selected from the group consisting of hydrogen, optionally substituted aliphatic, optionally substituted carbocyclyl, optionally substituted heterocyclyl, optionally substituted aryl, and optionally substituted heteroaryl;

each $R^B$ is independently selected from the group consisting of hydrogen, optionally substituted aliphatic, optionally substituted carbocyclyl, optionally substituted heterocyclyl, optionally substituted aryl, and optionally substituted heteroaryl, or two $R^B$ groups are taken together with their intervening atoms to form an optionally substituted heterocyclic ring;

$R^{4a}$ and $R^{4b}$ are independently selected from the group consisting of hydrogen, halo, —CN, —OR$^A$, —N(R$^B$)$_2$, and optionally substituted aliphatic, or $R^{4a}$ and $R^{4b}$ are taken together with their intervening atoms to form an optionally substituted 3- to 7-membered saturated carbocyclic or heterocyclic ring;

$R^{5a}$ and $R^{5b}$ are independently selected from the group consisting of hydrogen, halo, —CN, —OR$^A$, —N(R$^B$)$_2$, optionally substituted aliphatic, optionally substituted aryl, and optionally substituted heteroaryl, or $R^{5a}$ and $R^{5b}$ are taken together with their intervening atoms to form an optionally substituted 3- to 7-membered saturated carbocyclic or heterocyclic ring; and $R^{6a}$ and $R^{6b}$ are independently selected from the group consisting of hydrogen, halo, —CN, —OR$^A$, —N(R$^B$)$_2$, and optionally substituted aliphatic, or $R^{6a}$ and $R^{6b}$ are taken together with their intervening atoms to form an optionally substituted 3- to 7-membered saturated carbocyclic or heterocyclic ring.

Embodiment 62

The method of embodiment 61, wherein the CK1 is CK1δ.

Embodiment 63

The method of embodiment 62, wherein the CK1δ-mediated disorder is ADHD.

Embodiment 64

The method of any one of embodiments 35-63, wherein the compound is of formula II:

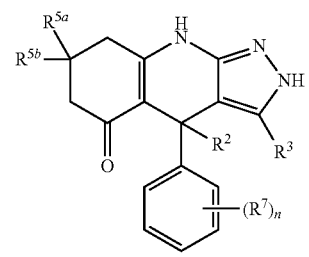

or a pharmaceutically acceptable salt thereof,
wherein:

each $R^7$ is independently selected from the group consisting of hydrogen, halo, —CN, —NO$_2$, optionally substituted aliphatic, optionally substituted phenyl, optionally substituted heterocyclyl, optionally substituted heteroaryl, —OR$^A$, —N(R$^B$)$_2$, —SR$^A$, —C(=O)R$^A$, —C(=O)OR$^A$, —C(=O)SR$^A$, —C(=O)N(R$^B$)$_2$, —OC(=O)R$^A$, —NR$^B$C(=O)R$^A$, —NR$^B$C(=O)N(R$^B$)$_2$, —OC(=O)N(R$^B$)$_2$, —NR$^B$C(=O)OR$^A$, —SC(=O)R$^A$, —C(=NR$^B$)R$^A$, —C(=NR$^B$)N(R$^B$)$_2$, —NR$^B$C(=NR$^B$)R$^B$, —C(=S)R$^A$, —C(=S)N(R$^B$)$_2$, —NR$^B$C(=S)R$^A$, —S(=O)R$^A$, —SO$_2$R$^A$, —NR$^B$SO$_2$R$^A$, and —SO$_2$N(R$^B$)$_2$; or two adjacent $R^7$ groups are taken together with their intervening atoms to form an optionally substituted carbocyclic or heterocyclic fused ring; or $R^2$ and $R^7$ are taken together with their intervening atoms to form an optionally substituted carbocyclic or heterocyclic fused ring; and n is 0, 1, 2, 3, or 4.

Embodiment 65

The method of any one of embodiments 35-63, wherein the compound is of formula III:

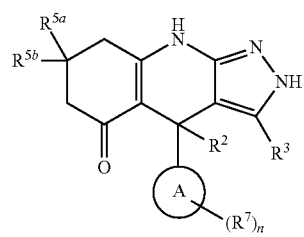

or a pharmaceutically acceptable salt thereof,
wherein:

Ring A is a 5- to 6-membered heteroaryl;

each $R^7$ is independently selected from the group consisting of hydrogen, halo, —CN, —NO$_2$, optionally substituted aliphatic, optionally substituted phenyl, optionally substituted heterocyclyl, optionally substituted heteroaryl, —OR$^A$, —N(R$^B$)$_2$, —SR$^A$, —C(=O)R$^A$, —C(=O)OR$^A$, —C(=O)SR$^A$, —C(=O)N(R$^B$)$_2$, —OC(=O)R$^A$, —NR$^B$C(=O)R$^A$, —NR$^B$C(=O)N(R$^B$)$_2$, —OC(=O)N(R$^B$)$_2$, —NR$^B$C(=O)OR$^A$, —SC(=O)R$^A$, —C(=NR$^B$)R$^A$, —C(=NR$^B$)N(R$^B$)$_2$, —NR$^B$C(=NR$^B$)R$^B$, —C(=S)R$^A$, —C(=S)N(R$^B$)$_2$, —NR$^B$C(=S)R$^A$, —S(=O)R$^A$, —SO$_2$R$^A$, —NR$^B$SO$_2$R$^A$, and —SO$_2$N(R$^B$)$_2$; or two adjacent $R^7$ groups are taken together with their intervening atoms to form an optionally substituted carbocyclic or heterocyclic fused ring; or $R^2$ and $R^7$ are taken together with their intervening atoms to form an optionally substituted carbocyclic or heterocyclic fused ring; and n is 0, 1, 2, 3, or 4.

Embodiment 66

The method of any one of embodiments 39-65, wherein $R^3$ is hydrogen.

Embodiment 67

The method of any one of embodiments 39-65, wherein $R^3$ or $R^{3'}$ is fluoro.

Embodiment 68

The method of any one of embodiments 39-65, wherein $R^3$ or $R^{3'}$ is optionally substituted aliphatic.

Embodiment 69

The method of embodiment 68, wherein $R^3$ or $R^{3'}$ is methyl.

Embodiment 70

The method of embodiment 68, wherein $R^3$ or $R^{3'}$ is trifluoromethyl.

Embodiment 71

The method of embodiment 68, wherein $R^3$ or $R^{3'}$ is tert-butyl or isobutyl.

Embodiment 72

The method of embodiment 68, wherein $R^3$ or $R^{3'}$ is cyclopropyl.

Embodiment 73

The method of embodiment 68, wherein $R^3$ or $R^{3'}$ is difluorocyclobutyl.

Embodiment 74

The method of any one of embodiments 39-65, wherein $R^2$ or $R^{2'}$ is optionally substituted aliphatic.

Embodiment 75

The method of embodiment 74, wherein $R^2$ or $R^{2'}$ is methyl.

Embodiment 76

The method of embodiment 74, wherein $R^2$ or $R^{2'}$ is ethyl or propyl.

Embodiment 77

The method of any one of embodiments 39-64, wherein the compound is one of the following:

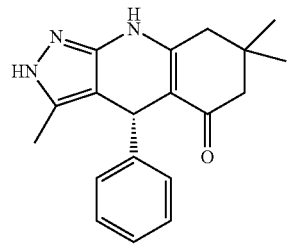

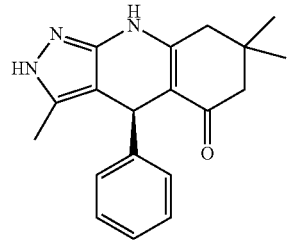

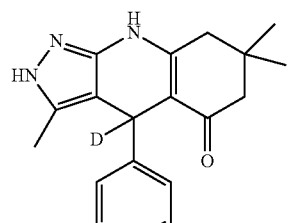

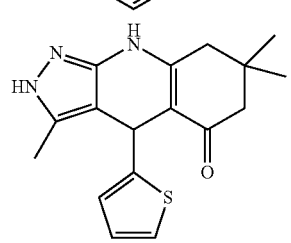

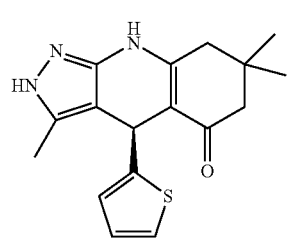

125
-continued
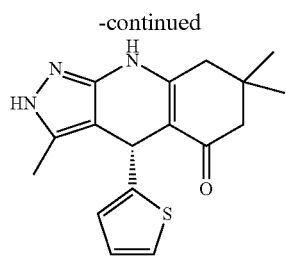
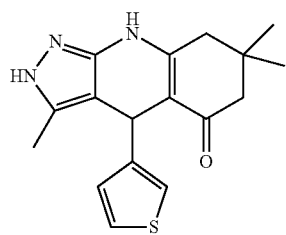
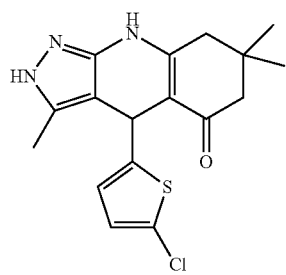
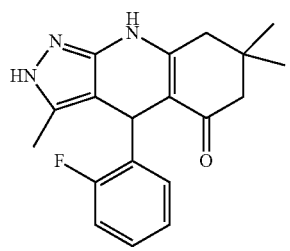
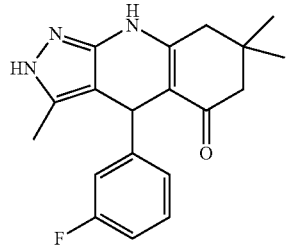
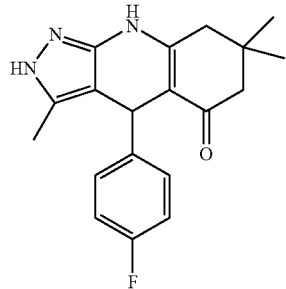
126
-continued
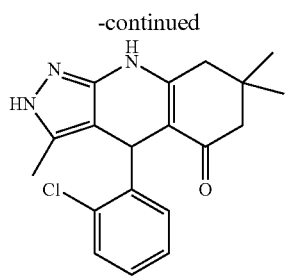
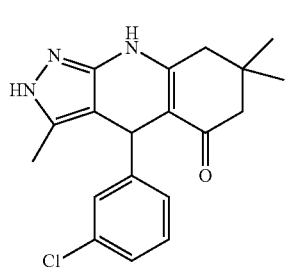
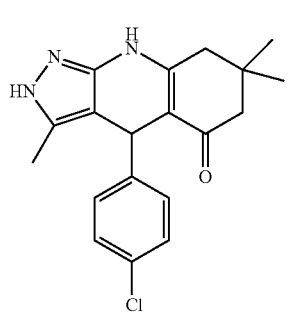
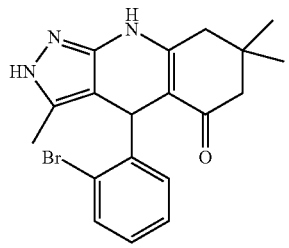
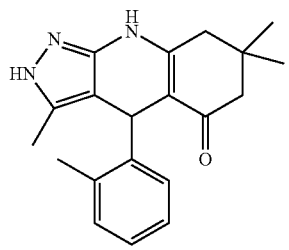

127
-continued
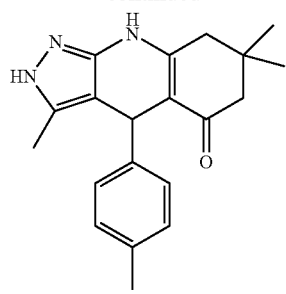
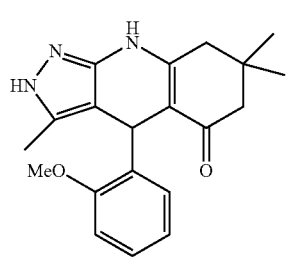
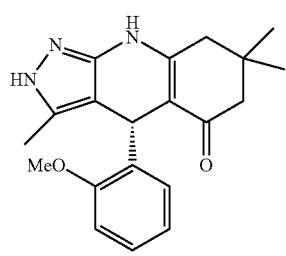
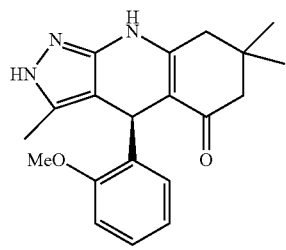
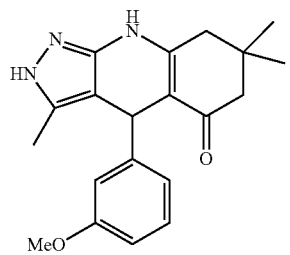
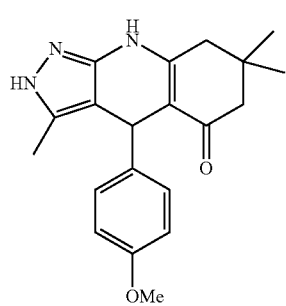
128
-continued
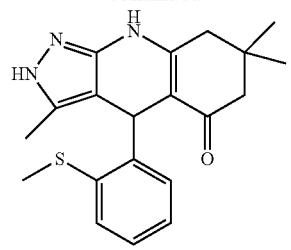
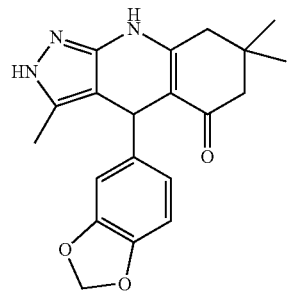
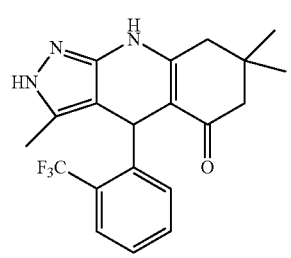
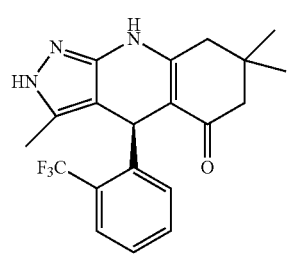
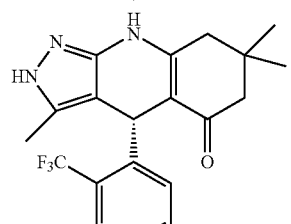
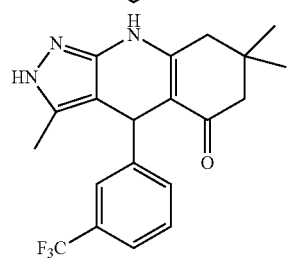

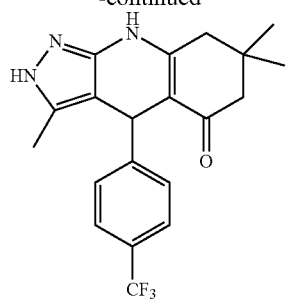
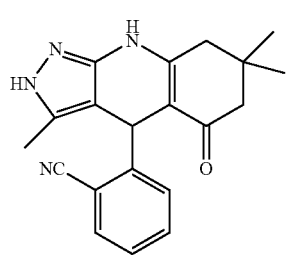
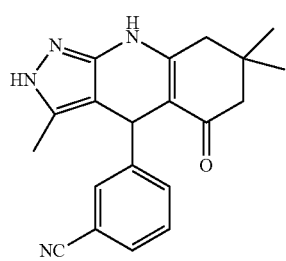
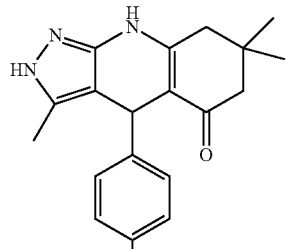
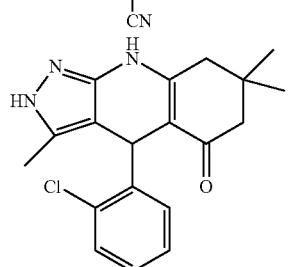
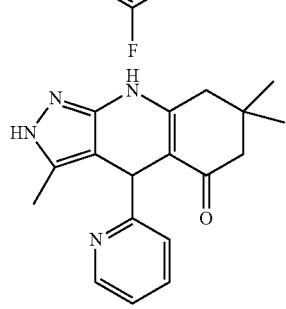
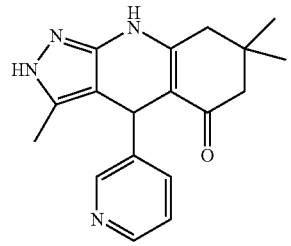
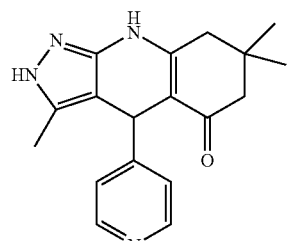
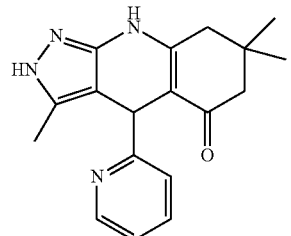
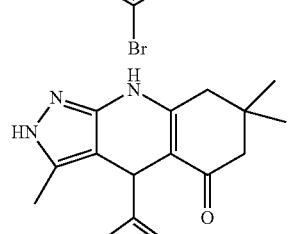
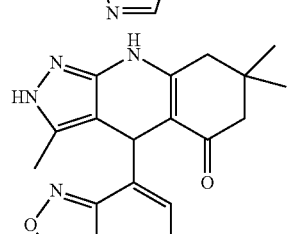
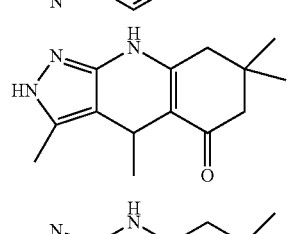
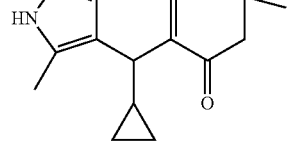

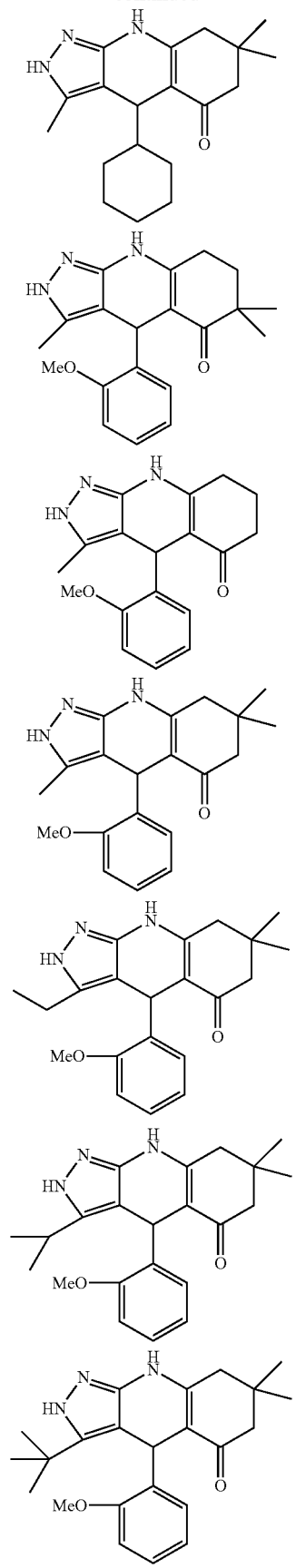
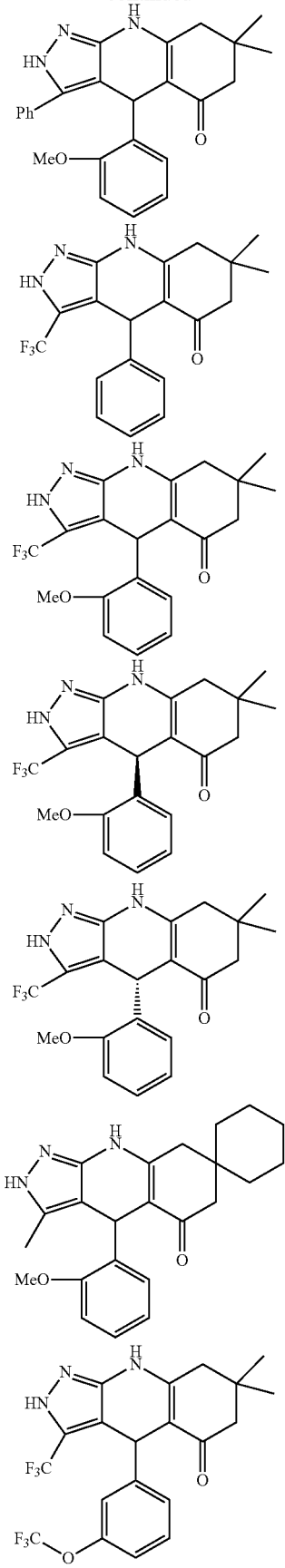

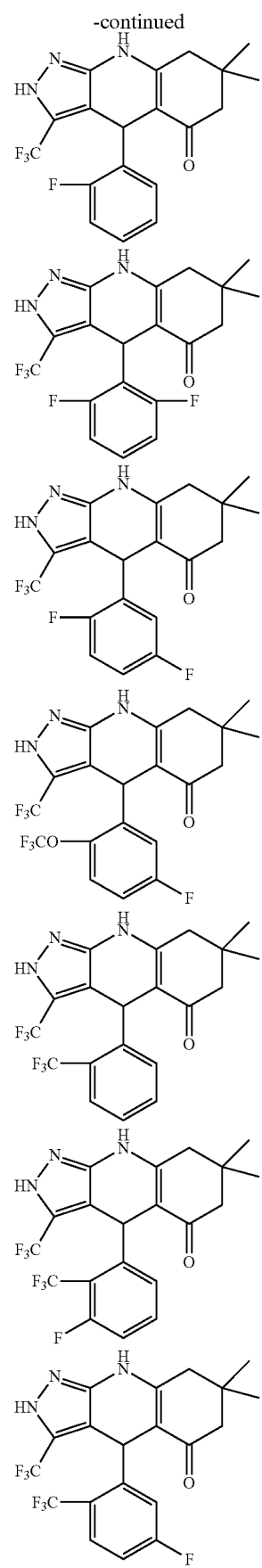
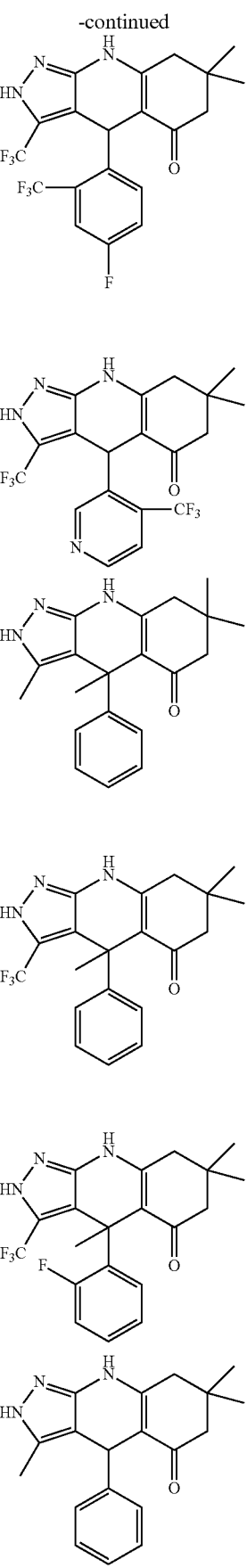

135
-continued
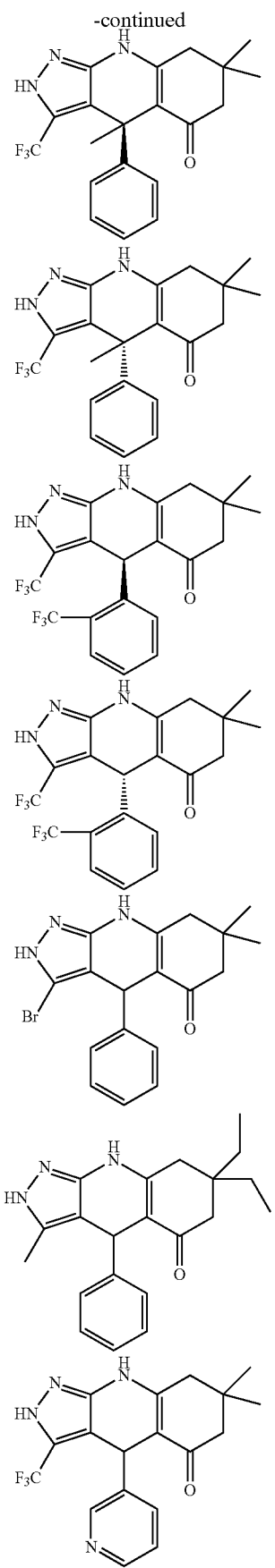
136
-continued
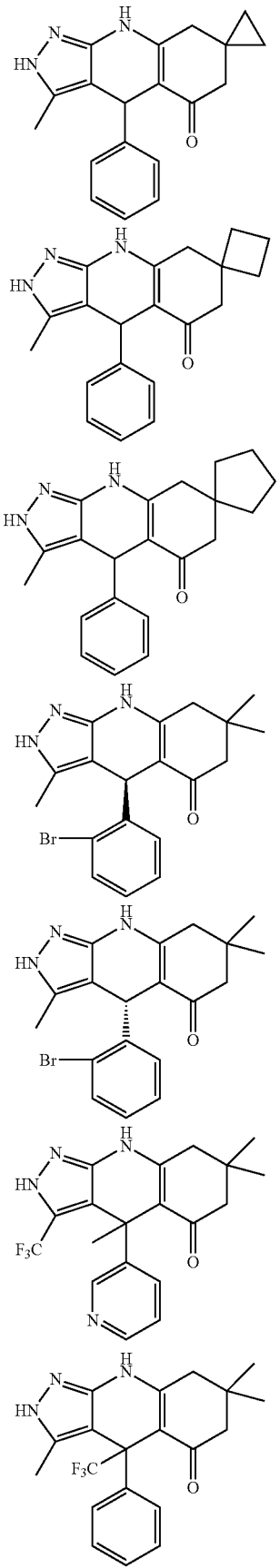

137
-continued
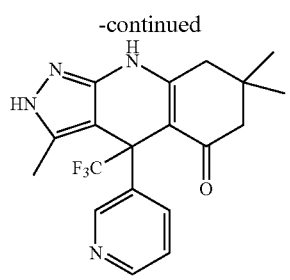
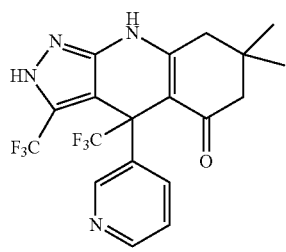
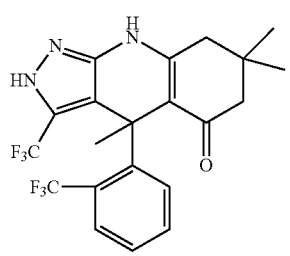
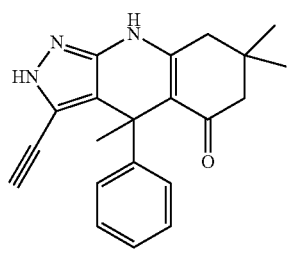
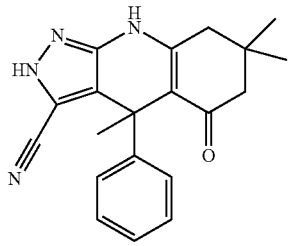
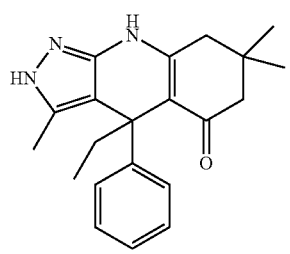
138
-continued
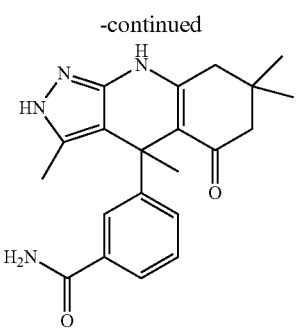
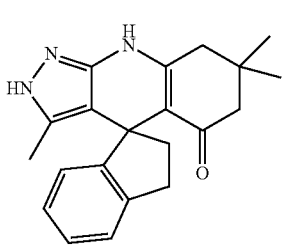
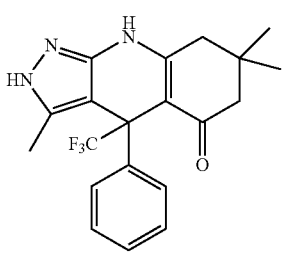
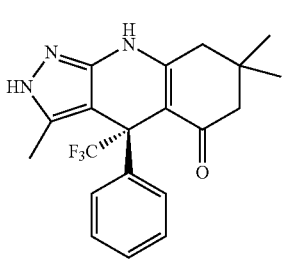
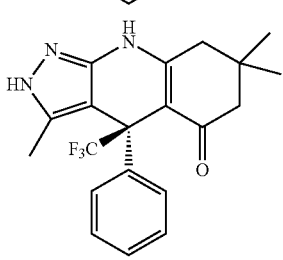
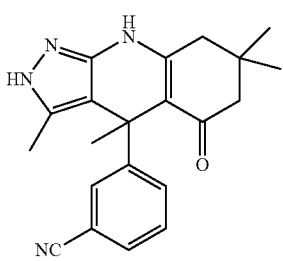

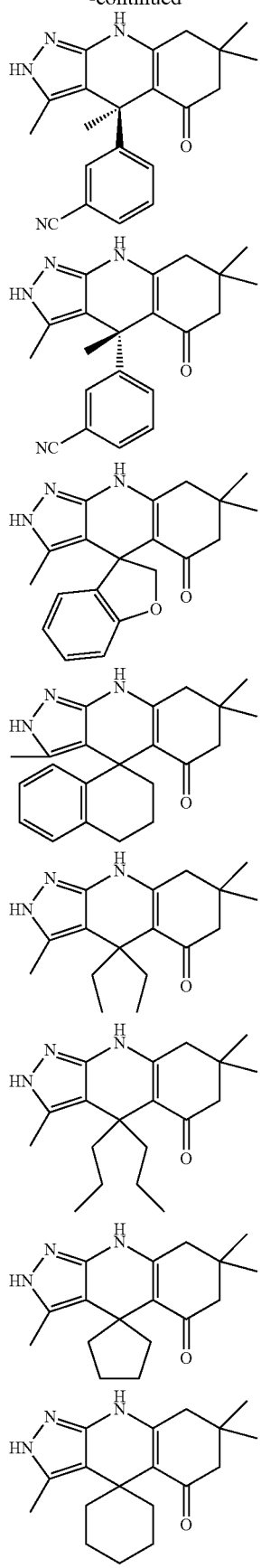
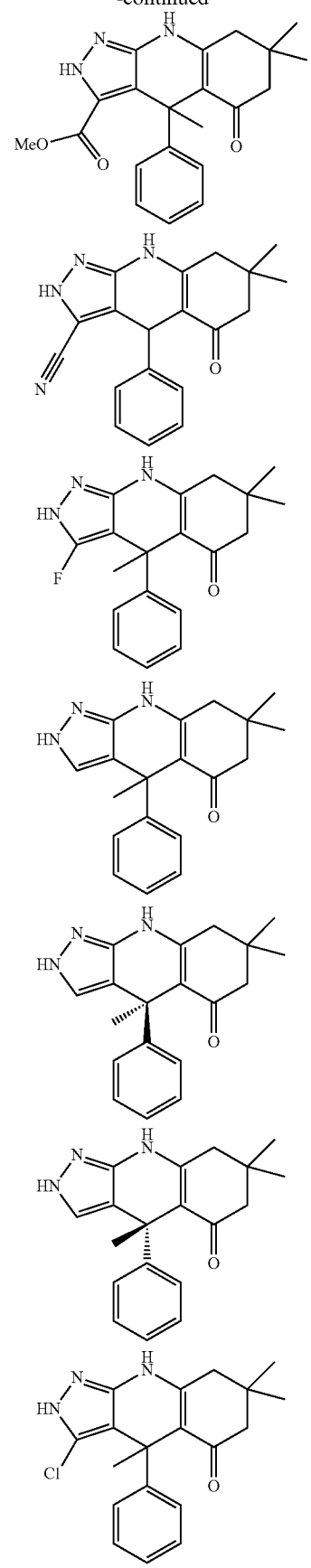

141
-continued
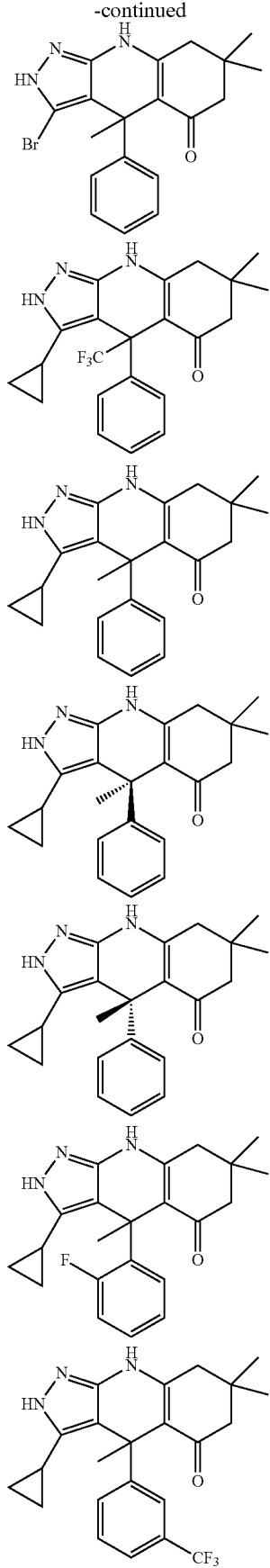
142
-continued
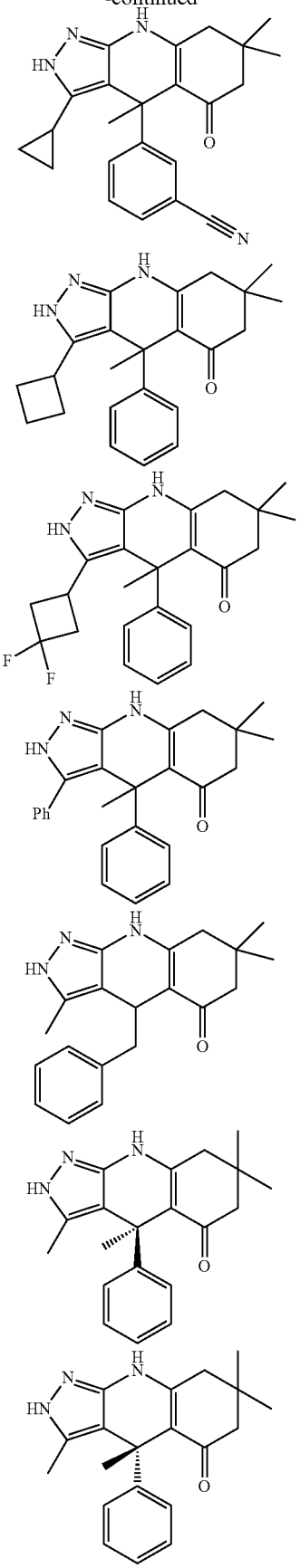

-continued
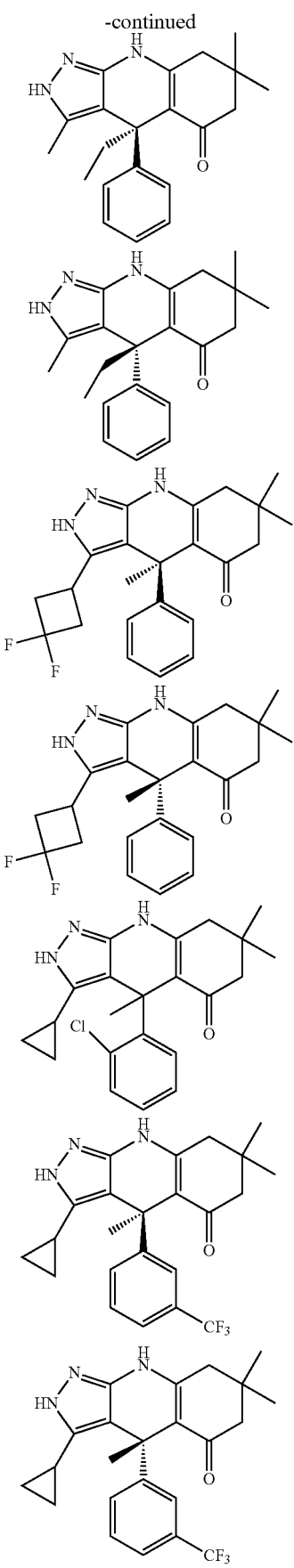
-continued
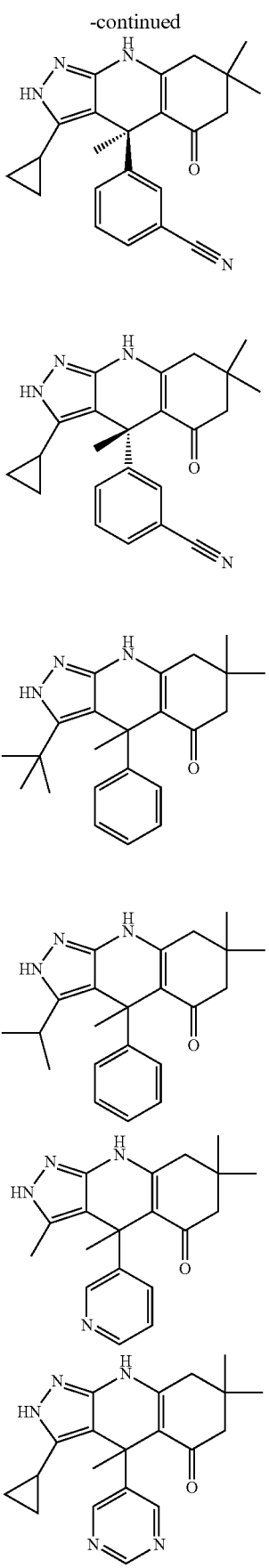

-continued
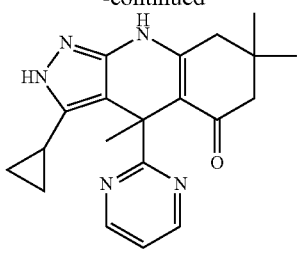
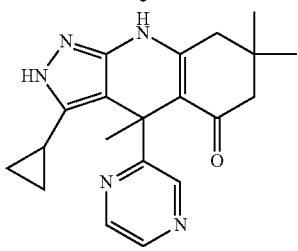
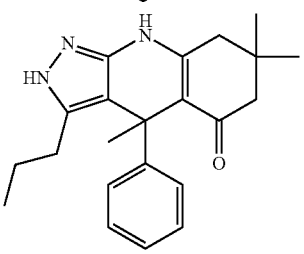
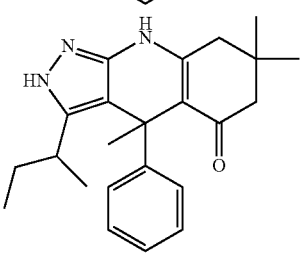
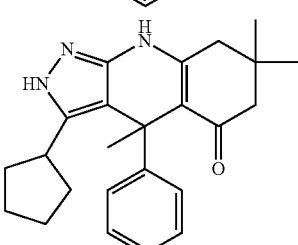
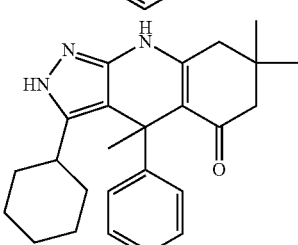
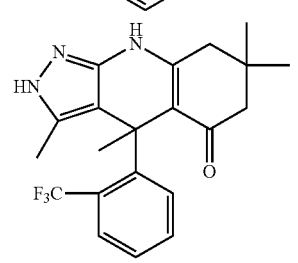
-continued
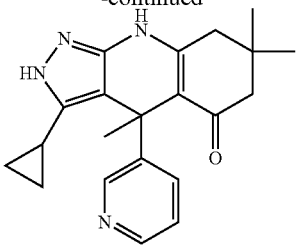
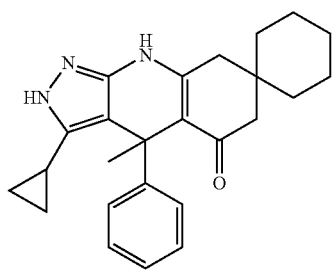
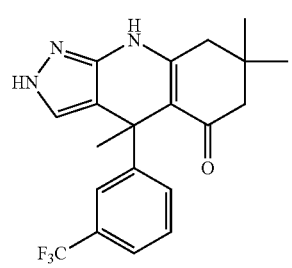
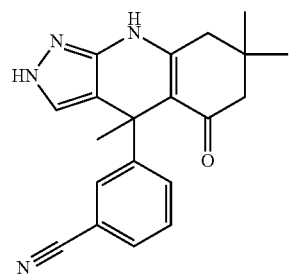
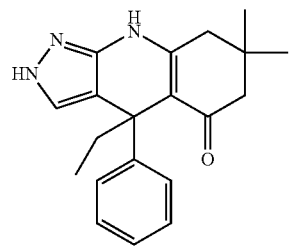
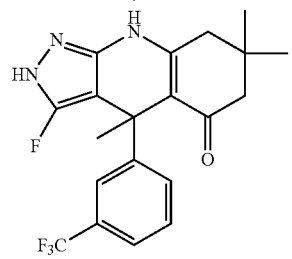

-continued

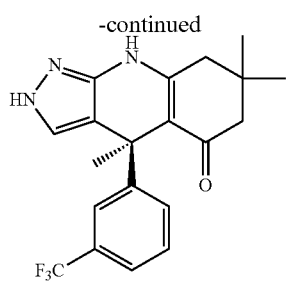
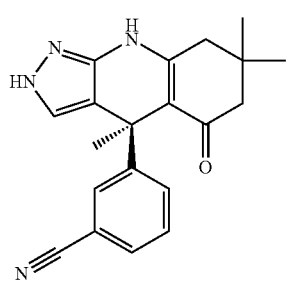
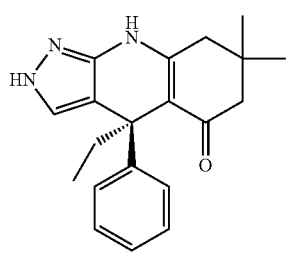
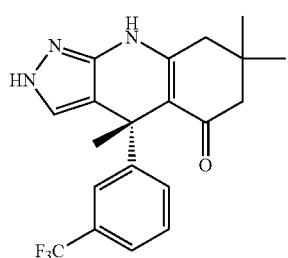
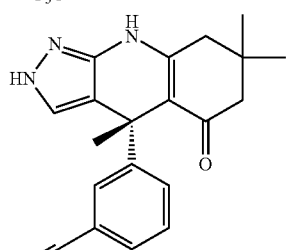
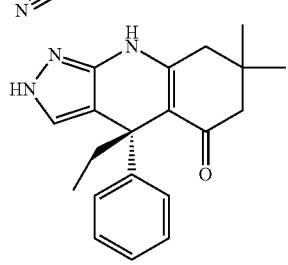

-continued

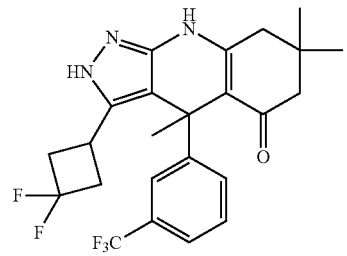
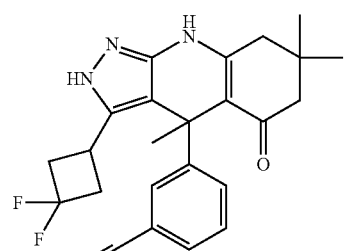
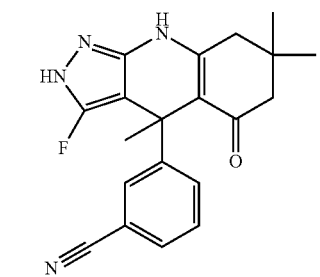

and pharmaceutically acceptable salts thereof.

Embodiment 78

A kit comprising:

a compound of any one of embodiments 1-30, or a pharmaceutically acceptable salt thereof, or a composition of any one of embodiments 31-34; and instructions for using the kit.

Embodiment 79

A method of preparing a compound of formula I:

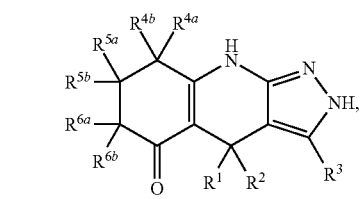

or a salt thereof, the method comprising contacting a compound of formula A, or a salt thereof, with a compound of formula B, or a salt thereof, and a compound of formula C, or a salt thereof, under suitable conditions to provide the compound of formula I, or salt thereof:

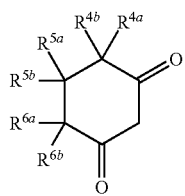

A

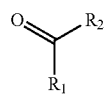

B

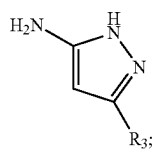

C wherein:

R¹ and R² are independently selected from the group consisting of hydrogen, optionally substituted aliphatic, optionally substituted aryl, and optionally substituted heteroaryl, wherein R¹ and R² are not simultaneously hydrogen; or R¹ and R² are taken together with their intervening atoms to form an optionally substituted 3- to 7-membered saturated carbocyclic or heterocyclic ring, wherein the ring formed by R¹ and R² may be optionally fused to an aryl or heteroaryl ring;

R³ is selected from the group consisting of hydrogen, halo, —CN, —NO₂, optionally substituted aliphatic, optionally substituted phenyl, optionally substituted heterocyclyl, optionally substituted heteroaryl, —OR$^A$, —N(R$^B$)₂, —SR$^A$, —C(=O)R$^A$, —C(=O)OR$^A$, —C(=O)SR$^A$, —C(=O)N(R$^B$)₂, —OC(=O)R$^A$, —NR$^B$C(=O)R$^A$, —NR$^B$C(=O)N(R$^B$)₂, —OC(=O)N(R$^B$)₂, —NR$^B$C(=O)OR$^A$, —SC(=O)R$^A$, —C(=NR$^B$)R$^A$, —C(=NR$^B$)N(R$^B$)₂, —NR$^B$C(=NR$^B$)R$^B$, —C(=S)R$^A$, —C(=S)N(R$^B$)₂, —NR$^B$C(=S)R$^A$, —S(=O)R$^A$, —SO₂R$^A$, —NR$^B$SO₂R$^A$, and —SO₂N(R$^B$)₂;

each R$^A$ is independently selected from the group consisting of hydrogen, optionally substituted aliphatic, optionally substituted carbocyclyl, optionally substituted heterocyclyl, optionally substituted aryl, and optionally substituted heteroaryl;

each R$^B$ is independently selected from the group consisting of hydrogen, optionally substituted aliphatic, optionally substituted carbocyclyl, optionally substituted heterocyclyl, optionally substituted aryl, and optionally substituted heteroaryl, or two R$^B$ groups are taken together with their intervening atoms to form an optionally substituted heterocyclic ring;

R$^{4a}$ and R$^{4b}$ are independently selected from the group consisting of hydrogen, halo, —CN, —OR$^A$, —N(R$^B$)₂, and optionally substituted aliphatic, or R$^{4a}$ and R$^{4b}$ are taken together with their intervening atoms to form an optionally substituted 3- to 7-membered saturated carbocyclic or heterocyclic ring;

R$^{5a}$ and R$^{5b}$ are independently selected from the group consisting of hydrogen, halo, —CN, —OR$^A$, —N(R$^B$)₂, optionally substituted aliphatic, optionally substituted aryl, and optionally substituted heteroaryl, or R$^{5a}$ and R$^{5b}$ are taken together with their intervening atoms to form an optionally substituted 3- to 7-membered saturated carbocyclic or heterocyclic ring; and R$^{6a}$ and R$^{6b}$ are independently selected from the group consisting of hydrogen, halo, —CN, —OR$^A$, —N(R$^B$)₂, and optionally substituted aliphatic, or R$^{6a}$ and R$^{6b}$ are taken together with their intervening atoms to form an optionally substituted 3- to 7-membered saturated carbocyclic or heterocyclic ring.

Embodiment 80

A method of preparing a compound of formula I':

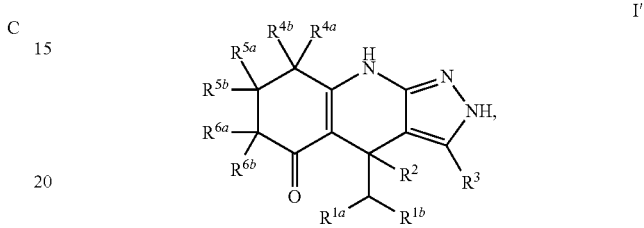

I' or a salt thereof, the method comprising:

contacting a compound of formula C, or a salt thereof, with a compound of formula D, or a salt thereof, under suitable conditions to provide a compound of formula E, or a salt thereof:

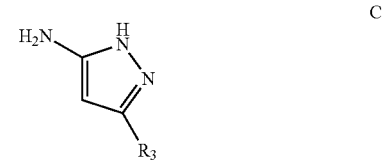

C

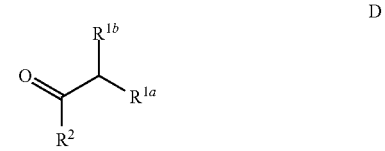

D

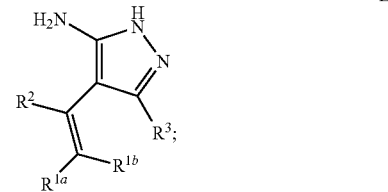

E conjugating the compound of formula E, or salt thereof, to a compound of formula A, or a salt thereof, under suitable conditions to provide a compound of formula F, or a salt thereof:

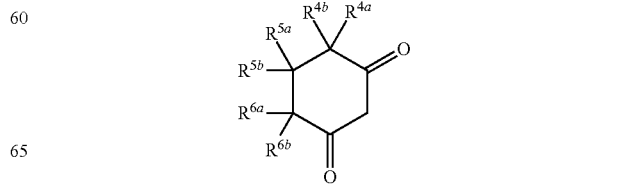

A

151

-continued

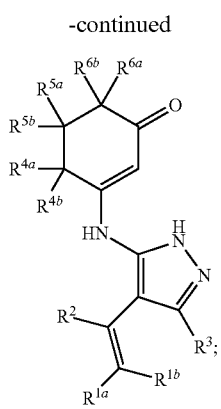

F and cyclizing the compound of formula F, or salt thereof, under suitable conditions to provide the compound of formula I', or salt thereof, wherein:

$R^{1a}$ and $R^{1b}$ are independently selected from the group consisting of hydrogen and optionally substituted aliphatic, or $R^{1a}$ and $R^{1b}$ are taken together with their intervening atoms to form an optionally substituted 3- to 7-membered saturated or unsaturated carbocyclic or heterocyclic ring, wherein the ring formed by $R^{1a}$ and $R^{1b}$ may be optionally fused to an aryl or heteroaryl ring;

$R^2$ is selected from the group consisting of optionally substituted aliphatic, optionally substituted aryl, and optionally substituted heteroaryl, or $R^{1a}$ and $R^2$ are taken together with their intervening atoms to form an optionally substituted 3- to 7-membered saturated or unsaturated carbocyclic or heterocyclic ring, wherein the ring formed by $R^{1a}$ and $R^2$ may be optionally fused to an aryl or heteroaryl ring;

$R^3$ is selected from the group consisting of hydrogen, halo, —CN, —NO$_2$, optionally substituted aliphatic, optionally substituted phenyl, optionally substituted heterocyclyl, optionally substituted heteroaryl, —OR$^A$, —N(R$^B$)$_2$, —SR$^A$, —C(=O)R$^A$, —C(=O)OR$^A$, —C(=O)SR$^A$, —C(=O)N (R$^B$)$_2$, —OC(=O)R$^A$, —NR$^B$C(=O)R$^A$, —NR$^B$C(=O)N (R$^B$)$_2$, —OC(=O)N(R$^B$)$_2$, —NR$^B$C(=O)OR$^A$, —SC(=O) R$^A$, —C(=NR$^B$)R$^A$, —C(=NR$^B$)N(R$^B$)$_2$, —NR$^B$C (=NR$^B$)R$^B$, —C(=S)R$^A$, —C(=S)N(R$^B$)$_2$, —NR$^B$C(=S) R$^A$, —S(=O)R$^A$, —SO$_2$R$^A$, —NR$^B$SO$_2$R$^A$, and —SO$_2$N (R$^B$)$_2$;

each $R^A$ is independently selected from the group consisting of hydrogen, optionally substituted aliphatic, optionally substituted carbocyclyl, optionally substituted heterocyclyl, optionally substituted aryl, and optionally substituted heteroaryl;

each $R^B$ is independently selected from the group consisting of hydrogen, optionally substituted aliphatic, optionally substituted carbocyclyl, optionally substituted heterocyclyl, optionally substituted aryl, and optionally substituted heteroaryl, or two $R^B$ groups are taken together with their intervening atoms to form an optionally substituted heterocyclic ring;

$R^{4a}$ and $R^{4b}$ are independently selected from the group consisting of hydrogen, halo, —CN, —OR$^A$, —N(R$^B$)$_2$, and optionally substituted aliphatic, or $R^{4a}$ and $R^{4b}$ are taken together with their intervening atoms to form an optionally substituted 3- to 7-membered saturated carbocyclic or heterocyclic ring;

$R^{5a}$ and $R^{5b}$ are independently selected from the group consisting of hydrogen, halo, —CN, —OR$^A$, —N(R$^B$)$_2$, optionally substituted aliphatic, optionally substituted aryl,

152 and optionally substituted heteroaryl, or $R^{5a}$ and $R^{5b}$ are taken together with their intervening atoms to form an optionally substituted 3- to 7-membered saturated carbocyclic or heterocyclic ring; $R^{6a}$ and $R^{6b}$ are independently selected from the group consisting of hydrogen, halo, —CN, —OR$^A$, —N(R$^B$)$_2$, and optionally substituted aliphatic, or $R^{6a}$ and $R^{6b}$ are taken together with their intervening atoms to form an optionally substituted 3- to 7-membered saturated carbocyclic or heterocyclic ring; and $R^{1a}$ and $R^{1b}$ are independently selected from the group consisting of hydrogen and optionally substituted aliphatic.

Embodiment 81

A method of preparing a compound of formula I':

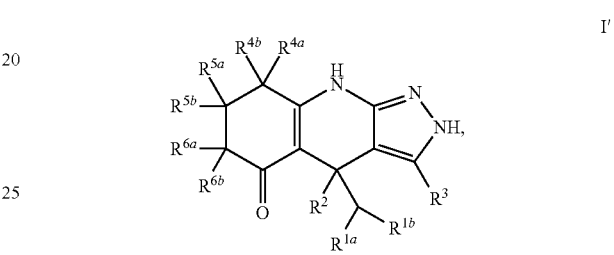

I' or a salt thereof, the method comprising:

protecting the primary amino group of a compound of formula C, or a salt thereof, to provide a compound of formula G, or a salt thereof:

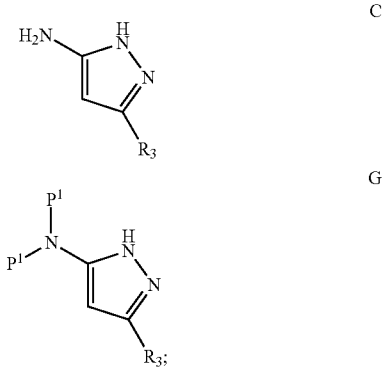

halogenating the compound of formula G, or salt thereof, to provide a compound of formula H, or a salt thereof:

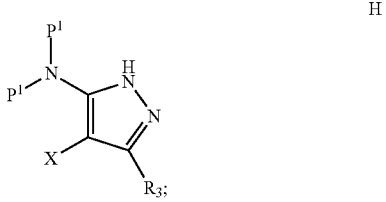

protecting the secondary amino group of the compound of formula H, or salt thereof, to provide a compound of formula J, or a salt thereof;

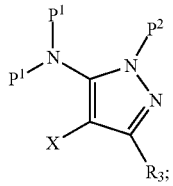
J coupling the compound of formula J, or salt thereof, with a boronic acid or ester of formula K, or a salt thereof, to provide a compound of formula L, or a salt thereof:

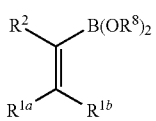
K

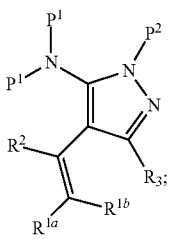
L deprotecting the primary amino group the compound of formula L, or salt thereof, to provide a compound of formula M, or a salt thereof:

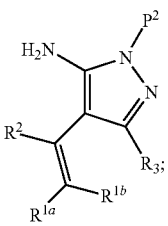
M conjugating the compound of formula M, or salt thereof, to a compound of formula A, or a salt thereof, to provide a compound of formula N, or a salt thereof:

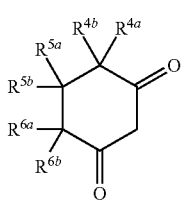
A

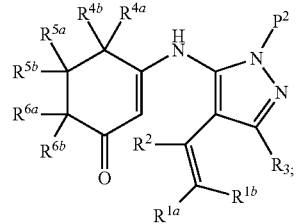
N deprotecting the secondary amino group the compound of formula N, or salt thereof, to provide a compound of formula F, or a salt thereof:

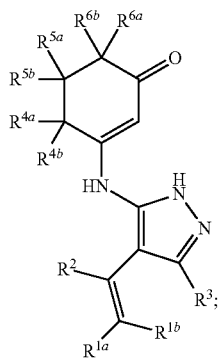
F cyclizing the compound of formula F, or salt thereof, under suitable conditions to provide the compound of formula I', or salt thereof, wherein:

$R^{1a}$ and $R^{1b}$ are independently selected from the group consisting of hydrogen and optionally substituted aliphatic, or $R^{1a}$ and $R^{1b}$ are taken together with their intervening atoms to form an optionally substituted 3- to 7-membered saturated or unsaturated carbocyclic or heterocyclic ring, wherein the ring formed by $R^{1a}$ and $R^{1b}$ may be optionally fused to an aryl or heteroaryl ring;

$R^2$ is selected from the group consisting of hydrogen, optionally substituted aliphatic, optionally substituted aryl, and optionally substituted heteroaryl, or $R^{1a}$ and $R^2$ are taken together with their intervening atoms to form an optionally substituted 3- to 7-membered saturated or unsaturated carbocyclic or heterocyclic ring, wherein the ring formed by $R^{1a}$ and $R^2$ may be optionally fused to an aryl or heteroaryl ring;

$R^3$ is selected from the group consisting of hydrogen, halo, —CN, —NO$_2$, optionally substituted aliphatic, optionally substituted phenyl, optionally substituted heterocyclyl, optionally substituted heteroaryl, —OR$^A$, —N(R$^B$)$_2$, —SR$^A$, —C(=O)R$^A$, —C(=O)OR$^A$, —C(=O)SR$^A$, —C(=O)N(R$^B$)$_2$, —OC(=O)R$^A$, —NR$^B$C(=O)R$^A$, —NR$^B$C(=O)N(R$^B$)$_2$, —OC(=O)N(R$^B$)$_2$, —NR$^B$C(=O)OR$^A$, —SC(=O)R$^A$, —C(=NR$^B$)R$^A$, —C(=NR$^B$)N(R$^B$)$_2$, —NR$^B$C(=NR$^B$)R$^B$, —C(=S)R$^A$, —C(=S)N(R$^B$)$_2$, —NR$^B$C(=S)R$^A$, —S(=O)R$^A$, —SO$_2$R$^A$, —NR$^B$SO$_2$R$^A$, and —SO$_2$N(R$^B$)$_2$;

each $R^A$ is independently selected from the group consisting of hydrogen, optionally substituted aliphatic, optionally substituted carbocyclyl, optionally substituted heterocyclyl, optionally substituted aryl, and optionally substituted heteroaryl;

each $R^B$ is independently selected from the group consisting of hydrogen, optionally substituted aliphatic, optionally substituted carbocyclyl, optionally substituted heterocyclyl, optionally substituted aryl, and optionally substituted heteroaryl, or two $R^B$ groups are taken together with their intervening atoms to form an optionally substituted heterocyclic ring;

$R^{4a}$ and $R^{4b}$ are independently selected from the group consisting of hydrogen, halo, —CN, —$OR^A$, —$N(R^B)_2$, and optionally substituted aliphatic, or $R^{4a}$ and $R^{4b}$ are taken together with their intervening atoms to form an optionally substituted 3- to 7-membered saturated carbocyclic or heterocyclic ring;

$R^{5a}$ and $R^{5b}$ are independently selected from the group consisting of hydrogen, halo, —CN, —$OR^A$, —$N(R^B)_2$, optionally substituted aliphatic, optionally substituted aryl, and optionally substituted heteroaryl, or $R^{5a}$ and $R^{5b}$ are taken together with their intervening atoms to form an optionally substituted 3- to 7-membered saturated carbocyclic or heterocyclic ring;

$R^{6a}$ and $R^{6b}$ are independently selected from the group consisting of hydrogen, halo, —CN, —$OR^A$, —$N(R^B)_2$, and optionally substituted aliphatic, or $R^{6a}$ and $R^{6b}$ are taken together with their intervening atoms to form an optionally substituted 3- to 7-membered saturated carbocyclic or heterocyclic ring;

each instance of $P^1$ is independently a nitrogen protecting group, or two instances of $P^1$ are joined to form an optionally substituted heterocyclic ring;

X is halogen;

$P^2$ is a nitrogen protecting group and is different from any instance of $P^1$;

$R^{2a}$ and $R^{2b}$ are independently selected from the group consisting of hydrogen and optionally substituted aliphatic; and each instance of $R^8$ is independently hydrogen, substituted or unsubstituted acyl, substituted or unsubstituted alkyl, substituted or unsubstituted carbocyclyl, substituted or unsubstituted heterocyclyl, substituted or unsubstituted aryl, or substituted or unsubstituted heteroaryl, or two instances of $R^8$ are joined to form a substituted or unsubstituted heterocyclic ring.

Embodiment 82

The method of embodiment 79, wherein $R^1$ is hydrogen.

Embodiment 83

The method of embodiment 80 or 81, wherein $R^{1a}$ and $R^{1b}$ are each hydrogen.

Embodiment 84

The method of any one of embodiments 79-83, wherein $R^3$ is hydrogen, fluorine, chlorine, or methyl.

Embodiment 85

The method of any one of embodiments 79-84, wherein $R^{4a}$, $R^{4b}$, $R^{6a}$, and $R^{6b}$ are each hydrogen.

Embodiment 86

The method of any one of embodiments 81 and 83-85, wherein X is iodine or bromine.

Embodiment 87

The method of any one of embodiments 81 and 83-86, wherein two instances of $R^8$ are each hydrogen, or two instances of $R^8$ are joined to form a heterocyclic ring of the formula:

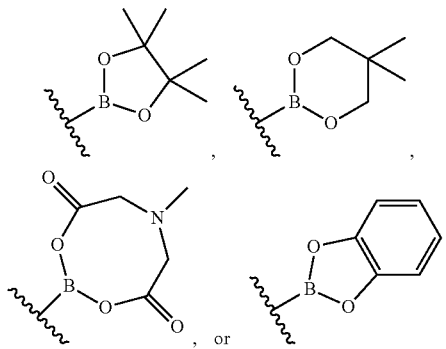

Embodiment 88

The method of any one of embodiments 79-87, wherein the suitable conditions comprise the presence of an acid or a temperature of at least about 25° C., or a combination thereof.

Examples

In order that the invention described herein may be more fully understood, the following examples are set forth. It should be understood that these examples are for illustrative purposes only and are not to be construed as limiting this invention in any manner.

A library of over three hundred twenty thousand compounds was screened against human GSK3β. Among the inhibitors identified, Compound 1 showed decent potency and excellent selectivity inhibiting only four other kinases out of over three hundred kinases at 10 μM by over fifty percent. Subsequent chemical modifications of Compound 1, guided by a co-crystal structure with GSK3β, and a battery of biochemical and cell-based assays led to Compound 54 that inhibits GSK3β with an $IC_{50}$ between 10-30 nM. Compound 54 has a superior kinome-wide selectivity profile compared to CHIR99021. Further, Compound 54 demonstrates excellent cellular activity in inhibiting GSK3β-mediated Tau phosphorylation in SH-SY5Y neuroblastoma cells ($IC_{50}$ of 1 μM), and in relieving negative regulation by GSK3β on cellular β-catenin degradation and TCF/LEF promoter activities with $EC_{50}$ of 5 μM in both assays. At the same time, no cellular toxicity by Compound 54 was observed in SH-SY5Y cells at the highest testing concentration of 30 μM. Taken together, Compound 54 is a potent and highly selective small molecular probe against GSK3β, allowing better investigation and interpretation of GSK3β cellular functions previously known inhibitors. Compound 54 scaffold also holds the promise to deliver additional compounds with further improved biochemical, cellular, and pharmacokinetic properties suitable for investigating in vivo roles of GSK3β in pertinent animal physiology and pathology.

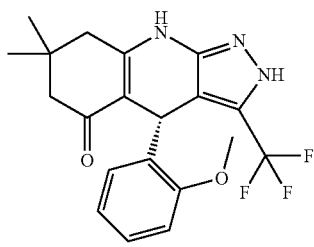

Compound 54

| Compound number | Target Name | Target IC$_{50}$ (nM) | Anti-target Name | Anti-target IC$_{50}$ (μM) | Fold Selective | Phospho-Tau ELISA in SHSY5Y Cells (IC$_{50}$, μM) |
|---|---|---|---|---|---|---|
| 54 | GSK3β | 24 | CDK5 | 8.9 | 380 | 1.03 |

Synthetic Methods

General Details.

All oxygen and/or moisture-sensitive reactions were carried out under nitrogen (N$_2$) atmosphere in glassware that had been flame-dried under vacuum (approximately 0.5 mm Hg) and purged with N$_2$ prior to use. All reagents and solvents were purchased from commercial vendors and used as received, or synthesized according to methods already reported. NMR spectra were recorded on a Bruker 300 (300 MHz $^1$H, 75 MHz $^{13}$C) or Varian UNITY INOVA 500 (500 MHz $^1$H, 125 MHz $^{13}$C) spectrometer. Proton and carbon chemical shifts are reported in ppm (δ) referenced to the NMR solvent. Data are reported as follows: chemical shifts, multiplicity (br=broad, s=singlet, d=doublet, t=triplet, q=quartet, m=multiplet; coupling constant(s) in Hz).

Unless otherwise indicated, NMR data were collected at 25° C. Flash chromatography was performed using 40-60 μm Silica Gel (60 Å mesh) on a Teledyne Isco Combiflash R$_f$. Tandem Liquid Chromatography/Mass Spectrometry (LC/MS) was performed on a Waters 2795 separations module and 3100 mass detector. Analytical thin layer chromatography (TLC) was performed on EM Reagent 0.25 mm silica gel 60-F plates. Visualization was accomplished with ultraviolet (UV) light and aqueous potassium permanganate (KMnO$_4$) stain followed by heating. High-resolution mass spectra were obtained at the MIT Mass Spectrometry Facility (Bruker Daltonics APEXIV 4.7 Tesla Fourier Transform Ion Cyclotron Resonance Mass Spectrometer).

In Synthesis Protocol A (Scheme 1a), 1,3-dione (1.0 equivalents), aldehyde (1.0 equivalents) and amine (1.35 equivalents) were dissolved in ethanol (0.4 M) and mixture was heated at 150° C. in the microwave for 15 minutes. The reaction mixture was cooled and ethanol was evaporated. The crude reaction mixture was purified by column chromatography on silica (ISCO).

Scheme 1a. Synthesis Protocol A

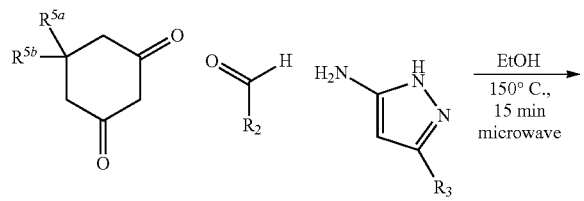

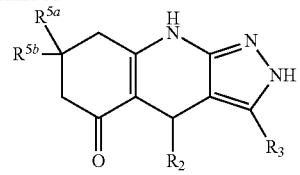

4-(2-methoxyphenyl)-7,7-dimethyl-3-(trifluoromethyl)-6,7,8,9-tetrahydro-2H-pyrazolo[3,4-b]quinolin-5(4H)-one

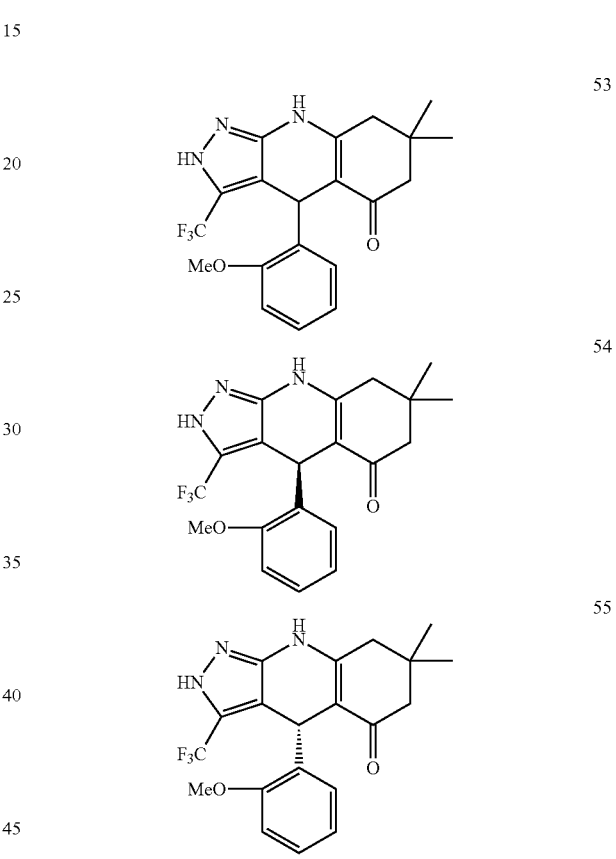

5,5-Dimethylcyclohexane-1,3-dione (824 mg, 5.88 mmol), 2-methoxybenzaldehyde (800 mg, 5.88 mmol) and 3-(trifluoromethyl)-1H-pyrazol-5-amine (1199 mg, 7.93 mmol) were mixed together in a microwave vial and ethanol (14.7 mL, 0.4 M) was added to it. The reaction mixture was heated in microwave for 15 min at 150° C. The mixture was cooled and the solvent was evaporated. The resultant mixture was then purified by column chromatography over silica gel (hexane/ethyl acetate: 100/0 to 20/80) to afford the desired product as a white solid (372.0 mg). $^1$H NMR (300 MHz, MeOD) δ 7.19 (d, J=7.4 Hz, 1H), 7.12-7.03 (m, 1H), 6.78 (dd, J=13.8, 7.4 Hz, 2H), 5.39 (s, 1H), 3.67 (s, 3H), 2.56 (d, J=16.8 Hz, 1H), 2.42 (d, J=16.7 Hz, 1H), 2.24 (d, J=16.5 Hz, 1H), 2.04 (d, J=16.5 Hz, 1H), 1.08 (s, 3H), 0.97 (s, 3H). LRMS (ESI+) (M+): 391.82.

The racemic mixture was separated by chiral HPLC to provide (R)-4-(2-methoxyphenyl)-7,7-dimethyl-3-(trifluoromethyl)-6,7,8,9-tetrahydro-2H-pyrazolo[3,4-b]quinolin-5 (4H)-one (Compound 54) and (S)-4-(2-methoxyphenyl)-7, 7-dimethyl-3-(trifluoromethyl)-6,7,8,9-tetrahydro-2H-pyrazolo[3,4-b]quinolin-5(4H)-one (Compound 55).

In Synthesis Protocol B, 1,3-dione (1.0 equivalents) was dissolved in trifluoroacetic acid (0.45 M) followed by addition of ketone (10.0 equivalents) in one portion. The reaction was refluxed for at 190° C. 3 hours, followed by addition of amine (1.5 equivalents) and continued reflux for additional 2.5 hours at 190° C. The reaction mixture was cooled and evaporated (to remove TFA). The crude reaction mixture was purified by HPLC.

In a 25 mL rb flask, 5,5-dimethylcyclohexane-1,3-dione (1402.0 mg, 10.0 mmol, 1.0 equivalent) was dissolved in trifluoroacetic acid (10.0 mL, 0.47 molar), followed by addition of acetophenone (11.44 mL, 100.0 mmol, 10.0 equivalent) in one portion. The reaction was refluxed for 3 hours at 190° C., followed by addition of 3-(trifluoromethyl)-1H-pyrazol-5-amine (1511.0 mg, 10.0 mmol, 1.5 equivalent) and continued reflux for additional 2.5 hours at 190° C. The reaction mixture was cooled and evaporated to remove TFA. The crude reaction mixture was purified by HPLC to afford the desired product as a white solid (17.0 mg). $^1$H NMR (300 MHz, DMSO) δ 7.24 (d, J=7.6 Hz, 2H), 7.14 (t, J=7.6 Hz, 2H), 6.99 (t, J=7.1 Hz, 1H), 2.43 (d, J=4.7 Hz, 2H), 2.01 (d, J=15.8 Hz, 1H), 1.92 (s, 3H), 1.86 (d, J=15.8 Hz, 1H), 0.99 (s, 3H), 0.92 (s, 3H). LRMS (ESI+) (M+H): 376.24, retention time 0.67 min.

The racemic mixture was separated by chiral HPLC to provide Compound 70 or Compound 71.

7,7-dimethyl-4-phenyl-3-(trifluoromethyl)-6,7,8,9-tetrahydro-2H-pyrazolo[3,4-b]quinolin-5(4H)-one

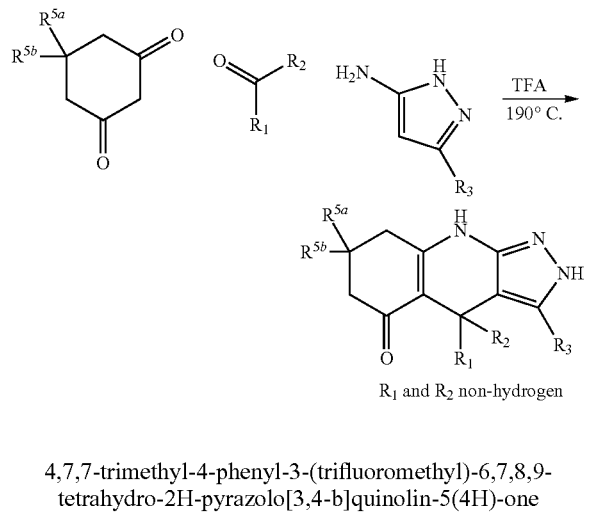

4,7,7-trimethyl-4-phenyl-3-(trifluoromethyl)-6,7,8,9-tetrahydro-2H-pyrazolo[3,4-b]quinolin-5(4H)-one

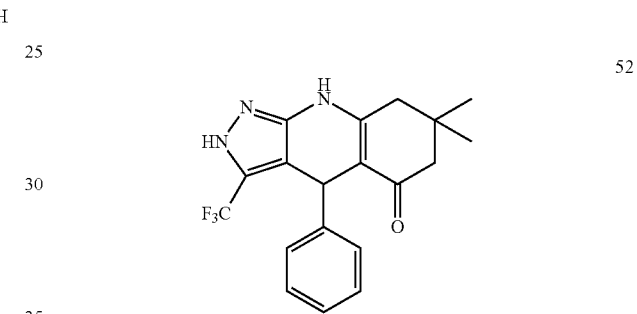

$^1$H NMR (300 MHz, d$^6$-DMSO) δ 10.14 (s, 1H), 7.23-7.12 (m, 2H), 7.12-7.00 (m, 3H), 5.07 (s, 1H), 2.56-2.35 (m, 2H), 2.15-2.09 (m, 1H), 1.95-1.90 (m, 1H), 1.01 (s, 3H), 0.88 (s, 3H). LRMS (ESI+): 362 ([M+H]+), retention time 0.62 min.

3,7,7-trimethyl-4-(thiophen-2-yl)-6,7,8,9-tetrahydro-1H-pyrazolo[3,4-b]quinolin-5(4H)-one

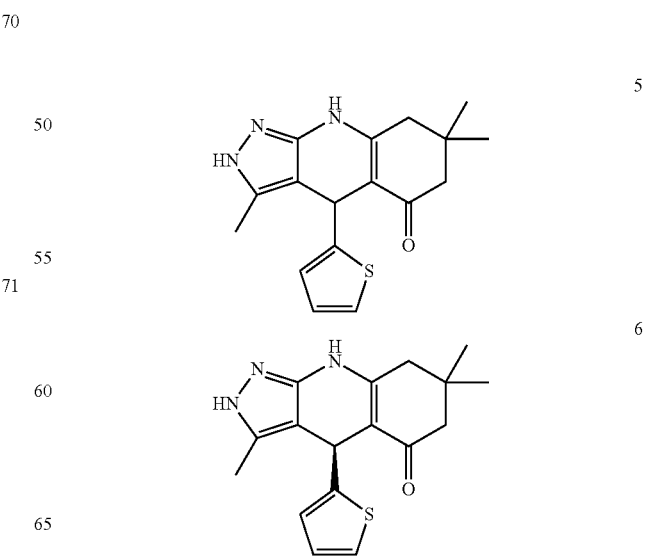

-continued

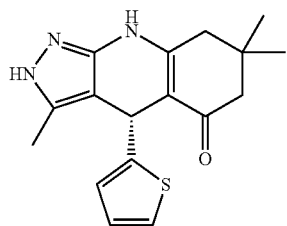

7

¹H NMR (300 MHz, d⁶-DMSO) δ 11.63 (s, 1H), 9.54 (s, 1H), 6.9 (d, J=3.0 Hz, 1H), 6.57 (t, J=3.0, 6.0 Hz, 1H), 6.51 (d, J=3.0 Hz, 1H), 5.07 (s, 1H), 2.18-2.08 (m, 2H), 1.95-1.76 (m, 2H), 1.90 (s, 3H), 0.77 (s, 3H), 0.75 (s, 3H). LRMS (ESI+): 314 ([M+H]+), retention time 0.57 min. The racemic mixture was separated by chiral HPLC to provide Compound 6 and Compound 7.

3,7,7-trimethyl-4-(thiophen-3-yl)-6,7,8,9-tetrahydro-1H-pyrazolo[3,4-b]quinolin-5(4H)-one

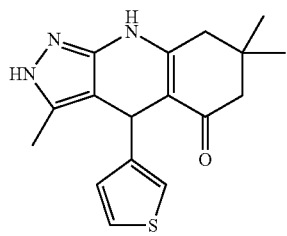

8

¹H NMR (300 MHz, d⁶-DMSO) δ 11.77 (s, 1H), 9.68 (s, 1H), 7.26 (s, 1H), 6.95 (d, J=3.0 Hz, 1H), 6.78 (d, J=3.0 Hz, 1H), 5.09 (s, 1H), 2.49-2.33 (m, 2H), 2.17-2.08 (m, 2H), 2.0 (s, 3H), 1.00 (s, 3H), 0.94 (s, 3H). LRMS (ESI+): 314 ([M+H]+), retention time 0.57 min.

4-(5-chlorothiophen-2-yl)-3,7,7-trimethyl-6,7,8,9-tetrahydro-1H-pyrazolo[3,4-b]quinolin-5(4H)-one

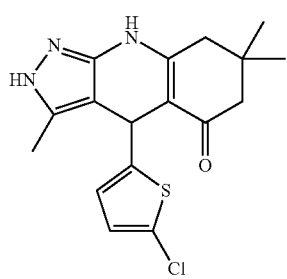

9

¹H NMR (300 MHz, d⁶-DMSO) δ 11.71 (s, 1H), 9.62 (s, 1H), 6.54 (d, J=3.0 Hz, 1H), 6.3 (d, J=3.0 Hz, 1H), 4.99 (s, 1H), 2.3-2.07 (m, 2H), 1.9 (s, 3H), 1.95-1.81 (m, 2H), 0.75 (s, 3H), 0.73 (s, 3H). LRMS (ESI+): 348 ([M+H]+), retention time 0.64 min.

4-(2-fluorophenyl)-3,7,7-trimethyl-6,7,8,9-tetrahydro-1H-pyrazolo[3,4-b]quinolin-5(4H)-one

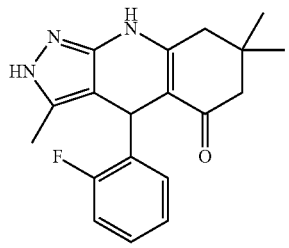

10

¹H NMR (300 MHz, d⁶-DMSO) δ 11.77 (s, 1H), 9.76 (s, 1H), 7.10-7.01 (m, 4H), 5.18 (s, 1H), 2.45-2.32 (m, 2H), 2.15-1.95 (m, 2H), 1.88 (s, 1H), 1.01 (s, 3H), 0.96 (s, 3H). LRMS (ESI+): 327 ([M+H]+), retention time 0.59 min.

4-(3-fluorophenyl)-3,7,7-trimethyl-6,7,8,9-tetrahydro-1H-pyrazolo[3,4-b]quinolin-5(4H)-one

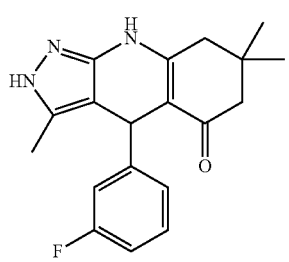

11

¹H NMR (300 MHz, d⁶-DMSO) δ 11.8 (s, 1H), 9.76 (s, 1H), 7.23 (m, 1H), 6.95 (d, J=9.0 Hz, 1H), 6.90-6.84 (m, 2H), 4.97 (s, 1H), 2.44-2.37 (m, 2H), 2.15-1.93 (m, 2H), 1.91 (s, 3H), 1.00 (s, 3H), 0.94 (s, 3H). LRMS (ESI+): 327 ([M+H]+), retention time 0.61 min.

4-(4-fluorophenyl)-3,7,7-trimethyl-6,7,8,9-tetrahydro-1H-pyrazolo[3,4-b]quinolin-5(4H)-one

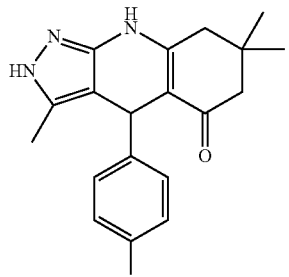

12

¹H NMR (300 MHz, d⁶-DMSO) δ 11.77 (s, 1H), 9.73 (s, 1H), 7.13 (d, J=6.0 Hz, 2H), 6.99 (d, J=6.0 Hz, 2H), 4.94 (s, 1H), 2.43-2.35 (m, 2H), 2.14-1.91 (m, 2H), 1.89 (s, 3H), 1.00 (s, 3H), 0.93 (s, 3H). LRMS (ESI+): 327 ([M+H]+), retention time 0.60 min.

4-(3-chlorophenyl)-3,7,7-trimethyl-6,7,8,9-tetrahydro-1H-pyrazolo[3,4-b]quinolin-5(4H)-one

14

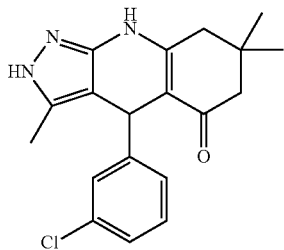

¹H NMR (300 MHz, d⁶-DMSO) δ 11.57 (s, 1H), 9.54 (s, 1H), 7.00-6.95 (m, 1H), 6.87-6.83 (m, 3H) 4.7 (s, 1H), 2.25-2.12 (m, 2H), 1.91-1.69 (m, 2H), 1.66 (s, 3H), 0.76 (s, 3H), 0.69 (s, 3H). LRMS (ESI+): 342 ([M+H]+), retention time 0.62 min.

4-(4-chlorophenyl)-3,7,7-trimethyl-6,7,8,9-tetrahydro-1H-pyrazolo[3,4-b]quinolin-5(4H)-one

15

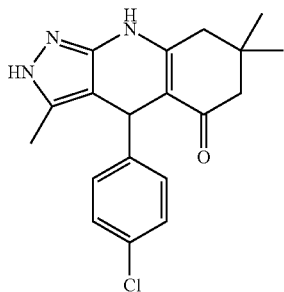

¹H NMR (300 MHz, d⁶-DMSO) δ 11.60 (s, 1H), 9.57 (s, 1H), 7.05 (d, J=9.0 Hz, 2H), 6.95 (d, J=9.0 Hz, 2H), 4.74 (s, 1H), 2.25-2.22 (m, 2H), 1.95-1.72 (m, 2H), 1.70 (s, 3H), 0.81 (s, 3H), 0.74 (s, 3H). LRMS (ESI+): 342 ([M+H]+), retention time 0.64 min.

3,7,7-trimethyl-4-(p-tolyl)-6,7,8,9-tetrahydro-1H-pyrazolo[3,4-b]quinolin-5(4H)-one

19

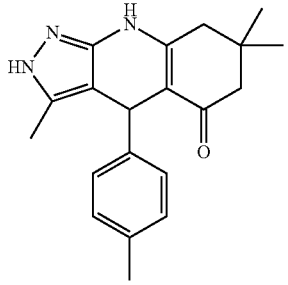

¹H NMR (300 MHz, d⁶-DMSO) δ 11.65 (s, 1H), 9.61 (s, 1H), 6.99 (m, 4H), 4.89 (s, 1H), 2.44-2.30 (m, 2H), 2.25 (s, 3H), 2.24-2.19 (m, 2H), 2.18 (s, 3H), 1.00 (s, 3H), 0.95 (s, 3H). LRMS (ESI+): 322 ([M+H]+), retention time 0.62 min.

4-(2-methoxyphenyl)-3,7,7-trimethyl-6,7,8,9-tetrahydro-1H-pyrazolo[3,4-b]quinolin-5(4H)-one

20

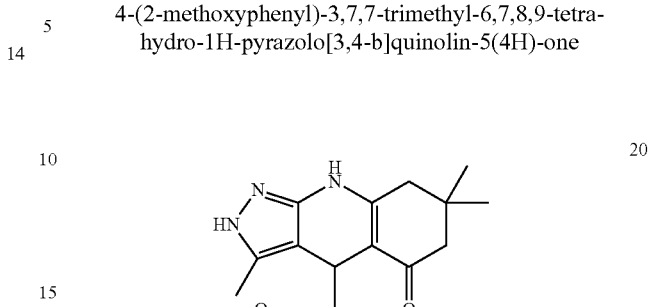

22

21

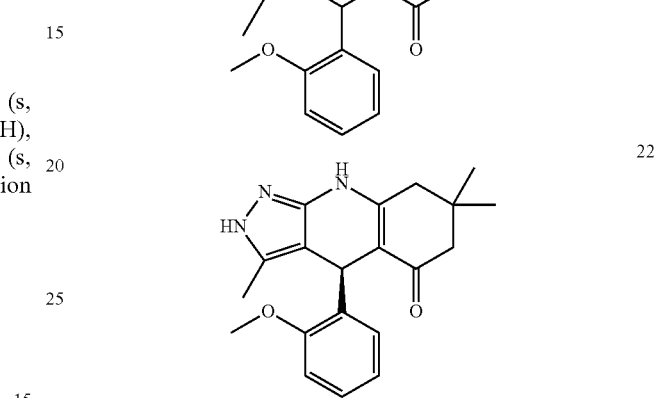

¹H NMR (300 MHz, DMSO) δ 11.39 (s, 1H), 9.38 (s, 1H), 6.79 (t, J=6.0, 15.0 Hz, 1H), 6.70 (d, J=6.0 Hz, 1H), 6.65 (d, J=9.0 Hz, 1H), 6.52 (t, J=6.0, 15.0 Hz, 1H), 5.08 (s, 1H), 3.6 (s, 3H), 2.22-2.14 (m, 2H), 1.90-1.71 (m, 2H), 1.67 (s, 3H), 0.78 (s, 3H), 0.75 (s, 3H). LRMS (ESI+): 339 ([M+H]+), retention time 0.58-0.59 min.

4-(3-methoxyphenyl)-3,7,7-trimethyl-6,7,8,9-tetrahydro-1H-pyrazolo[3,4-b]quinolin-5(4H)-one

23

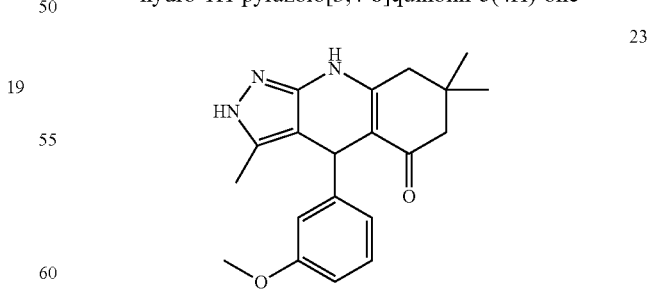

¹H NMR (300 MHz, d⁶-DMSO) δ 11.5 (s, 1H), 9.45 (s, 1H), 6.85 (t, J=6.0, 15.0 Hz, 1H), 6.48-6.37 (m, 3H), 4.66 (s, 1H), 3.43 (s, 3H), 2.21-2.12 (m, 2H), 1.92-1.71 (m, 2H), 1.69 (s, 3H), 0.77 (s, 3H), 0.72 (s, 3H). LRMS (ESI+): 339 ([M+H]+), retention time 0.59 min.

4-(4-methoxyphenyl)-3,7,7-trimethyl-6,7,8,9-tetra-
hydro-1H-pyrazolo[3,4-b]quinolin-5(4H)-one

24

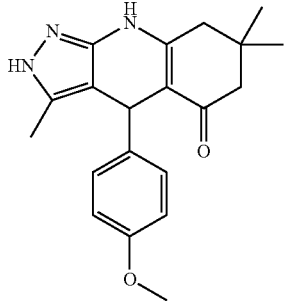

$^1$H NMR (300 MHz, d$^6$-DMSO) δ 11.71 (s, 1H), 9.65 (s, 1H), 7.2 (d, J=9.0 Hz, 2H), 6.72 (d, J=9.0 Hz, 2H), 4.87 (s, 1H), 3.66 (s, 3H), 2.42-2.34 (m, 2H), 2.13-1.96 (m, 2H), 1.89 (s, 3H), 1.00 (s, 3H), 0.93 (s, 3H). LRMS (ESI+): 339 ([M+H]+), retention time 0.58 min.

4-(benzo[d][1,3]dioxol-5-yl)-3,7,7-trimethyl-6,7,8,9-
tetrahydro-1H-pyrazolo[3,4-b]quinolin-5(4H)-one

26

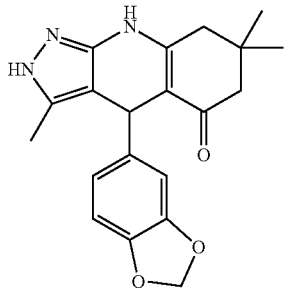

$^1$H NMR (300 MHz, d$^6$-DMSO) δ 11.75 (s, 1H), 6.70 (d, J=9.0 Hz, 1H), 6.59 (m, 2H), 5.90 (d, J=6.0 Hz, 2H), 4.86 (s, 1H), 2.42-2.35 (m, 2H), 2.14-1.95 (m, 2H), 1.92 (s, 3H), 1.00 (s, 3H), 0.94 (s, 3H). LRMS (ESI+): 352 ([M+H]+), retention time 0.57 min.

4-(2-chloro-4-fluorophenyl)-3,7,7-trimethyl-6,7,8,9-
tetrahydro-1H-pyrazolo[3,4-b]quinolin-5(4H)-one

35

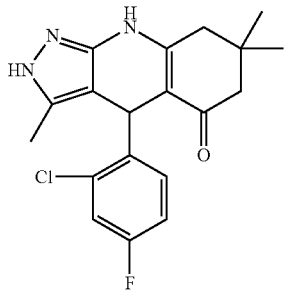

$^1$H NMR (300 MHz, d$^6$-DMSO) δ 11.56 (s, 1H), 9.56 (s, 1H), 6.97 (m, 1H), 6.83 (m, 2H), 5.06 (s, 1H), 2.20-2.11 (m, 2H), 1.88-1.69 (m, 2H), 1.63 (s, 3H), 0.76 (s, 3H), 0.70 (s, 3H). LRMS (ESI+): 360 ([M+H]+), retention time 0.64 min.

3,7,7-trimethyl-4-(pyridin-2-yl)-6,7,8,9-tetrahydro-
1H-pyrazolo[3,4-b]quinolin-5(4H)-one

36

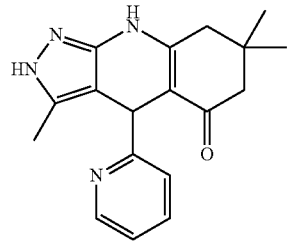

$^1$H NMR (300 MHz, d$^6$-DMSO) δ 11.52 (s, 1H), 9.51 (s, 1H), 8.17 (d, J=3.0 Hz, 1H), 7.41 (t, J=6.0 Hz, 15.0 Hz, 1H), 6.95 (d, J=9.0 Hz, 1H), 6.87 (t, J=6.0, 12.0 Hz, 1H), 4.89 (s, 1H), 2.31-2.26 (m, 2H), 1.97-1.76 (m, 5H), 0.83 (s, 6H). LRMS (ESI+): 310 ([M+H]+), retention time 0.50 min.

3,7,7-trimethyl-4-(pyridin-3-yl)-6,7,8,9-tetrahydro-
1H-pyrazolo[3,4-b]quinolin-5(4H)-one

37

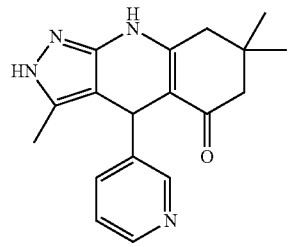

$^1$H NMR (300 MHz, d$^6$-DMSO) δ 11.64 (s, 1H), 9.62 (s, 1H), 8.20 (s, 1H), 8.06 (d, J=6.0 Hz, 1H), 7.25 (d, J=9.0 Hz, 1H), 7.01 (t, J=6.0, 12.0 Hz, 1H), 5.57 (s, 1H), 2.26-2.22 (m, 2H), 1.96-1.73 (m, 2H), 1.69 (s, 3H), 0.81 (s, 3H), 0.73 (s, 3H). LRMS (ESI+): 310 ([M+H]+), retention time 0.49 min.

3,7,7-trimethyl-4-(pyridin-4-yl)-6,7,8,9-tetrahydro-
1H-pyrazolo[3,4-b]quinolin-5(4H)-one

38

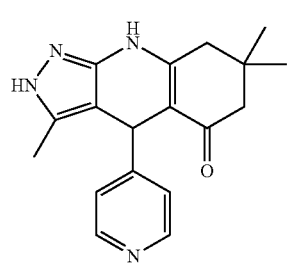

¹H NMR (300 MHz, d⁶-DMSO) δ 11.61 (s, 1H), 9.6 (s, 1H), 8.12 (d, J=6.0 Hz, 2H), 6.88 (d, J=6.0 Hz, 2H), 4.7 (s, 1H), 2.21-2.14 (m, 2H), 1.92-1.70 (m, 2H), 1.66 (s, 3H), 0.77 (s, 3H), 0.71 (s, 3H). LRMS (ESI+): 310 ([M+H]+), retention time 0.48 min.

4-(5-bromopyridin-2-yl)-3,7,7-trimethyl-6,7,8,9-tetrahydro-1H-pyrazolo[3,4-b]quinolin-5(4H)-one

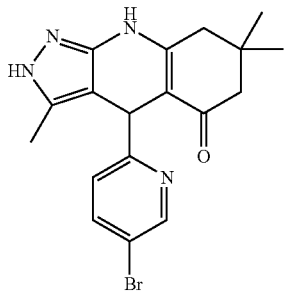

¹H NMR (300 MHz, d⁶-DMSO) δ 11.52 (s, 1H), 9.51 (s, 1H), 8.23 (s, 1H), 7.61 (d, J=9.0 Hz, 1H), 6.92 (d, J=9.0 Hz, 1H), 4.83 (s, 1H), 2.20-2.17 (m, 2H), 1.91-1.71 (m, 2H), 1.69 (s, 3H), 0.77 (s, 3H), 0.75 (s, 3H). LRMS (ESI+): 389 ([M+H]+), retention time 0.57 min.

3,7,7-trimethyl-4-(1H-pyrazol-5-yl)-6,7,8,9-tetrahydro-1H-pyrazolo[3,4-b]quinolin-5(4H)-one

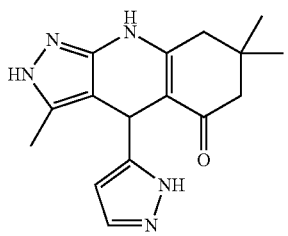

¹H NMR (300 MHz, d⁶-DMSO) δ 12.20-11.40 (m, 1H), 9.60-9.25 (m, 1H), 7.25-6.80 (m, 1H), 5.70-5.30 (m, 1H), 4.90-4.75 (m, 1H), 2.20 (br s, 3H), 2.00-1.75 (m, 4H), 0.80-0.70 (br s, 6H). LRMS (ESI+): 299 ([M+H]+), retention time 0.45 min.

4-(2-chlorophenyl)-3,7,7-trimethyl-6,7,8,9-tetrahydro-2H-pyrazolo[3,4-b]quinolin-5(4H)-one

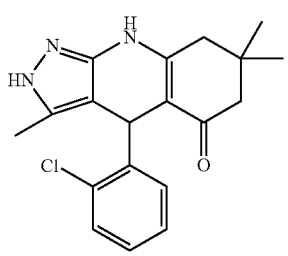

¹H NMR (300 MHz, d⁶-DMSO) δ 11.77 (s, 1H), 9.77 (s, 1H), 7.27 (d, J=7.6, 1H), 7.19-7.02 (m, 3H), 5.34 (s, 1H), 2.48-2.23 (m, 2H), 2.17-2.04 (m, 1H), 1.88 (s, 3H), 1.96-1.81 (m, 1H), 1.01 (s, 3H), 0.95 (s, 3H); LRMS (ESI+): 342 ([M+H]+), retention time 0.61 min.

3,7,7-trimethyl-4-(o-tolyl)-6,7,8,9-tetrahydro-2H-pyrazolo[3,4-b]quinolin-5(4H)-one

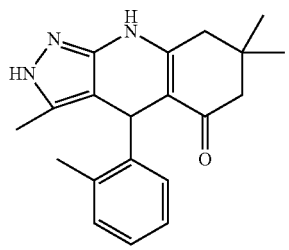

¹H NMR (300 MHz, d⁶-DMSO) δ 11.70 (s, 1H), 9.69 (s, 1H), δ 6.98 (t, J=6.9 Hz, 2H), 6.93-6.87 (m, 2H), 5.05 (s, 1H), 3.17 (d, J=5.2, 3H), 2.49-2.31 (m, 2H), 2.15-2.03 (m, 1H), 1.96-1.85 (m, 1H), 1.79 (s, 3H), 1.00 (s, 1H), 0.91 (s, 1H); LRMS (ESI+): 322 ([M+H]+), retention time 0.62 min.

3,7,7-trimethyl-4-(4-(trifluoromethyl)phenyl)-6,7,8,9-tetrahydro-2H-pyrazolo[3,4-b]quinolin-5(4H)-one

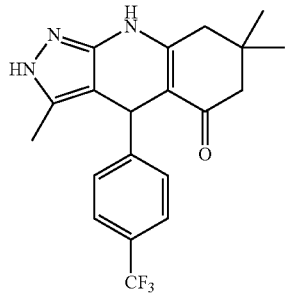

¹H NMR (300 MHz, d⁶-DMSO) δ 11.83 (s, 1H), 9.83 (s, 1H), 7.56 (d, J=8.1, 2H), 7.34 (d, J=8.0, 2H), 5.03 (s, 1H), 2.49-2.35 (m, 2H), 2.17-2.08 (m, 1H), 1.98-1.90 (m, 1H), 1.88 (s, 3H), 1.00 (s, 3H), 0.93 (s, 3H); LRMS (ESI+): 376 ([M+H]+), retention time 0.68 min.

3,4,7,7-tetramethyl-6,7,8,9-tetrahydro-2H-pyrazolo[3,4-b]quinolin-5(4H)-one

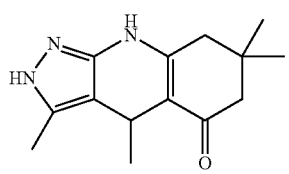

$^1$H NMR (300 MHz, d$^6$-DMSO) δ 11.70 (s, 1H), 9.45 (s, 1H), δ 3.84 (q, J=6.4 Hz, 1H), 2.29 (s, 2H), 2.12 (s, 3H), 2.09 (d, J=3.6 Hz, 2H), 1.03 (d, J=6.4 Hz, 3H), 1.00 (s, 3H), 0.98 (s, 3H); LRMS (ESI+): 246 ([M+H]+), retention time 0.52 min.

4-cyclohexyl-3,7,7-trimethyl-6,7,8,9-tetrahydro-2H-pyrazolo[3,4-b]quinolin-5(4H)-one

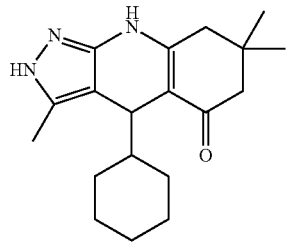

44

$^1$H NMR (300 MHz, d$^6$-DMSO) δ 11.72 (s, 1H), 9.40 (s, 1H), 3.76 (s, 1H), δ 2.37-2.38 (m, 2H), 2.20-2.04 (m, 5H), 1.71-1.39 (m, 6H), 1.39-1.20 (m, 2H), 1.02 (s, 3H), 0.99 (s, 3H), 0.63-0.46 (m, 2H); LRMS (ESI+): 314 ([M+H]+), retention time 0.65 min.

4-deutero-3,7,7-trimethyl-4-phenyl-6,7,8,9-tetrahydro-2H-pyrazolo[3,4-b]quinolin-5(4H)-one

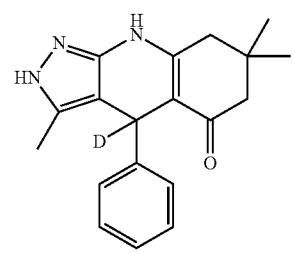

4

$^1$H NMR (300 MHz, d$^6$-DMSO) δ 11.73 (s, 1H), 9.70 (s, 1H), δ 7.21-7.09 (m, 4H), 7.03 (t, J=6.9 Hz, 1H), 2.47-2.33 (m, 2H), 2.18-2.06 (m, 1H), 1.99-1.85 (m, 4H), 1.00 (s, 3H), 0.94 (s, 3H); LRMS (ESI+): 309 ([M+H]+), retention time 0.59 min.

4-cyclopropyl-3,7,7-trimethyl-6,7,8,9-tetrahydro-2H-pyrazolo[3,4-b]quinolin-5(4H)-one

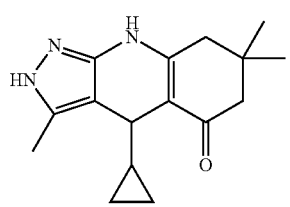

43

$^1$H NMR (300 MHz, d$^6$-DMSO) δ 11.80 (s, 1H), 9.44 (s, 1H), δ 3.91 (d, J=5.6 Hz, 1H), 2.35-2.28 (m, 2H), 2.19-2.06 (m, 5H), 1.03 (s, 3H), 0.99 (s, 3H), 0.96-0.87 (m, 1H), 0.20-0.02 (m, 3H), −0.12--0.22 (m, 1H); LRMS (ESI+): 272 ([M+H]+), retention time 0.56 min.

3,7,7-trimethyl-4-(m-tolyl)-6,7,8,9-tetrahydro-2H-pyrazolo[3,4-b]quinolin-5(4H)-one

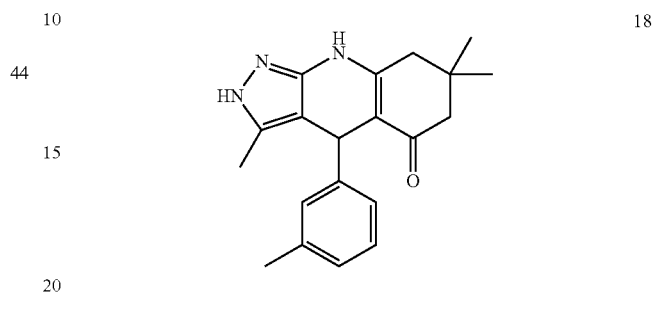

18

$^1$H NMR (300 MHz, d$^6$-DMSO) δ 11.72 (s, 1H), 9.67 (s, 1H), 7.09-7.01 (m, 1H), 6.94-6.82 (m, 3H), 4.87 (s, 1H), 2.46-2.33 (m, 2H), 2.20 (s, 3H), 2.16-2.04 (m, 1H), 2.01-1.83 (m, 4H), 1.00 (s, 3H), 0.95 (s, 3H); LRMS (ESI+): 322 ([M+H]+), retention time 0.61 min.

4-(2-methoxyphenyl)-3,6,6-trimethyl-6,7,8,9-tetrahydro-2H-pyrazolo[3,4-b]quinolin-5(4H)-one

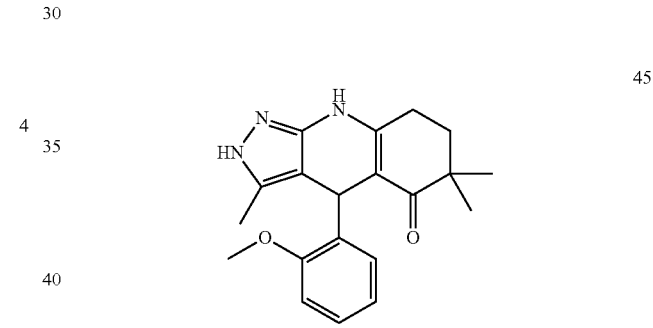

45

$^1$H NMR (300 MHz, d$^6$-DMSO) δ 11.60 (s, 1H), 9.54 (s, 1H), 7.05-6.98 (m, 1H), 6.92-6.84 (m, 2H), 6.77-6.69 (m, 1H), 5.31 (s, 1H), 3.82 (s, 3H), 2.30-2.24 (m, 2H), 1.91 (s, 3H), 1.79-1.70 (m, 2H), 0.94 (s, 3H), 0.85 (s, 3H); LRMS (ESI+): 338 ([M+H]+), retention time 0.62 min.

2-(3,7,7-trimethyl-5-oxo-4,5,6,7,8,9-hexahydro-2H-pyrazolo[3,4-b]quinolin-4-yl)benzonitrile

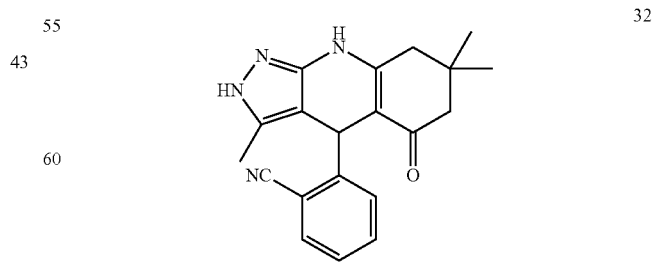

32

$^1$H NMR (300 MHz, DMSO) δ 11.74 (s, 1H), 9.70 (s, 1H), δ 7.21-6.99 (m, 4H), 4.91 (s, 1H), 2.46-2.33 (m, 2H), 2.16-2.07 (m, 1H), 1.98-1.85 (m, 4H), 1.00 (s, 1H), 0.94 (s, 1H); LRMS (ESI+): 333 ([M+H]+), retention time 0.57 min.

3-(3,7,7-trimethyl-5-oxo-4,5,6,7,8,9-hexahydro-2H-pyrazolo[3,4-b]quinolin-4-yl)benzonitrile

33

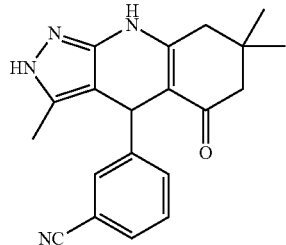

¹H NMR (300 MHz, DMSO) δ 11.89 (s, 1H), 9.93 (s, 1H), 7.69-7.63 (m, 1H), 7.56-7.48 (m, 1H), 7.29-7.18 (m, 2H), 5.23 (s, 1H), 2.48-2.33 (m, 2H), 2.18-2.05 (m, 1H), 1.97-1.80 (m, 4H), 1.01 (s, 3H), 0.95 (s, 3H); LRMS (ESI+): 333 ([M+H]+), retention time 0.58 min.

4-(3,7,7-trimethyl-5-oxo-4,5,6,7,8,9-hexahydro-2H-pyrazolo[3,4-b]quinolin-4-yl)benzonitrile

34

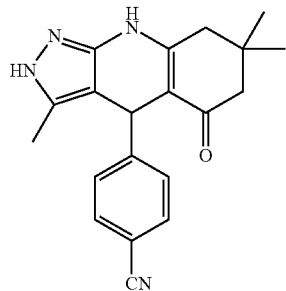

¹H NMR (300 MHz, DMSO) δ 11.84 (s, 1H), 9.84 (s, 1H), 7.66 (d, J=8.2 Hz, 2H), 7.32 (d, J=8.0 Hz, 2H), 5.05 (s, 1H), 2.44 (d, J=6.3 Hz, 2H), 2.12 (d, J=16.7 Hz, 1H), 1.94 (d, J=16.0 Hz, 1H), 1.87 (s, 3H), 1.00 (s, 3H), 0.92 (s, 3H); LRMS (ESI+): 333 ([M+H]+), retention time 0.54 min.

3,4,7,7-tetramethyl-4-phenyl-6,7,8,9-tetrahydro-2H-pyrazolo[3,4-b]quinolin-5(4H)-one

67

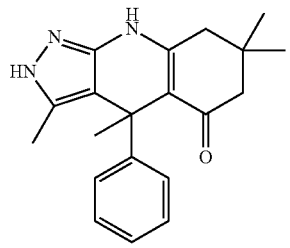

¹H NMR (300 MHz, DMSO) δ 11.69 (s, 1H), 9.69 (s, 1H), 7.27-7.22 (m, 1H), 7.08-6.92 (m, 3H), 5.44 (s, 1H), 2.48-2.32 (m, 2H), 2.16-2.04 (m, 1H), 1.95-1.84 (m, 4H), 1.00 (s, 3H), 0.95 (s, 3H).; LRMS (ESI+): 322 ([M+H]+), retention time 0.62 min.

4-(2-methoxyphenyl)-3-methyl-6,7,8,9-tetrahydro-2H-pyrazolo[3,4-b]quinolin-5(4H)-one

46

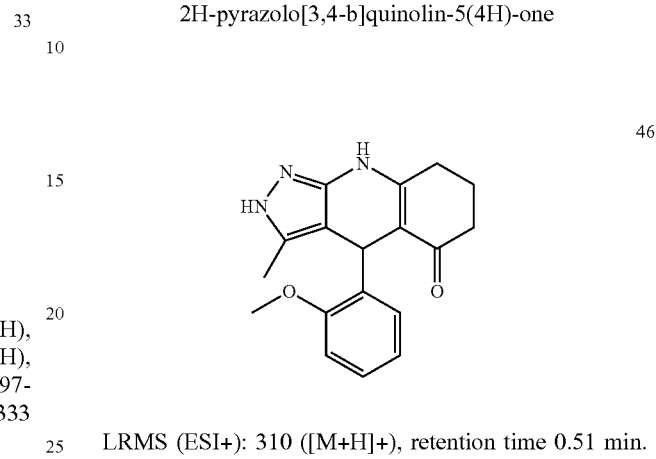

LRMS (ESI+): 310 ([M+H]+), retention time 0.51 min.

3,7,7-trimethyl-4-(2-(trifluoromethyl)phenyl)-6,7,8,9-tetrahydro-2H-pyrazolo[3,4-b]quinolin-5(4H)-one

27

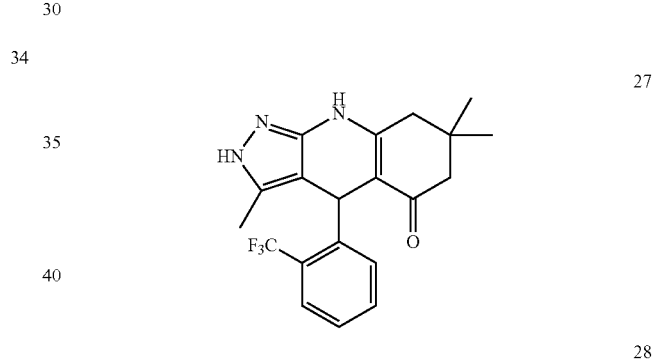

28

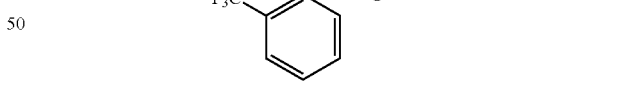

29

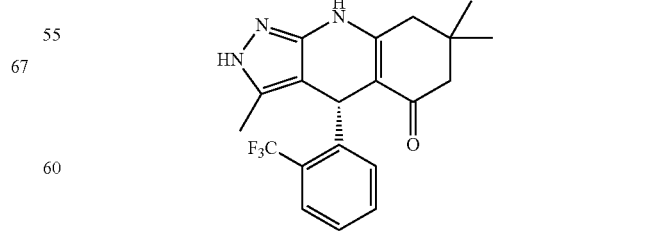

LRMS (ESI+): 376 ([M+H]+), retention time 0.64-0.66 min. The racemic mixture was separated by chiral HPLC to provide Compound 28 and Compound 29.

173

3,7,7-trimethyl-4-(3-(trifluoromethyl)phenyl)-6,7,8,
9-tetrahydro-2H-pyrazolo[3,4-b]quinolin-5(4H)-one

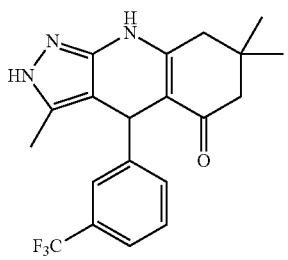

LRMS (ESI+): 376 ([M+H]+), retention time 0.66 min.

4-(2-methoxyphenyl)-7,7-dimethyl-6,7,8,9-tetra-
hydro-2H-pyrazolo[3,4-b]quinolin-5(4H)-one

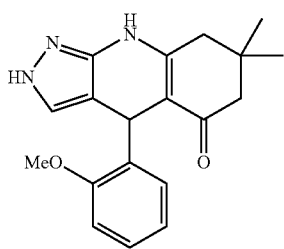

LRMS (ESI+): 324 ([M+H]+), retention time 0.57 min.

3-isopropyl-4-(2-methoxyphenyl)-7,7-dimethyl-6,7,
8,9-tetrahydro-2H-pyrazolo[3,4-b]quinolin-5(4H)-
one

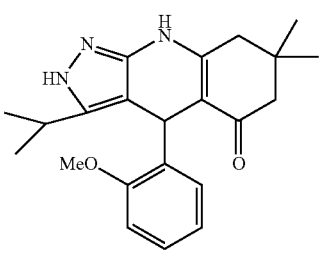

LRMS (ESI+): 366 ([M+H]+), retention time 0.63 min.

174

4-(2-methoxyphenyl)-7,7-dimethyl-3-phenyl-6,7,8,9-
tetrahydro-2H-pyrazolo[3,4-b]quinolin-5(4H)-one

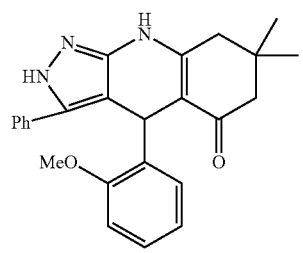

LRMS (ESI+): 400 ([M+H]+), retention time 0.67 min.

3-(tert-butyl)-4-(2-methoxyphenyl)-7,7-dimethyl-6,
7,8,9-tetrahydro-2H-pyrazolo[3,4-b]quinolin-5(4H)-
one

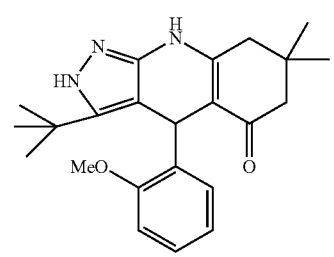

LRMS (ESI+): 380 ([M+H]+), retention time 0.65 min.

3-ethyl-4-(2-methoxyphenyl)-7,7-dimethyl-6,7,8,9-
tetrahydro-2H-pyrazolo[3,4-b]quinolin-5(4H)-one

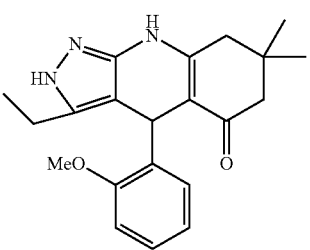

LRMS (ESI+): 352 ([M+H]+), retention time 0.62 min.

175

3,7,7-trimethyl-4-(2-(methylthio)phenyl)-6,7,8,9-tetrahydro-2H-pyrazolo[3,4-b]quinolin-5(4H)-one

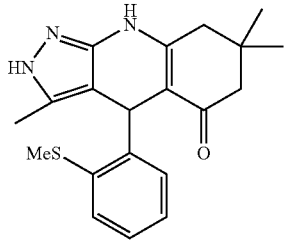

LRMS (ESI+): 354 ([M+H]+), retention time 0.62 min.

4-(benzo[c][1,2,5]oxadiazol-4-yl)-3,7,7-trimethyl-6,7,8,9-tetrahydro-2H-pyrazolo[3,4-b]quinolin-5(4H)-one

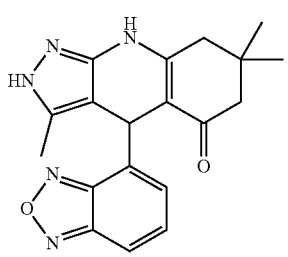

LRMS (ESI+): 350 ([M+H]+), retention time 0.54 min.

4'-(2-methoxyphenyl)-3'-methyl-4',6',8',9'-tetrahydrospiro[cyclohexane-1,7'-pyrazolo[3,4-b]quinolin]-5'(2'H)-one

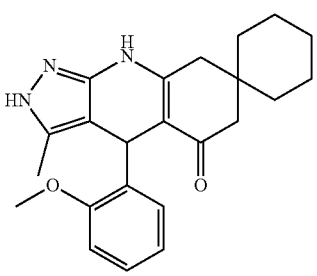

$^1$H NMR (300 MHz, d$^6$-DMSO) 9.57 (s, 1H), 7.06-6.97 (m, 1H), 6.94-6.83 (m, 2H), 6.78-6.69 (m, 1H), 5.27 (s, 1H), 3.78 (s, 3H), 2.62-2.40 (m, 4H), 2.07 (s, 2H), 1.88 (s, 3H), 1.50-1.26 (m, 10H). LRMS (ESI+) ([M+H]+): 378, retention time 0.67 min.

176

4-(2-fluorophenyl)-7,7-dimethyl-3-(trifluoromethyl)-6,7,8,9-tetrahydro-2H-pyrazolo[3,4-b]quinolin-5(4H)-one

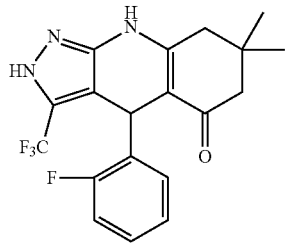

$^1$H NMR (300 MHz, d$^6$-DMSO) δ 10.32 (s, 1H), 6.96-6.83 (m, 1H), 6.79-6.70 (m, 1H), 6.70-6.57 (m, 2H), 5.29 (s, 1H), 2.48-2.32 (m, 2H), 2.28-2.12 (m, 1H), 2.09-1.94 (m, 1H), 1.01 (s, 3H), 0.87 (s, 3H). LRMS (ESI+) ([M]+): 379, retention time 0.59 min.

4-(5-fluoro-2-(trifluoromethyl)phenyl)-7,7-dimethyl-3-(trifluoromethyl)-6,7,8,9-tetrahydro-2H-pyrazolo[3,4-b]quinolin-5(4H)-one

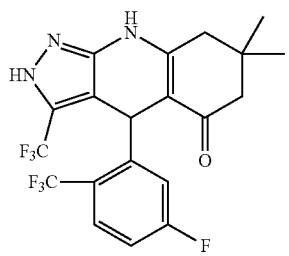

$^1$H NMR (300 MHz, d$^6$-DMSO) δ 10.29 (s, 1H), 7.66-7.61 (m, 1H), 7.22-7.09 (m, 1H), 6.93-6.86 (m, 1H), 5.68 (s, 1H), 2.51-2.40 (m, 2H), 2.19-2.09 (m, 1H), 2.01-1.91 (m, 1H), 1.01 (s, 3H), 0.89 (s, 3H). LRMS (ESI+) ([M+H]+): 448, retention time 0.55 min.

4-(3-fluoro-2-(trifluoromethyl)phenyl)-7,7-dimethyl-3-(trifluoromethyl)-6,7,8,9-tetrahydro-2H-pyrazolo[3,4-b]quinolin-5(4H)-one

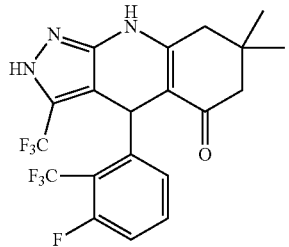

$^1$H NMR (300 MHz, d$^6$-DMSO) δ 10.28 (s, 1H), 7.53-7.42 (m, 1H), 7.21-7.11 (m, 1H), 6.99-6.92 (m, 1H), 5.78 (s,

1H), 2.49-2.30 (m, 2H), 2.19-2.10 (m, 1H), 2.0-1.87 (m, 1H), 1.01 (s, 3H), 0.85 (s, 3H). LRMS (ESI+) ([M+H]+): 448, retention time 0.66 min.

4-(5-fluoro-2-(trifluoromethoxy)phenyl)-7,7-dimethyl-3-(trifluoromethyl)-6,7,8,9-tetrahydro-2H-pyrazolo[3,4-b]quinolin-5(4H)-one

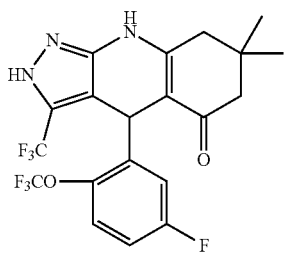

$^1$H NMR (300 MHz, d$^6$-DMSO) δ 10.30 (s, 1H), 7.25-7.14 (m, 1H), 7.14-7.02 (m, 2H), 5.31 (s, 1H), 2.48-2.34 (m, 2H), 2.18-2.07 (m, 1H), 2.01-1.92 (m, 1H), 1.01 (s, 3H), 0.92 (s, 3H). LRMS (ESI+) ([M+H]+): 464, retention time 0.58 min.

4-(2,5-difluorophenyl)-7,7-dimethyl-3-(trifluoromethyl)-6,7,8,9-tetrahydro-2H-pyrazolo[3,4-b]quinolin-5(4H)-one

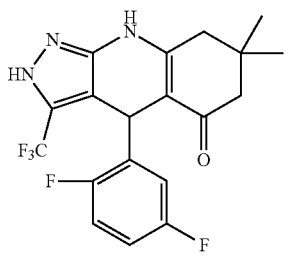

$^1$H NMR (300 MHz, d$^6$-DMSO) δ 10.35 (s, 1H), 6.81-6.69 (m, 2H), 6.69-6.60 (m, 2H), 6.55-6.43 (m, 2H), 5.25 (s, 2H), 2.48-2.34 (m, 2H), 2.25-2.13 (m, 1H), 2.08-1.96 (m, 1H), 1.01 (s, 3H), 0.89 (s, 3H). LRMS (ESI+) ([M]+): 397, retention time 0.48 min.

4-(2-fluorophenyl)-4,7,7-trimethyl-3-(trifluoromethyl)-6,7,8,9-tetrahydro-2H-pyrazolo[3,4-b]quinolin-5(4H)-one

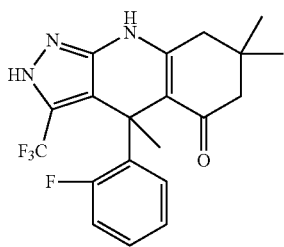

$^1$H NMR (300 MHz, d$^4$-MeOD) δ 7.63-7.52 (m, 1H), 7.17-7.01 (m, 2H), 6.88-6.74 (m, 1H), 2.46 (q, J=16.5 Hz, 2H), 2.18-2.01 (m, 2H), 1.99 (s, 3H), 1.07 (s, 3H), 1.01 (s, 3H). LRMS (ESI+) ([M+H]+): 394, retention time 0.67 min.

7,7-dimethyl-3-(trifluoromethyl)-4-(2-(trifluoromethyl)phenyl)-6,7,8,9-tetrahydro-2H-pyrazolo[3,4-b]quinolin-5(4H)-one

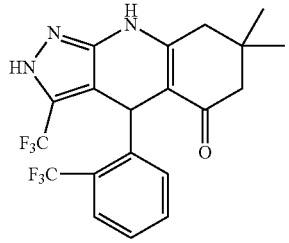

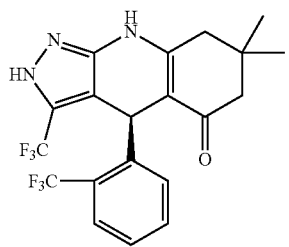

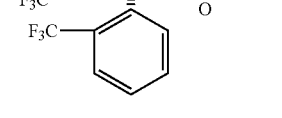

$^1$H NMR (300 MHz, d$^6$-DMSO) δ 10.22 (s, 1H), 7.52-7.40 (m, 2H), 7.31-7.22 (m, 1H), 7.20-7.13 (m, 1H), 5.69 (s, 1H), 2.60-2.34 (m, 2H), 2.21-2.05 (m, 1H), 1.96-1.86 (m, 1H), 1.01 (s, 3H), 0.86 (s, 3H). LRMS (ESI+) ([M+H]+): 430, retention time 0.66 min. The racemic mixture was separated by chiral HPLC to provide Compound 72 and Compound 73.

4-(4-fluoro-2-(trifluoromethyl)phenyl)-7,7-dimethyl-3-(trifluoromethyl)-6,7,8,9-tetrahydro-2H-pyrazolo[3,4-b]quinolin-5(4H)-one

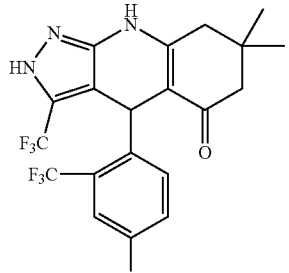

$^1$H NMR (300 MHz, d$^6$-DMSO) δ 10.28 (s, 1H), 7.41-7.30 (m, 2H), 7.25-7.15 (m, 1H), 5.66 (s, 1H), 2.59-2.35 (m,

2H), 2.19-2.08 (m, 1H), 1.98-1.88 (m, 1H), 1.01 (s, 3H), 0.87 (s, 3H). LRMS (ESI+) ([M+H]+): 448, retention time 0.56 min.

4-(2,6-difluorophenyl)-7,7-dimethyl-3-(trifluoromethyl)-6,7,8,9-tetrahydro-2H-pyrazolo[3,4-b]quinolin-5(4H)-one

59

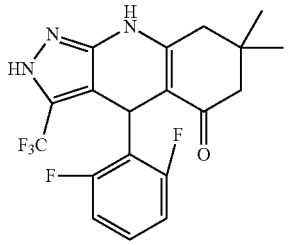

¹H NMR (300 MHz, d⁶-DMSO) δ 10.08 (s, 1H), 6.97-6.81 (m, 1H), 6.55-6.34 (m, 2H), 5.50 (s, 1H), 2.51-2.41 (m, 1H), 2.39-2.24 (m, 1H), 2.12-2.08 (m, 1H), 2.03-1.88 (m, 1H), 1.01 (s, 3H), 0.91 (s, 3H). LRMS (ESI+): 397 ([M]+), retention time 0.50 min.

7,7-dimethyl-4-(3-(trifluoromethoxy)phenyl)-3-(trifluoromethyl)-6,7,8,9-tetrahydro-2H-pyrazolo[3,4-b]quinolin-5(4H)-one

57

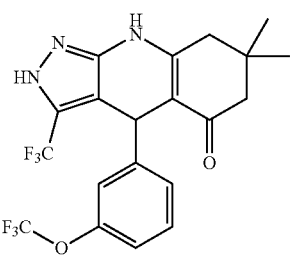

¹H NMR (300 MHz, MeOD) δ 7.31-7.23 (m, 1H), 7.18-7.12 (m, 1H), 7.08-6.96 (m, 2H), 5.24 (s, 1H), 2.63-2.42 (m, 2H), 2.32-2.22 (m, 1H), 2.15-2.03 (m, 1H), 1.09 (s, 3H), 0.95 (s, 3H). LRMS (ESI+) ([M+H]+): 446.

7,7-dimethyl-3-(trifluoromethyl)-4-(4-(trifluoromethyl)pyridin-3-yl)-6,7,8,9-tetrahydro-2H-pyrazolo[3,4-b]quinolin-5(4H)-one

66

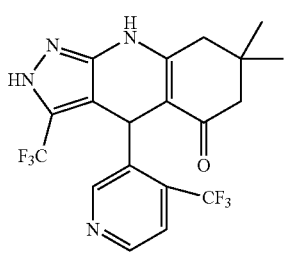

LRMS (ESI+) ([M+H]+): 431.

3-bromo-7,7-dimethyl-4-phenyl-6,7,8,9-tetrahydro-2H-pyrazolo[3,4-b]quinolin-5(4H)-one

74

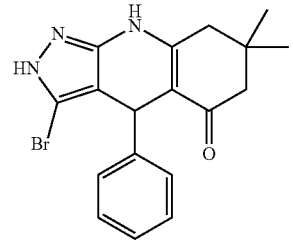

¹H NMR (400 MHz, d⁶-DMSO): δ 12.72 (s, 1H), 9.89 (s, 1H), 7.20-7.04 (m, 5H), 4.85 (s, 1H), 2.50-2.30 (m, 2H), 2.13 (d, J=16.4 Hz, 1H), 1.96 (d, J=16.0 Hz, 1H), 1.00 (s, 3H), 0.926 (s, 3H). ESI+ LCMS: m/z 372 ([M+H]+).

7,7-diethyl-3-methyl-4-phenyl-6,7,8,9-tetrahydro-2H-pyrazolo[3,4-b]quinolin-5(4H)-one

75

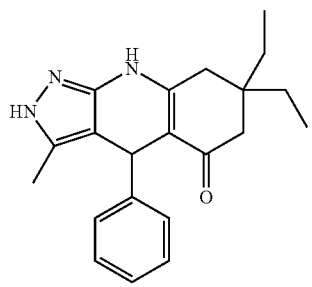

¹H NMR (500 MHz, CD₃OD): δ 7.18-7.15 (m, 4H), 7.06-7.04 (m, 1H), 5.00 (s, 1H), 2.58-2.47 (m, 2H), 2.22-2.11 (m, 2H), 1.93 (s, 3H), 1.46-1.37 (m, 4H), 0.85 (t, J=7 Hz, 3H), 0.78 (t, J=7.5 Hz, 3H). ESI+ LCMS: m/z 336 ([M+H]+).

7,7-dimethyl-4-(pyridin-3-yl)-3-(trifluoromethyl)-6,7,8,9-tetrahydro-2H-pyrazolo[3,4-b]quinolin-5(4H)-one

76

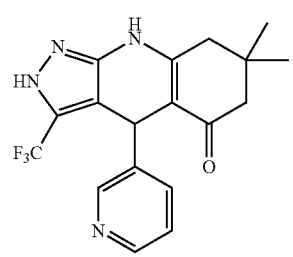

¹H NMR (400 MHz, d⁶-DMSO): δ 13.63 (bs, 0.5H), 13.32 (bs, 0.5H), 10.27-10.20 (m, 1H), 8.31 (d, J=22.0 Hz,

2H), 7.43-7.41 (m, 1H), 7.24-7.21 (m, 1H), 5.12-5.09 (m, 1H), 2.50-2.30 (m, 2H), 2.16 (d, J=16.4 Hz, 1H), 1.97 (d, J=16.4 Hz, 1H), 1.00 (s, 3H), 0.86 (s, 3H). ESI+ LCMS: m/z 363 ([M+H]+).

3'-methyl-4'-phenyl-4',6',8',9'-tetrahydrospiro[cyclopropane-1,7'-pyrazolo[3,4-b]quinolin]-5'(2'H)-one

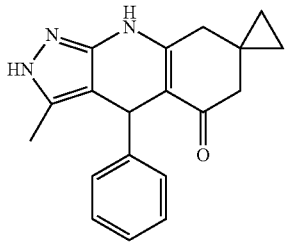

¹H NMR (500 MHz, d⁶-DMSO): δ 11.71 (bs, 1H), 9.68-9.66 (m, 1H), 7.20-7.16 (m, 4H), 7.04 (t, J=7 Hz, 1H), 4.98 (s, 1H), 2.59 (d, J=17 Hz, 1H), 2.35-2.25 (m, 2H), 1.93 (s, 3H), 1.87 (d, J=16.5 Hz, 1H), 0.41-0.27 (m, 4H). ESI+ LCMS: m/z 306 ([M+H]+).

3'-methyl-4'-phenyl-4',6',8',9'-tetrahydrospiro[cyclobutane-1,7'-pyrazolo[3,4-b]quinolin]-5'(2'H)-one

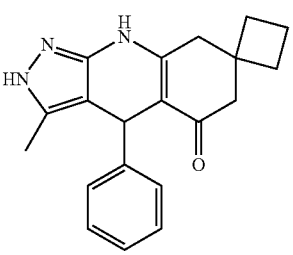

¹H NMR (500 MHz, d⁶-DMSO): δ 11.68 (s, 1H), 9.68 (s, 1H), 7.16-6.99 (m, 5H), 4.90 (s, 1H), 2.71-2.59 (m, 2H), 2.30-2.25 (m, 2H), 1.90 (s, 3H), 1.85-1.72 (m, 5H), 1.62-1.57 (m, 1H). ESI+ LCMS: m/z 320 ([M+H]+).

3'-methyl-4'-phenyl-4',6',8',9'-tetrahydrospiro[cyclopentane-1,7'-pyrazolo[3,4-b]quinolin]-5'(2'H)-one

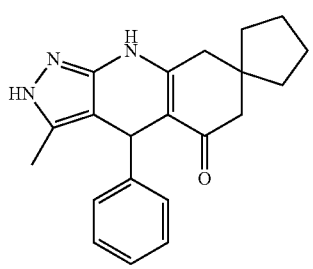

¹H NMR (500 MHz, d⁶-DMSO): δ 11.69 (s, 1H), 9.64 (s, 1H), 7.19-7.10 (m, 4H), 7.03 (t, J=7 Hz, 1H), 4.91 (s, 1H),
2.65-2.50 (m, 2H), 2.21 (d, J=16 Hz, 1H), 2.06 (d, J=16 Hz, 1H), 1.90 (s, 3H), 1.62-1.51 (m, 4H), 1.49-1.37 (m, 3H), 1.30-1.26 (m, 1H). ESI+ LCMS: m/z 334 ([M+H]+).

4-(2-bromophenyl)-3,7,7-trimethyl-6,7,8,9-tetrahydro-2H-pyrazolo[3,4-b]quinolin-5(4H)-one

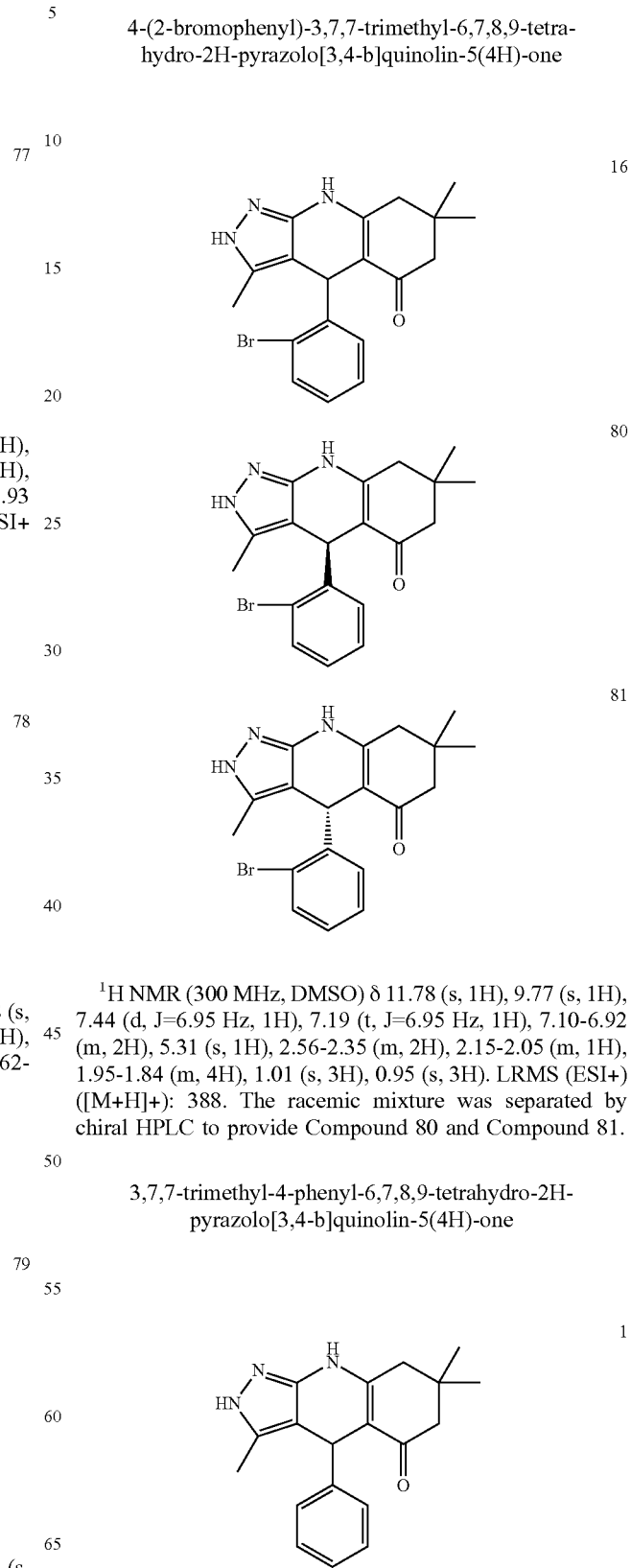

¹H NMR (300 MHz, DMSO) δ 11.78 (s, 1H), 9.77 (s, 1H), 7.44 (d, J=6.95 Hz, 1H), 7.19 (t, J=6.95 Hz, 1H), 7.10-6.92 (m, 2H), 5.31 (s, 1H), 2.56-2.35 (m, 2H), 2.15-2.05 (m, 1H), 1.95-1.84 (m, 4H), 1.01 (s, 3H), 0.95 (s, 3H). LRMS (ESI+) ([M+H]+): 388. The racemic mixture was separated by chiral HPLC to provide Compound 80 and Compound 81.

3,7,7-trimethyl-4-phenyl-6,7,8,9-tetrahydro-2H-pyrazolo[3,4-b]quinolin-5(4H)-one

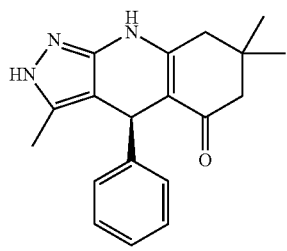

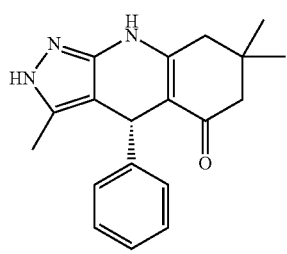

LRMS (ESI+): 308 ([M+H]+). The racemic mixture was separated by chiral HPLC to provide Compound 3 and Compound 2.

Compounds described herein may also be prepared according to Synthesis Protocols C to F as shown in Scheme 1c.

Scheme 1c. Synthesis Protocols C to F.

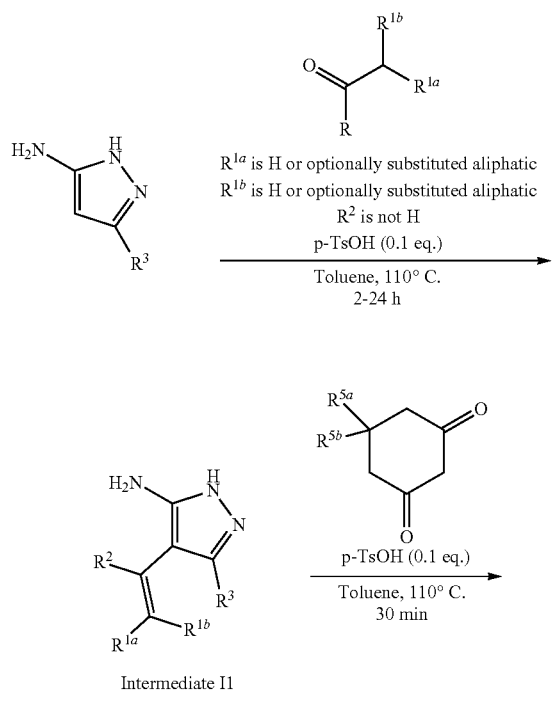

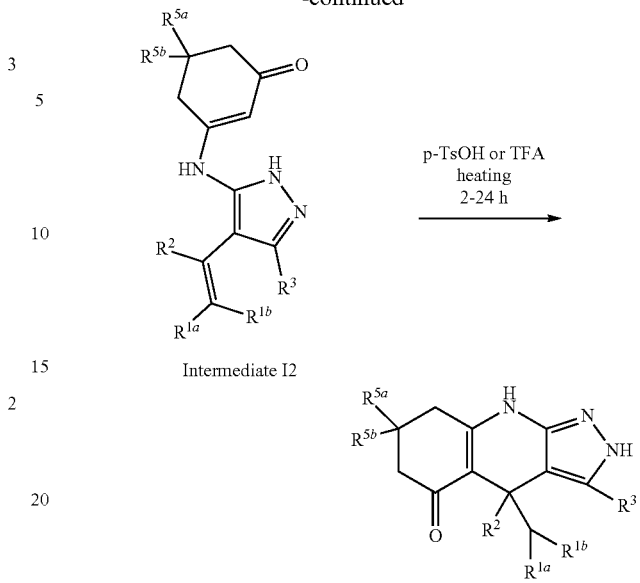

In Synthesis Protocol C (Scheme 1c), the ketone (1.0 equivalent) and the amine (1.0 equivalent) were dissolved in toluene (0.1-0.5 M). p-Toluenesulfonic acid (0.1 equivalent) was added, and the mixture was heated at 110° C. The reaction mixture was cooled, and toluene was evaporated. The crude reaction mixture was purified by column chromatography on silica to afford intermediate I1. The resulting intermediate I1 (1.0 equivalent) was then dissolved in toluene, and the 1,3-diketone (1.0 equivalent) followed by p-toluenesulfonic acid (0.1 equivalent) were added. The mixture was heated at 110° C. for 30-60 minutes to afford the uncyclized intermediate I2 quantitatively. Toluene was evaporated to remove the water generated in the enamine formation reaction. Fresh toluene was added and the mixture was heated at 110° C. After complete conversion of the uncyclized intermediate I2, toluene was evaporated, and the crude mixture was purified by column chromatography on silica to afford the cyclized product.

In Synthesis Protocol D, the uncyclized intermediate I2 was dissolved in toluene and trifluoroacetic acid (1.0 equivalent) was added. The mixture was heated at 150° C. in a microwave reactor. After complete conversion of the uncyclized intermediate, volatiles were evaporated, and the crude mixture was purified by column chromatography on silica to afford the cyclized product.

In Synthesis Protocol E, the uncyclized intermediate I2 was dissolved in trifluoroacetic acid (0.5 M), and the mixture was heated at 73° C. After complete conversion of the uncyclized intermediate, volatiles were evaporated, and the crude mixture was purified by column chromatography on silica to afford the cyclized product.

In Synthesis Protocol F, the uncyclized intermediate I2 was dissolved in trifluoroacetic acid (0.5 M), and the mixture was heated at 140° C. in a microwave reactor. After complete conversion of the uncyclized intermediate, volatiles were evaporated, and the crude mixture was purified by column chromatography on silica to afford the cyclized product.

Compounds described herein may also be prepared according to Synthesis Protocol G as shown in Scheme 1d, where $R^3$ is —$CF_3$, isopropyl, or a group larger than —$CF_3$ or isopropyl.

Scheme 1d. Synthesis Protocol G.

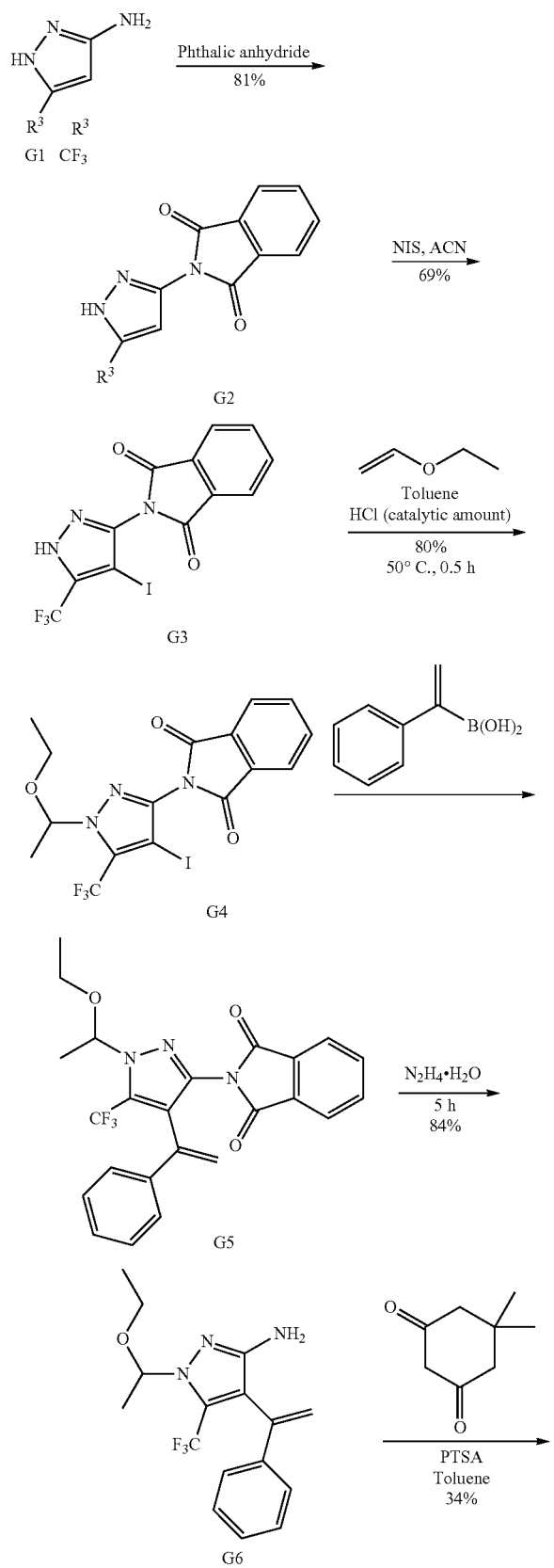

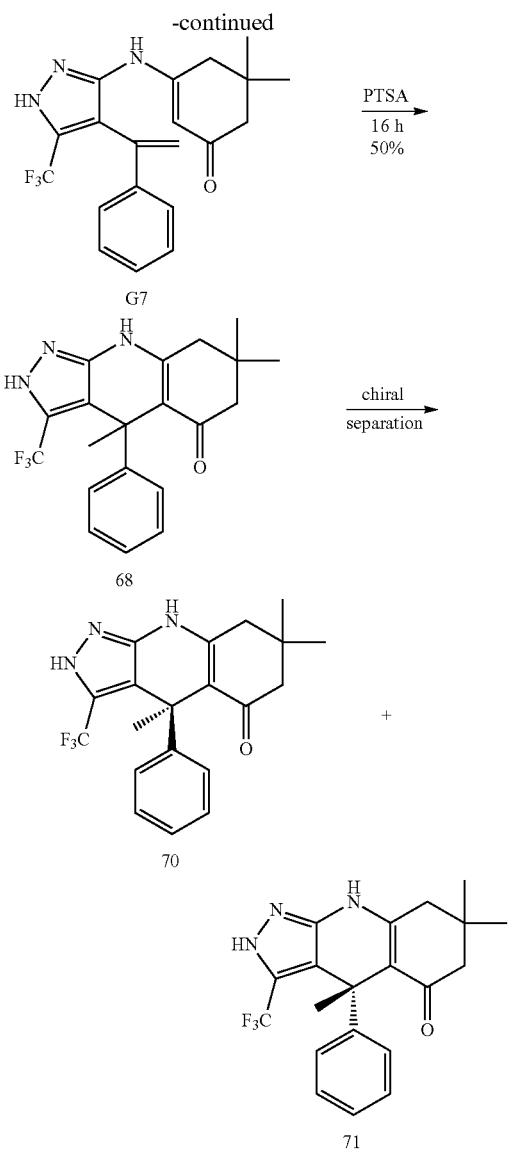

To a stirred solution of 5-trifluoromethyl-1H-pyrazol-3-amine (compound G1) (2 g, 1.0 eq) in dioxane (30 mL) was added phthalic anhydride (2.15 g, 1.1 eq) under nitrogen atmosphere at room temperature. The reaction mixture was refluxed for 24 h. Volatiles were evaporated under reduced pressure to afford a crude residue (compound G2). The crude compound G2 was used in the next step as such without further purification (crude yield: 3 g, 81% yield).

To a stirred solution of crude compound G2 (3 g, 1.0 eq.) in ACN (acetonitrile, 50 mL) was added N-iodosuccinimide (NIS, 5.04 g, 2 eq.) under nitrogen atmosphere at room temperature. The reaction mixture was refluxed for 16 h, and the reaction mixture was quenched with a saturated aqueous sodium sulfite solution and extracted with EtOAc. The organic layer was separated, washed with water and brine, dried over $Na_2SO_4$, filtered, and concentrated under reduced pressure to give crude compound G3. The crude compound G3 was used in the next step as such without further purification (crude yield: 3 g, 69% yield).

To a stirred solution of crude compound G3 (2 g, 1.0 eq.) in toluene (20 mL) were added ethylvinylether (0.92 mL, 2 eq) and a catalytic amount of concentrated HCl (5 drops)

under nitrogen atmosphere at room temperature. The reaction mixture was stirred at 50° C. for 30 min. After reaction completion, the reaction mixture was quenched with saturated aqueous NaHCO₃ solution and extracted with EtOAc. The organic layer was separated, washed with water and brine, dried over Na₂SO₄, filtered, and concentrated under reduced pressure to give crude compound G4. The crude compound G4 was purified by column chromatography on silica gel eluting with 30% EtOAc in hexanes to afford pure compound G4: 1.88 g, 80% yield.

A mixture of compound G4 (500 mg, 1 eq.), the boronic acid as shown in Scheme 1d (230 mg, 1.5 eq.), Pd(PPh₃)₄ (120 mg, 0.1 eq.), and K₂CO₃ (288 mg, 2 eq.) in a solvent mixture [toluene (3 mL), water (3 mL), and ethanol (1 mL)] was degassed with argon and heated at 100° C. in a microwave reactor for 1 h. After completion, the reaction was diluted with water, and the product was extracted with EtOAc. The organic layer was separated, washed with water and brine, dried over Na₂SO₄, and concentrated under reduced pressure to give crude compound G5. The crude compound G5 was purified by column chromatography eluting with 20% EtOAc in hexanes to afford a mixture of compounds that contains compound G5. An LCMS analysis of the isolated mixture showed 56% of the desired mass of compound G5. The crude compound G5 was used in the next step as such without further purification.

To a stirred solution of crude compound G5 (1 g, 1 eq.) in methanol (20 mL) was added N₂H₄.H₂O (0.5 mL, 2.8 eq.). The reaction mixture was stirred at room temperature for 5 h. After completion, the reaction mixture was quenched with water, and the product was extracted with EtOAc. The organic layer was washed with water and brine, dried over Na₂SO₄, filtered, and concentrated under reduced pressure to give crude compound G6. The crude compound G6 was purified by column chromatography eluting with 30% EtOAc in hexanes to afford pure compound G6: 0.6 g, 84% yield.

To a stirred solution of compound G6 (600 mg, 1.0 eq.) in toluene (20 mL) were added dimedone (388 mg, 1.5 eq.), PTSA (p-toluenesulfonic acid, 702 mg, 2 eq.) under nitrogen atmosphere at room temperature. The reaction mixture was refluxed for 2 h. After completion (monitored by TLC), the reaction was quenched with a saturated aqueous NaHCO₃ solution and extracted with EtOAc. The organic layer was separated, washed with water and brine, dried over anhydrous Na₂SO₄, and concentrated under reduced pressure to afford a crude residue. The crude residue was purified by column chromatography on silica gel eluting with 2% MeOH in DCM (dichloromethane) to afford a mixture of compounds that contains compound G7 (62.8% of desired mass of compound G7 and 23% of an imine impurity; crude yield 240 mg, 34% yield). The crude compound G7 was used for next step as such without any further purification.

To a stirred solution of crude compound G7 (240 mg, 1.0 eq.) in toluene (10 mL) was added PTSA (486 mg, 4 eq.) under nitrogen atmosphere at room temperature. The reaction mixture was refluxed for 12 h. After completion (monitored by TLC), the reaction was quenched with saturated aqueous NaHCO₃ solution and extracted with EtOAc. The organic layer was washed with water and brine, dried over anhydrous Na₂SO₄, and concentrated under reduced pressure to afford a crude residue. The crude residue was purified by column chromatography eluting with 2% MeOH in DCM to afford pure final compound 68: 120 mg (50% yield). After chiral separation, 40 mg of each one of the two enantiomers, compound 70 and compound 71, were obtained.

9-ethyl-1,6,6-trimethyl-9-phenyl-5,6,7,9-tetrahydro-2H-pyrazolo[3,4-b]quinolin-8(4H)-one (89)

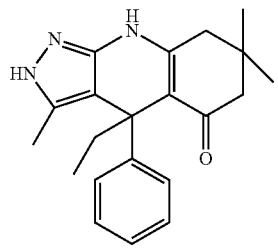

89

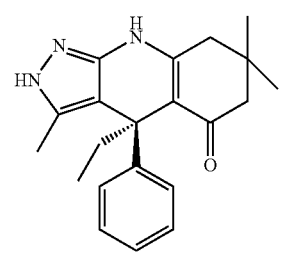

125

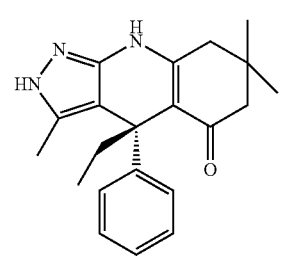

126

LCMS: m/z 336 [M+H]⁺; ¹H NMR (300 MHz, MeOD): 7.35 (d, J=7.3 Hz, 2H), 7.16 (t, J=7.3 Hz, 2H), 7.01 (t, J=7.3 Hz, 1H), 2.52 (s, 2H), 2.2-1.9 (m, 4H), 1.63 (s, 3H), 1.10 (s, 3H), 1.05 (s, 3H), 0.75 (t, J=7.3 Hz, 3H) ppm. The racemic mixture was separated by chiral HPLC to provide compound 125 and compound 126.

1,6,6-trimethyl-9-phenyl-9-(trifluoromethyl)-5,6,7,9-tetrahydro-2H-pyrazolo[3,4-b]quinolin-8(4H)-one (92, 93, and 94)

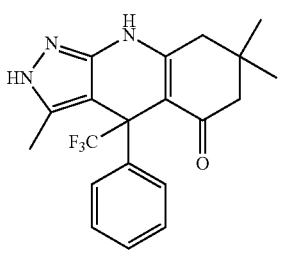

92

93

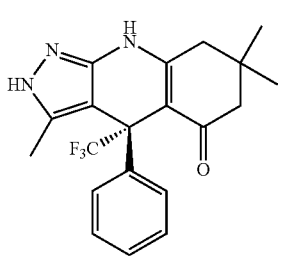

94

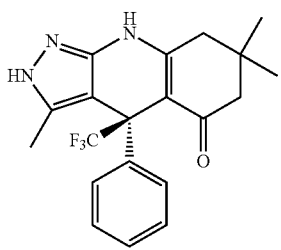

LCMS: m/z 376 [M+H]$^+$; $^1$H NMR (300 MHz, CD$_3$OD): δ 7.4-7.3 (m, 2H), 7.23 (t, J=7.3 Hz, 2H), 7.13 (t, J=7.3 Hz, 2H), 2.7-2.5 (m, 2H), 2.2-2.0 (m, 2H), 1.47 (s, 3H), 1.09 (s, 3H), 1.08 (s, 3H) ppm. The racemic mixture was separated by chiral HPLC to provide compound 93 and compound 94.

3-(1,6,6,9-tetramethyl-8-oxo-4,5,6,7,8,9-hexahydro-2H-pyrazolo[3,4-b]quinolin-9-yl)benzonitrile (95, 96, and 97)

95

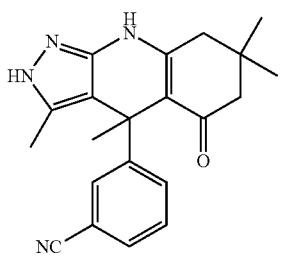

96

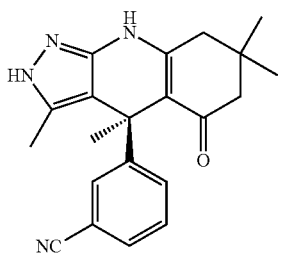

97

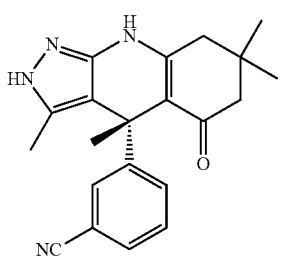

LCMS: m/z 347 [M+H]$^+$; $^1$H NMR (500 MHz, d$_6$-DMSO): 11.71 (s, 1H), 9.74 (s, 1H), 7.64 (s, 1H), 7.56 (d, J=8.5 Hz, 1H), 7.48 (d, J=7.5 Hz, 1H), 7.38 (t, J=8.0 Hz, 1H), 2.42-2.35 (m, 2H), 1.98 (d, J=30.0 Hz, 1H), 1.89 (d, J=30.0 Hz, 1H), 1.81 (s, 3H), 1.60 (s, 3H), 0.98 (s, 3H), 0.94 (s, 3H) ppm. The racemic mixture was separated by chiral HPLC to provide compound 96 and compound 97.

3-(3,4,7,7-tetramethyl-5-oxo-4,5,6,7,8,9-hexahydro-2H-pyrazolo[3,4-b]quinolin-4-yl)benzamide (90)

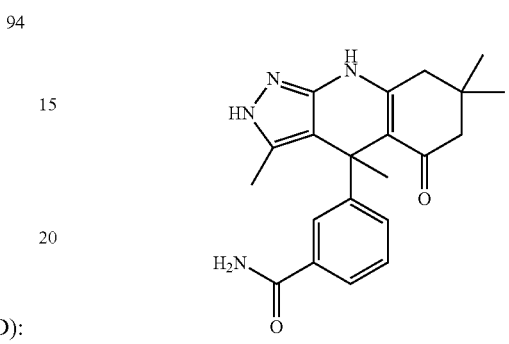

LCMS: m/z 365 [M+H]$^+$; $^1$H NMR (400 MHz, DMSO-d$_6$): δ 11.62 (s, 1H), 9.64 (s, 1H), 7.87 (bs, 1H), 7.83 (bs, 1H), 7.53 (d, J=7.6 Hz, 1H), 7.39 (d, J=8.4 Hz, 1H), 7.24-7.19 (m, 2H), 2.50-2.40 (m, 2H), 2.04-1.97 (m, 1H), 1.90-1.80 (m, 4H), 1.59 (s, 3H), 0.99 (s, 3H), 0.96 (s, 3H) ppm.

3',7',7'-trimethyl-2,3,6',7',8',9'-hexahydrospiro[indene-1,4'-pyrazolo[3,4-b]quinolin]-5'(2'H)-one (91)

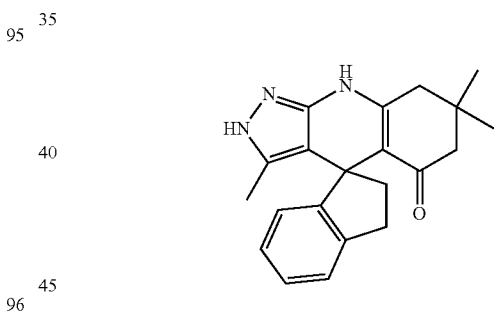

LCMS: m/z 334 [M+H]$^+$; $^1$H NMR (300 MHz, MeOD): δ 7.25-6.95 (m, 3H), 6.85-6.70 (m, 1H), 3.40-3.25 (m, 1H), 3.20-3.00 (m, 1H), 2.70-2.45 (m, 3H), 2.30-2.00 (m, 3H), 1.57 (s, 3H), 1.09 (s, 3H), 1.07 (s, 3H) ppm.

3',7',7'-trimethyl-6',7',8',9'-tetrahydro-2H-spiro[benzofuran-3,4'-pyrazolo[3,4-b]quinolin]-5'(2'H)-one (98)

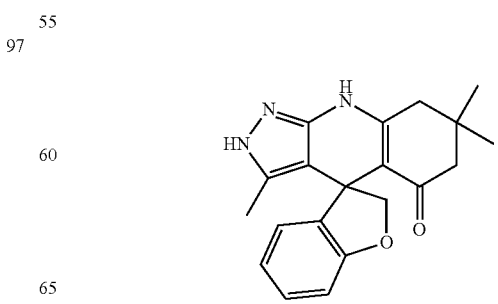

LCMS: m/z 334 [M−H]⁻; ¹H NMR (300 MHz, MeOD): δ 7.03 (td, J=7.1 Hz, J=1.6 Hz, 1H), 7.80-7-65 (m, 3H), 4.81 (d, J=8.2 Hz, 1H), 4.36 (d, J=8.2 Hz, 1H), 2.65-2.45 (m, 2H), 2.25-2.05 (m, 2H), 1.71 (s, 3H), 1.09 (s, 6H) ppm.

3',7',7'-trimethyl-3,4,6',7',8',9'-hexahydro-2H-spiro[naphthalene-1,4'-pyrazolo[3,4-b]quinolin]-5'(2'H)-one (99)

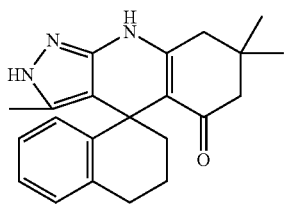

LCMS: m/z 346 [M−H]⁻; ¹H NMR (300 MHz, MeOD): δ 7.0-6.9 (m, 4H), 3.1-2.9 (m, 1H), 2.85-2.75 (m, 1H), 2.6-2.4 (m, 2H), 2.3-2.0 (m, 4H), 1.90-1.80 (m, 2H), 1.48 (s, 3H), 1.10 (s, 3H), 1.08 (s, 3H) ppm.

Compound 100

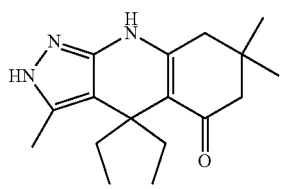

LCMS: m/z 288 [M+H]⁺; ¹H NMR (400 MHz, d₆-DMSO): δ 11.61 (s, 1H), 9.24 (s, 1H), 2.55-2.50 (m, 2H), 2.31 (bs, 3H), 2.12-2.05 (m, 5H), 1.38-1.28 (m, 2H), 1.00 (s, 6H), 0.54 (t, J=7.2 Hz, 5H) ppm.

Compound 101

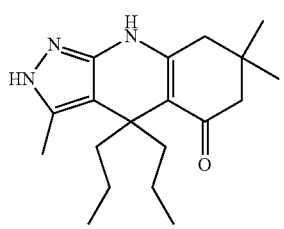

LCMS: m/z 316 [M+H]⁺; ¹H NMR (300 MHz, CD₃OD): δ 2.65-2.50 (m, 2H), 2.41-2.35 (m, 2H), 2.24-2.10 (m, 5H), 1.47-1.20 (m, 5H), 1.12-0.95 (m, 7H), 0.84-0.72 (m, 6H) ppm.

Compound 102

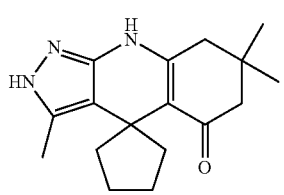

LCMS: m/z 286 [M+H]⁺; ¹H NMR (400 MHz, d₆-DMSO): δ 11.66 (s, 1H), 9.43 (s, 1H), 2.32-2.28 (m, 2H), 2.18-2.12 (m, 5H), 2.10-2.06 (m, 2H), 2.04-1.94 (m, 2H), 1.79 (d, J=5.0 Hz, 2H), 1.64-1.54 (m, 2H), 0.98 (s, 6H) ppm.

Compound 103

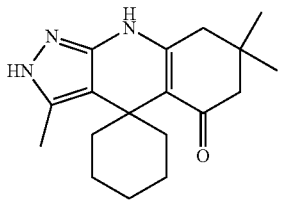

LCMS: m/z 299 [M]⁺; ¹H NMR (CD₃OD, 300 MHz): δ 2.60-2.40 (m, 5H), 2.25-1.55 (m, 12H), 1.10-1.00 (m, 6H) ppm.

Compound 104

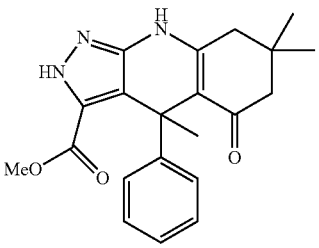

ESI+ MS: m/z 366 [M+H]⁺.

Compound 105

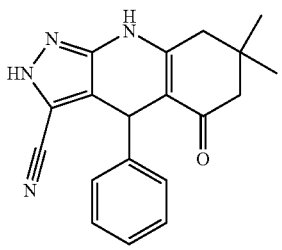

ESI+ LCMS: m/z 319 (M+H); ¹H NMR (400 MHz, d₆-DMSO): δ 13.62 (bs, 1H), 10.17 (s, 1H), 7.25-7.20 (m, 2H), 7.15-7.08 (m, 3H), 5.12 (s, 1H), 2.47-2.40 (m, 2H), 2.15 (d, J=16.0 Hz, 1H), 2.00 (d, J=16.0 Hz, 1H), 1.02 (s, 3H), 0.97 (s, 3H) ppm.

Compounds 107, 108, and 109

107

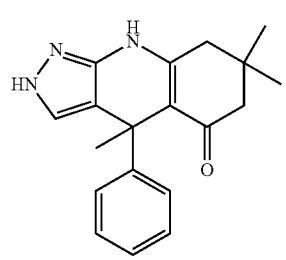

-continued

108

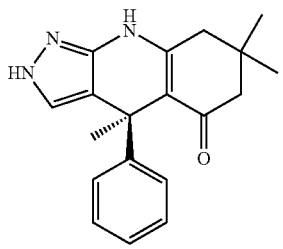

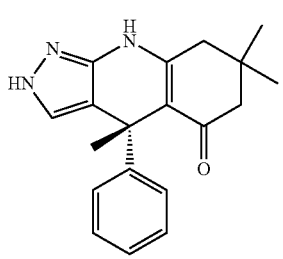

109

LCMS: m/z 308 [M+H]$^+$; $^1$H NMR (400 MHz, DMSO-d$_6$): δ 11.90 (s, 1H), 9.67 (s, 1H), 7.27 (d, J=7.2 Hz, 2H), 7.16 (t, J=7.6 Hz, 2H), 7.08 (s, 1H), 6.99 (t, J=7.2 Hz, 1H), 2.44 (s, 2H), 2.05 (d, J=15.6 Hz, 1H), 1.97-1.95 (m, 1H), 1.92 (s, 3H), 1.01 (s, 3H), 0.99 (s, 3H) ppm. The racemic mixture was separated by chiral HPLC to provide compound 108 and compound 109.

Compound 106

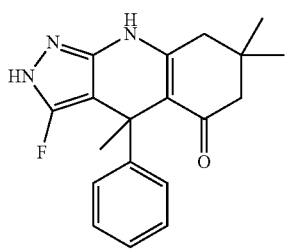

LCMS: m/z 326 [M+H]$^+$; $^1$H NMR (300 MHz, CD$_3$OD): δ 7.36-7.25 (m, 2H), 7.25-7.13 (m, 2H), 7.12-7.00 (m, 1H), 2.50 (bs, 2H), 2.25-1.90 (m, 5H), 1.09 (s, 3H), 1.06 (s, 3H) ppm.

Compound 110

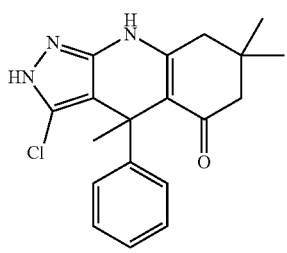

ESI+ MS: m/z 341 [M]$^+$.

Compound 111

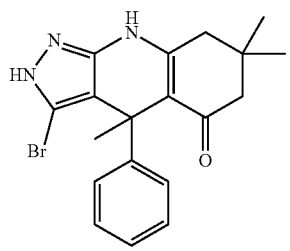

LCMS: m/z 386 [M]$^+$: $^1$H NMR (400 MHz, DMSO-d$_6$): δ 12.57 (s, 1H), 9.80 (s, 1H), 7.26 (d, J=7.6 Hz, 2H), 7.16 (t, J=7.6 Hz, 2H), 7.00 (t, J=7.2 Hz, 1H), 2.45-2.35 (m, 2H), 2.05-2.00 (m, 1H), 1.94 (s, 3H), 1.90-1.85 (m, 1H), 0.99 (s, 3H), 0.95 (s, 3H) ppm.

Compounds 113, 114, and 115

113

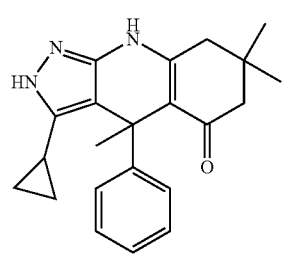

114

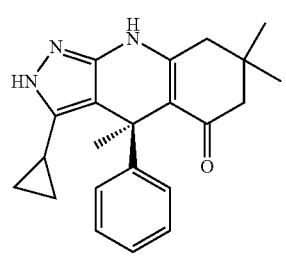

115

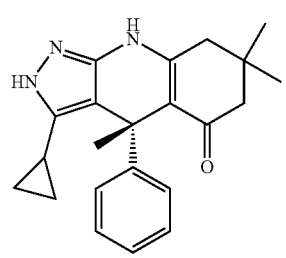

ESI+ MS: m/z 348 [M+H]$^+$; $^1$H NMR (CD$_3$OD, 300 MHz): δ 7.36 (d, J=3.0 Hz, 2H), 7.16 (t, J=6.0 Hz, 2H), 7.10-6.98 (m, 1H), 2.52-2.48 (m, 2H), 2.25-2.00 (m, 2H), 2.01 (s, 3H), 1.25-1.00 (m, 1H), 1.08 (s, 3H), 1.08 (s, 3H), 1.04 (s, 3H), 0.80-0.73 (m, 1H), 0.60-0.46 (m, 1H), 0.46-0.26 (m, 1H), 0.26-0.15 (m, 1H) ppm. The racemic mixture was separated by chiral HPLC to provide compound 114 and compound 115.

Compound 112

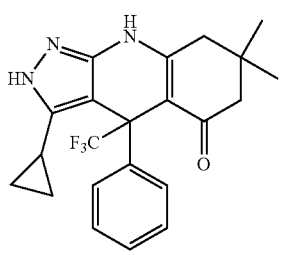

ESI+ MS: m/z 402 [M+H]⁺.

Compound 116

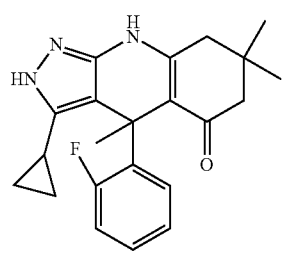

ESI+ MS: m/z 366 ([M+H]⁺); $^1$H NMR (400 MHz, DMSO-$d_6$): δ 11.37 (s, 1H), 9.59 (s, 1H), 7.57-7.51 (m, 1H), 7.11-7.03 (m, 2H), 6.89-6.83 (m, 1H), 2.42 (d, J=16.0 Hz, 1H), 2.30 (d, J=16.0 Hz, 1H), 2.02 (d, J=16.0 Hz, 1H) 1.92 (s, 3H), 1.85 (d, J=16.0 Hz, 1H), 1.13-1.05 (m, 1H), 0.99 (s, 3H), 0.93 (s, 3H), 0.70-0.65 (m, 1H), 0.51-0.46 (m, 1H), 0.33-0.21 (m, 2H) ppm.

Compounds 118, 130, and 131

118

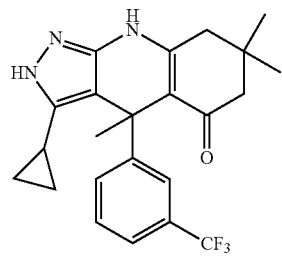

130

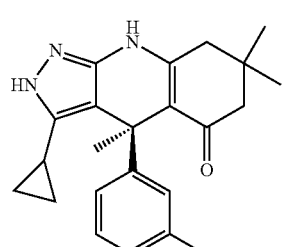

131

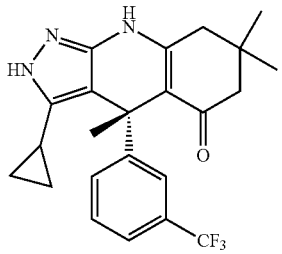

LCMS: m/z 416 [M+H]⁺. The racemic mixture was separated by chiral HPLC to provide compound 130 and compound 131.

Compounds 117, 132, and 133

117

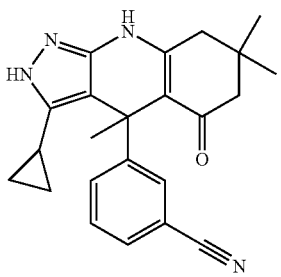

132

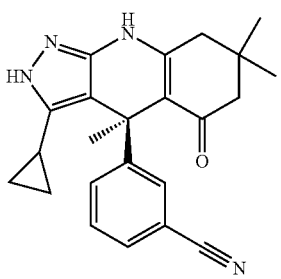

133

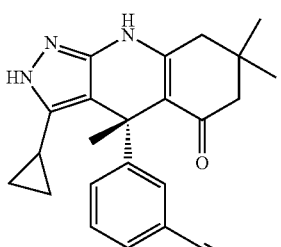

ESI+ MS: m/z 373 [M+H]⁺; $^1$H NMR (400 MHz, $d_6$-DMSO): δ 11.55 (s, 1H), 9.76 (s, 1H), 7.66 (d, J=1.6 Hz, 1H), 7.59 (d, J=8 Hz, 1H), 7.50 (d, J=7.6 Hz, 1H), 7.38 (t, J=7.6 Hz, 1H), 2.45 (s, 2H), 2.00 (d, J=15.6 Hz, 1H), 1.93-1.88 (m, 1H), 1.93 (s, 3H), 1.18-1.10 (m, 1H), 0.99 (s, 3H), 0.95 (s, 3H), 0.75-0.68 (m, 1H), 0.60-0.52 (m, 1H), 0.37-0.28 (m, 1H), 0.15-0.08 (m, 1H) ppm. The racemic mixture was separated by chiral HPLC to provide compound 132 and compound 133.

Compound 119

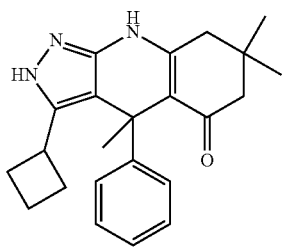

LCMS: m/z 361 [M]+.

Compound 120, 127, and 128

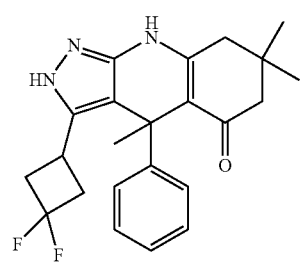

120

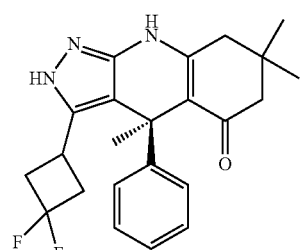

127

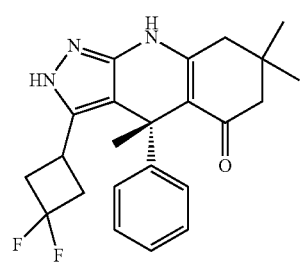

128

LCMS: m/z 397 [M+H]+; ¹H NMR (300 MHz, CD₃OD): δ 7.36 (d, J=6.0 Hz, 2H), 7.19 (t, J=9.0 Hz, 2H), 7.05 (t, 9.0 Hz, 1H), 2.90-2.60 (m, 3H), 2.49 (s, 2H), 2.20-1.75 (m, 3H), 1.90 (s, 3H), 1.80-1.60 (m, 1H), 1.07 (s, 3H), 1.03 (s, 3H) ppm. The racemic mixture was separated by chiral HPLC to provide compound 127 and compound 128.

4,7,7-trimethyl-3,4-diphenyl-6,7,8,9-tetrahydro-2H-pyrazolo[3,4-b]quinolin-5(4H)-one (121)

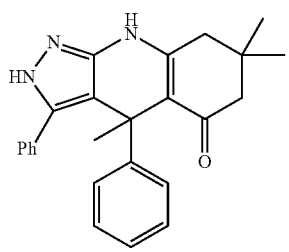 [SMILES: CC1(C)CC(=O)C2=C(C1)Nc1n[nH]c(-c3ccccc3)c1C2(C)c1ccccc1]

LCMS: m/z 384 [M+H]+, ¹H NMR (300 MHz, CDCl₃): δ 7.40-7.25 (m, 3H), 7.26-7.02 (m, 5H), 6.59 (d, J=9.0 Hz, 2H), 2.40-2.25 (m, 2H), 2.25-2.00 (m, 2H), 1.81 (s, 3H), 1.06 (s, 3H), 0.99 (s, 3H) ppm.

Compound 122

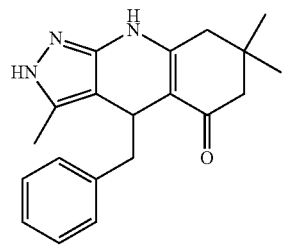

LCMS: m/z 321 [M]+; ¹H NMR (300 MHz, DMSO-d₆): δ 11.58 (s, 1H), 9.39 (s, 1H), 7.22-7.10 (m, 3H), 6.88 (d, J=6.0 Hz, 2H), 4.08 (dd, J=3.0, 9.0 Hz, 1H), 2.80-2.60 (m, 1H), 2.50-2.13 (m, 5H), 1.41 (s, 3H), 0.99 (s, 3H), 0.98 (s, 3H) ppm.

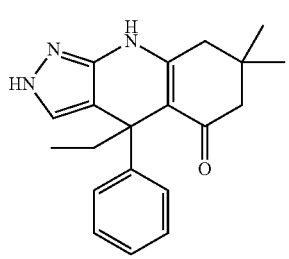 [SMILES: CCC1(c2ccccc2)C2=C(CC(C)(C)CC2=O)Nc2n[nH]cc21]

ESI+ MS: m/z 322 ([M+H]+): ¹H NMR (500 MHz, d₆-DMSO): δ 11.91 (s, 1H), 9.63 (s, 1H), 7.28 (d, J=7.5 Hz, 2H), 7.15 (t, J=7.2 Hz, 2H), 7.05 (s, 1H), 7.01-6.97 (m, 1H), 2.92-2.88 (m, 1H), 2.50-2.42 (m, 2H), 2.07-1.97 (m, 3H), 1.04 (s, 3H), 1.02 (s, 3H), 0.65 (t, J=7.5 Hz, 3H) ppm.

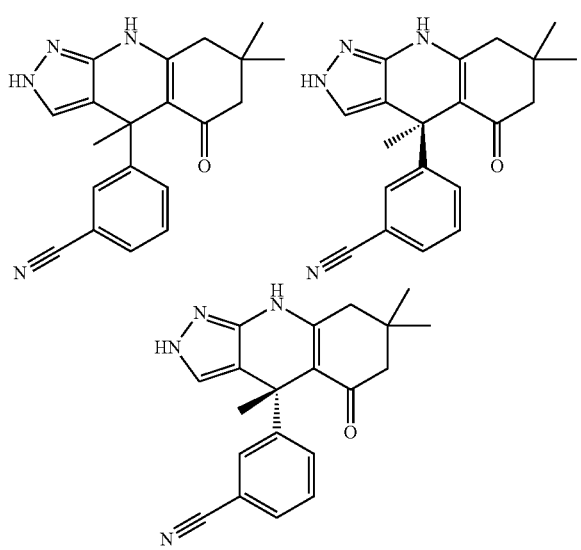

ESI⁺ MS: m/z 333 ([M+H]⁺); ¹H NMR (400 MHz, CD₃OD): δ 7.72-7.64 (m, 2H), 7.01 (s, 1H), 2.60-2.50 (m, 1H), 2.16 (d, J=16.0 Hz, 1H), 2.08 (d, J=16.4 Hz, 1H), 1.98 (s, 3H), 1.10 (s, 3H), 1.07 (s, 3H) ppm.

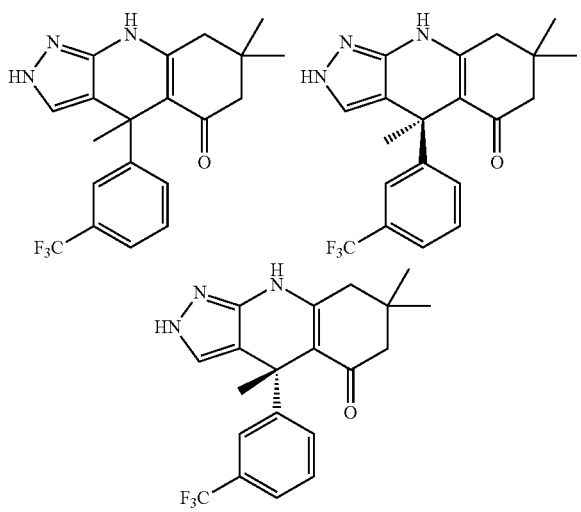

ESI⁺ MS: m/z 376 ([M+H]⁺); ¹H NMR (500 MHz, d₆-DMSO): δ 12.01 (s, 1H), 9.81 (s, 1H), 7.60 (d, J=8 Hz, 1H), 7.53 (s, 1H), 7.45-7.36 (m, 2H), 7.17 (s, 1H), 2.50-2.40 (m, 2H), 2.08 (d, J=15.5 Hz, 1H), 1.93 (s, 3H), 1.94-1.90 (m, 1H), 1.01 (s, 3H), 0.97 (s, 3H) ppm.

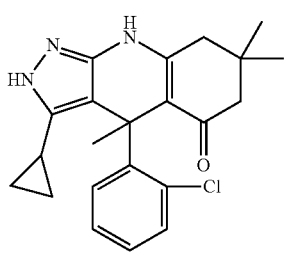 [SMILES: CC1(C)CC(=O)C2=C(C1)Nc1n[nH]c(C3CC3)c1C2(C)c1ccccc1Cl]

ESI⁺ MS: m/z 382 ([M+H]⁺); ¹H NMR (400 MHz, d₆-DMSO): δ 11.32 (s, 1H), 9.66 (s, 1H), 7.75 (dd, J=1.2 Hz, 7.6 Hz, 1H), 7.27-7.21 (m, 1H), 7.17-7.13 (m, 1H), 7.11-7.05 (m, 1H), 2.42-2.26 (m, 2H), 2.01-1.84 (m, 5H), 0.99 (s, 3H), 0.98 (s, 3H), 0.95-0.87 (m, 1H), 0.64-0.55 (m, 1H), 0.53-0.45 (m, 1H), 0.25-0.14 (m, 2H) ppm.

Other Compounds.

Any other compounds described herein can be made in a similar fashion to the methods described above. They can be analyzed by UPLC as described below.

Retention Time UPLC Method

Compound purity and identity were determined by UPLC-MS (Waters, Milford, Mass.). Purity was measured by UV absorbance at 210 nm. Identity was determined on a SQ mass spectrometer by positive and negative electrospray ionization. Mobile phase A consisted of either 0.1% ammonium hydroxide or 0.1% trifluoroacetic acid in water, while mobile phase B consisted of the same additives in acetonitrile. The gradient ran from 5% to 95% mobile phase B over 0.8 minutes at 0.45 mL/min. An Acquity BEH C18, 1.7 um, 1.0×50 mm column was used with column temperature maintained at 65° C. Compounds were dissolved in DMSO at a nominal concentration of 1 mg/mL, and 0.25 μL of this solution was injected.

Additional Analytical Assays

Solubility.

Solubility was determined in phosphate buffered saline (PBS) pH 7.4 with 1% DMSO. Each compound was prepared in duplicate at 100 μM in both 100% DMSO and PBS with 1% DMSO. Compounds were allowed to equilibrate at room temperature with a 250 rpm orbital shake for 24 hours. After equilibration, samples were analyzed by UPLC-MS (Waters, Milford, Mass.) with compounds detected by SIR detection on a single quadrupole mass spectrometer. The DMSO samples were used to create a two point calibration curve to which the response in PBS was fit. The results are shown in Table 3.

PBS Stability.

Stability was determined in the presence of PBS pH 7.4 with 0.1% DMSO. Each compound was prepared in duplicate on six separate plates and allowed to equilibrate at room temperature with a 250 rpm orbital shake for 48 hours. One plate was removed at each time point (0, 2, 4, 8, 24, and 48 hours). An aliquot was removed from each well and analyzed by UPLC-MS (Waters, Milford, Mass.) with compounds detected by SIR detection on a single quadrupole mass spectrometer. Additionally, to the remaining material at each time point, acetonitrile was added to force dissolution of compound (to test for recovery of compound). An aliquot of this was also analyzed by UPLC-MS.

GSH Stability.

Stability was determined in the presence of PBS pH 7.4 μM and 50 μM glutathione with 0.1% DMSO. Each compound was prepared in duplicate on six separate plates and allowed to equilibrate at room temperature with a 250 rpm orbital shake for 48 hours. One plate was removed at each time point (0, 2, 4, 8, 24, and 48 hours). An aliquot was removed from each well and analyzed by UPLC-MS (Waters, Milford, Mass.) with compounds detected by SIR detection on a single quadrupole mass spectrometer. Additionally, to the remaining material at each time point, acetonitrile was added to force dissolution of compound (to test for recovery of compound). An aliquot of this was also analyzed by UPLC-MS.

Plasma Protein Binding.

Plasma protein binding was determined by equilibrium dialysis using the Rapid Equilibrium Dialysis (RED) device (Pierce Biotechnology, Rockford, Ill.) for both human and mouse plasma. Each compound was prepared in duplicate at 5 µM in plasma (0.95% acetonitrile, 0.05% DMSO) and added to one side of the membrane (200 µl) with PBS pH 7.4 added to the other side (350 µl). Compounds were incubated at 37° C. for 5 hours with a 250 rpm orbital shake. After incubation, samples were analyzed by UPLC-MS (Waters, Milford, Mass.) with compounds detected by SIR detection on a single quadrupole mass spectrometer. The results are shown in Table 3.

Plasma Stability.

Plasma stability was determined at 37° C. at 5 hours in both human and mouse plasma. Each compound was prepared in duplicate at 5 µM in plasma diluted 50/50 (v/v) with PBS pH 7.4 (0.95% acetonitrile, 0.05% DMSO). Compounds were incubated at 37° C. for 5 hours with a 250 rpm orbital shake with time points taken at 0 and 5 hours. Samples were analyzed by UPLC-MS (Waters, Milford, Mass.) with compounds detected by SIR detection on a single quadrupole mass spectrometer. The results are shown in Table 3.

Primary HTS

The GSK3β primary screen was conducted in assay ready 1536 plates (Aurora 29847) that contain 2.5 nL/well of 10 mM compound. Human GSK3β as a GST fusion expressed in baculoviral system was purchased from BPS Bioscience (San Diego, Calif.). The GSK3β peptide substrate was from American Peptide (Sunnyvale, Calif.; Cat 311153). 1 µL/well of CABPE (22.5 nM GSK3β, 8 µM peptide in AB buffer (12.5 mM DTT, 0.25 mg/mL BSA, 0.5 unit/mL Heparin)), 0.5 µL/well of 125 µM of ATP, and 1 µL/well of positive control 50 µM of GW8510 (positive control) or AB (DMSO only neutral control) in respective wells according to plate design using BioRAPTR (Beckman, Brea, Calif.). Reactions were incubated at room temperature for 60 minutes. 2.5 µL/well of ADP-Glo (Promega, V9103) was added with BioRAPTR, and incubated at room temperature for 40 minutes followed by addition of 5 µL/well of ADP-Glo detection reagent (Promega, V9103) with Combi nL (Thermo, Waltham, Mass.) and incubation at room temperature for 30 minutes. The plates were read on a ViewLux (PerkinElmer, Waltham, Mass.) for luminescence. Data were scaled using the positive and neutral controls and fitted for $IC_{50}$ as described below.

1 µL/well of CABPE, 0.5 µL of ATP, and 1 µL of positive control GW8510 or AB were dispensed in respective wells according to plate design to 1536-well assay ready plates (Aurora 29847) that contain 2.5 nL/well of 10 mM compound using BioRAPTR (Beckman) to start the reaction. Plates were incubated at room temperature for 60 minutes. 2.5 µL/well of ADP-Glo (Promega, V9103) with BioRAPTR were added, and plates were incubated at room temperature for 40 minutes. 5 µL/well of ADP-Glo (Promega, V9103) with Combi nL (Thermo) were added, and plates were incubated at room temperature for 30 minutes. Plates were read on ViewLux (PerkinElmer) for luminescence.

Solutions:

AB:

| 25 | mM | Tris7.5 |
|---|---|---|
| 10 | mM | $MgCl_2$ |

GW8510 (in AB, Sigma G7791)

| 50 | µM | GW8510 |
|---|---|---|

CABPE (in AB):

| 12.5 | mM | DTT (Sigma 43816) |
|---|---|---|
| 0.25 | mg/ml | BSA (Sigma A4503) |
| 0.5 | U/ml | Heparin (Baxter NDC 0641-2440-41) |
| 8 | µM | Peptide (American Peptide) |
| 22.5 | nM | GSK3β (BPS Biosciences) |

(SEQ ID NO.: 1)
Peptide: Tyr-Arg-Arg-Ala-Ala-Val-Pro-Pro-Ser-Pro-Ser-Leu-Ser-Arg-His-Ser-Ser-Pro-His-Gln-Ser(PO₃H₂)-Glu-Asp-Glu-Glu-Glu ATP (in AB, Promega V9103 Component):

| 125 | µM | ATP |
|---|---|---|

Confirmatory Assay

The confirmatory assay was a retest of active compounds in primary HTS above and along with some of their negative analogues. The assay was performed in the same manner as the primary screen except the compounds were tested in doses and with replicates.

1 µL/well of CABPE, 0.5 µL of ATP, and 1 µL of positive control GW8510 or AB were dispensed in respective wells according to plate design to 1536-well assay ready plates (Aurora 29847) that contain 2.5 nL/well of 10 mM compound using BioRAPTR (Beckman) to start the reaction. Plates were incubated at room temperature for 60 minutes. 2.5 µL/well of ADP-Glo (Promega, V9103) with BioRAPTR were added, and plates were incubated at room temperature for 40 minutes. 5 µL/well of ADP-Glo (Promega, V9103) with Combi nL (Thermo) were added, and plates were incubated at room temperature for 30 minutes. Plates were read on ViewLux (PerkinElmer) for luminescence.

Solutions:

AB:

| 25 | mM | Tris7.5 |
|---|---|---|
| 10 | mM | $MgCl_2$ |

GW8510 (in AB, Sigma G7791)

| 50 | µM | GW8510 |
|---|---|---|

CABPE (in AB):

| 12.5 | mM | DTT (Sigma 43816) |
|---|---|---|
| 0.25 | mg/ml | BSA (Sigma A4503) |
| 0.5 | U/ml | Heparin (Baxter NDC 0641-2440-41) |
| 8 | µM | Peptide (American Peptide) |
| 22.5 | nM | GSK3β (BPS Biosciences) |

(SEQ ID NO.: 1)
Peptide: Tyr-Arg-Arg-Ala-Ala-Val-Pro-Pro-Ser-Pro-Ser-Leu-Ser-Arg-His-Ser-Ser-Pro-His-Gln-Ser(PO₃H₂)-Glu-Asp-Glu-Glu-Glu ATP (in AB, Promega V9103 Component):

| 125 | µM | ATP |
|---|---|---|

Counter Screen of ADP-Glo Reagents

The ADP-Glo reagent counter screen is to identify false positives due to inhibition of the ADP-Glo detection system. 2.5 µL of 5 µM of ADP were incubated directly with compounds in doses at room temperature for 60 minutes. 2.5 µL/well of ADP-Glo (Promega, V9103) was added with BioRAPTR, and incubated at room temperature for 40 minutes followed by addition of 5 µL/well of ADP-Glo Detection (Promega, V9103) with Combi nL (Thermo, Waltham, Mass.) and incubation at room temperature for 30 minutes. The plates were read on a ViewLux (PerkinElmer, Waltham, Mass.) for luminescence. Data were scaled using the positive and neutral controls and fitted for IC50 as described below.

2.5 µL of 5 µM ADP or buffer AB were dispensed into wells on 1536-well assay ready plates according to plate design (Aurora 29847) generated by acoustic transfer using Labcyte Echo that contain 7.5 nL/well of compound in doses. 2.5 µL/well of ADP-Glo (Promega, V9103) with Combi nL (Thermo) were added, and plates were incubated at room temperature for 40 minutes. 5 µL/well of ADP-Glo (Promega, V9103) with Combi nL (Thermo) were added, and plates were incubated at room temperature for 35 minutes. Plates were read on ViewLux (PerkinElmer) for luminescence.

Solutions:
AB: 25 mM TrisCl pH7.5, 10 mM MgCl$_2$
ADP: 5 µM ADP (in AB, Promega V9103 component)
Single Point Inhibitory Analysis of Selected Compounds (Carna Biosciences)

Briefly, a selection of compounds was screened against a panel of kinases at a single concentration of 10 µM. The kinases were selected from all families of the kinome and in all represented 60% of the entire kinome for a total of 311 kinases screened. This was completed utilizing one of two assays depending on the kinase being examined.

Test compounds were dissolved in and diluted with dimethylsulfoxide (DMSO) to generate a 100× sample solution. These were then diluted to 4× sample solutions in assay buffer to make the final test compound solutions. Reference compounds for assay control were prepared similarly.

IMAP Assay.

A solution of 4× inhibitor (5 µL), 4× substrate/ATP/Metal solution (5 µL), and 2× kinase solution (10 µL) was prepared with assay buffer (20 mM HEPES, 0.01% Tween-20, 2 mM DTT, pH 7.4) and mixed/incubated in 384 well black plates for 1 hour at room temperature. A solution of IMAP binding reagent (IMAP Screening Express kit; Molecular Devices) (60 µL) was added to each well and incubated for 30 minutes. Level of kinase activity was then evaluated by fluorescence polarization at 485 nM (exc) and 530 nM (emm) of each well.

Off-Chip Mobility Shift Assay (MSA).

A solution of 4× inhibitor (5 µL), 4× substrate/ATP-Metal solution (5 µL), and 2× Kinase solution (10 µL) was prepared with assay buffer (20 mM HEPES, 0.01% Triton X-100, 2 mM DTT, pH 7.5) and mixed/incubated in 384 well plates for 1 or 5 hours depending on the kinase being examined, at room temperature. A solution of termination buffer (QuickScout Screening assist MSA; Carna Biosciences) (60 µL) was added to each well. The entire reaction mixture was then applied to a LabChip3000 system (Caliper Life Science) and the product and substrate peptide peaks were separated and quantified. Evaluation of kinase activity was then determined based on ratio of calculated peak heights of product (P) and substrate (S) peptides (P/(P+S)).

Dose Response IC50 Determination of Selected Compounds Against Selected Kinases

A selection of compounds was screened against a selected panel of kinases based on single point inhibitory ability to determine absolute inhibitory activity, leading to selectivity measurements. The assay utilized was identical to that of the single point inhibitory activity determination (MSA) but run in dose response. A solution of 4× inhibitor (5 µL), 4× substrate/ATP Metal solution (5 µL), and 2× Kinase solution (10 µL) was prepared with assay buffer (20 mM HEPES, 0.01% Triton X-100, 2 mM DTT, pH 7.5) and mixed/incubated in 384 well plates for 1 or 5 hours depending on the kinase, at room temperature. A solution of termination buffer (QuickScout Screening assist MSA; Carna Biosciences) (60 µL) was added to each well. The entire reaction mixture was then applied to a LabChip3000 system (Caliper Life Science) and the product and substrate peptide peaks were separated and quantified. Evaluation of kinase activity was then determined based on ratio of calculated peak heights of product (P) and substrate (S) peptides (P/(P+S)).

Tau Phosphorylation and Total Tau Assay

SH-SY5Y cells were maintained in DMEM supplemented with 10% heat-inactivated FBS and 1% penicillin-streptomycin (Invitrogen) unless otherwise stated. ELISA kits for phospho-Tau (Ser199) and total Tau detection were purchased from Invitrogen (KHB0041, and KHB7041 respectively). Briefly, SH-SY5Y cells were seeded at 50,000 cells/200 µL/well in 96 well plates and after overnight incubation, treated with various doses of chemical compounds at 0.2 µL/well. The next day cells were washed with PBS twice before being lysed in 100 µL Lysis buffer/well. 50 µL of cell lysate of each sample was transferred to an ELISA vial coated with the capture antibody, and the mixture was incubated at room temperature for 2 hours, before the supernatant was aspired, and each vial washed four times. 100 µL of detection antibody was then added to each well, incubated for 1 hour, and then washed four times. The amount of phospho-Tau and total Tau was measured by adding 100 µL of anti-rabbit IgG Horseradish peroxidase working solution to each well, and absorbance of each well at 450 nM was read on EnVision (PerkinElmer, Waltham, Mass.). Data were scaled using the positive and neutral controls and fitted for IC50.

A standard protocol using an immunoassay kit to quantify total Tau protein and phospho-Tau (Ser199) protein in SH-SY5Y human neuroblastoma cells was employed. Human Tau (Total) ELISA kit (#KHB0041) and human phosphor-Tau (Ser199) ELISA kit were purchased from Invitrogen (#KHB7041)

50,000 cells were seeded in 200 µl per well in cell culture media (250,000 cells/ml). Cells were incubated overnight @37° C. Cells were induced with appropriate doses of inhibitors and incubated for approximately 24 hrs @37° C. Cell lysates were harvested by washing cells once with cold PBS and adding 100 µl cold lysis buffer and pipette up and down vigorously. Lysate was transferred to 96 well PCR plate and centrifuged at 4,000 rpm for 20 minutes at 4° C.

Human Tau (Total) Standard was reconstituted with 1300 µl Standard Diluent Buffer. Serial dilutions of the standard were made according to the following table:

| Standard: | Add | Into |
| --- | --- | --- |
| 2000 pg/ml | | |
| 1000 pg/ml | 300 µL of 2000 pg/ml standard | 300 µL Diluent Buffer |
| 500 pg/ml | 300 µL of 1000 pg/ml standard | 300 µL Diluent Buffer |
| 250 pg/ml | 300 µL of 500 pg/ml standard | 300 µL Diluent Buffer |
| 125 pg/ml | 300 µL of 250 pg/ml standard | 300 µL Diluent Buffer |
| 62.5 pg/ml | 300 µL of 125 pg/ml standard | 300 µL Diluent Buffer |
| 32.1 pg/ml | 300 µL of 62.5 pg/ml standard | 300 µL Diluent Buffer |
| 0 pg/ml | 300 µL Diluent Buffer | Empty Tube |

Human pTau (Ser199) Standard was reconstituted with 1730 µl of Standard Diluent Buffer, gently mixed, and allowed to rest for 10 minutes. Serial dilutions of the standard were made according to the following table:

| Standard: | Add | Into |
| --- | --- | --- |
| 1000 pg/ml | | |
| 500 pg/ml | 300 µL of 1000 pg/ml standard | 300 µL Diluent Buffer |
| 250 pg/ml | 300 µL of 500 pg/ml standard | 300 µL Diluent Buffer |
| 125 pg/ml | 300 µL of 250 pg/ml standard | 300 µL Diluent Buffer |
| 62.5 pg/ml | 300 µL of 125 pg/ml standard | 300 µL Diluent Buffer |
| 31.2 pg/ml | 300 µL of 62.5 pg/ml standard | 300 µL Diluent Buffer |
| 15.6 pg/ml | 300 µL of 31.2 pg/ml standard | 300 µL Diluent Buffer |
| 0 pg/ml | 300 µL Diluent Buffer | Empty Tube |

Anti-rabbit IgG HRP for both Human Tau (Total) and Human pTau (Ser199) was diluted by allowing it to reach room temperature, then use the following table:

| # of 8 well Strips | Vol of anti-rabbit IgG HRP | Vol of HRP Diluent |
| --- | --- | --- |
| 2 | 20 µL | 2 ml |
| 4 | 40 µL | 4 ml |
| 6 | 60 µL | 6 ml |
| 8 | 80 µL | 8 ml |
| 10 | 100 µL | 10 ml |
| 12 | 120 µL | 12 ml |

Wash buffer was diluted from 25× concentrate according to the following: Amount of wash buffer=(x)*(8)*(400)*(4)*(3), where x=number of strips of ELISA plate Diluted 24 volumes with deionized water (ie 5 ml concentrate into 120 ml water).

Well strips were warmed and inserted into the frame. 100µ of standard diluent buffer were loaded into ZERO wells, and 100 ul of each standard concentrations (both total Tau and pTau) were loaded into wells in duplicate. Samples were loaded to each well that would be analyzed for total Tau, 85 µl standard diluent buffer and 15 µl cell lysate were added. To each well that will be analyzed for pTau (Ser199) 50 µl standard diluent buffer+50 µl cell lysate were added. Plates were tapped gently on the side to mix. Certain wells were left empty for chromogen blank. Plates were covered and incubated for 2 hours at room temperature. Wells were aspirated 4 times (400 µl diluted wash buffer, left for 30 seconds, aspirated all wells; alternatively used automated plate washer and programmed in a 30 second hold between each cycle). 100 µl of detection antibody solution were added to each well except chromogen blanks. Anti-total Tau was added to wells being analyzed for total Tau, anti-pTau (Ser199) was added to wells being analyzed for pTau (Ser199), and plates were tapped gently on the side to mix. Plates were covered and incubated for 1 hour at room temperature, then wells were aspirated and washed 4 times as described above. 100 µl of anti-rabbit IgG HRP working solution (prepared ahead) were added to each well except chromogen blanks, and plates were covered and incubated for 30 minutes at room temperature, then wells were aspirated and washed 4 times as described above. 100 µl of stabilized chromogen were added to each well (the liquid turned blue). Plates were incubates for 30 minutes at room temperature in the dark, then 100 µl of stop solution were added to each well, and plates were tapped gently on the side to mix. Absorbance of each well was read at 450 nm (within 2 hours of adding stop solution).

β-Catenin Nuclear Localization Assay

U2-OS cells stably expressing two complimentary β-galactosidase fragments (one part on β-Catenin and the other constitutively expressed in the cell nucleus) were maintained in DMEM F12 supplemented with 10% FBS. When β-catenin translocates to the nucleus, the complimentary fragments form a complete β-galactosidase, the amount of which is then quantified by β-galactosidase activity (DiscoveRx). Cells were seeded in a 384-well CulturPlate (Perkin Elmer, Boston, Mass.) with 10,000 per well in 20 µL DMEM F12 containing 10% FCS, 100 U/ml penicillin and 100 µg/mL streptomycin. After overnight incubation at 37° C., cells were stimulated with 100 nL test compound/well and then returned to the incubator for 6 h. Cells were disrupted using 12 µL substrate-containing lysis buffer from the PathHunter Detection Kit in the formulation specified by the supplier (DiscoveRx). Plates were incubated in the dark for 1 h at room temperature before measurement of β-galactosidase activity (luminescence) on an EnVision plate reader (PerkinElmer, Waltham, Mass.). Distance between plate and detector was 0.2 mm. Measurement time(s)=0.1; Glow (CT2) correction factor=0.

TCF/LEF Reporter Assay

HEK293-pBARL cells were derived from HEK293 cells and they stably expressed a firefly-luciferase reporter gene driven by a promoter containing 12 copies of TCF/LEF binding sequences. These cells were maintained in DMEM and supplemented with 10% FBS and 1% penicillin-streptomycin (Invitrogen). Reporter gene assays were conducted in anti-biotic free media. TCF/LEF reporter gene activity was assayed as described previously (Pan et al., 2011, Neuropsychopharmacology). These cells also contained a renilla-luciferase reporter gene driven by the ubiquitous EF1α promoter as a control. HEK293-pBarl reporter cell lines were seeded into 384-well culture plates (Corning) at 6000 cells/well. 24 hours after plating, cells were treated overnight with relevant compounds and assayed using Dual-Glo assay kit (Promega). Luminescent intensities were read by EnVision (PerkinElmer, Waltham, Mass.). Firefly luciferase intensity is normalized by renilla luciferase intensity. The detailed protocol is discussed below.

Reagents:

Dual-Glo Luciferase Assay Reagent from Promega (E2940) (Luciferase Buffer, Luciferase Substrate, Stop & Glo Luciferase Buffer, Stop & Glo Luciferase Substrate);

Plate Type:

Corning 384 well white, TC treated culture plates (3707)

Cells were cultured in 384 well plates to appropriate density (40 µl total plating volume). 24 hours after plating, cells were treated with 100 nl compounds. 24 hours after incubation with compounds (48 hours after plating), assay reagents were prepared by mixing Luciferase Assay solution with Luciferase substrate and Stop & Glo solution to Stop & Glo substrate (extra reagents can be aliquoted and frozen for future use and are stable for at least one freeze/thaw cycle). A volume of luciferase reagent was added equal to ¼ the volume of media to each well (for example, in a 384-well plate with 40 µl in each well, 10 µl were added to give a final volume of 50 µl). The plate was spun down and 10 minutes were allowed for signal stabilization. Luciferase signal on the Perkin Elmer EnVision using the following parameters: Distance between plate & detector (mm)=0.2; Measurement time(s)=0.1; Glow (CT2) correction factor=0. Once the initial data is secure, a volume of Stop & Glo was added equal to each well equal to the volume of Luciferase reagent added above (If 10 µl Luciferase Reagent was added, 10 µl Stop & Glo was also added). The plate was spun down and 10 minutes were allowed for signal stabilization. The plate was read on the EnVision using the same parameters detailed above.

Secondary Surface Plasmon Resonance Affinity Determination

Approximately 20,000 Response Units (RU) of anti GST-antibody (GE Healthcare Life Sciences) were immobilized on Flow Cell (FC) 1 and FC2 of a new, freshly conditioned CM5 SensorChip (GE Healthcare Life Sciences) in a Biacore T100 instrument utilizing the immobilization wizard of the T100 software package. Approximately 1,200 RU of recombinant GST (GE Healthcare Life Sciences) was then captured on FC1 utilizing the capture wizard protocol of the T100 software package. FC1 is used as a reference subtraction point for this and all SPR assays. Approximately 2,500 RU of recombinant GST-GSK3β was then captured on FC2 utilizing the capture wizard protocol of the T100 software package. FC2 is used as the active flowcell for this and all SPR assays. The analyte plate is generated in dose response fashion in TBS buffer containing a final concentration of 2% DMSO, with a final analyte concentration of 10 µM to 10 nM with a 2× dilution factor. A zero value is determined by running injections of buffer containing only 2% DMSO and no analyte. All injections are run in duplicate and are reference subtracted from FC1. A method consisting of a 60 second contact time and 60 second wash time with a flow rate of 30 µL/min was developed. The internal standard curve for DMSO values was generated with seven injections of DMSO consisting of 1, 1.25, 1.5, 2, 2.25, 2.5 and 3% DMSO in TBS running buffer. Analysis of compounds was done using the 1:1 binding model and affinity measurements in the Biacore T100 evaluation software package.

Buffer Generation:

PBS: Mixed 900 mL filtered DI water with 100 mL 10×PBS buffer solution (Invitrogen).

In house TBS: Added 1.21 g Tris and 8.7 g NaCl to 950 mL filtered DI water. pH was adjusted using 6M HCl to 7.35. Filled to 1000 mL mark. Filtered and collected 900 mL in one bottle, and filtered and collected 100 mL in second bottle. Added 450 µL P20 detergent (GE Healthcare Life Sciences) to bottle 1, added 50 µL P20 detergent to bottle 2, and mixed thoroughly. Transferred 18 mL buffer from bottle 1 to bottle 2 to make TBS running buffer. Added 18 mL DMSO (Aldrich) to bottle 1 to make a 2% DMSO running buffer.

GSK3β CM5 Sensor Chip Generation:

Conditioning new chip: PBS immobilization buffer was loaded into buffer shelf and insert buffer line A. Unused CM5 sensor chip was loaded into instrument per user manual. Chip was primed with 6 minutes of buffer injection at 30 µL/min. Manual run was initiated and injected over flow cell (FC) 1 and 2 alternating injections of Lysine buffer (GE Healthcare Life Sciences) and Sodium Hydroxide buffer (GE Healthcare Life Sciences) at a flow rate of 30 µL/min for 30 seconds per injection. Immobilization of anti GST antibody: Primed chip again as described above. Generated anti GST antibody solution by mixing 4.5 µL anti GST antibody (GE Healthcare Life Sciences, GST Capture Kit) with 95.5 µL immobilization buffer (GE Healthcare Life Sciences, GST Capture Kit). Put solution into 700 µL small vial and cap. Repeated. Placed both vials in reagent rack 1 of Biacore T100 instrument and insert into machine per user manual. Initiated immobilization of anti GST antibody by utilizing the immobilization Wizard protocol of Biacore T100 software. Immobilized approximately 20,000 Response Units (RU) of anti GST antibody on FC1 and FC2. Capture Reference and Active Proteins on FC1 and FC2 respectively: Removed PBS immobilization buffer from buffer rack and replace with TBS 2% DMSO running buffer. Inserted buffer line A. Repeated prime procedure. Generated GST protein solution by mixing 2 µL of recombinant GST (GE Healthcare Life Sciences, GST Capture Kit) with 98 µL TBS 2% DMSO buffer. Generated GST-GSK3β protein solution by mixing 5 µL of recombinant GST-GSK3β with 95 µL TBS 2% DMSO running buffer. Placed GST protein solution in position B1 on reagent rack 1. Placed GST-GSK3β protein solution in position C1 on reagent rack 1. Initiated a manual injection run and inject for 30 seconds at 5 µL/min GST protein solution on FC1 to generate reference flow cell. Initiated a manual injection run and inject for 30 seconds at 5 µL/min GST-GSK3β protein solution on FC2 to generate active flow cell. Captured approximately 1000 RU GST protein on FC1. Captured approximately 2500 RU GST-GSK3β protein on FC2.

Analysis of Small Molecule GSK3β Inhibitors:

An analyte plate was generated for the assay. Using a standard deep volume 384 well plate, placed 100 µL of a 10 µM TBS 2% DMSO solution of the desired analyte in wells A1 and A2. Placed 100 µL of a 5 µM TBS 2% DMSO solution of desired analyte in wells A3 and A4. Placed 100 µL of a TBS 2% DMSO solution 2.5 µm solution of desired analyte in wells A5 and A6. Repeated these steps with serially diluted analytes to 10 nM in wells A21 and A22. Placed 100 µL of TBS 2% DMSO running buffer in wells A23 and A24. Repeated steps for subsequent analytes. Placed analyte plate in Biacore T100 per user manual. Generated method that consists of the following: Analyte injection over FC1 and FC2 with reference subtraction; 30 µL/min flow rate of analyte, 60 second contact time of analyte; 60 second wash time of running buffer; DMSO standard curve generation using 1, 1.5, 1.75, 2, 2.5, 2.75 and 3% DMSO in TBS running buffer. Analysis of compounds was run, and compounds were ranked according to KD determination utilizing the affinity measurement option in Biacore T100 software.

CK1δ CM5 Sensor Chip Generation:

Approximately 20,000 Response Units (RU) of anti GST-antibody (GE Healthcare Life Sciences) were immobilized on Flow Cell (FC) 1 and FC2 of a new, freshly conditioned CM5 SensorChip (GE Healthcare Life Sciences) in a Biacore T100 instrument utilizing the immobilization wizard of the T100 software package. Approximately 1,500 RU of recombinant GST (GE Healthcare Life Sciences) was then captured on FC1 utilizing the capture wizard protocol of the T100 software package. FC1 is used as a reference subtraction point for this and all SPR assays. Approximately 2,700 RU of recombinant GST-CK1δ was then captured on FC2 utilizing the capture wizard protocol of the T100 software package. FC2 is used as the active flowcell for this and all SPR assays. The analyte plate is generated in dose response fashion in TBS buffer containing a final concentration of 2% DMSO, with a final analyte concentration of 10 µM, 100 nM and 10 nM. A zero value is determined by running injections of buffer containing only 2% DMSO and no analyte. All injections are run in duplicate and are reference subtracted from FC1. A method consisting of a 60 second contact time and 60 second wash time with a flow rate of 30 μL/min was employed. The internal standard curve for DMSO values was generated with seven injections of DMSO consisting of 1, 1.25, 1.5, 2, 2.25, 2.5 and 3% DMSO in TBS running buffer. Analysis of compounds was done using the 1:1 binding model and affinity measurements in the Biacore T100 evaluation software package.

CK1δ CM5 Sensor Chip Generation:

Conditioning new chip: PBS immobilization buffer was loaded into buffer shelf and insert buffer line A. Unused CM5 sensor chip was loaded into instrument per user manual. Chip was primed with 6 minutes of buffer injection at 30 μL/min. Manual run was initiated and injected over flow cell (FC) 1 and 2 alternating injections of Lysine buffer (GE Healthcare Life Sciences) and Sodium Hydroxide buffer (GE Healthcare Life Sciences) at a flow rate of 30 μL/min for 30 seconds per injection.

Immobilization of Anti GST Antibody:

Primed chip again as described above. Generated anti GST antibody solution by mixing 4.5 μL anti GST antibody (GE Healthcare Life Sciences, GST Capture Kit) with 95.5 μL immobilization buffer (GE Healthcare Life Sciences, GST Capture Kit). Put solution into 700 μL small vial and cap. Repeated. Placed both vials in reagent rack 1 of Biacore T100 instrument and insert into machine per user manual. Initiated immobilization of anti GST antibody by utilizing the immobilization Wizard protocol of Biacore T100 software. Immobilized approximately 20,000 Response Units (RU) of anti GST antibody on FC1 and FC2. Capture Reference and Active Proteins on FC1 and FC2 respectively: Removed PBS immobilization buffer from buffer rack and replace with TBS 2% DMSO running buffer. Inserted buffer line A. Repeated prime procedure. Generated GST protein solution by mixing 2 μL of recombinant GST (GE Healthcare Life Sciences, GST Capture Kit) with 98 μL TBS 2% DMSO buffer. Generated GST-CK1δ protein solution by mixing 5 μL of recombinant GST-CK1δ with 95 μL TBS 2% DMSO running buffer. Placed GST protein solution in position B1 on reagent rack 1. Placed GST-CK1δ protein solution in position C1 on reagent rack 1. Initiated a manual injection run and inject for 30 seconds at 5 μL/min GST protein solution on FC1 to generate reference flow cell. Initiated a manual injection run and inject for 30 seconds at 5 μL/min GST-GSK3β protein solution on FC2 to generate active flow cell. Captured approximately 1500 RU GST protein on FC1. Captured approximately 2700 RU GST-CK1δ protein on FC2.

Analysis of Small Molecule CK1δ Ligands:

An analyte plate was generated for the assay. Using a standard deep volume 384 well plate, placed 100 μL of a 10 μM analyte in TBS 2% DMSO solution wells A1 and A2. Placed 100 μL of a 50 nM analyte in TBS 2% DMSO solution in wells A3 and A4. Placed 100 μL of a 10 nM analyte in TBS 2% DMSO solution in wells A5 and A6. Placed 100 μL of TBS 2% DMSO running buffer in wells A7 and A8. Repeated steps for subsequent analytes. Placed analyte plate in Biacore T100 per user manual. Generated method that consists of the following: Analyte injection over FC1 and FC2 with reference subtraction; 30 μL/min flow rate of analyte, 60 second contact time of analyte; 60 second wash time of running buffer; DMSO standard curve generation using 1, 1.5, 1.75, 2, 2.5, 2.75 and 3% DMSO in TBS running buffer. Analysis of compounds was run, and compounds were ranked according to KD determination utilizing the affinity measurement option in Biacore T100 software.

GSK3β Microfluidic Mobility-Shift Assay

Purified GSK3β was incubated with tested compounds in doses in the presence of 4.3 μM of ATP and 1.5 μM peptide substrate (Peptide 15 from Caliper) for 60 minutes at room temperature in 384-well plates (Seahorse Bioscience, MA), in assay buffer that contained 100 mM HEPES (pH 7.5), 10 mM $MgCl_2$, 2.5 mM DTT, 0.004% Tween-20 and 0.003% Briji-35. Reactions were terminated by the addition of 10 mM EDTA. Substrate and product were separated electrophoretically and fluorescence intensity of the substrate and product was determined by Labchip EZ Reader II (Caliper Life Sciences, MA). The kinase activity was measured as percent conversion. The reactions were performed in duplicate for each sample. Positive control (GW8510 at 20 μM; CID 6539118) was included in each plate and used to scale the data in conjunction with in-plate DMSO controls. The results were analyzed by Genedata Assay Analyzer. The percent inhibition was plotted against the compound concentration and the IC50 value was determined from the logistic dose-response curve fitting.

ADP Glo Assay Protocol (10 μM ATP) in 384-Well Format

20 μL/well of 4.7 nM GSK3β and 7 μM peptide in KBA (250 mM HEPES (pH 7.5), 50 mM MgCl2, 5 mM EGTA, 0.05% BRIJ-35) were dispensed onto white opaque 384-well plate. 100 nL/well compounds were pinned. 1 μL/well of 140 μM ATP in KBA was dispensed. Incubated at room temperature for 60 minutes. Added 20 μL/well of ADP-glo (Promega, V9103) with Combi, and incubated at room temperature for 40 minutes. Added 40 μL/well of ADP-glo (Promega, V9103) with Combi, incubated at room temperature for 30 minutes. Read on Envision for luminescence.

AIH In Vivo Protocol

Amphetamine-induced hyperactivity was performed as described in Pan et al. Neuropsychopharmacology, 2011).

Surgery:

Mice receiving intracranial infusions were implanted with stainless steel guide cannula (Plastics One, Roanoke, Va.) aimed at the dorsal third ventricle. Mice were anesthetized with ketamine/xylazine (150 mg/kg and 10 mg/kg respectively; 5 mls/kg injection volume). Using a stereotaxic apparatus, guide cannula (C232GC, 26 gauge, Plastics One) with inserted dummy cannula (C232DC) were directed toward the dorsal third ventricle (−0.5 mm posterior to Bregma, ±0.0 lateral to midline, and −3.0 (injection site) ventral to the skull surface), (Paxinos, 2001). Mice recovered for at least 5 days prior to testing. During infusions, mice were gently restrained. Dummy cannula were replaced with injection cannula (26 gauge; extending 1.0 mm beyond the tip of the 2.0 mm guide; C232I) attached to polyethylene tubing (PE50) connected to a 10 μl Hamilton syringe. Infusions were controlled by a microinfusion pump (KDS 100, KD Scientific; New Hope, Pa.).

Behavioral Procedures Regarding Mice Dosed with Compound 22:

Amphetamine-induced hyperactivity (AIH) was examined in eight identical open-field chambers (16.5"×16"×12"; AccuScan Instruments, Columbus, Ohio). Activity was detected by infrared beam breaks and recorded automatically by VersaMax software (AccuScan). Daily sessions were automatically binned in 5 minute intervals (VersaDat; AccuSacn) for statistical analysis. AIH was run over three consecutive days as follows:

Day 1: Mice were acclimated to the infusion procedure by gently restraining them and removing the dummy cannula. Mice were restrained for three minutes at which point the dummy cannula was replaced. Mice were then placed into the open-field for 20 minutes and then removed for a saline injection. Mice were placed back into the open-field for an additional 30 minutes, at which point the mice were returned to their home cage.

Day 2 was run identically to Day 1, with the exception that the second day lasted for one hour (20 minutes→injection→40 minutes), and the restraint acclimation included an ICV saline infusion (2 minute infusion followed by one minute for drug diffusion away from the injection cannula).

Day 3 was the amphetamine challenge day. Mice were pre-treated with an infusion of compound 22 or vehicle 40 minutes prior to being placed in the open-field. After 20 minutes, mice were removed and challenged with amphetamine, and placed back in the open-field for 80 minutes.

Figure 7:
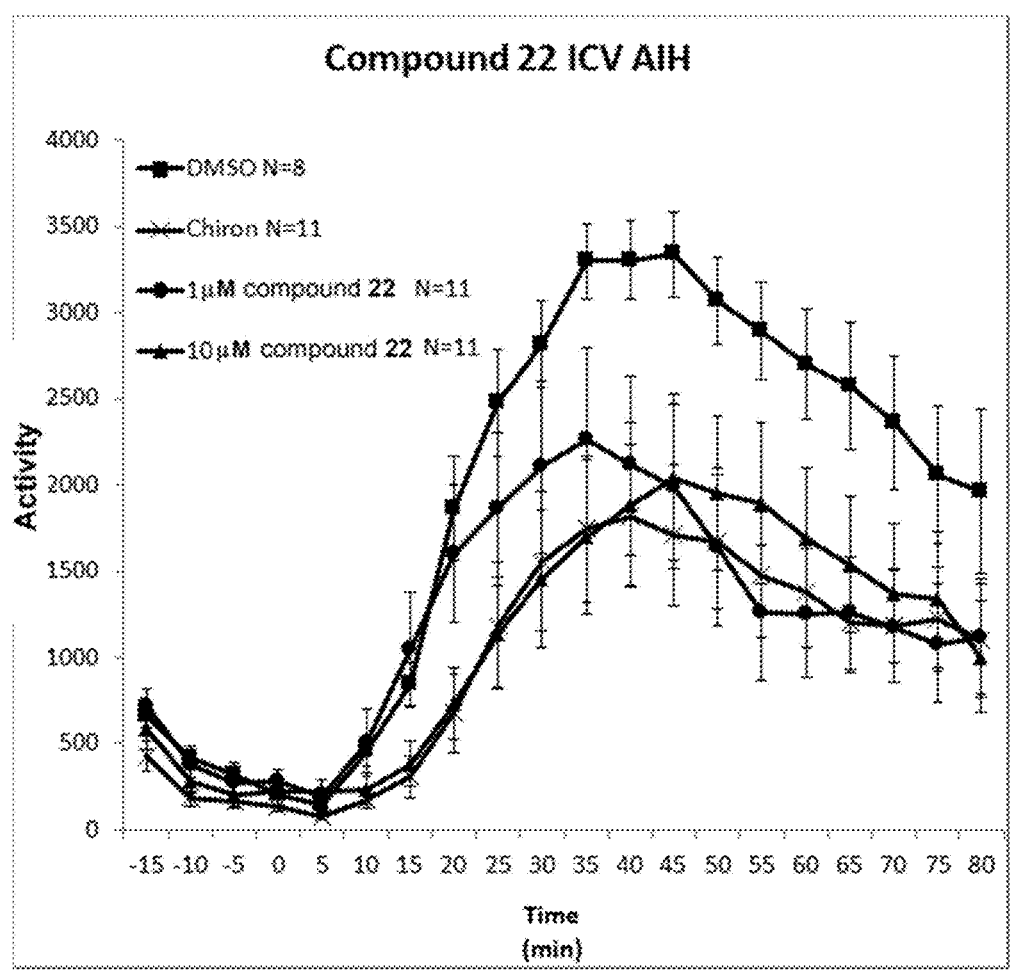
FIG. 7 shows the effect of Compound 22 in comparison to vehicle to attenuate amphetamine-induced hyperactivity over time following intracerebroventricular ICV injection.
Figure 8:
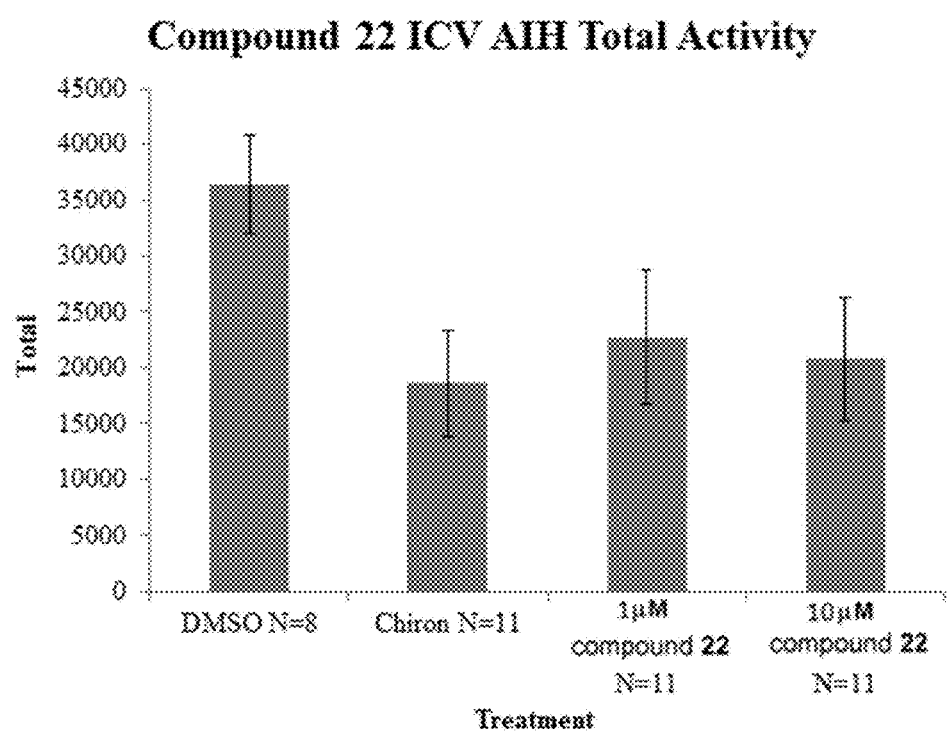
FIG. 8 shows the effect of Compound 22 on the total activity of amphetamine-induced hyperactivity total activity, in comparison to a vehicle.
Figure 9:
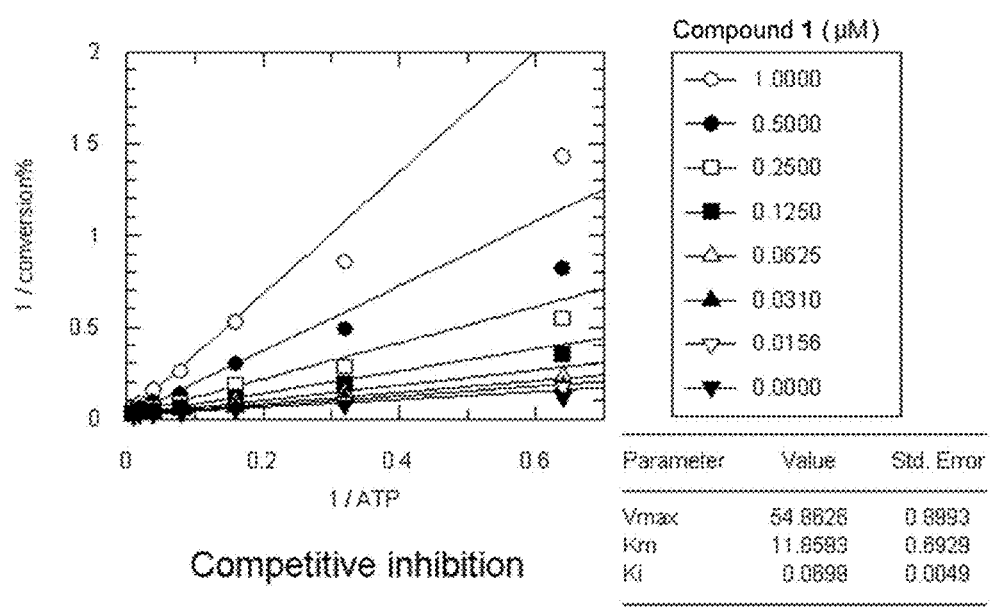
FIG. 9 shows a Lineweaver-Burk plot of competitive inhibition of Compound 22 for GSK3β.

Dosage: 3 mg/kg, 10 mg/kg, or 30 mg/kg. Vehicle: 45% PEG400, 45% Saline; 10% DMSO. The results are shown in FIGS. 7 and 8.

Behavioral Procedures Regarding Mice Dosed with Compound 70

Amphetamine-induced hyperactivity (AIH) was examined in eight identical open-field chambers (16.5"×16"×12"; AccuScan Instruments). Activity was detected by infrared beam breaks and recorded automatically by VersaMax software (AccuScan Instruments). Daily sessions were automatically binned in 5 minute intervals (VersaDat; AccuSacn) for statistical analysis. AIH was run over three consecutive days as follows:

Day 1: Mice were placed into the open-field for 20 minutes prior to removal for a saline injection. Mice were then placed back into the open-field for an additional 30 minutes, at which point the mice were returned to their home cage.

Day 2 was run identically to Day 1, with the exception that, in Day 2, the total time was one hour (20 minutes pre-injection followed by 40 minutes of activity monitoring).

Day 3 was the amphetamine challenge day. Mice were pre-treated with compound 137 (i.p. (intraperitoneal)) 30 minutes prior to being placed in the open fields. After 20 minutes, mice were removed, challenged with amphetamine, and placed back in the open-field for 80 minutes.

Figure 11A:
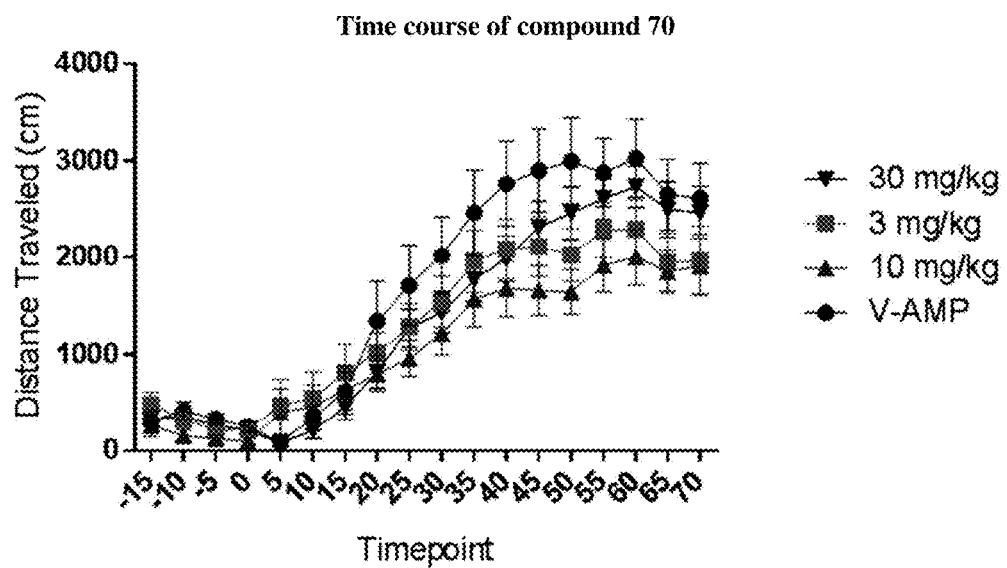
FIG. 11A shows the effect of compound 70 in comparison to vehicle to attenuate amphetamine-induced hyperactivity over time following systemic intraperitoneal injection.
Figure 11B:
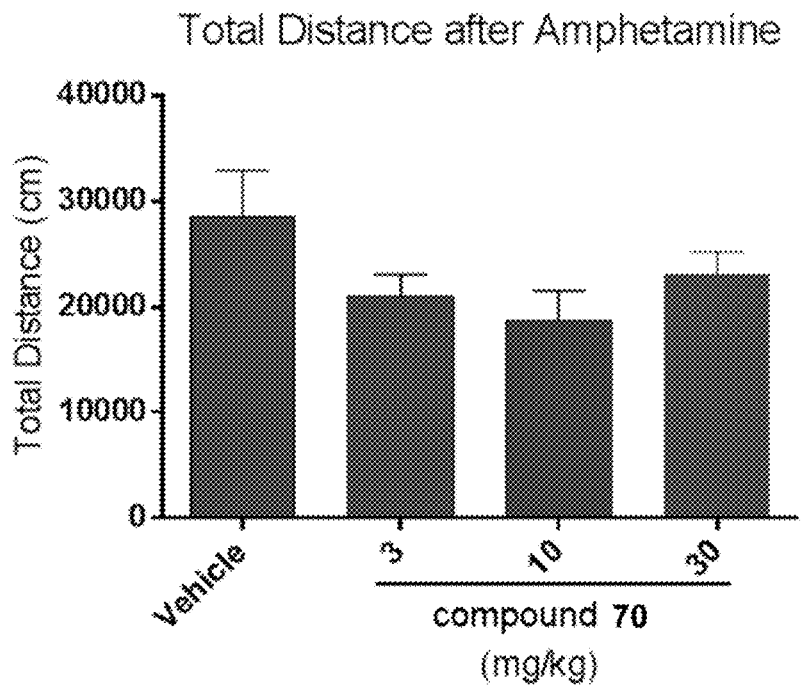
FIG. 11i shows the effect of compound 70 on the total activity of amphetamine-induced hyperactivity, in comparison to a vehicle.

Dosage: 3 mg/kg, 10 mg/kg, or 30 mg/kg. Vehicle: 45% PEG400, 45% Saline; 10% DMSO. The results are shown in FIG. 11.

Results

Summary of Screening Results

Figure 2:
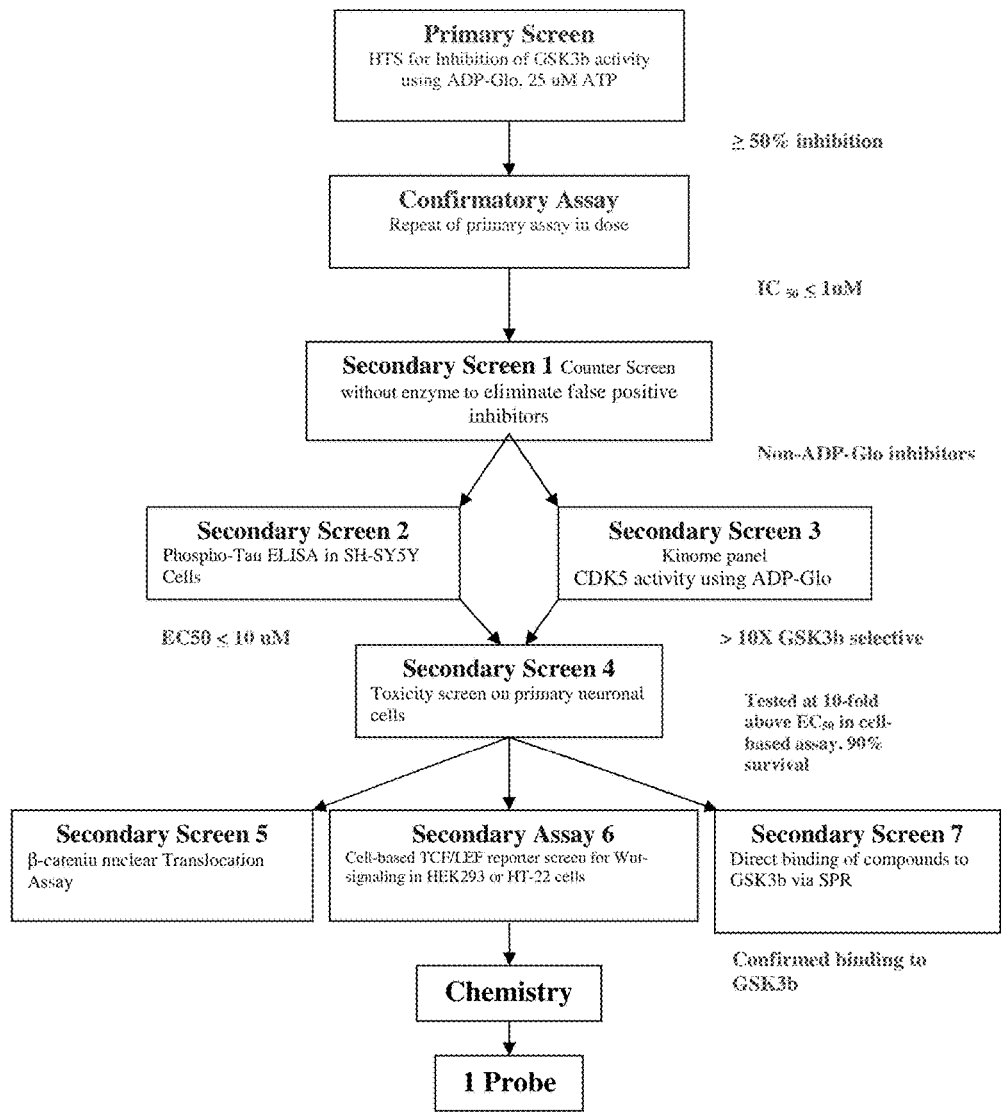
FIG. 2 shows an exemplary path for probe development.
Figure 3:
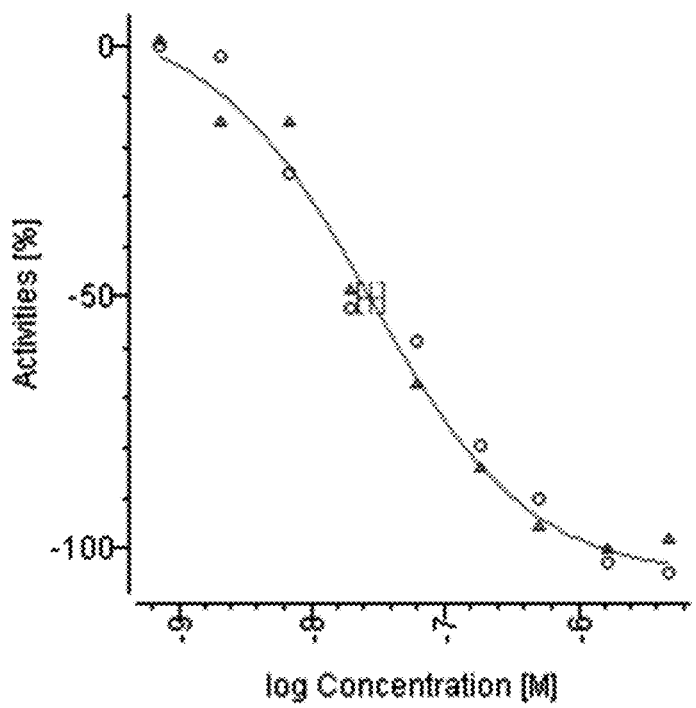
FIG. 3 shows dose-dependent activity of Compound 54 in target (GSK3β, top) and anti-target (CDK5, bottom). Representative curves with duplicated data (circles and triangles) are shown.
Figure 3:
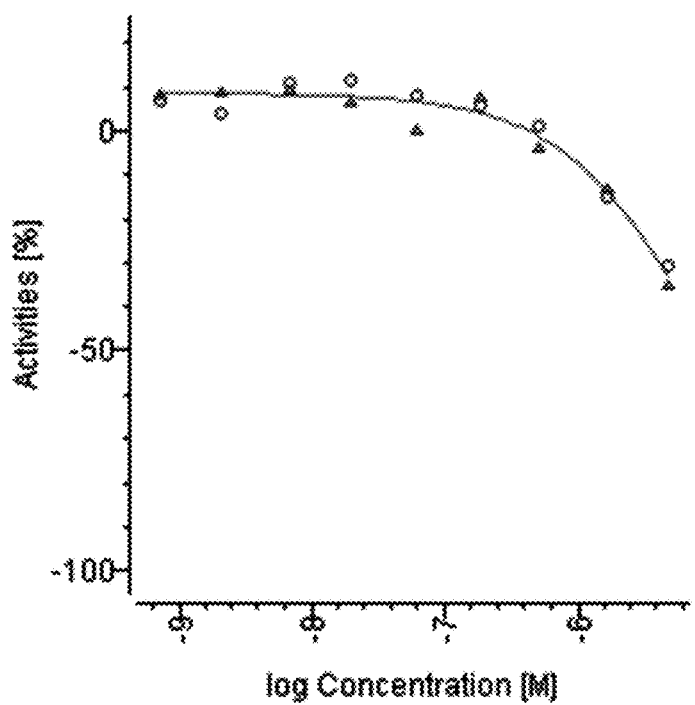

FIG. 2 displays an exemplary path for probe development.

A high-throughput screen of approximately 320,000 compounds was completed against human GSK3β in 1536-well plate format. The screen featured an average Z'>0.8. Approximately 1,000 compounds showed more than 25% inhibition were selected as actives.

These active compounds, along with approximately 1,000 of their negative analogues in the library, were cherry-picked and their potencies ($IC_{50}$s) against GSK3β assessed in doses in confirmatory retest. In parallel, a counter screen to rule out false positives due to inhibition of detection reagents was also completed. Compounds with promising potency ($IC_{50}$<10 μM against GSK3β at this stage) but not inhibiting detection reagents were further evaluated for structural features that are likely to render novelty, selectivity, and tractability.

Highly selective and potent GSK3β inhibitors were desired. Given that a great deal of work has been done on the GSK3β target, focus was made on structural series that do not possess scaffolds common to known kinase inhibitors. This initial filter allowed for the selection of a limited number of scaffolds from the original library of more than 320,000 small molecules screened. The selection of the pyrazolodihydropyridine scaffold (Scheme 1) as an initial probe starting point was done based on results from ADP-Glo experiments (vide infra, Table 2, Entry 1) that indicated a potency against GSK3β in the sub-micromolar range. Based on a search of PubChem, this scaffold had been analyzed in a large selection of assays (>600) but was confirmed as active in only one assay other than the assays described herein, which did not pertain to kinase inhibition. Secondly, as illustrated in Scheme 1a and b, the synthesis of this scaffold lent itself to rapid introduction of chemical diversity. This high synthetic tractability made for an attractive target from a chemistry vantage point. An initial selectivity analysis was done to determine the percent of the kinome inhibited by our initial HTS hit (Compound 1) using a kinome-wide profile (Carna Biosciences). The selectivity assay described above examined the inhibitory ability of the pyrazolodihydropyridine compound 1 against 311 kinases (representing 60% of the existing kinome) at a held concentration of 10 μM. Captured in Table 1 below are the results of the only kinases inhibited greater than 50% by treatment with Compound 1 at 10 μM.

TABLE 1

Percent Inhibition of Selected Kinases by HTS Hit (Compound 1) at 10 μM.

| Kinase | % Inhibition at 10 μM of Compound 1 | $IC_{50}$ for Compound 3 (μM) |
|---|---|---|
| GSK3α | 100.7 | 0.161 |
| GSK3β | 99.4 | 0.232 |
| CK1δ | 94.4 | 21.40 |
| CK1α | 57.2 | >30 |
| CK1ε | 50.0 | >30 |

CHIR99021 (or CHIR 99021), is a state of the art GSK3β inhibitor. When this compound was compared for selectivity with the same criteria as the HTS hit, CHIR99021 inhibited 21 kinases greater than 50% at 10 μM. This initial selectivity analysis combined with excellent potency led to the conclusion that the pyrazolodihydropyridine scaffold would be an excellent choice for further analysis as a probe candidate or as a potential therapeutic. Compound 3, an enantiomer of Compound 1, was examined for activity against the list of kinases previously determined (Table 1), illustrating that Compound 3 was selective for GSK3α/β and did not inhibit any of the CK1 family as seen when examining the racemic mixture.

Surface Plasmon Resonance Examination

A direct binding assay was then utilized as a secondary analysis of compound activity. Surface Plasmon Resonance (SPR), was employed to examine a small collection of pyrazolodihydropyridine derivatives described herein. Upon examination using this assay, it was discovered that substitution of the aryl ring at the 2-position led to a two-fold increase in affinity of these molecules for GSK3β. The HTS hit (Compound 1) has an experimentally determined $K_D$ of 130 nM. Compound 20 has an experimentally determined $K_D$ of 60 nM.

Separation of Enantiomers

Separation of the two enantiomers of Compound 20 was completed to arrive at a single compound. Compound 22, the R-enantiomer of Compound 20, inhibited 8 kinases at greater than 50% at 10 μM, and was selective for the GSK3 by more than 22-fold (22-fold to the next closest kinase, CDK5) (see Table 5). The absolute stereochemistry of the enantiomer was determined through co-crystallization of Compound 22 with GSK3β (see FIG. 4). The crystal structure also confirmed that the compound binds in the ATP binding site. To generate GSK3β/compound 22 co-crystals, the following procedure was used: (1) A 5-fold molar excess of compound 22 (in 100% DMSO) was added to a dilute GSK3β and then gently mixed; and (2) The GSK3β/compound 22 complex was incubated on ice for 30 minutes, concentrated to 5 mg/mL, and then screened with the methods described above. Crystals nucleated within four days and grew to maximum size after a week. Crystals for GSK3β/compound 22 were transported to the NSLS synchrotron facility at Brookhaven National Laboratory and evaluated using the X29 beamline.

Compounds were designed and synthesized to explore SAR at different chemical moieties of the pyrazolodihydropyridine scaffold, enhance desired properties including potency, selectivity, solubility, and in some instances, microsomal stability, and decrease liabilities. Racemic mixtures of certain analogs were separated and activities of enantiomers were measured (Table 2).

Biochemical characterization of these synthesized compounds were assayed against GSK3β and CDK5/p25, with CDK5/p25 serving as a counter target of GSK3β selectivity. Additional biochemical characterization for potency and selectivity were also performed at Carna Biosciences. A battery of cell-based assays were also performed to assess the cellular activity of a subset of these compounds. These cell-based assays include phosphorylation of Tau in SH-SY5Y human pathophysiology cells, beta-catenin nuclear translocation, and the TCF/LEF reporter assay that monitors the Wnt signaling pathway in HEK293 cells. The effects of these compounds on survival of SH-SY5Y pathophysiology cells were also monitored. Compound 54 consistently demonstrates 10-20 nM potency against GSK3β, 150-380 fold selectivity relative to CDK5/p25, superior kinome selective profile as compared to CHIR99021, and potent cellular activity.

A search of PubChem for the hit compound from the primary screen (Compound 1) revealed that it had been tested in 652 bioassays and was confirmed as active only in one assay other than the assays described herein. The assay was a screen for inhibitors of hydroxysteroid (17-beta) dehydrogenase 4 (HSD17B4) with a potency of 25.1 μM. Based on this information the compound does not seem to be a promiscuous inhibitor, also the scaffold does not contain any obvious chemical liabilities.

SAR Analysis

Results are described in Table 2.

TABLE 2

Exemplary assay results.

| Compound No. | ADP Glo Assay GSK3β (10 μM ATP) | Caliper Assay, GSK3α $IC_{50}$ (μM) | Caliper Assay, GSK3β $IC_{50}$ (μM) | SPR GSK3β ($K_d$) (μM) | SPR CK1δ ($K_d$) (μM) | ADP Glo Assay GSK3β vs CDK5 fold selectivity |
|---|---|---|---|---|---|---|
| 1 | B |   | B | B | B | >100X |
| 2 | D | B | C |   |   |   |
| 3 | B | B | B |   |   | 219X |
| 4 | B | A | B |   |   |   |
| 5 | B | B | B | B | B |   |
| 6 | C | B | B |   |   |   |
| 7 | D | B | C |   |   |   |
| 8 | C | B | B | B | B |   |
| 9 | C | B | B | B | C |   |
| 10 | B |   | A | C | B | 111X |
| 11 | B | A | B | C | B | 61X |
| 12 | C | C | C | C | A |   |
| 13 | B | A | A |   |   | 6X |
| 14 | B | A | B | B | B |   |
| 15 | C | B | C | C | C |   |
| 16 | B | A | A |   |   | 14X |
| 17 | B | A | B |   |   | 14X |
| 18 | B | B | B |   |   |   |
| 19 | C | B | C |   |   |   |
| 20 | B | A | A | A | D | 57X |
| 21 | C | B | C |   |   |   |
| 22 | A | A | A |   |   |   |
| 23 | B | B | B | D | C |   |
| 24 | D | D | C | C | C |   |
| 25 | A | A | A |   |   | 124X |
| 26 | C | B | C | C | B |   |
| 27 | A | A | A |   |   | 34X |
| 28 | A | A | A |   |   | 12X |
| 29 | D | B | C |   |   |   |
| 30 | B | B | B |   |   | 81X |
| 31 | D |   | D |   |   |   |
| 32 | B | A | A |   |   | 30X |
| 33 | A | A | A |   |   | 131X |
| 34 | D | C | D |   |   |   |
| 35 | C | B | B | D | D | 7X |
| 36 | B | C | B | B | D |   |
| 37 | B | B | B | B | C |   |
| 38 | D | C | C | B | D |   |
| 39 | C | C | C | D | D |   |
| 40 | C | B | B | D | D |   |
| 41 | A | A | A |   |   | 51X |
| 42 | C | B | B |   |   | 23X |
| 43 | C | C | C |   |   |   |
| 45 | B | B | B |   |   | 20X |
| 46 | C | B | B |   |   | 6X |
| 47 | B | A | B |   |   | 34X |
| 48 | B | A | A |   |   | 35X |
| 49 | B | B | A |   |   | 14X |
| 50 | B | C | B |   |   |   |
| 51 | C | B | B |   |   |   |
| 52 | A | A | A |   |   | 615X |
| 53 | A |   | A |   |   | 1076X |
| 54 | A | A | A |   |   | 105X |
| 55 | C | C | C |   |   |   |
| 56 | B | B | B |   |   |   |
| 57 |   | A | A |   |   |   |
| 58 | B | A | A |   |   |   |
| 59 | A | B | A |   |   |   |
| 60 | B | B | B |   |   |   |
| 61 | B | B | B |   |   |   |
| 62 | A | A | A |   |   | 165X |
| 63 | A | A | A |   |   | 276X |
| 64 | A | A | A |   |   | 162X |
| 65 | B | B | B |   |   | 130X |
| 66 |   | C | C |   |   |   |
| 67 | B | A | B |   |   | 47X |
| 68 | A | A | A |   |   | 244X |
| 69 |   | A | A |   |   |   |
| 70 |   | A | A |   |   |   |
| 71 | B | C |   |   |   |   |
| 72 |   | A | A |   |   |   |
| 73 | B | B |   |   |   |   |
| 74 |   | A | A |   |   |   |
| 75 | B | B |   |   |   |   |
| 76 | B | A |   |   |   |   |
| 77 | B | B |   |   |   |   |
| 78 | B | B |   |   |   |   |
| 79 |   | B |   |   |   |   |
| 80 | A | A |   |   |   |   |
| 81 | B | C |   |   |   |   |
| 83 |   | A | A |   |   |   |

TABLE 2-continued

Exemplary assay results.

| Compound No. | ADP Glo Assay GSK3β (10 μM ATP) | Caliper Assay, GSK3α IC$_{50}$ (μM) | Caliper Assay, GSK3β IC$_{50}$ (μM) | SPR GSK3 β (K$_d$) (μM) | SPR CK1δ (K$_d$) (μM) | ADP Glo Assay GSK3β vs CDK5 fold selectivity |
|---|---|---|---|---|---|---|
| 123 |   | A | A |   |   |   |
| 124 |   | C | D |   |   |   |
| 89  |   | A | B |   |   |   |
| 125 |   | A | A |   |   |   |
| 126 |   | C | C |   |   |   |
| 93  |   | A | A |   |   |   |
| 94  |   | C | C |   |   |   |
| 95  |   | A | A |   |   |   |
| 96  |   | A | B |   |   |   |
| 97  |   | C | D |   |   |   |
| 90  |   | A | A |   |   |   |
| 91  |   | A | B |   |   |   |
| 98  |   | B | B |   |   |   |
| 99  |   | B | B |   |   |   |
| 100 |   | B | C |   |   |   |
| 101 |   | B | B |   |   |   |
| 102 |   | B | B |   |   |   |
| 104 |   | A | A |   |   |   |
| 105 |   | A | B |   |   |   |
| 107 |   | B | C |   |   |   |
| 108 |   | A | B |   |   |   |
| 109 |   | D | E |   |   |   |
| 106 |   | B | C |   |   |   |
| 110 |   | A | A |   |   |   |
| 111 |   | A | A |   |   |   |
| 113 |   | A | A |   |   |   |
| 114 |   | A | A |   |   |   |
| 115 |   | C | C |   |   |   |
| 112 |   | A | A |   |   |   |
| 116 |   | A | A |   |   |   |
| 118 |   | A | A |   |   |   |
| 117 |   | A | A |   |   |   |
| 119 |   | B | A |   |   |   |
| 120 |   | B | B |   |   |   |
| 127 |   | B | A |   |   |   |
| 128 |   | D | B |   |   |   |
| 121 |   | B | B |   |   |   |

For Table 2, "A" indicates an IC$_{50}$ or K$_d$ of ≤0.100 μM, "B" indicates an IC$_{50}$ or K$_d$ of 0.101-1.000 μM, "C" indicates an IC$_{50}$ or K$_d$ of 1.001-5.000 μM, "D" indicates an IC$_{50}$ or K$_d$ of 5.001-30.000 μM, and "E" indicates an IC$_{50}$ or K$_d$>30 μM.

Figure 4:
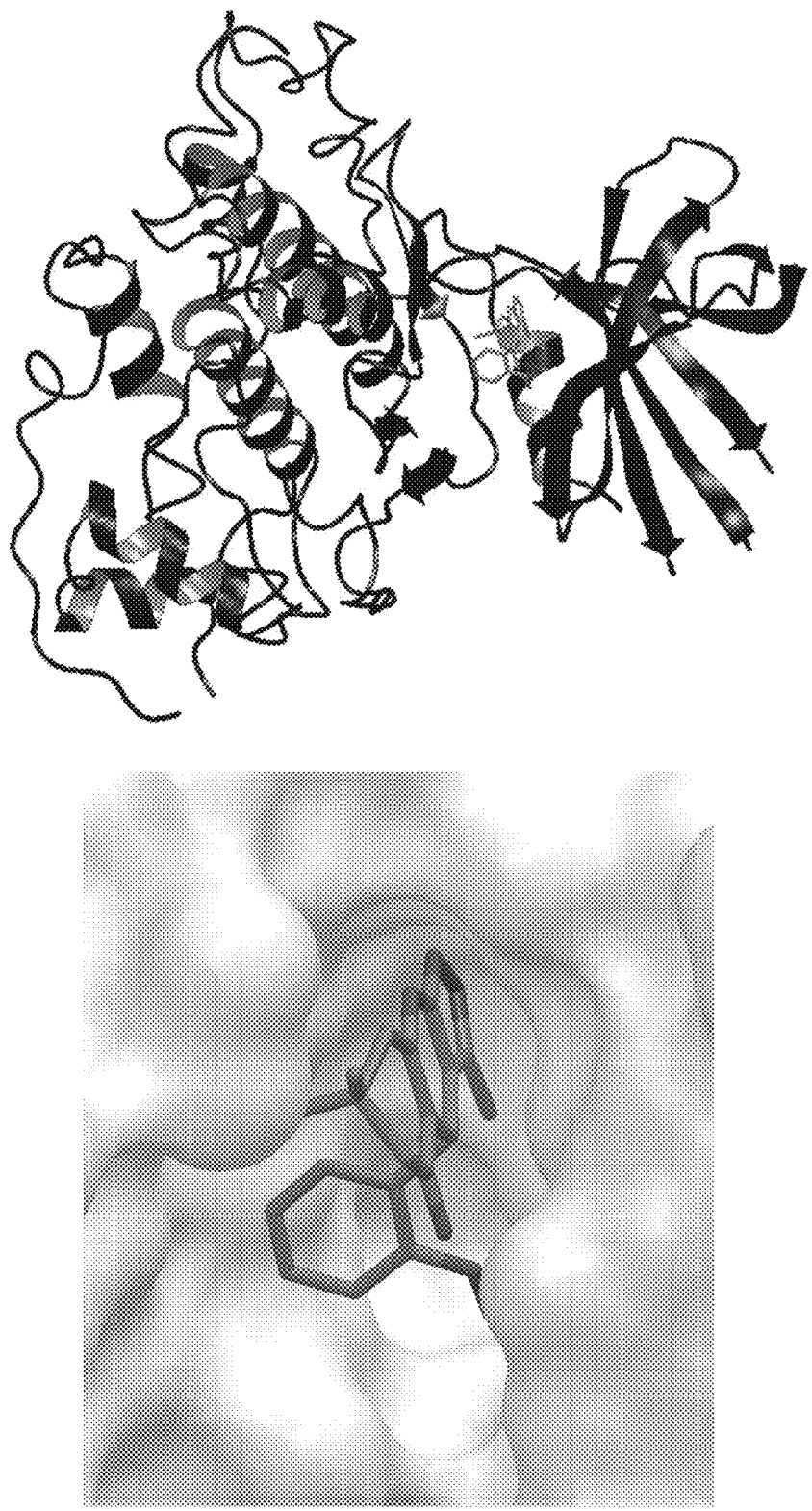
FIG. 4 shows a) a ribbon diagram depicting the crystal structure of GSK3β bound to Compound 22 in the ATP binding pocket and b) surface representation showing the binding site, binding orientation, and absolute configuration of Compound 22 in the crystal structure.

While keeping R$^3$ as a methyl group, various substitutions on the phenyl ring were explored. The nature of the substituent had little effect on the potency of the compound, fluoro, chloro, trifluormethyl, methyl, methoxy, and cyano all resulted in compounds with similar potency. The position of the substituent however, had a more profound impact on the activity. Substitution at the ortho-position resulted in the most potent compounds though, in general, the lowest selectivity versus CDK5. Compounds substituted at the meta-position were slightly less potent, but displayed higher selectivity over CDK5. Compounds which were substituted at the para-position resulted in a significant drop in GSK3 activity which can be predicted based on the binding observed in the crystal structure (FIG. 4). The crystal structure shows that while there are pockets for substituents at the 2- and 3-position, the binding at the 4-position of the phenyl ring is too tight to tolerate groups larger than hydrogen. Compounds that were particularly interesting due to their activity in the primary assay and cell assays were the 2-fluoro compound, 2-trifluoromethyl, 2-methoxy, 2-methylthio, 3-trifluoromethyl, and 3-cyano.

In instances where R$^3$ was kept constant as a methyl group, replacement of the phenyl group with heteroaromatics was explored. Replacement of the phenyl group with thiophenes resulted in a drop in potency against GSK3 and no increase in cell activity. Imidazole replacement also led to a drop in potency against GSK3. Replacement with a 3-pyridyl group resulted in a compound that was equipotent with the hit compound and increased solubility, however had no appreciable cell activity. Other pyridyl replacements resulted in a drop in potency compared to the hit compound.

Having investigated a range of common replacements and substitutions for the phenyl group, the 2-methoxy phenyl was chosen for its potency, selectivity and physical properties to use as the base compound for further SAR studies. Movement of the geminal dimethyl group to the α-position of the carbonyl, resulted in a compound that had a drop in potency in the primary assay and a loss of activity in the cell assays. Removal of the geminal dimethyl group resulted in a moderate loss of activity. Replacement of the six-membered ring with a five member ring provided the aromatized compound, which had no activity against GSK3. Removal of the keto containing-ring resulted in a significant drop in activity. Replacement of the germinal dimethyl with a cyclohexyl group provided a compound that was similarly potent to the lead compound, however lost activity in the cell assays.

Compounds for which the pyrazole has been replaced or substituted at the methyl group were explored. Removal of the methyl group from the pyrazole results in a compound that has comparable potency to the lead compound indicating that the methyl group is not vital for activity. Replacement of the methyl with larger alkyl groups, such as ethyl, iso-propyl, and tert-butyl display a trend of lowering the activity as the group increases in size. This can be explained by the crystal structure as there is a small pocket at this position that can be exploited for substitution allowing the increase in size to ethyl, however further increases result in negative interactions. The phenyl replacement results in a drop in potency and a decrease in activity in the cell assays. The trifluoromethyl-containing pyrazole, while similarly potent to the lead compound in the primary assay shows a significant improvement in the cell assays, presumably due to increase permeability. Replacement of the pyrazole with an oxazole or phenyl provides compounds with limited activity.

The microsomal stability of certain compounds is poor. Primarily the benzylic position appears to be prone to oxidation. As mentioned previously, the aromatized analog of the hit compound is inactive. Since our primary mode of metabolism presumably results in aromatized products compounds were synthesized to block this site of metabolism. To test whether P450 mediated hydroxylation of the benzylic position was key to the poor metabolic stability profile of the series a compound in which the hydrogen at the benzylic position was replaced with a deuterium was synthesized in an effort to potentially take advantage of a secondary isotope effect and provide an analog with improved metabolic stability. The deuterium replacement provides a compound that had similar activity to the hit compound, however, there was no improvement in microsomal stability. The crystal structure indicated that substitution at the benzylic position with a methyl group may be tolerated, e.g., Compound 67 displayed improved microsomal stability (6% to 32%) and also did not result in a loss in potency against GSK3, however this compound displayed no activity in the cell assays. Future efforts will be directed towards compounds that have a methyl at the benzylic position with improved cell activity.

Based on the results from substitution of the phenyl and pyrazole shown in Table 2, several hybrid compounds were synthesized. Replacement of the methyl on the pyrazole of the hit compound with a trifluoromethyl results in an increase in potency in the primary assay and activity in the cell assays indicating that the trifluoromethyl is beneficial for cell permeability. Mono- or di-substitution of the phenyl with fluoro and trifluoromethyl groups, lead to compounds that while potent in the primary assay, lose activity in the cell-based assays.

The results from Table 2 indicated that one enantiomer in the racemic mixtures of the compounds was responsible for the activity observed which was then explained by the binding of the active enantiomer in the crystal structure, therefore separation of the enantiomers of several compounds was carried out. For these compounds, it was found that the enantiomer wherein the aryl group was "down" as shown in the structures below was typically more potent for GSK3β.

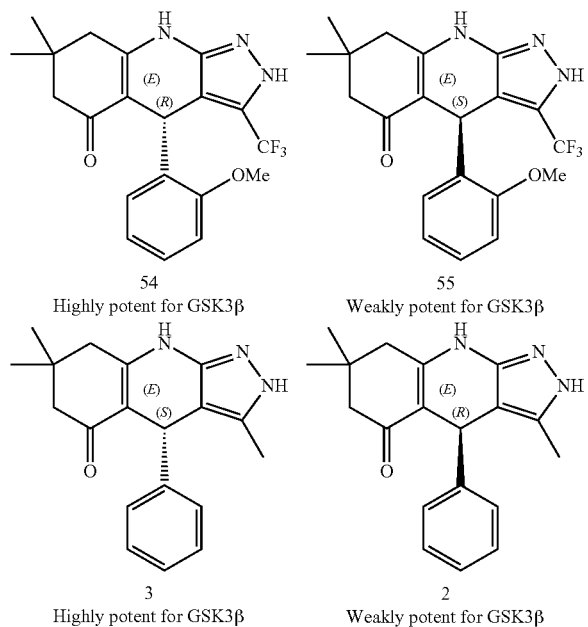

54
Highly potent for GSK3β

55
Weakly potent for GSK3β

3
Highly potent for GSK3β

2
Weakly potent for GSK3β

Chemical Characterization of Compound 54

Compound 54 was analyzed by UPLC, $^1$H and $^{13}$C NMR spectroscopy, and high-resolution mass spectrometry. The data obtained from NMR and mass spectroscopy were consistent with the structure of Compound 54 (data not shown), and UPLC indicated an isolated purity of >95%.

The solubility of Compound 54 was experimentally determined to be 85 μM in phosphate buffered saline (PBS, pH 7.4, 23° C.) solution. Plasma protein binding (PPB) was determined to be 93% bound in human plasma. Compound 54 is stable in human plasma, with approximately 97% remaining after a 5-hour incubation period. The compound was found to be stable in glutathione (GSH) with 99% remaining after 48 hours.

The stability of Compound 54 in PBS (0.1% DMSO) was measured over 48 hours. The concentration of Compound 54 steadily increased over 48 hours to about 200% (data not shown). Without wishing to be bound by theory, it is believed that the gradual increase in concentration is the direct result of more compound dissolving in PBS over time. In other words, the PBS stability assay was performed under the recommended conditions, the kinetic solubility of Compound 54 was measured in PBS and not its stability. Thus, the total amount of Compound 54 present in the well after the compound was treated with PBS alone was determined for a given length of time. Acetonitrile was added at various time points to wells containing Compound 54 in PBS and measured the total amount of the compound. This result is shown in FIG. 1. From these results, Compound 54 seems to be stable in PBS since more than 95% is still present after 48 hours of incubation.

Additional Analytical Analysis

Compound 54 was found to be 93% and 91% bound to human and mouse plasma respectively and stable in human and mouse plasma with 97% and 99% remaining after 5 hours. The hit compound, racemic probe and seven analogs were subjected to mouse microsomes for stability analysis (Table 3). The racemic probe was found to be unstable to mouse microsomes with <1% remaining after 1 hour. All other analogs that were unsubstituted at the benzylic position had <7% remaining after 1 hour, indicating that the primary metabolic liability is the benzylic position. Substitution at the benzylic position with a methyl group resulted in 32% compound remaining after 1 hour. Further compounds with substitution at the benzylic position may yield increased potency while maintaining or improving this metabolic stability gain.

TABLE 3

Solubility, protein binding, plasma stability, and microsomal stability of select compounds.

| | Solubility | Analytical (in mice) | | |
|---|---|---|---|---|
| Compound number | in PBS no DMSO (μM) | Protein binding % bound | Plasma stability % remaining | Microsomal stability 60 min |
| 1 | 20.6 | 83.7 | 96.9 | 6.0 |
| 4 | | 83.2 | 98.6 | 6.8 |
| 20 | 130.2 | 77.1 | 87.2 | |
| 53 | | 94.7 | 98.7 | 0.3 |
| 67 | 388.1 | 84.8 | 99.7 | 32 |
| 83 | 409.6 | 89.8 | 1016 | 51.5 |
| 108 | >500 | 79.4 | 96.6 | 108.2 |
| 95 | 253.2 | 86.8 | 99.0 | 68.2 |
| 113 | 107.8 | 90.0 | 90.5 | 44.8 |

All values are the average of at least two replicates

Cellular Activity

GSK3β is constitutively active and often serves as a negative regulator of cellular signaling. The inhibition of GSK3β removes this negative regulation resulting in the activation of various cellular pathways. Many proteins, including beta-catenin in the Wnt signaling pathway and Tau protein in the microtubule dynamics, are subject to GSK3β phosphorylation. Specifically, GSK3β directly phosphorylates Tau protein at Ser199 and modulates Tau's self-assembly. Hyperphosphorylation of Tau is implicated in the pathophysiology of Alzheimer's disorder. Beta-catenin is phosphorylated by GSK3β in the N-terminal region and this phosphorylation marks the protein for degradation. Accumulation of beta-catenin following GSK3β inhibition translocates to the nucleus and activates TCF/LEF promoter driven genes in the canonical Wnt pathway. Tau and β-catenin were chosen as two independent substrates to evaluate GSK3β inhibition in three cellular assays:

1) Assess the amount of Tau-phosphorylation (Ser199) in SH-SY5Y cells upon GSK3β inhibition (AID 624057);

2) Evaluate the amount of beta-catenin nuclear accumulation following GSK3β inhibition in U20S cells (AID 624086) and subsequent activation of TCF/LEF by increased nuclear beta-catenin in HEK293 cells (AID 624088).

Mono substitution on the phenyl group was explored, and some of the enzymatically active compounds were further evaluated in cellular assays. chloro-, methoxy, and trifluoromethyl substitution at 2-position of the phenyl group generated compounds with <1 µM $IC_{50}$ in enzymatic assays, and were active in inhibiting Tau-phosphorylation ($IC_{50}$<10 µM) by GSK3β. A 3-substitution with a trifluoromethyl group on the phenyl ring was also active phospho-Tau assay. These compounds were similarly active in the beta-catenin nuclear translocation assay and TCF/LEF reporter assay with $EC_{50}$ between 5 and 25 µM.

Based on the 2-methoxy on the phenyl ring, substitutions on the pyrazole were explored. Trifluorosubstitution on the pyrazole had the best cellular activity within the series, with a submicromolar (0.48 µM) $IC_{50}$ in p-Tau ELISA, and an $EC_{50}$ in the TCF/LEF reporter assay of <10 µM.

The trifluorosubstitution on the pyrazole was fixed and substitution on the phenyl ring was further evaluated in enzymatic and cellular assays, and 2-methoxy on the phenyl ring is found to have a superior cellular activity profile.

As expected, enzymatically active enantiomers were also found to be active in cells. While Compound 47, Compound 50, and Compound 51 have similar enzymatic activities, Compound 50 demonstrated reduced selectivity against CDK5. Compound 54 was chosen as a probe due to its excellent potency and selectivity.

Figure 14A:
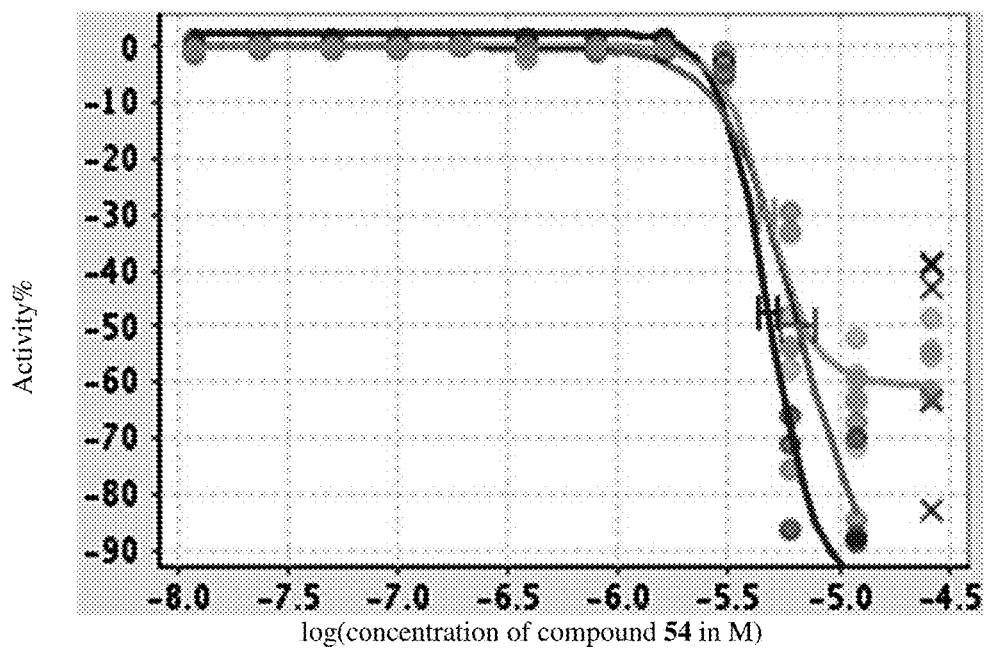
FIG. 14A to 14B show the results of compound 54 in a p-Tau ELISA SH-SY5Y assay and TCF/LEF reporter assay.
Figure 14B:
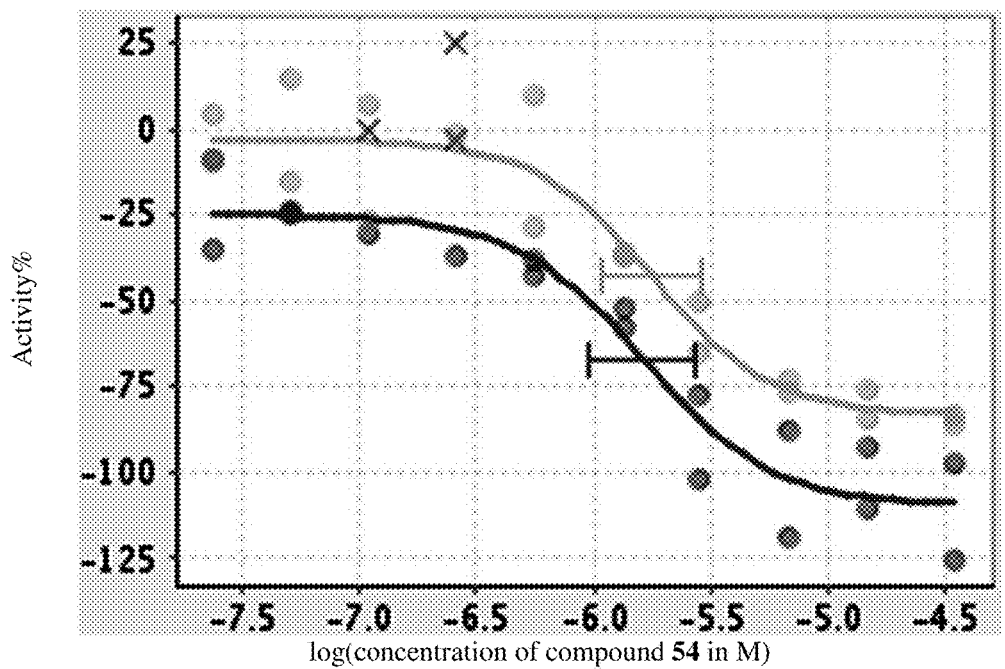

Results from the Tau, β-Catenin, and TCF/LEF assays are shown in Table 4 and FIGS. 14A to 14B.

TABLE 4

Results from exemplary Tau, β-Catenin, and TCF/LEF assays.

| Compound No. | p-Tau Inhibition ELISA $EC_{50}$ SH-SY5Y (µM) | beta-Catenin translocation $EC_{50}$ (µM) | TCF/LEF $EC_{50}$ (µM) |
|---|---|---|---|
| 1 | >30 | >50 | >25 |
| 2 | >30 | >50 | >25 |
| 3 | 11.51 | >50 | 31 |
| 4 | NT | >50 | >25 |
| 5 | NT | NT | >25 |
| 8 | NT | NT | >25 |
| 9 | NT | NT | >25 |
| 10 | 5.02 | NT | 12.69 |
| 11 | NT | NT | >25 |
| 12 | NT | NT | >25 |
| 13 | 2.49 | 41.1 | 24.0 |
| 14 | NT | NT | 31.3 |
| 15 | NT | NT | >25 |
| 17 | NT | >50 | >25 |
| 18 | NT | >50 | >25 |
| 19 | NT | NT | >25 |
| 20 | 9.14 | NT | 17.85 |
| 21 | >30 | NT | >25 |
| 23 | NT | NT | >25 |
| 24 | NT | NT | >25 |
| 25 | 2.85 | 10.94 | 4.34 |
| 26 | | | >25 |
| 27 | 4.24 | 12.0 | 9.59 |
| 28 | 1.80 | 6.32 | 4.80 |
| 29 | >30 | >50 | >25 |
| 30 | 4.68 | 11.2 | 7.67 |
| 31 | NT | >50 | >25 |
| 32 | NT | NT | 23.4 |
| 33 | 2.50 | 11.99 | 5.16 |
| 34 | NT | NT | >25 |
| 35 | | | >25 |
| 36 | NT | NT | >25 |
| 37 | NT | NT | >25 |
| 38 | NT | NT | >25 |
| 39 | NT | NT | >25 |
| 40 | NT | NT | >25 |
| 41 | 2.27 | 11.79 | 6.70 |
| 42 | NT | >50 | >25 |
| 43 | >30 | >50 | >25 |
| 44 | NT | >50 | >25 |
| 45 | NT | >50 | >25 |
| 46 | NT | >50 | >25 |
| 47 | NT | 30.37 | 11.40 |
| 48 | NT | 24.56 | 16.20 |
| 49 | NT | >50 | >25 |
| 50 | NT | >50 | >25 |
| 51 | NT | >50 | >25 |
| 52 | 0.507 | 13.10 | 9.32 |
| 53 | 1.76 | 14.00 | 16.85 |
| 54 | 1.70 | 6.97 | 5.35 |
| 55 | >30 | >50 | >25 |
| 56 | NT | >50 | >25 |
| 58 | NT | NT | >25 |
| 59 | | | >25 |
| 60 | NT | NT | >25 |
| 61 | | | >25 |
| 62 | 0.652 | 4.23 | 3.93 |
| 63 | 1.38 | 3.34 | 4.83 |
| 64 | NT | NT | >25 |
| 65 | | | >25 |
| 67 | NT | NT | >25 |
| 68 | 1.58 | 10.83 | 7.77 |
| 69 | 2.41 | | 20.75 |
| 70 | 0.819 | | 1.86 |
| 71 | >30 | | |
| 72 | 0.426 | | 1.49 |
| 73 | 22.0 | | >25 |
| 74 | 2.09 | | 6.19 |
| 76 | 2.09 | | 6.19 |
| 80 | | | 5.63 |
| 89 | 22.19 | | |
| 92 | 20.41 | | |
| 95 | 6.35 | | |
| 104 | 4.48 | | |
| 110 | 4.55 | | |
| 111 | 2.98 | | |
| 113 | 4.80 | | |

NT = not tested

Profiling Assays

Kinome Wide Selectivity.

Figure 5:
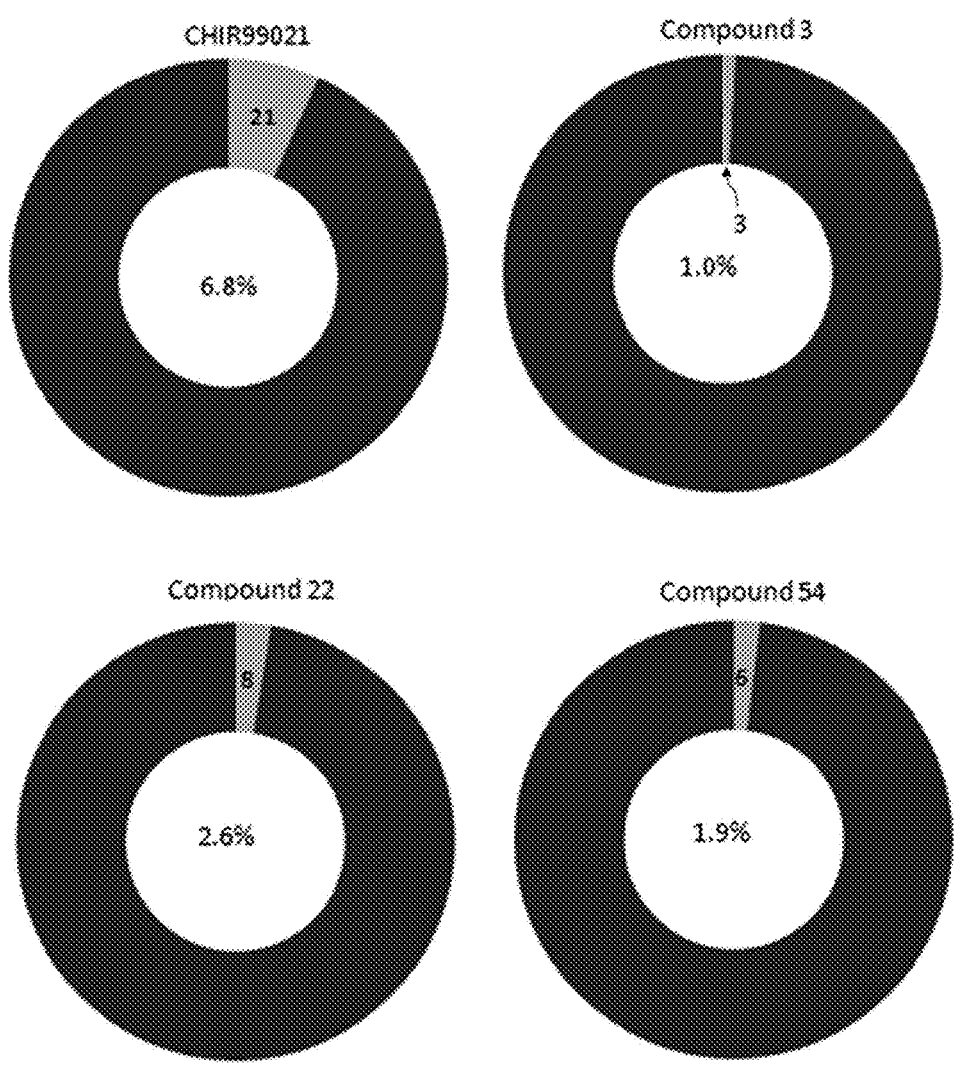
FIG. 5 shows the percent of the kinome (311 kinases) inhibited by CHIR99021 and three compounds of the present disclosure.

A key component to generating a useful probe for determining the role of GSK3β in CNS is solidifying selectivity of action. Illustrated in FIG. 5 are graphs that depict the percentage of the kinome that is inhibited by each compound investigated. As shown, CHIR99021 is of very low selectivity in comparison to the pyrazolodihydropyridines described herein. The HTS hit (Compound 1) shows excellent functional selectivity against this panel of 311 kinases, inhibiting only 5 kinases as described earlier. Two other compounds examined in this fashion (Compound 22 and Compound 54) showed similar impressive selectivity marks, inhibiting only 2.3 and 2.6% of the kinome (311 kinases) respectively, with markedly improved potencies discussed in the next section.

Absolute Selectivity Determination.

A second delimiter utilized in arriving at Compound 54 was the absolute selectivity in $IC_{50}$ of each compound against the target kinase (e.g., GSK3β) and the next closest anti-target. In the three cases above (Compound 1, Compound 22, and Compound 54) the choice of which compound to pursue became very clear when looking at these values. Illustrated below (Table 5) are the $IC_{50}$ determinations for two of these compounds against selected kinases that were inhibited more than 50% at a concentration of 10 µM.

TABLE 5

Absolute Selectivity of Selected Compounds.

| Kinase | Compound 22 $IC_{50}$ µM | Selectivity Factor | Kinase | Compound 54 $IC_{50}$ µM | Selectivity Factor |
|---|---|---|---|---|---|
| GSK3α | 0.027 | — | GSK3α | 0.013 | — |
| GSK3β | 0.061 | — | GSK3β | 0.012 | — |
| CDK2/CycA2 | 1.5 | 25 | CDK2/CycA2 | 3.9 | 325 |
| CDK2/CycE1 | 2.2 | 36 | CDK2/CycE1 | 4.4 | 367 |
| CDK5 | 1.4 | 23 | CDK5 | 1.8 | 150 |

Utilizing an absolute measurement instead of a general selectivity profile allows for the conclusion that Compound 54 is much more selective than Compound 22 (selectivity factor of 150 compared to 23 against CDK5 the kinase inhibited by the highest % at 10 µM). The selectivity factor in this case is determined by comparing the $IC_{50}$ of the compound against GSK3β, to that against the other competing kinases. The matter of selectivity is discussed in more detail in the discussion section.

Pharmacokinetics and Brain Distribution of Compound 70

Figure 10:
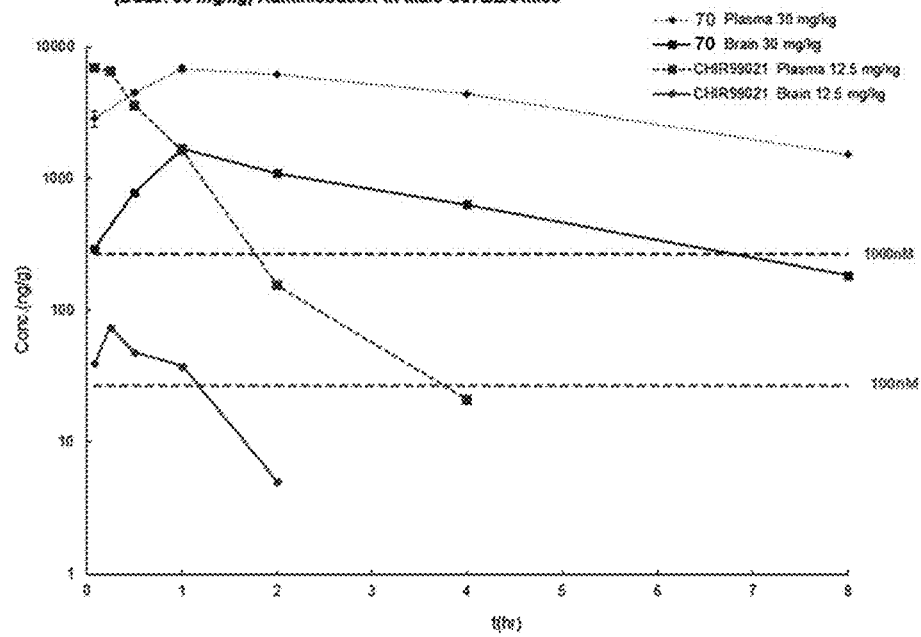
FIG. 10 shows that, compared to compound CHIR99021, compound 137 showed an improved pharmacokinetic profile, such as systemic exposure and brain distribution, when dosed in male C57BL/6 mice. Conc.: concentration. AUC: area under the curve. $T_{1/2}$: half life. Cmax: maximum concentration.
Figure 10:
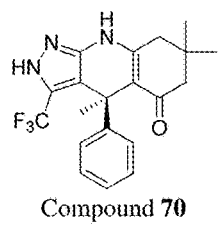

A single intraperitoneal dose of compound 70 (structure shown in FIG. 10) or CHIR99021 were administered to male C57BL/6 mice at 30 mg/kg or 12.5 mg/kg, respectively. The pharmacokinetics (e.g., concentration in plasma and brain distribution) of compounds 70 and CHIR99021 were measured after the dose at different time points (up to about 8 hours). The results (shown in FIG. 10) indicate that, compared to compound CHIR99021, compound 70 showed an improved pharmacokinetic profile, such as systemic exposure and brain distribution.

Figure 12:
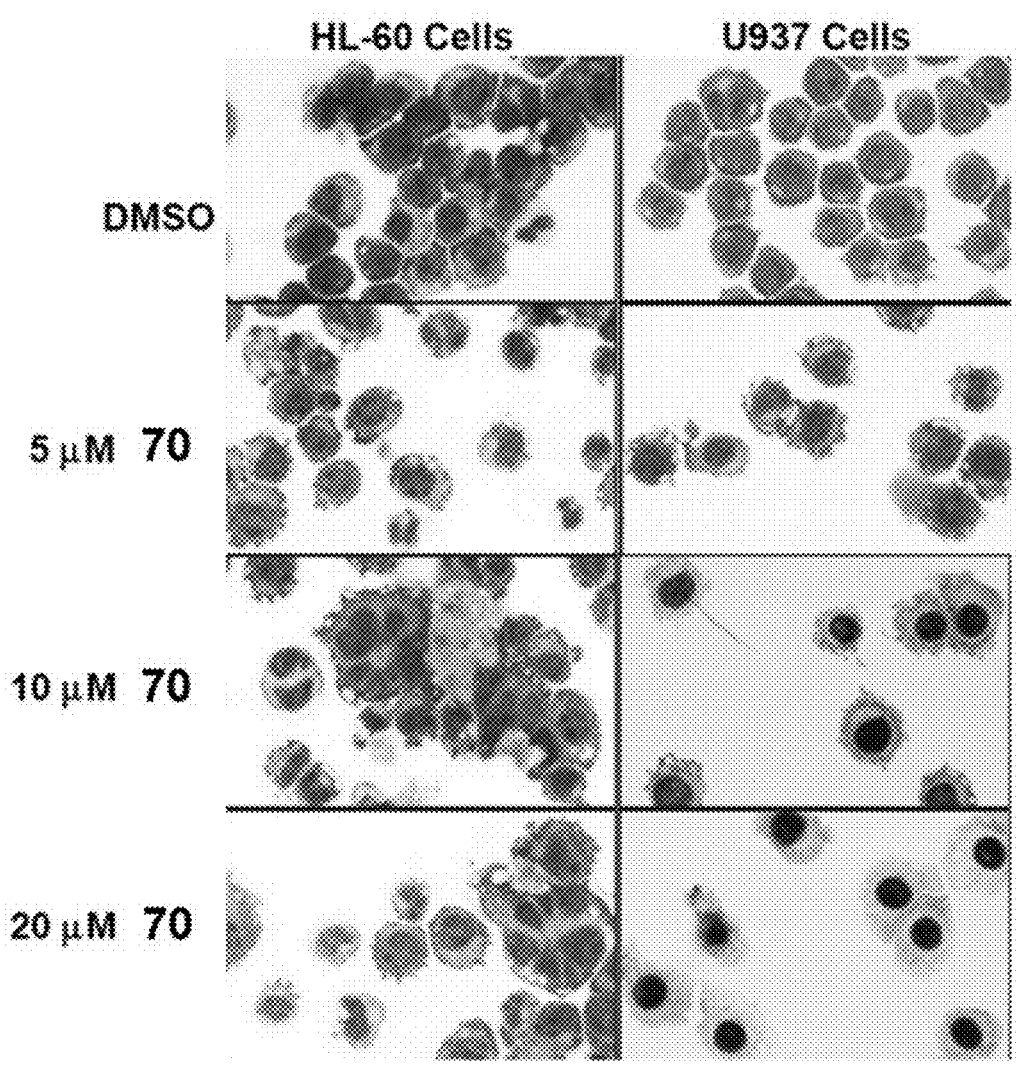
FIG. 12 shows that selective GSK3 inhibitor 70 induces morphological evidence of AML (acute myeloid leukemia) differentiation. May-Grunwald Giemsa staining of AML cell lines three days after treatment with compound 70 demonstrated cellular differentiation compared to vehicle-treated controls.

Compound 70 Induces Morphological Changes in AML Cell Lines Consistent with Myeloid Differentiation On day three post-chemical treatment, cytospin preparations were performed. Changes in cellular morphology were evaluated by May-Grunwald Giemsa staining (Sigma Aldrich). Images were acquired by light microscopy at 400× magnification. The results showed that May-Grunwald Giemsa staining of AML cell lines three days after treatment with compound 70 demonstrated cellular differentiation compared to vehicle-treated controls (FIG. 12).

Figure 13A:
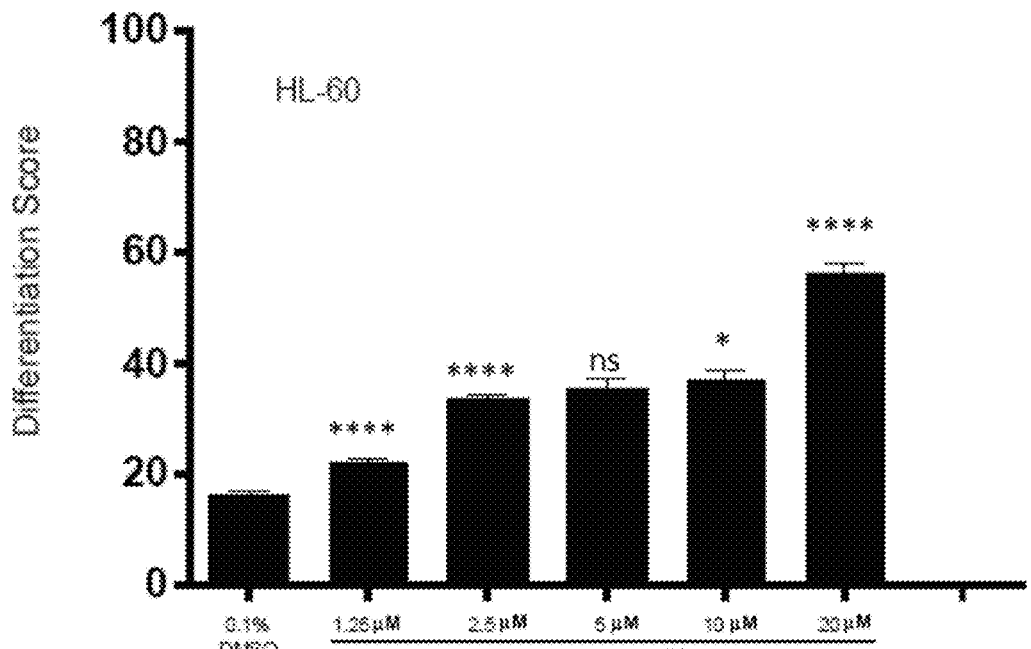
FIGS. 13A to 13B show that compound 70 induces AML (acute myeloid leukemia) differentiation by GE-HTS signature. HL-60 and U937 cells were treated for three days with compound 70 or vehicle. A 32-gene differentiation signature was quantified by the LMA/bead-based approach and a Weighted Summed Score (Differentiation Score) calculated for all genes was determined for each condition. Error bars denote the mean±SD of 8 replicates and statistical significance of the differences between these differentiation scores was derived using a one-way ANOVA with a Bonferroni correction.
Figure 13B:
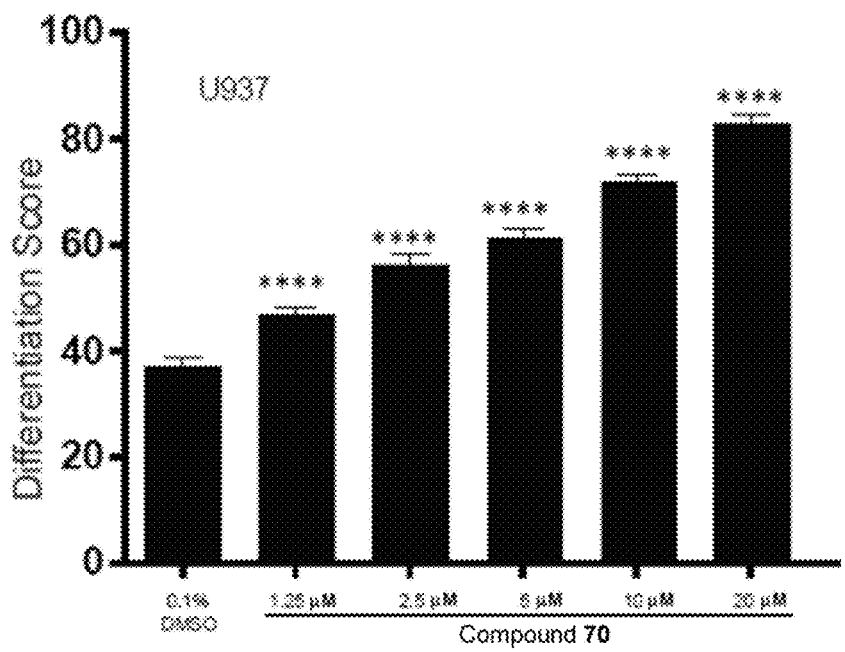

Compound 70 Induces a Gene Expression Signature in AML Cell Lines Consistent with Myeloid Differentiation GE-HTS was conducted using methods previously described to assess for an expression signature composed of genes that distinguish AML from either the neutrophil or monocyte differentiated state (Banerji V, Frumm S M, Ross K N, Li L S, Schinzel A C, Hahn C K, Kakoza R M, Chow K T, Ross L, Alexe G, Tolliday N, Inguilizian H, Galinsky I, Stone R M, DeAngelo D J, Roti G, Aster J C, Hahn W C, Kung A L, Stegmaier K. The intersection of genetic and chemical genomic screens identifies GSK-3alpha as a target in human acute myeloid leukemia. *J Clin Invest.* 2012; 122:935-947; Hahn C K, Berchuck J E, Ross K N, Kakoza R M, Clauser K, Schinzel A C, Ross L, Galinsky I, Davis T N, Silver S J, Root D E, Stone R M, DeAngelo D J, Carroll M, Hahn W C, Carr S A, Golub T R, Kung A L, Stegmaier K. Proteomic and genetic approaches identify Syk as an AML target. *Cancer Cell.* 2009; 16:281-294). The 32 marker genes for myeloid differentiation were chosen using previously published Affymetrix AML-related data sets (Stegmaier K, Ross K N, Colavito S A, O'Malley S, Stockwell B R, Golub T R. Gene expression-based high-throughput screening (GE-HTS) and application to leukemia differentiation. *Nat Genet.* 2004; 36:257-263). These genes have been shown to distinguish AML from either neutrophil or monocyte with p<0.05 by t-test and to distinguish undifferentiated versus HL-60 differentiated with ATRA, Phorbol 12-myristate 13-acetate, or 1,25-dihydroxyvitamin D3 with p<0.05 by t-test. This assay uses ligation-mediated amplification with a fluorescent bead-based detection system to quantify the expression of up to 500 genes in a single well. Two primary scoring methods are used to quantify induction of the 32-gene myeloid differentiation signature. The Summed Score combines expression ratios (marker gene/control gene) by summing them with a sign determined by the expected direction of regulation from ATRA-treated positive controls. The Weighted Summed Score combines expression ratios by summing them with a weight and sign determined by the signal-to-noise ratio of each expression ratio for the positive control (ATRA-treated) and negative control (DMSO-treated) samples. To assess the statistical significance of the differences between these differentiation scores a one-way ANOVA with a Bonferroni correction as a post-hoc test was employed. The results show that compound 70 induced a gene expression signature in AML cell lines consistent with myeloid differentiation (FIGS. 13A and 13B).

Discussion

Beginning from the hit from HTS, the SAR of four regions of the molecule was investigated through the synthesis of multiple compounds, the benzylic position, the pyrazole moiety, the phenyl ring, and the diketone derived ring on the western portion of the molecule guided by crystal structure analysis (see FIG. 4). Substitution at the benzylic position with a methyl group was tolerated. Oxidation of the central ring led to a loss in activity. Modifications to the pyrazole were tolerated, such as substitution with a trifluoromethyl group. Through SAR of the phenyl ring, it was found that compounds having substitution at the 2- or 3-position were particularly active. Substitution with heteroaromatics was tolerated. Compounds with substitution at the 4-position were found to display some activity. Compound having trifluoromethyl or methoxy substitution at the 2- or 3-position were found to be particularly active in cells. Compound 54 was identified as much more potent than the hit compound, especially in cellular assays in which the hit compound was weakly active.

Overall, the data support the identification of a potent (e.g., $IC_{50}$=0.02 µM) probe (Compound 54) that inhibits GSK3 and is selective against 309 other kinases with greater than 150-fold selectivity (vida infra). Compound 54 was found to be active in three different cell assays that display the compound's ability to inhibit GSK3 in different cellular contexts.

Advantages Over Previously Disclosed Inhibitors

Other inhibitors of GSK3β exist; however, these compounds that have been tested against other kinases have been found lacking in selectivity (Leclerc, et al. *J Biol Chem,* 2001; 276: 251-260; Meijer, et al. *Chem Biol,* 2003; 10:1255-1266; Polychronopoulos, et al. *J Med Chem,* 2004; 47:935-946; Leost, et al. *Eur J Biochem,* 2000; 267:5983-

Figure 6:
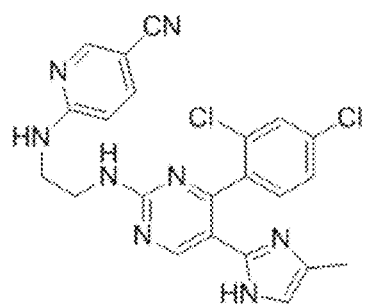
FIG. 6 shows known GSK3 inhibitors.
Figure 6:
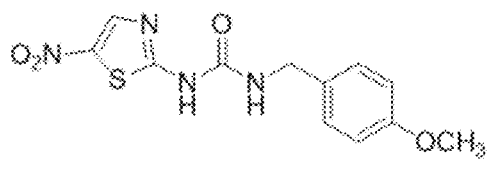
Figure 6:
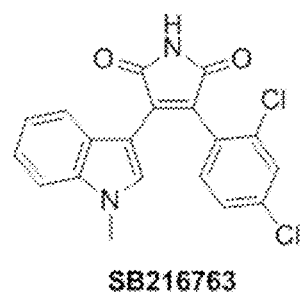
Figure 6:
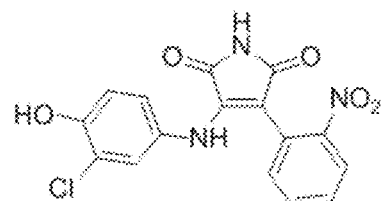
Figure 6:
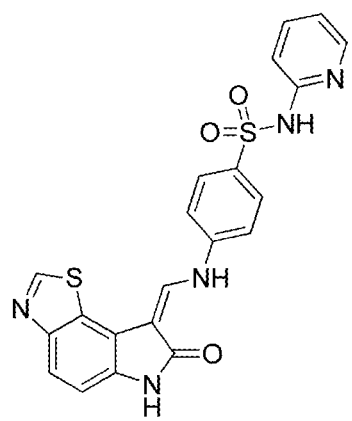

5994; Chang, et al. Chem Biol, 1999; 7:51-63). The kinases that the compounds most often inhibit are the cyclin-dependent kinases (CDKs), to which GSK3 is most closely related. Selectivity profiles were compared with previously existing GSK3 inhibitors such as CHIR 99021 (FIG. 6). CHIR 99021 was tested in a screen against >300 kinases confirming that the compound inhibits CDK2 along with many other kinases including CDK5, CDK9, LIMK1, CLK1, PLK1, ERK5 at greater than 50% at 10 µM. A comparison of the activity and physical properties of Compound 54 and CHIR 99021 is shown in Table 6 and a comparison of Compound 54 activity to the kinase profile of CHIR 99021 is shown in Table 7. As can been seen in the tables below, Compound 54 displays comparable potency to CHIR 99021 in all assays while displaying significantly greater selectivity against the kinome. Furthermore, based on the microsomal data in Table 3, there is promise for developing a GSK3 inhibitor of this class with microsomal stability and potency, allowing for in vivo studies that are not possible with CHIR 99021 due to its poor physical properties. Compared to GSK3 inhibitors known in the art, the compounds described are more stable in microsomes and show improved pharmacokinetic and/or selectivity profiles.

TABLE 6

Comparison of Activity and Physical Properties of CHIR99021 and Compound 54.

| Description | CHIR99021 | Compound 54 |
|---|---|---|
| $IC_{50}$ ADP Glo GSK3β (µM) | 0.008 | 0.02 |
| TCF/LEF (µM) | 6.0 | 4.8 |
| beta-Catenin Translocation (µM) | 10.0 | 5.28 |
| p-Tau (µM) | 0.44 | 1.03 |
| cLogP | 3.57 | 4.34 |
| tPSA | 115 | 67 |
| Log BBB (calculated) | −0.38 | 0.33 |
| Microsomal Stability | M: 4% | M: 0% |

TABLE 7

Comparison of CHIR 99021 Kinase profile and Compound 54 (% Inhibition at 10 µM).

| Kinase | CHIR99021 | Compound 54 |
|---|---|---|
| GSK3α | 99.9 | 99.9 |
| GSK3β | 99.9 | 99.9 |
| BRAF | 53.8 | 10.8 |
| CDK2/CycA2 | 79.3 | 78.7 |
| CDK2/CycE1 | 67.2 | 73.5 |
| CDK4 | 65.3 | 19 |
| CDK5 | 51.2 | 86.7 |
| CDK9 | 88.1 | 20.5 |
| CK1g1 | 85.8 | 0.5 |
| CK1g3 | 70.5 | 3.2 |
| DYKR1B | 70.5 | 52.5 |
| Erk5 | 61.3 | 0.6 |
| HIPK4 | 55.5 | 3.2 |
| LIMK1 | 78.9 | 6.7 |
| MAP2K6 | 65.3 | 0.1 |
| MELK | 53.5 | 4.5 |
| MLK3 | 52.7 | 18.8 |
| PKR | 57.1 | 0.1 |
| PLK1 | 59.2 | 21.3 |
| RSK3 | 53.6 | 0.1 |

Mechanism of Action Studies

Compound 54 demonstrates inhibitory characteristics consistent with it being an ATP-competitive inhibitor. $IC_{50}$s were measured against GSK3β at two different ATP concentrations. Compared with an $IC_{50}$ of 24 nM at 7 µM ATP, the IC50 of Compound 54 at 100 µM of ATP increased to 143 nM, suggesting ATP-competitive inhibition.

Cellularly, inhibition of GSK3β by Compound 54 removes negative regulation of two important signaling pathways in microtubule dynamics and Wnt signaling. Beta-catenin in the Wnt pathway and Tau protein in the microtubule dynamics, are subject to GSK3β phosphorylation. GSK3β is constitutively active and often serves as a negative regulator of cellular signaling. Specifically, inhibition of GSK3β inhibits the phosphorylation of Tau protein, and the inhibition of beta-catenin phosphorylation prevents the b-catenin degradation, promotes its nuclear translocation and subsequently activates TCF/LEF reporter. As such, this compound and others described herein would be excellent tools to investigate Wnt pathway as well as probe for microtubule dynamics in cells and potentially in animals.

Compounds 22 and 54 were tested in cellular assays, including as a tool to probe the GSK/Wnt molecular pathways in vitro through the use of human and rodent neural progenitor cells to determine their ability to promote neurogenesis. Through the use of induced pluripotent stem cells-neural progenitor cells (iPSC-NPCs) from patients with neuropsychiatric disorders, such as bipolar disorder and schizophrenia, the question of whether there are differences in response to GSK3 modulators was explored. This allowed for determination of the role of dysregulated GSK3 signaling in the underlying pathologies. What was also determined is the effect of selective GSK3 inhibition on cells which have a genetic variation in DISC1 to help understand the role of DISC1/GSK3 signaling in the pathophysiology of neuropsychiatric disorders.

Neurogenesis Assay

Figure 15:
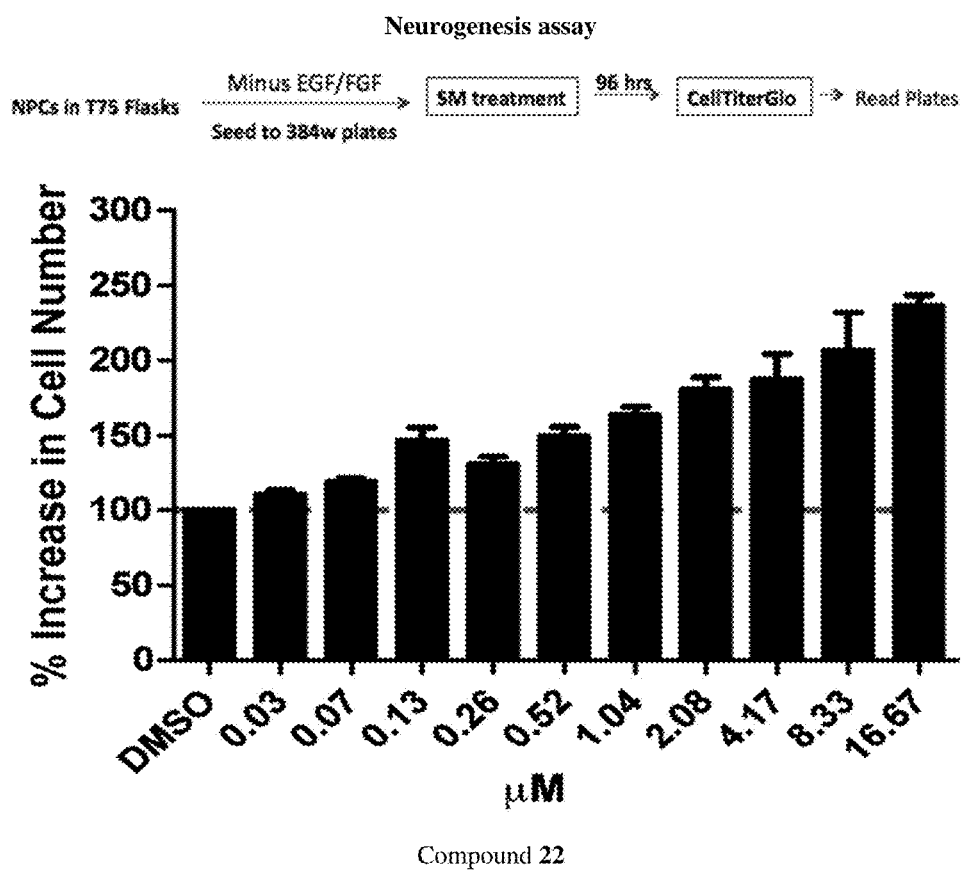
FIG. 15 shows the results of compound 22 in a neurogenesis assay.

Human neuroprogenitor cells were generated and derived according to methods known in the art. See, e.g., Zhao et al., J Biomol Screen. 2012 October; 17(9):1252-63. Single-cell suspensions were prepared from the human iPSC-NPCs, stably integrated with the TCF/LEF-luciferase reporter, and dispensed into 96- or 384-well plates at the seeding densities of 20,000 or 6,000 per well, respectively, using a Matrix WellMate (Thermo Scientific) microplate dispenser. A 96-well plate format was used for measuring Wnt3a and lithium (lithium chloride solution, 10 M; Fluka, St. Louis, Mo.) dose-response effects, whereas a 384-well plate format was used for all small-molecule probe treatments and chemical screening. The next day, cells were subjected to various 24-h treatments. Just prior to the luminescence reading, the plates were taken out of a 37° C. incubator and equilibrated to room temperature for 30 min before the SteadyGlo reagent (Promega, Madison, Wis.) was dispensed (volume equal 1:1 SteadyGlo:culture medium). Luminescence was measured after a 10-min incubation using an EnVision multilabel plate reader (PerkinElmer, Waltham, Mass.). Exemplary results are shown in FIG. 15, which indicates that compound 22 promoted neurogenesis.

Compounds described herein can also be tested in vivo, such as testing the effect of selective GSK3 inhibitors on mouse models for neuropsychiatric disorders, such as the amphetamine induced hyperactivity model (AIH) for mania and the forced swim test and learned helplessness tests for depression.

Other Embodiments

The foregoing has been a description of certain non-limiting embodiments of the invention. Those of ordinary skill in the art will appreciate that various changes and modifications to this description may be made without departing from the spirit or scope of the present invention, as defined in the following claims.

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

---

---

What is claimed is:

1. A method of treating Fragile X syndrome comprising administering to a subject suffering from Fragile X syndrome an effective amount of a compound of formula I:

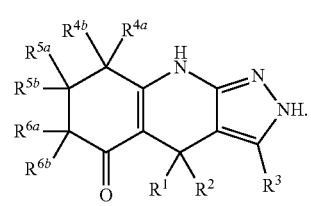

or a pharmaceutically acceptable salt thereof, wherein:
R$^1$ is selected from the group consisting of optionally substituted phenyl and optionally substituted heteroaryl;
R$^2$ is unsubstituted C$_{1-6}$ aliphatic or C$_{1-6}$ aliphatic substituted with one or more instances of halogen;
or R$^1$ and R$^2$ are taken together with their intervening atoms to form optionally substituted, 3- to 7-membered, monocyclic, saturated, carbocyclyl or heterocyclyl, wherein the carbocyclyl or heterocyclyl formed by taking together R$^1$ and R$^2$ is optionally fused to optionally substituted phenyl or optionally substituted heteroaryl;
R$^3$ is selected from the group consisting of hydrogen, halogen, —CN, —NO$_2$, optionally substituted C$_{1-6}$ aliphatic, —OR$^A$, —N(R$^B$)$_2$, and —SR$^A$;
each R$^A$ is independently selected from the group consisting of hydrogen and optionally substituted C$_{1-6}$ aliphatic;
each R$^B$ is independently selected from the group consisting of hydrogen and optionally substituted C$_{1-6}$ aliphatic;
R$^{4a}$ and R$^{4b}$ are each hydrogen;
R$^{5a}$ and R$^{5b}$ are each independently selected from the group consisting of hydrogen, halogen, —CN, —OR$^A$, —N(R$^B$)$_2$, unsubstituted C$_{1-6}$ aliphatic, and C$_{1-6}$ aliphatic substituted with one or more instances of halogen, or R$^{5a}$ and R$^{5b}$ are taken together with their intervening atoms to form unsubstituted, 3- to 7-membered, monocyclic, saturated, carbocyclyl or heterocyclyl; and
R$^{6a}$ and R$^{6b}$ are each hydrogen;
wherein:
each instance of the heteroaryl is independently 5- or 6-membered, monocyclic heteroaryl comprising 1 to 4 ring heteroatoms independently selected from the group consisting of nitrogen, oxygen, and sulfur, as valency allows;
each instance of the heterocyclyl independently comprises 1 to 4 ring heteroatoms independently selected from the group consisting of nitrogen, oxygen, and sulfur, as valency allows;
when any one of the aliphatic, carbocyclyl, heterocyclyl, phenyl, and heteroaryl referred to above is substituted with one or more substituents at a carbon atom, the one or more substituents at the carbon atom are independently selected from Group (i);
when any one of the heterocyclyl and heteroaryl referred to above is substituted with one or more substituents at a nitrogen atoms, the one or more substituents at the nitrogen atom are independently selected from Group (ii);
Group (i) consists of halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3$$^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$—C(=S)N(R$^{bb}$)$_2$, —C(=O)SR$^{aa}$, —C(=S)SR$^{aa}$, —SC(=S)SR$^{aa}$, —SC(=O) SR$^{aa}$, —OC(=O)SR$^{aa}$, —SC(=O)OR$^{aa}$, —SC(=O)R$^{aa}$, —P(=O)(R$^{aa}$)$_2$, —OP(=O)(R$^{aa}$)$_2$, —OP(=O)(OR$^{cc}$)$_2$, —P(=O)(NR$^{bb}$)$_2$, —OP(=O)(NR$^{bb}$)$_2$, —NR$^{bb}$P(=O)(OR$^{cc}$)$_2$, —NR$^{bb}$P(=O)(NR$^{bb}$)$_2$, —P(R$^{cc}$)$_2$, —OP(R$^{cc}$)$_2$, —B(R$^{aa}$)$_2$, —B(OR$^{cc}$)$_2$, —BR$^{aa}$(OR$^{cc}$), C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, carbocyclyl, heterocyclyl, aryl, and heteroaryl is independently substituted with 0, 1, 2, 3, 4, or 5 R$^{dd}$ groups; or two geminal hydrogens on a carbon atom are replaced with the group =O, =S, =NN(R$^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$, or =NOR$^{cc}$; and
Group (ii) consists of hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{bb}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)(R$^{aa}$)$_2$, —P(=O)(NR$^{cc}$)$_2$, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, carbocyclyl, heterocyclyl, aryl, and heteroaryl is independently substituted with 0, 1, 2, 3, 4, or 5 R$^{dd}$ groups;
wherein:
each instance of R$^{aa}$ is, independently, selected from C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;
each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR, —SOR$^{aa}$, —C(=S)N(R$^{cc}$)$_2$, —C(=O)SR$^{cc}$, —C(=S)SR$^{cc}$, —P(=O)(R$^{aa}$)$_2$, —P(=O)(NR$^{cc}$)$_2$, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;
each instance of R$^{cc}$ is, independently, selected from hydrogen, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups;

each instance of $R^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3$$^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)(R$^{ee}$)$_2$, —OP(=O)(R$^{ee}$)$_2$, —OP(=O)(OR$^{ee}$)$_2$, C$_{1-6}$ alkyl, C$_{1-6}$ perhaloalkyl, C$_{2-6}$ alkenyl, C$_{2-6}$ alkynyl, C$_{3-10}$ carbocyclyl, 3-10 membered heterocyclyl, C$_{6-10}$ aryl, 5-10 membered heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups, or two geminal R$^{dd}$ substituents can be joined to form =O or =S;

each instance of R$^{ee}$ is, independently, selected from C$_{1-6}$ alkyl, C$_{1-6}$ perhaloalkyl, C$_{2-6}$ alkenyl, C$_{2-6}$ alkynyl, C$_{3-10}$ carbocyclyl, C$_{6-10}$ aryl, 3-10 membered heterocyclyl, and 3-10 membered heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups;

each instance of R$^{ff}$ is, independently, selected from hydrogen, C$_{1-6}$ alkyl, C$_{1-6}$ perhaloalkyl, C$_{2-6}$ alkenyl, C$_{2-6}$ alkynyl, C$_{3-10}$ carbocyclyl, 3-10 membered heterocyclyl, C$_{6-10}$ aryl and 5-10 membered heteroaryl, or two R$^{ff}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{gg}$ groups;

each instance of R$^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3$$^+$X$^-$, —NH(C$_{1-6}$ alkyl)$_2$$^+$X$^-$, —NH$_2$(C$_{1-6}$ alkyl)$^+$X$^-$, —NH$_3$$^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(=NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$ —C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)(C$_{1-6}$ alkyl)$_2$, —OP(=O)(C$_{1-6}$ alkyl)$_2$, —OP(=)(OC$_{1-6}$ alkyl)$_2$, C$_{1-6}$ alkyl, C$_{1-6}$ perhaloalkyl, C$_{2-6}$ alkenyl, C$_{2-6}$ alkynyl, C$_{3-10}$ carbocyclyl, C$_{6-10}$ aryl, 3-10 membered heterocyclyl, 5-10 membered heteroaryl; or two geminal R$^{gg}$ substituents can be joined to form =O or =S; and X$^-$ is a counterion, wherein the counterion is a halide ion, NO$_3$$^-$, ClO$_4$$^-$, OH$^-$, H$_2$PO$_4$$^-$, HSO$_4$$^-$, a sulfonate ion, or a carboxylate ion.

2. The method of claim 1, wherein R$^1$ is optionally substituted phenyl.

3. The method of claim 1, wherein R$^{5a}$ and R$^{5b}$ are each unsubstituted methyl.

4. The method of claim 1, wherein the compound is of the formula:

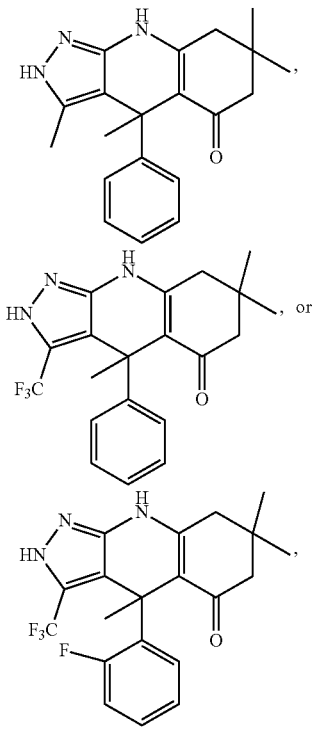

or a pharmaceutically acceptable salt thereof.

5. A method of treating bipolar disorder comprising administering to a subject suffering from a mood disorder an effective amount of a compound of formula I:

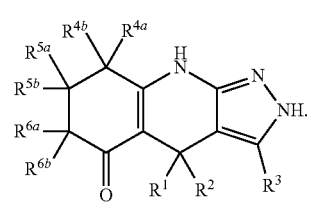

or a pharmaceutically acceptable salt thereof, wherein:
R$^1$ is selected from the group consisting of optionally substituted phenyl and optionally substituted heteroaryl;
R$^2$ is unsubstituted C$_{1-6}$ aliphatic or C$_{1-6}$ aliphatic substituted with one or more instances of halogen;
or R$^1$ and R$^2$ are taken together with their intervening atoms to form optionally substituted, 3- to 7-membered, monocyclic, saturated, carbocyclyl or heterocyclyl, wherein the carbocyclyl or heterocyclyl formed by taking together R$^1$ and R$^2$ is optionally fused to optionally substituted phenyl or optionally substituted heteroaryl;
R$^3$ is selected from the group consisting of hydrogen, halogen, —CN, —NO$_2$, optionally substituted C$_{1-6}$ aliphatic, —OR$^A$, —N(R$^B$)$_2$, and —SR$^A$;
each R$^A$ is independently selected from the group consisting of hydrogen and optionally substituted C$_{1-6}$ aliphatic;
each R$^B$ is independently selected from the group consisting of hydrogen and optionally substituted C$_{1-6}$ aliphatic;
R$^{4a}$ and R$^{4b}$ are each hydrogen;
R$^{5a}$ and R$^{5b}$ are each independently selected from the group consisting of hydrogen, halogen, —CN, —OR$^A$, —N(R$^B$)$_2$, unsubstituted C$_{1-6}$ aliphatic, and C$_{1-6}$ aliphatic substituted with one or more instances of halogen, or R$^{5a}$ and R$^{5b}$ are taken together with their intervening atoms to form unsubstituted, 3- to 7-membered, monocyclic, saturated, carbocyclyl or heterocyclyl; and
R$^{6a}$ and R$^{6b}$ are each hydrogen;
wherein:
  each instance of the heteroaryl is independently 5- or 6-membered, monocyclic heteroaryl comprising 1 to 4 ring heteroatoms independently selected from the group consisting of nitrogen, oxygen, and sulfur, as valency allows;
  each instance of the heterocyclyl independently comprises 1 to 4 ring heteroatoms independently selected from the group consisting of nitrogen, oxygen, and sulfur, as valency allows;
  when any one of the aliphatic, carbocyclyl, heterocyclyl, phenyl, and heteroaryl referred to above is substituted with one or more substituents at a carbon atom, the one or more substituents at the carbon atom are independently selected from Group (i);
  when any one of the heterocyclyl and heteroaryl referred to above is substituted with one or more substituents at a nitrogen atoms, the one or more substituents at the nitrogen atom are independently selected from Group (ii);
  Group (i) consists of halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3$$^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$—C(=S)N(R$^{bb}$)$_2$, —C(=O)SR$^{aa}$, —C(=S)SR$^{aa}$, —SC(=S)SR$^{aa}$, —SC(=O) SR$^{aa}$, —OC(=O)SR$^{aa}$, —SC(=O)OR$^{aa}$, —SC(=O)R$^{aa}$, —P(=O)(R$^{aa}$)$_2$, —OP(=O)(R$^{aa}$)$_2$, —OP(=O)(OR$^{cc}$)$_2$, —P(=O)(NR$^{bb}$)$_2$, —OP(=O)(NR$^{bb}$)$_2$, —NR$^{bb}$P(=O)(OR$^{cc}$)$_2$, —NR$^{bb}$P(=O)(NR$^{bb}$)$_2$, —P(R$^{cc}$)$_2$, —OP(R$^{cc}$)$_2$, —B(R$^{aa}$)$_2$, —B(OR$^{cc}$)$_2$, —BR$^{aa}$(OR$^{cc}$), C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, carbocyclyl, heterocyclyl, aryl, and heteroaryl is independently substituted with 0, 1, 2, 3, 4, or 5 R$^{dd}$ groups; or two geminal hydrogens on a carbon atom are replaced with the group =O, =S, =NN(R$^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$, or =NOR$^{cc}$; and Group (ii) consists of hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{bb}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)(R$^{aa}$)$_2$, —P(=O)(NR$^{cc}$)$_2$, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, carbocyclyl, heterocyclyl, aryl, and heteroaryl is independently substituted with 0, 1, 2, 3, 4, or 5 R$^{dd}$ groups;

wherein:
  each instance of R$^{aa}$ is, independently, selected from C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;
  each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R, —SO$_2$OR, —SOR$^{aa}$, —C(=S)N(R$^{cc}$)$_2$, —C(=O)SR$^{cc}$, —C(=S)SR$^{cc}$, —P(=O)(R$^{aa}$)$_2$, —P(=O)(NR$^{cc}$)$_2$, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;
  each instance of R$^{cc}$ is, independently, selected from hydrogen, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups;

each instance of $R^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$)OR$^{ee}$, —C(=NR)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)(R$^{ee}$)$_2$, —OP(=O)(R$^{ee}$)$_2$, —OP(=O)(OR$^{ee}$)$_2$, C$_{1-6}$ alkyl, C$_{1-6}$ perhaloalkyl, C$_{2-6}$ alkenyl, C$_{2-6}$ alkynyl, C$_{3-10}$ carbocyclyl, 3-10 membered heterocyclyl, C$_{6-10}$ aryl, 5-10 membered heteroaryl, wherein each alkyl, alkenyl, alkynyl, carbocyclyl, heterocyclyl, aryl, and heteroaryl is independently substituted with 0, 1, 2, 3, 4, or 5 $R^{gg}$ groups, or two geminal $R^{dd}$ substituents can be joined to form =O or =S;

each instance of $R^{ee}$ is, independently, selected from C$_{1-6}$ alkyl, C$_{1-6}$ perhaloalkyl, C$_{2-6}$ alkenyl, C$_{2-6}$ alkynyl, C$_{3-10}$ carbocyclyl, C$_{6-10}$ aryl, 3-10 membered heterocyclyl, and 3-10 membered heteroaryl, wherein each alkyl, alkenyl, alkynyl, carbocyclyl, heterocyclyl, aryl, and heteroaryl is independently substituted with 0, 1, 2, 3, 4, or 5 $R^{gg}$ groups;

each instance of $R^{ff}$ is, independently, selected from hydrogen, C$_{1-6}$ alkyl, C$_{1-6}$ perhaloalkyl, C$_{2-6}$ alkenyl, C$_{2-6}$ alkynyl, C$_{3-10}$ carbocyclyl, 3-10 membered heterocyclyl, C$_{6-10}$ aryl and 5-10 membered heteroaryl, or two R$^{ff}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{gg}$ groups;

each instance of $R^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3^+$X$^-$, —NH(C$_{1-6}$ alkyl)$_2^+$X$^-$, —NH$_2$(C$_{1-6}$ alkyl)$^+$X$^-$, —NH$_3^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl)$_2$, —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$ —C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)(C$_{1-6}$ alkyl)$_2$, —OP(=O)(C$_{1-6}$ alkyl)$_2$, —OP(=O)(OC$_{1-6}$ alkyl)$_2$, C$_{1-6}$ alkyl, C$_{1-6}$ perhaloalkyl, C$_{2-6}$ alkenyl, C$_{2-6}$ alkynyl, C$_{3-10}$ carbocyclyl, C$_{6-10}$ aryl, 3-10 membered heterocyclyl, 5-10 membered heteroaryl; or two geminal $R^{gg}$ substituents can be joined to form =O or =S; and X$^-$ is a counterion, wherein the counterion is a halide ion, NO$_3^-$, ClO$_4^-$, OH$^-$, H$_2$PO$_4^-$, HSO$_4^-$, a sulfonate ion, or a carboxylate ion.

6. A method of treating autism comprising administering to a subject suffering from autism an effective amount of a compound of formula I:

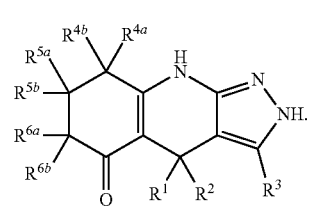

I or a pharmaceutically acceptable salt thereof, wherein:
  $R^1$ is selected from the group consisting of optionally substituted phenyl and optionally substituted heteroaryl;
  $R^2$ is unsubstituted C$_{1-6}$ aliphatic or C$_{1-6}$ aliphatic substituted with one or more instances of halogen;
  or $R^1$ and $R^2$ are taken together with their intervening atoms to form optionally substituted, 3- to 7-membered, monocyclic, saturated, carbocyclyl or heterocyclyl, wherein the carbocyclyl or heterocyclyl formed by taking together $R^1$ and $R^2$ is optionally fused to optionally substituted phenyl or optionally substituted heteroaryl;
  $R^3$ is selected from the group consisting of hydrogen, halogen, —CN, —NO$_2$, optionally substituted C$_{1-6}$ aliphatic, —OR$^A$, —N(R$^B$)$_2$, and —SR$^A$;
  each $R^A$ is independently selected from the group consisting of hydrogen and optionally substituted C$_{1-6}$ aliphatic;
  each $R^B$ is independently selected from the group consisting of hydrogen and optionally substituted C$_{1-6}$ aliphatic;
  $R^{4a}$ and $R^{4b}$ are each hydrogen;
  $R^{5a}$ and $R^{5b}$ are each independently selected from the group consisting of hydrogen, halogen, —CN, —OR$^A$, —N(R$^B$)$_2$, unsubstituted C$_{1-6}$ aliphatic, and C$_{1-6}$ aliphatic substituted with one or more instances of halogen, or $R^{5a}$ and $R^{5b}$ are taken together with their intervening atoms to form unsubstituted, 3- to 7-membered, monocyclic, saturated, carbocyclyl or heterocyclyl; and
  $R^{6a}$ and $R^{6b}$ are each hydrogen;
  wherein:
    each instance of the heteroaryl is independently 5- or 6-membered, monocyclic heteroaryl comprising 1 to 4 ring heteroatoms independently selected from the group consisting of nitrogen, oxygen, and sulfur, as valency allows;

each instance of the heterocyclyl independently comprises 1 to 4 ring heteroatoms independently selected from the group consisting of nitrogen, oxygen, and sulfur, as valency allows;

when any one of the aliphatic, carbocyclyl, heterocyclyl, phenyl, and heteroaryl referred to above is substituted with one or more substituents at a carbon atom, the one or more substituents at the carbon atom are independently selected from Group (i);

when any one of the heterocyclyl and heteroaryl referred to above is substituted with one or more substituents at a nitrogen atoms, the one or more substituents at the nitrogen atom are independently selected from Group (ii);

Group (i) consists of halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3$$^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$—C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)(R$^{aa}$)$_2$, —OP(=O)(R$^{aa}$)$_2$, —OP(=O)(OR$^{cc}$)$_2$, —P(=O)(NR$^{bb}$)$_2$, —OP(=O)(NR$^{bb}$)$_2$, —NR$^{bb}$P(=O)(OR$^{cc}$)$_2$, —NR$^{bb}$P(=O)(NR$^{bb}$)$_2$, —P(R$^{cc}$)$_2$, —OP(R$^{cc}$)$_2$, —B(R$^{aa}$)$_2$, —B(OR$^{cc}$)$_2$, —BR$^{aa}$(OR$^{cc}$), C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, carbocyclyl, heterocyclyl, aryl, and heteroaryl is independently substituted with 0, 1, 2, 3, 4, or 5 R$^{dd}$ groups; or two geminal hydrogens on a carbon atom are replaced with the group =O, =S, =NN(R$^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$, or =NOR$^{cc}$; and Group (ii) consists of hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{bb}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)(R$^{aa}$)$_2$, —P(=O)(NR$^{cc}$)$_2$, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, carbocyclyl, heterocyclyl, aryl, and heteroaryl is independently substituted with 0, 1, 2, 3, 4, or 5 R$^{dd}$ groups;

wherein:

each instance of R$^{aa}$ is, independently, selected from C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)(R$^{aa}$)$_2$, —P(=O)(NR$^{cc}$)$_2$, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{cc}$ is, independently, selected from hydrogen, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3$$^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)(R$^{ee}$)$_2$, —OP(=O)(R$^{ee}$)$_2$, —OP(=O)(OR$^{ee}$)$_2$, C$_{1-6}$ alkyl, C$_{1-6}$ perhaloalkyl, C$_{2-6}$ alkenyl, C$_{2-6}$ alkynyl, C$_{3-10}$ carbocyclyl, 3-10 membered heterocyclyl, C$_{6-10}$ aryl, 5-10 membered heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups, or two geminal R$^{dd}$ substituents can be joined to form =O or =S;

each instance of R$^{ee}$ is, independently, selected from C$_{1-6}$ alkyl, C$_{1-6}$ perhaloalkyl, C$_{2-6}$ alkenyl, C$_{2-6}$ alkynyl, C$_{3-10}$ carbocyclyl, C$_{6-10}$ aryl, 3-10 membered heterocyclyl, and 3-10 membered heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups;

each instance of R$^{ff}$ is, independently, selected from hydrogen, C$_{1-6}$ alkyl, C$_{1-6}$ perhaloalkyl, $C_{2-6}$ alkenyl, $C_{2-6}$ alkynyl, $C_{3-10}$ carbocyclyl, 3-10 membered heterocyclyl, $C_{6-10}$ aryl and 5-10 membered heteroaryl, or two $R^{ff}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{gg}$ groups;

each instance of $R^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3^+$X$^-$, —NH(C$_{1-6}$ alkyl)$_2^+$X$^-$, —NH$_2$(C$_{1-6}$ alkyl)$^+$X$^-$, —NH$_3^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$ —C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)(C$_{1-6}$ alkyl)$_2$, —OP(=O)(C$_{1-6}$ alkyl)$_2$, —OP(=O)(OC$_{1-6}$ alkyl)$_2$, C$_{1-6}$ alkyl, C$_{1-6}$ perhaloalkyl, C$_{2-6}$ alkenyl, C$_{2-6}$ alkynyl, C$_{3-10}$ carbocyclyl, C$_{6-10}$ aryl, 3-10 membered heterocyclyl, 5-10 membered heteroaryl; or two geminal $R^{gg}$ substituents can be joined to form =O or =S; and X$^-$ is a counterion, wherein the counterion is a halide ion, NO$_3^-$, ClO$_4^-$, OH$^-$, H$_2$PO$_4^-$, HSO$_4^-$, a sulfonate ion, or a carboxylate ion.

7. A method of treating acute myeloid leukemia (AML) comprising administering to a subject suffering from AML an effective amount of a compound of formula I:

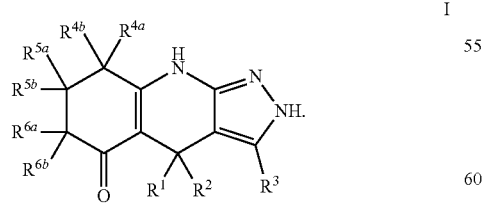

or a pharmaceutically acceptable salt thereof, wherein:

$R^1$ is selected from the group consisting of optionally substituted phenyl and optionally substituted heteroaryl;

$R^2$ is unsubstituted $C_{1-6}$ aliphatic or $C_{1-6}$ aliphatic substituted with one or more instances of halogen;

or $R^1$ and $R^2$ are taken together with their intervening atoms to form optionally substituted, 3- to 7-membered, monocyclic, saturated, carbocyclyl or heterocyclyl, wherein the carbocyclyl or heterocyclyl formed by taking together $R^1$ and $R^2$ is optionally fused to optionally substituted phenyl or optionally substituted heteroaryl;

$R^3$ is selected from the group consisting of hydrogen, halogen, —CN, —NO$_2$, optionally substituted $C_{1-6}$ aliphatic, —OR$^A$, —N(R$^B$)$_2$, and —SR$^A$;

each $R^A$ is independently selected from the group consisting of hydrogen and optionally substituted $C_{1-6}$ aliphatic;

each $R^B$ is independently selected from the group consisting of hydrogen and optionally substituted $C_{1-6}$ aliphatic;

$R^{4a}$ and $R^{4b}$ are each hydrogen;

$R^{5a}$ and $R^{5b}$ are each independently selected from the group consisting of hydrogen, halogen, —CN, —OR$^A$, —N(R$^B$)$_2$, unsubstituted $C_{1-6}$ aliphatic, and $C_{1-6}$ aliphatic substituted with one or more instances of halogen, or $R^{5a}$ and $R^{5b}$ are taken together with their intervening atoms to form unsubstituted, 3- to 7-membered, monocyclic, saturated, carbocyclyl or heterocyclyl; and $R^{6a}$ and $R^{6b}$ are each hydrogen;

wherein:

each instance of the heteroaryl is independently 5- or 6-membered, monocyclic heteroaryl comprising 1 to 4 ring heteroatoms independently selected from the group consisting of nitrogen, oxygen, and sulfur, as valency allows;

each instance of the heterocyclyl independently comprises 1 to 4 ring heteroatoms independently selected from the group consisting of nitrogen, oxygen, and sulfur, as valency allows;

when any one of the aliphatic, carbocyclyl, heterocyclyl, phenyl, and heteroaryl referred to above is substituted with one or more substituents at a carbon atom, the one or more substituents at the carbon atom are independently selected from Group (i);

when any one of the heterocyclyl and heteroaryl referred to above is substituted with one or more substituents at a nitrogen atoms, the one or more substituents at the nitrogen atom are independently selected from Group (ii);

Group (i) consists of halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$—C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)(R$^{aa}$)$_2$, —OP(=O)(R$^{aa}$)$_2$, —OP(=O)(OR$^{cc}$)$_2$, —P(=O)(NR$^{bb}$)$_2$, —OP(=O)(NR$^{bb}$)$_2$, —NR$^{bb}$P(=O)(OR$^{cc}$)$_2$, —NR$^{bb}$P(=O)(NR$^{bb}$)$_2$, —P(R$^{cc}$)$_2$, —OP(R$^{cc}$)$_2$, —B(R$^{aa}$)$_2$, —B(OR$^{cc}$)$_2$, —BR$^{aa}$(OR$^{cc}$), C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, carbocyclyl, heterocyclyl, aryl, and heteroaryl is independently substituted with 0, 1, 2, 3, 4, or 5 R$^{dd}$ groups; or two geminal hydrogens on a carbon atom are replaced with the group =O, =S, =NN(R$^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$, or =NOR$^{cc}$; and Group (ii) consists of hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{bb}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)(R$^{aa}$)$_2$, —P(=O)(NR$^{cc}$)$_2$, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, carbocyclyl, heterocyclyl, aryl, and heteroaryl is independently substituted with 0, 1, 2, 3, 4, or 5 R$^{dd}$ groups;

wherein:

each instance of R$^{aa}$ is, independently, selected from C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)(R$^{aa}$)$_2$, —P(=O)(NR$^{cc}$)$_2$, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{cc}$ is, independently, selected from hydrogen, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)(R$^{ee}$)$_2$, —OP(=O)(R$^{ee}$)$_2$, —OP(=O)(OR$^{ee}$)$_2$, C$_{1-6}$ alkyl, C$_{1-6}$ perhaloalkyl, C$_{2-6}$ alkenyl, C$_{2-6}$ alkynyl, C$_{3-10}$ carbocyclyl, 3-10 membered heterocyclyl, C$_{1-10}$ aryl, 5-10 membered heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups, or two geminal R$^{dd}$ substituents can be joined to form =O or =S;

each instance of R$^{ee}$ is, independently, selected from C$_{1-6}$ alkyl, C$_{1-6}$ perhaloalkyl, C$_{2-6}$ alkenyl, C$_{2-6}$ alkynyl, C$_{3-10}$ carbocyclyl, C$_{6-10}$ aryl, 3-10 membered heterocyclyl, and 3-10 membered heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups;

each instance of R$^{ff}$ is, independently, selected from hydrogen, C$_{1-6}$ alkyl, C$_{1-6}$ perhaloalkyl, C$_{2-6}$ alkenyl, C$_{2-6}$ alkynyl, C$_{3-10}$ carbocyclyl, 3-10 membered heterocyclyl, C$_{6-10}$ aryl and 5-10 membered heteroaryl, or two R$^{ff}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{gg}$ groups;

each instance of R$^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3^+$X$^-$, —NH(C$_{1-6}$ alkyl)$_2^+$X$^-$, —NH$_2$(C$_{1-6}$ alkyl)$^+$X$^-$, —NH$_3^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-4}$ alkyl)$_3$ —C(=S)N(C$_{1-6}$ alkyl)$_2$, C(=S)NH(C$_{1-6}$ alkyl), C(=S)

NH₂, —C(=O)S(C₁₋₆ alkyl), —C(=S)SC₁₋₆ alkyl, —SC(=S)SC₁₋₆ alkyl, —P(=O)(C₁₋₆ alkyl)₂, —OP(=O)(C₁₋₆ alkyl)₂, —OP(=)(OC₁₋₆ alkyl)₂, C₁₋₆ alkyl, C₁₋₆ perhaloalkyl, C₂₋₆ alkenyl, C₂₋₆ alkynyl, C₃₋₁₀ carbocyclyl, C₆₋₁₀ aryl, 3-10 membered heterocyclyl, 5-10 membered heteroaryl; or two geminal R^gg substituents can be joined to form =O or =S; and X⁻ is a counterion, wherein the counterion is a halide ion, NO₃⁻, ClO₄⁻, OH⁻, H₂PO₄⁻, HSO₄⁻, a sulfonate ion, or a carboxylate ion.

8. The method of claim 7, wherein the AML is acute promyelocytic leukemia.

9. The method of claim 1, wherein the compound is of formula:

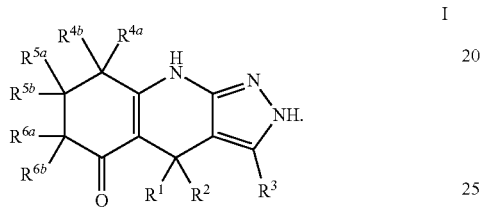

I or a pharmaceutically acceptable salt thereof.

10. The method of claim 1, wherein R¹ is optionally substituted heteroaryl.

11. The method of claim 1, wherein R¹ is optionally substituted pyridyl.

12. The method of claim 1, wherein R² is unsubstituted methyl.

13. The method of claim 1, wherein R² is substituted methyl or optionally substituted ethyl.

14. The method of claim 1, wherein R² is —CF₃ or unsubstituted ethyl.

15. The method of claim 1, wherein R³ is hydrogen or fluoro.

16. The method of claim 1, wherein R^{5a} and R^{5b} are taken together with their intervening atoms to form unsubstituted, 3- to 7-membered, monocyclic, saturated, carbocyclyl or heterocyclyl.

17. The method of claim 1, wherein the compound is of the formula:

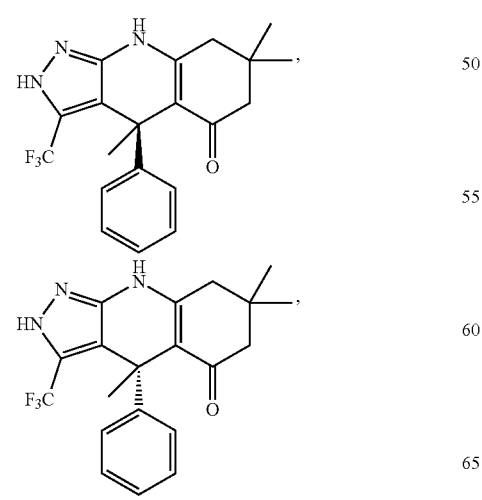

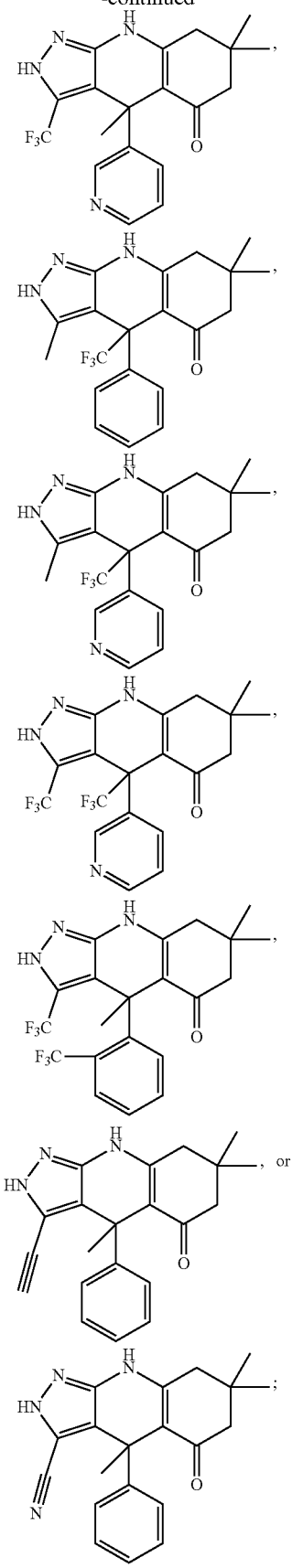

or a pharmaceutically acceptable salt thereof.
18. The method of claim 1, wherein the compound is of the formula:
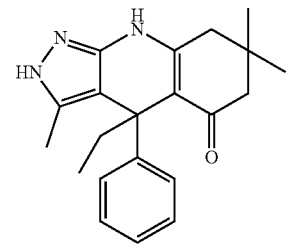
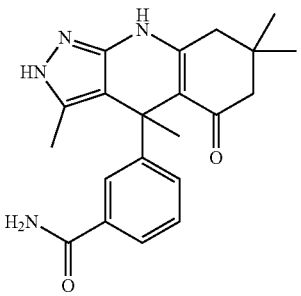
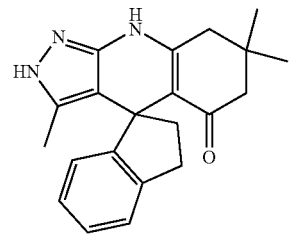
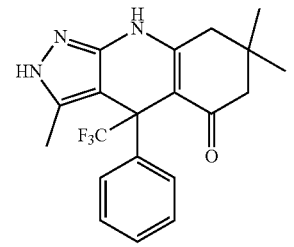
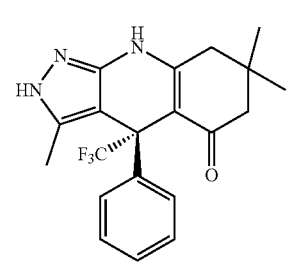
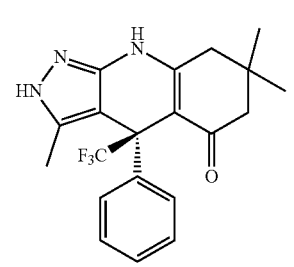
-continued
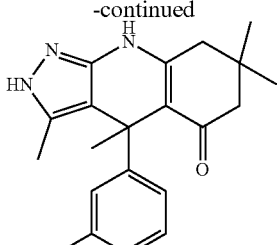
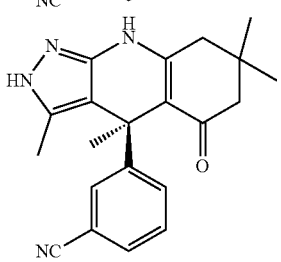
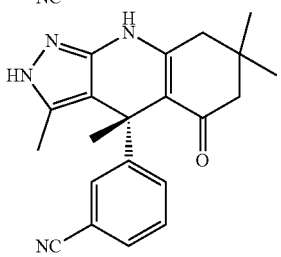
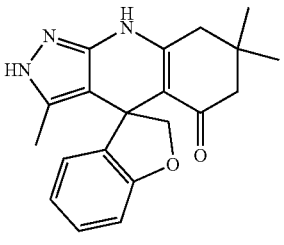
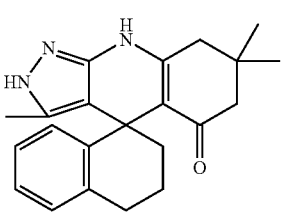
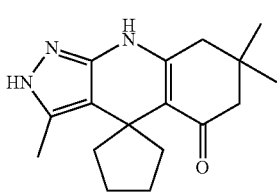
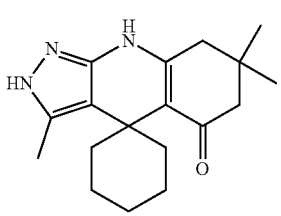

245
-continued
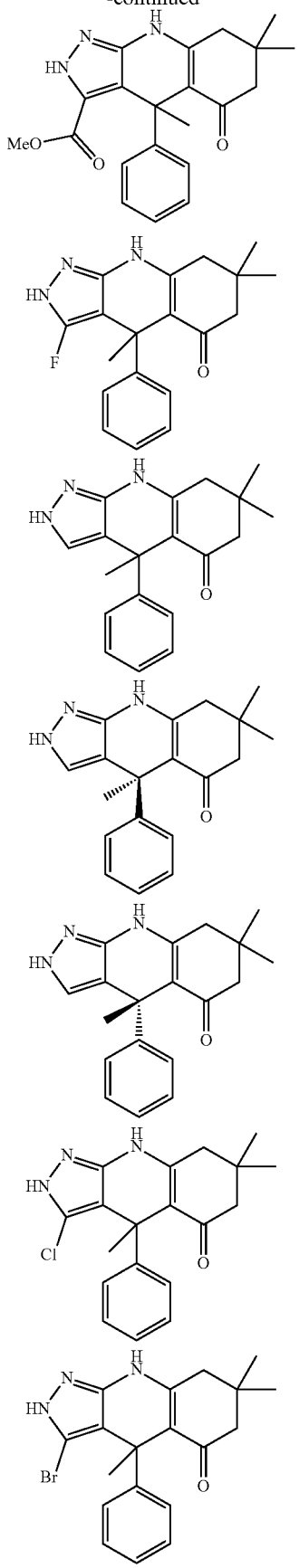
246
-continued
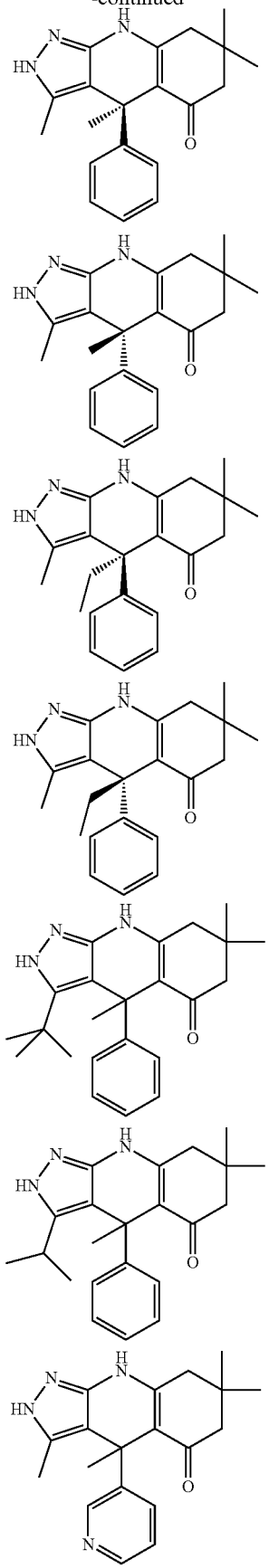

247
-continued
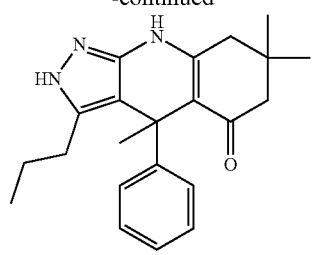
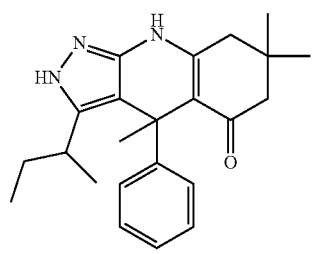
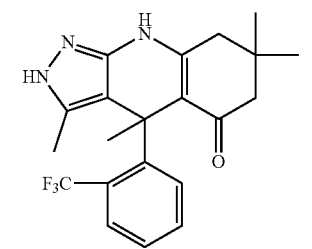
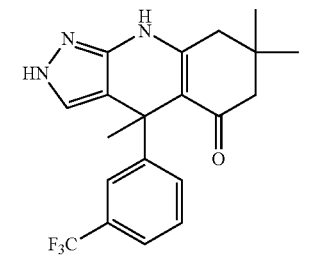
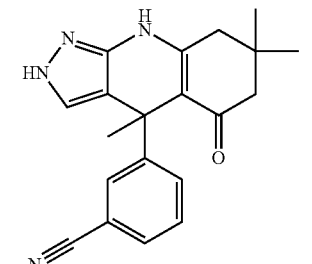
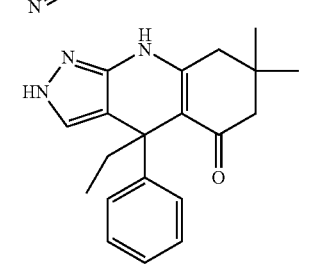
248
-continued
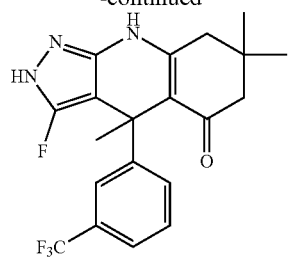
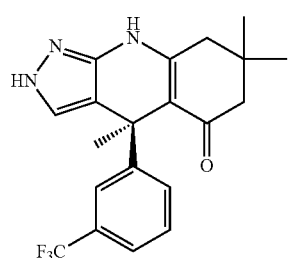
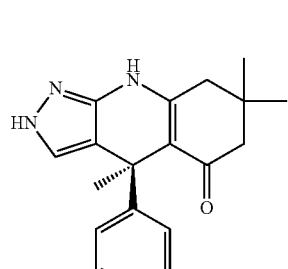
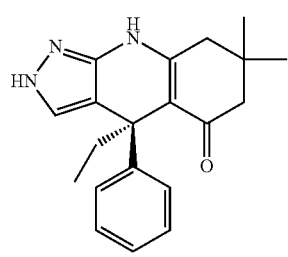
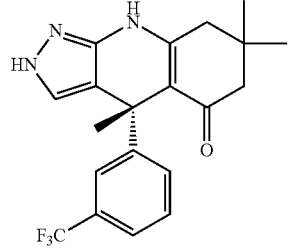
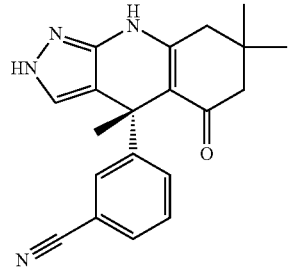

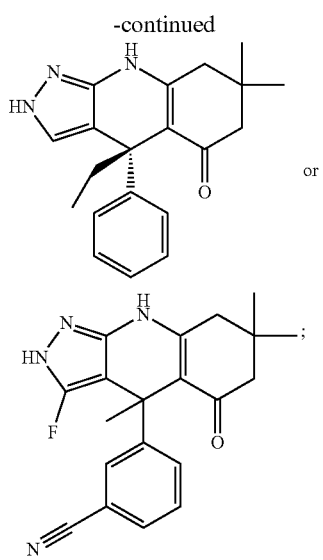

or a pharmaceutically acceptable salt thereof.

19. The method of claim 1, wherein the compound is of the formula:

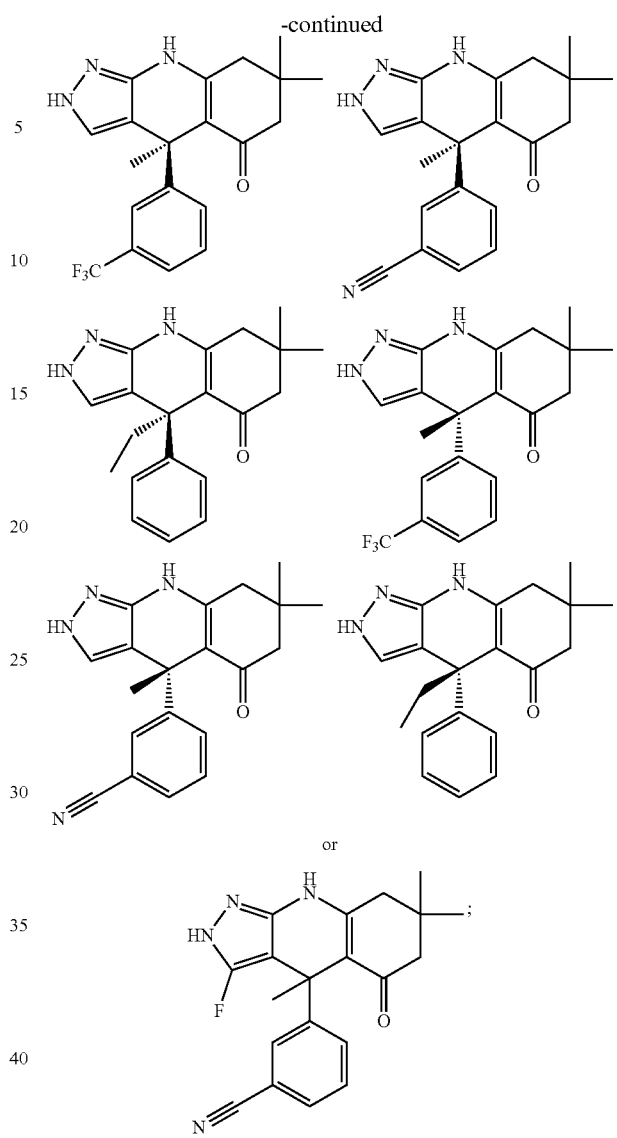

or a pharmaceutically acceptable salt thereof.

20. The method of claim 5, wherein $R^2$ is unsubstituted methyl.

21. The method of claim 5, wherein $R^1$ and $R^2$ are taken together with their intervening atoms to form optionally substituted, 3- to 7-membered, monocyclic, saturated, carbocyclyl or heterocyclyl, wherein the carbocyclyl or heterocyclyl formed by taking together $R^1$ and $R^2$ is optionally fused to optionally substituted phenyl or optionally substituted heteroaryl.

22. The method of claim 5, wherein $R^3$ is optionally substituted $C_{1-6}$ aliphatic.

23. The method of claim 5, wherein $R^3$ is optionally substituted ethyl, optionally substituted n-propyl, optionally substituted isopropyl, optionally substituted iso-butyl, optionally substituted tert-butyl, optionally substituted sec-butyl, optionally substituted n-pentyl, optionally substituted 3-pentanyl, optionally substituted amyl, optionally substituted 3-methyl-2-butanyl, or optionally substituted tertiary amyl.

24. The method of claim 5, wherein $R^3$ is optionally substituted neopentyl.

25. The method of claim 5, wherein R³ is optionally substituted cyclopropyl, optionally substituted cyclobutyl, optionally substituted cyclopentyl, or optionally substituted cyclohexyl.

26. The method of claim 5, wherein R³ is cyclobutyl substituted with one or more fluoro.

27. The method of claim 5, wherein R⁵ᵃ and R⁵ᵇ are each unsubstituted methyl.

28. The method of claim 5, wherein R⁵ᵃ and R⁵ᵇ are taken together with their intervening atoms to form unsubstituted, 3- to 7-membered, monocyclic, saturated, carbocyclyl or heterocyclyl.

29. The method of claim 5, wherein the compound is of the formula:

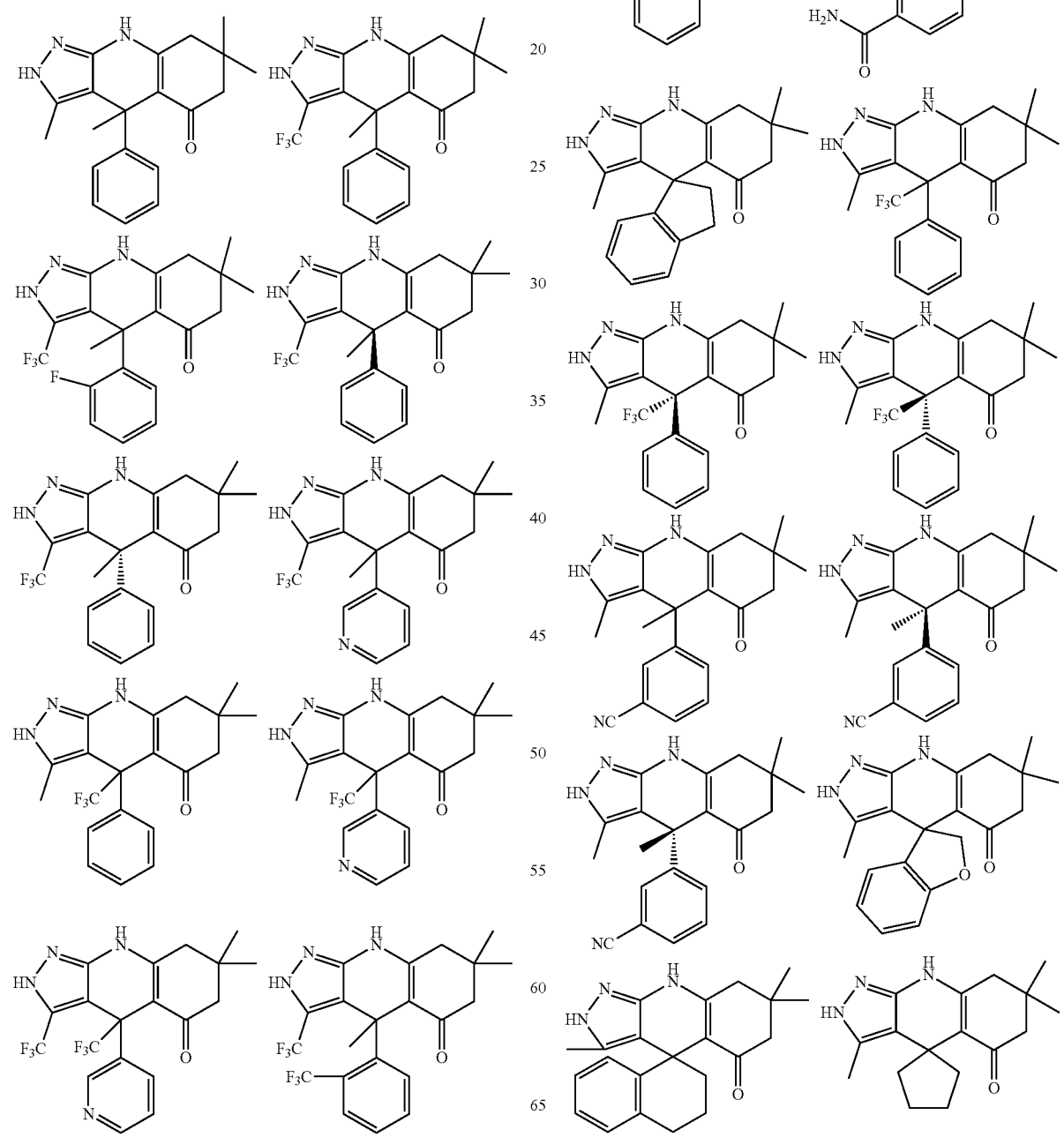

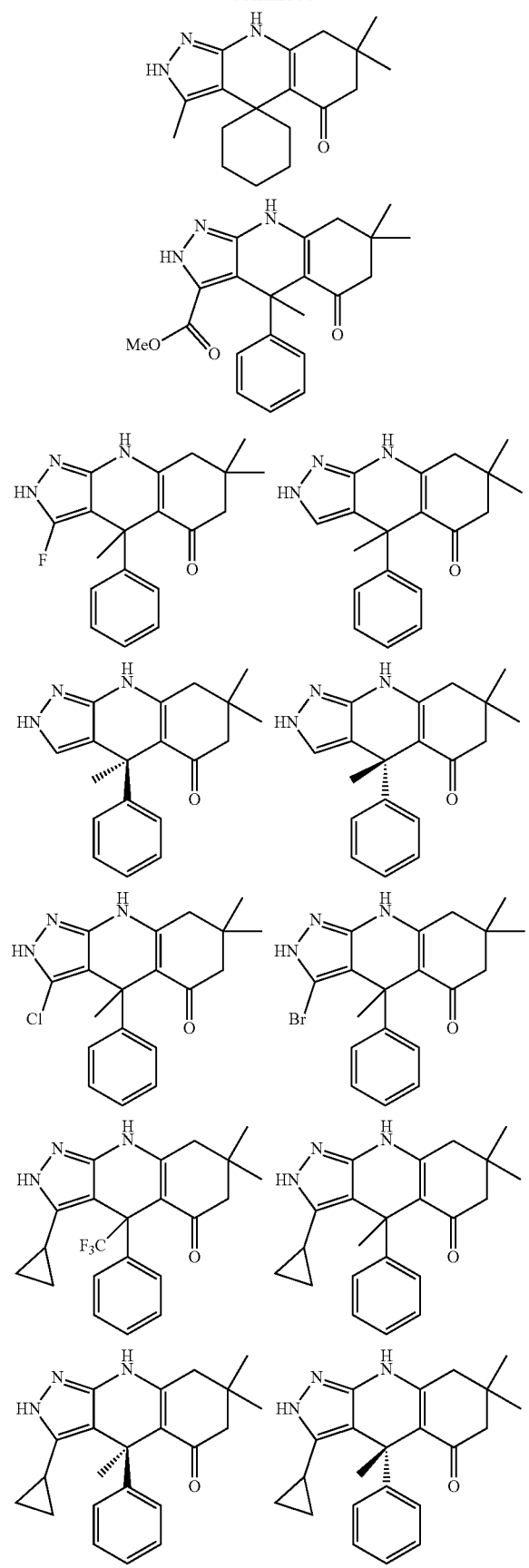
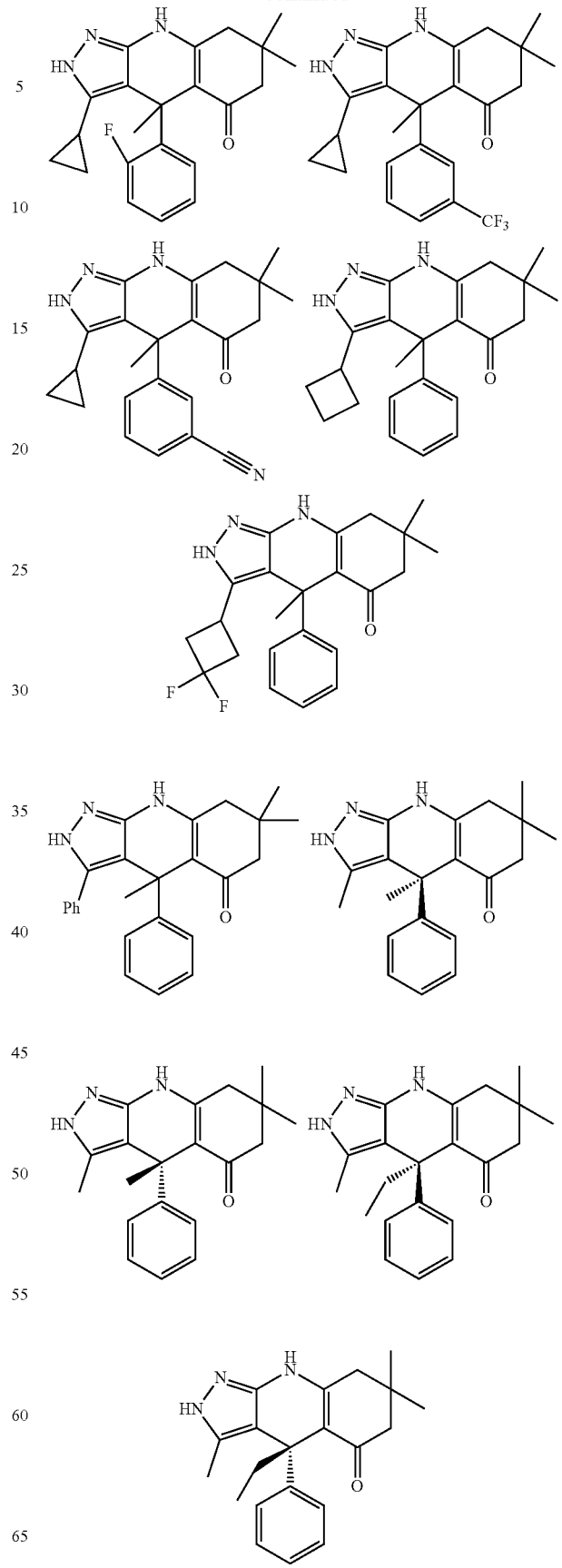

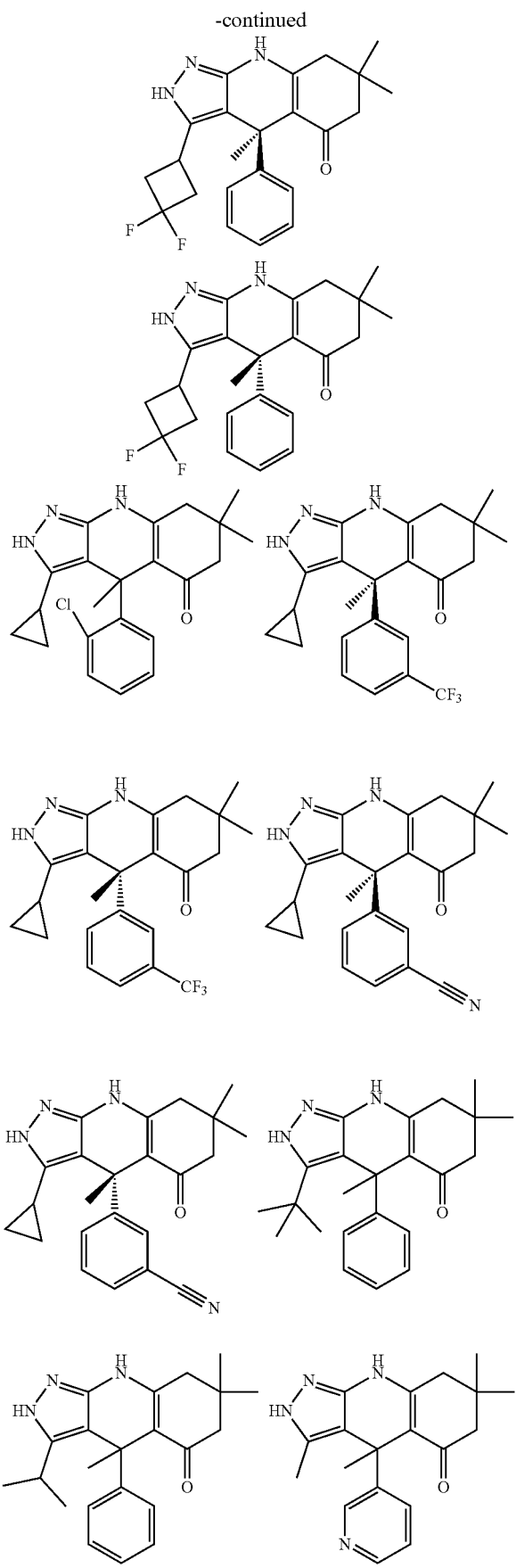
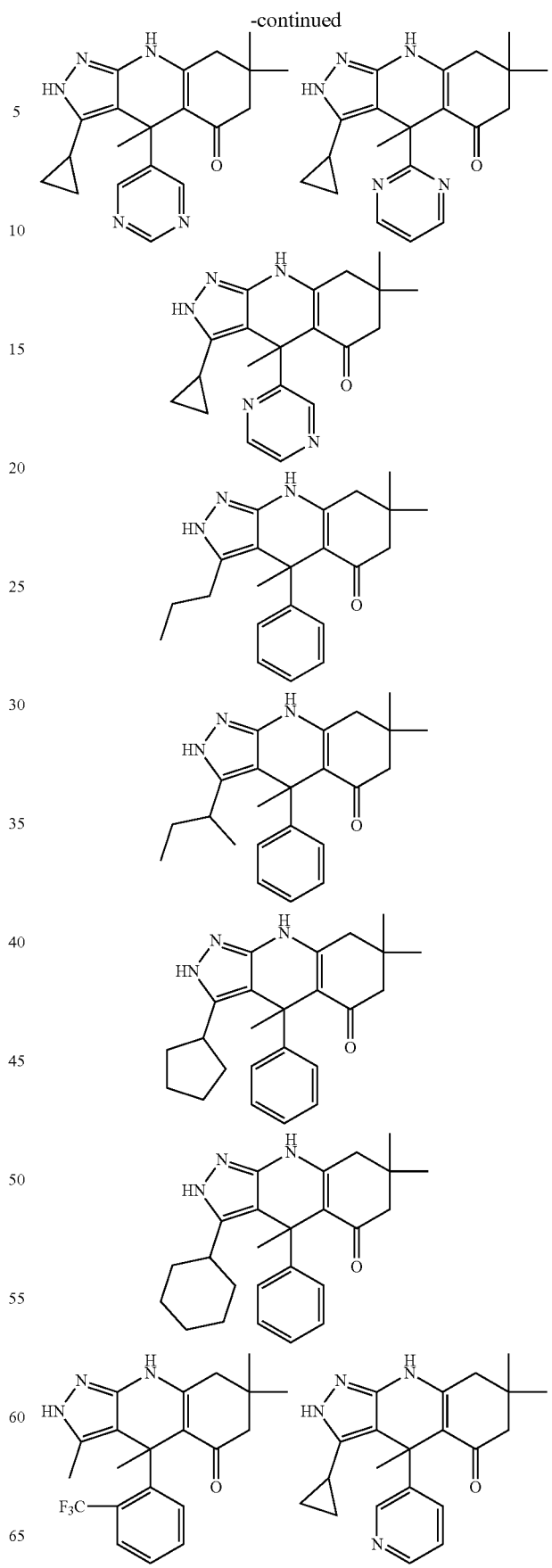

257
-continued

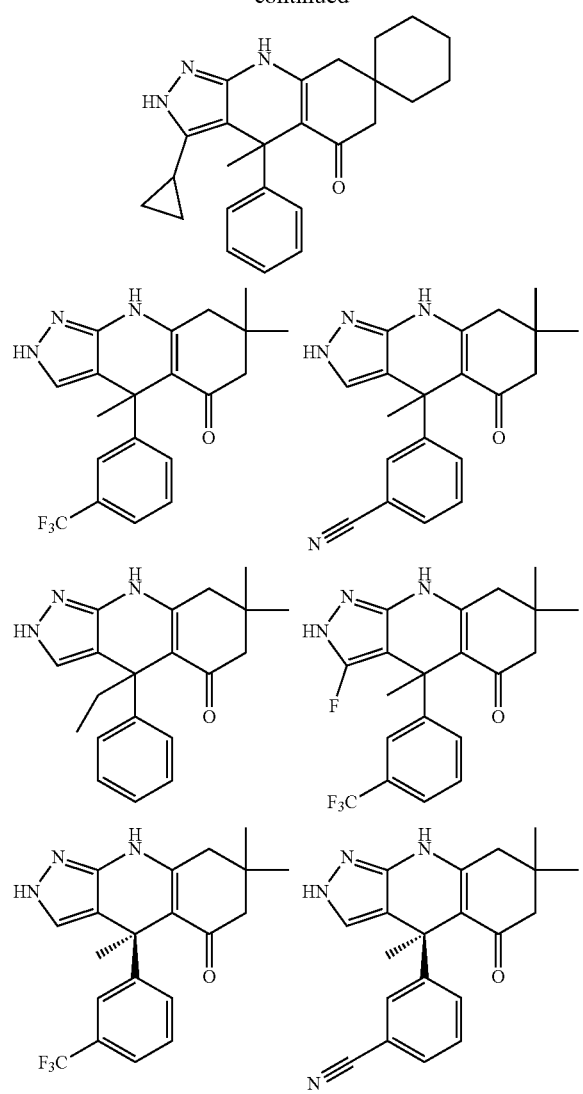

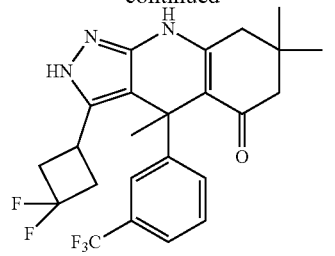

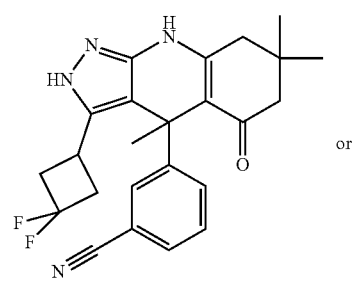

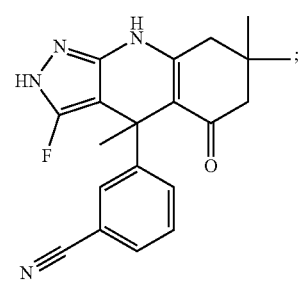

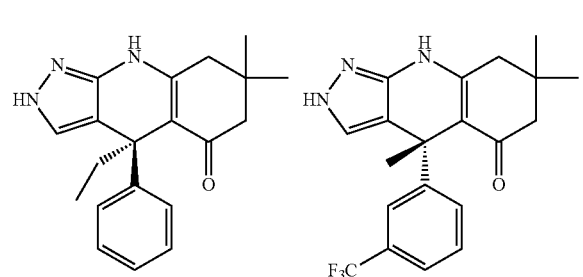

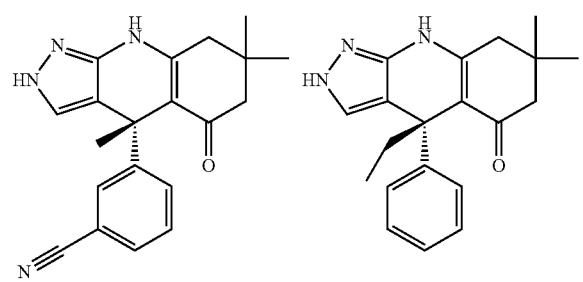

258
-continued

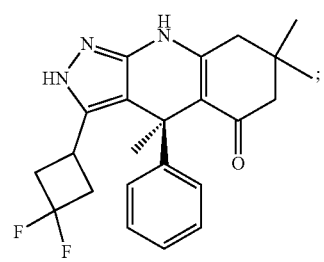 [SMILES: CC1(C)CC(=O)C2=C(C1)Nc1n[nH]c(C3CC(F)(F)C3)c1[C@]2(C)c1ccccc1]

or a pharmaceutically acceptable salt thereof.

30. The method of claim 5, wherein the compound is of the formula:

or a pharmaceutically acceptable salt thereof.

31. The method of claim 1, wherein $R^1$ and $R^2$ are taken together with their intervening atoms to form optionally substituted, 3- to 7-membered, monocyclic, saturated, carbocyclyl or heterocyclyl, wherein the carbocyclyl or heterocyclyl formed by taking together $R^1$ and $R^2$ is optionally fused to optionally substituted phenyl or optionally substituted heteroaryl.

32. The method of claim 5, wherein the compound is of formula:

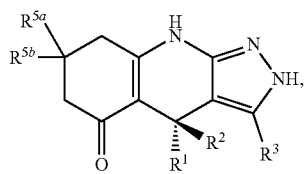

or a pharmaceutically acceptable salt thereof.

33. The method of claim 5, wherein $R^1$ is optionally substituted phenyl.

34. The method of claim 5, wherein $R^1$ is optionally substituted heteroaryl.

35. The method of claim 5, wherein $R^1$ is optionally substituted pyridyl.

36. The method of claim 5 wherein $R^2$ is —CF$_3$ or unsubstituted ethyl.

37. The method of claim 6, wherein $R^1$ and $R^2$ are taken together with their intervening atoms to form optionally substituted, 3- to 7-membered, monocyclic, saturated, carbocyclyl or heterocyclyl, wherein the carbocyclyl or heterocyclyl formed by taking together $R^1$ and $R^2$ is optionally fused to optionally substituted phenyl or optionally substituted heteroaryl.

38. The method of claim 6, wherein the compound is of formula:

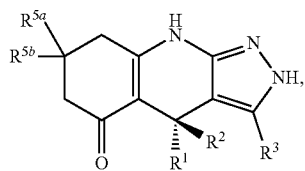

or a pharmaceutically acceptable salt thereof.

39. The method of claim 6, wherein $R^1$ is optionally substituted phenyl.

40. The method of claim 6, wherein $R^1$ is optionally substituted heteroaryl.

41. The method of claim 6, wherein $R^1$ is optionally substituted pyridyl.

42. The method of claim 6, wherein $R^2$ is unsubstituted methyl.

43. The method of claim 6, wherein $R^2$ is substituted methyl or optionally substituted ethyl.

44. The method of claim 6, wherein $R^2$ is —CF$_3$ or unsubstituted ethyl.

45. The method of claim 6, wherein $R^3$ is hydrogen or fluoro.

46. The method of claim 6, wherein $R^{5a}$ and $R^{5b}$ are each unsubstituted methyl.

47. The method of claim 6, wherein $R^{5a}$ and $R^{5b}$ are taken together with their intervening atoms to form unsubstituted, 3- to 7-membered, monocyclic, saturated, carbocyclyl or heterocyclyl.

48. The method of claim 6, wherein the compound is of the formula:

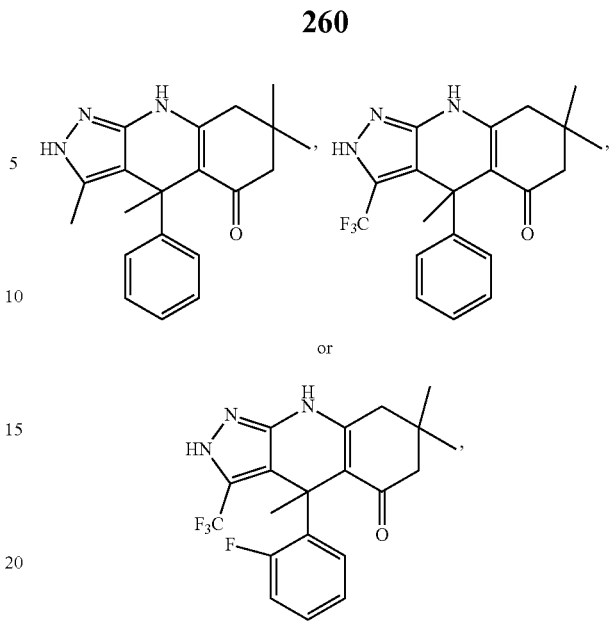

or a pharmaceutically acceptable salt thereof.

49. The method of claim 6, wherein the compound is of the formula:

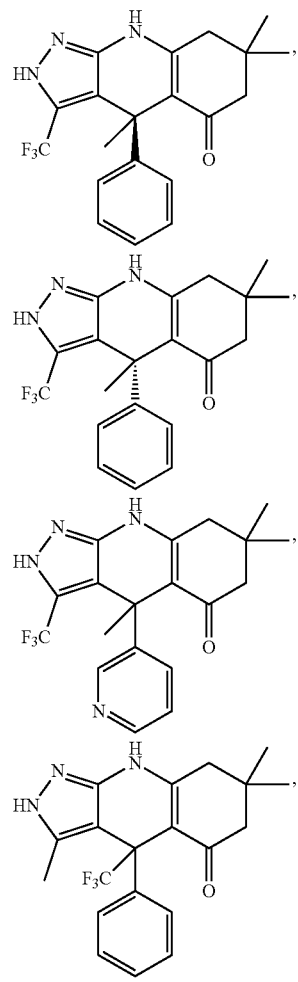

-continued
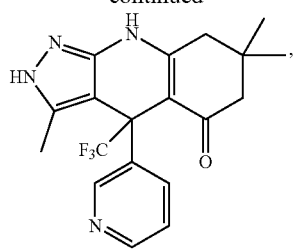
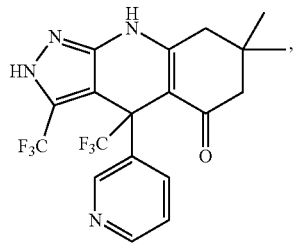
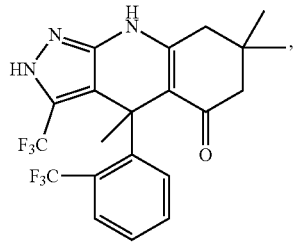
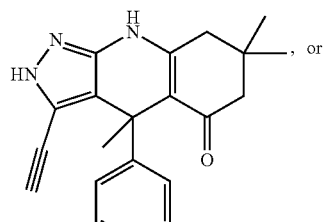, or
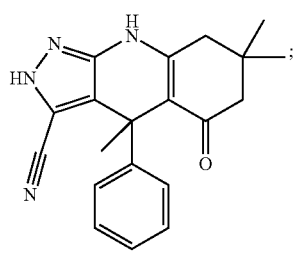;
or a pharmaceutically acceptable salt thereof.
50. The method of claim 6, wherein the compound is of the formula:
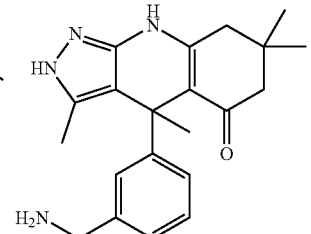
-continued
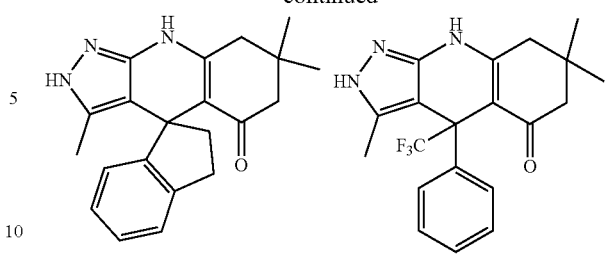
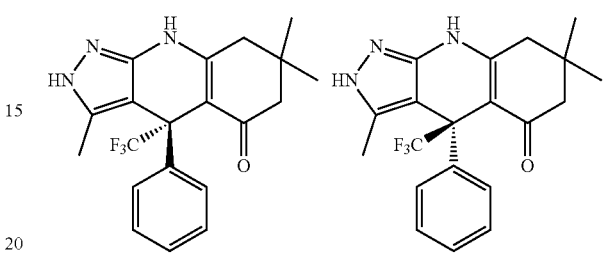
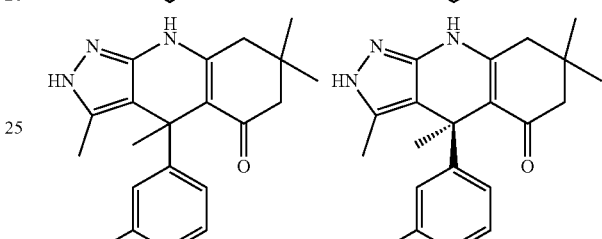
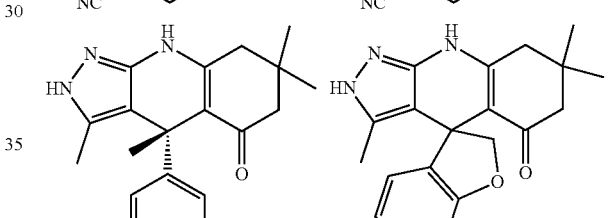
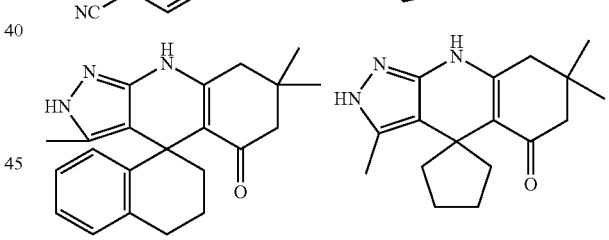
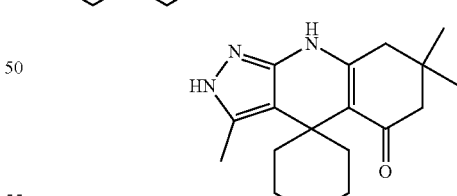
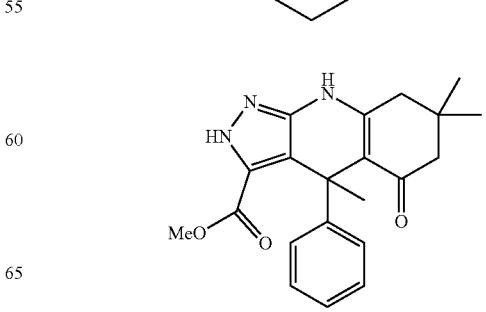

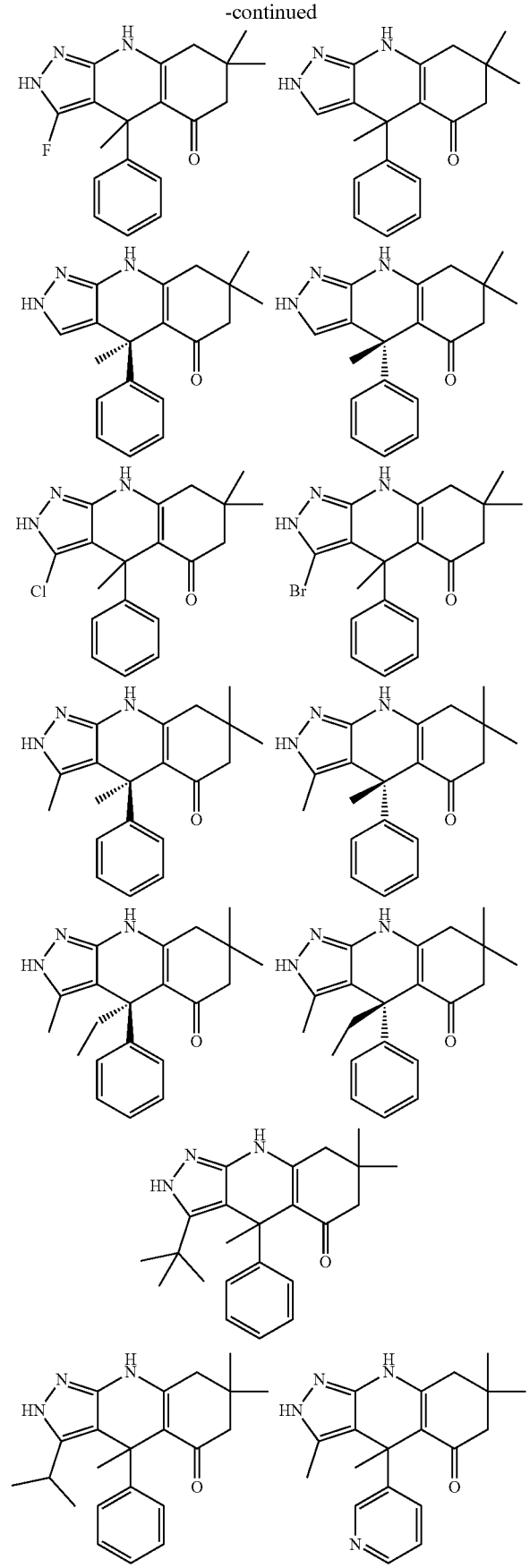
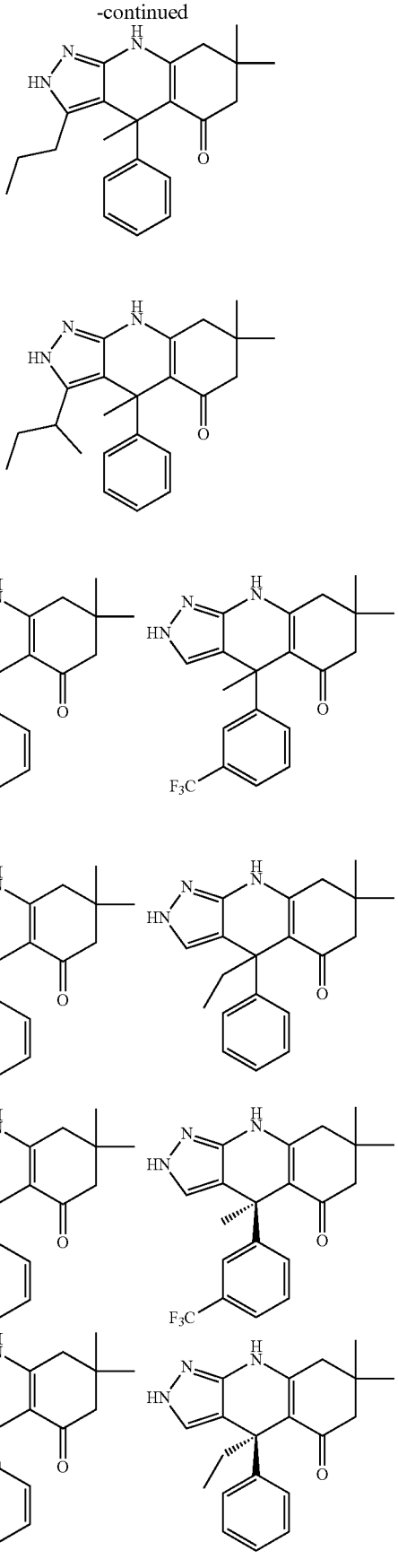

-continued

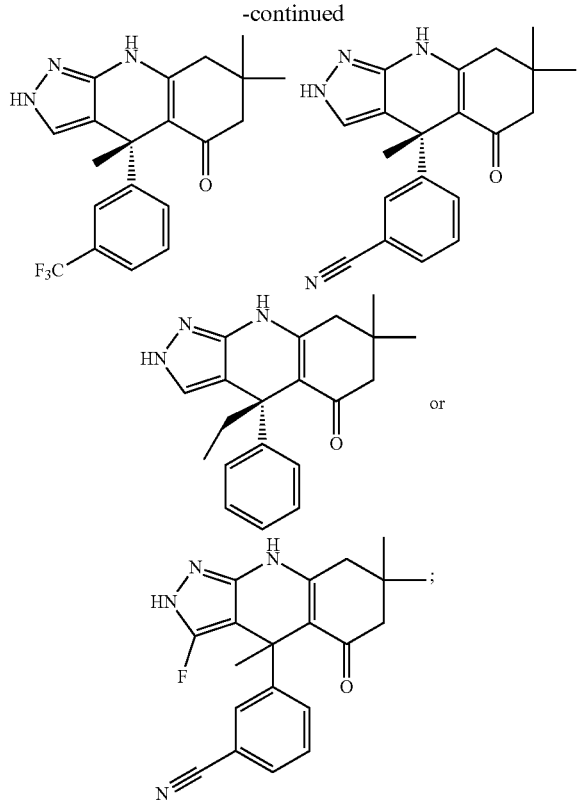

or a pharmaceutically acceptable salt thereof.

51. The method of claim 6, wherein the compound is of the formula:

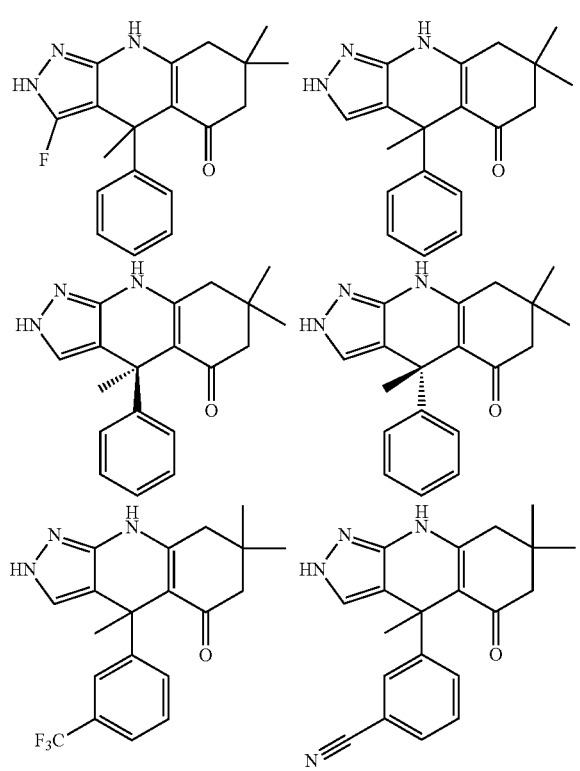

-continued

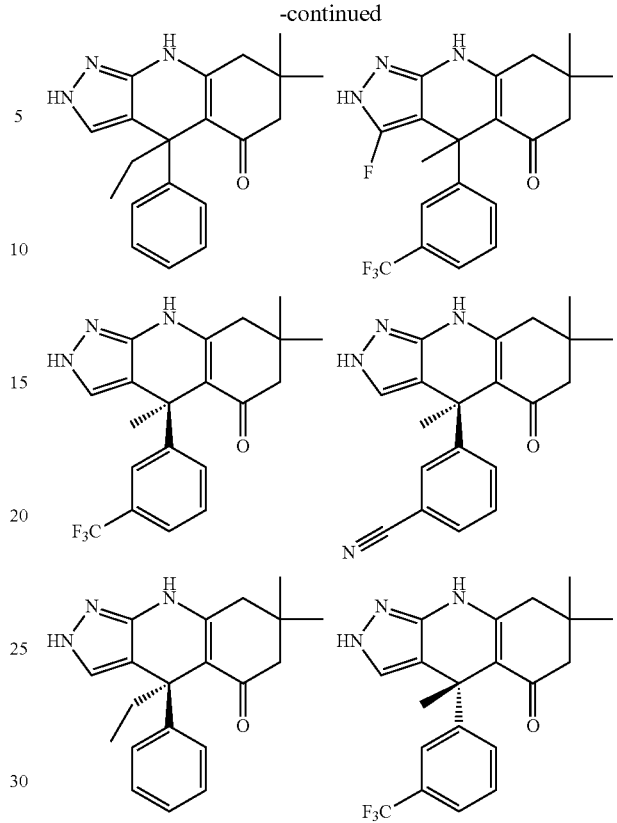

or

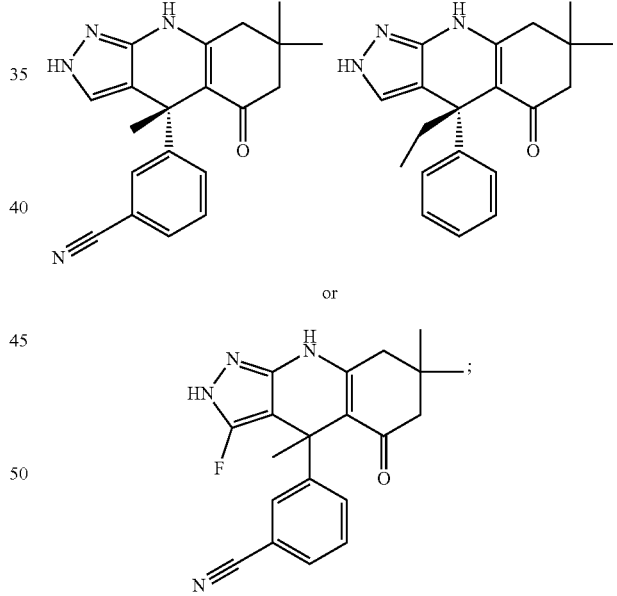

or a pharmaceutically acceptable salt thereof.

52. The method of claim 7, wherein $R^1$ and $R^2$ are taken together with their intervening atoms to form optionally substituted, 3- to 7-membered, monocyclic, saturated, carbocyclyl or heterocyclyl, wherein the carbocyclyl or heterocyclyl formed by taking together $R^1$ and $R^2$ is optionally fused to optionally substituted phenyl or optionally substituted heteroaryl.

53. The method of claim 7, wherein the compound is of formula:

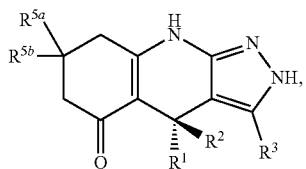

or a pharmaceutically acceptable salt thereof.

54. The method of claim 7, wherein $R^1$ is optionally substituted phenyl.

55. The method of claim 7, wherein $R^1$ is optionally substituted heteroaryl.

56. The method of claim 7 wherein $R^1$ is optionally substituted pyridyl.

57. The method of claim 7, wherein $R^2$ is unsubstituted methyl.

58. The method of claim 7, wherein $R^2$ is substituted methyl or optionally substituted ethyl.

59. The method of claim 7, wherein $R^2$ is —CF$_3$ or unsubstituted ethyl.

60. The method of claim 7, wherein $R^3$ is hydrogen or fluoro.

61. The method of claim 7, wherein $R^{5a}$ and $R^{5b}$ are each unsubstituted methyl.

62. The method of claim 7, wherein $R^{5a}$ and $R^{5b}$ are taken together with their intervening atoms to form unsubstituted, 3- to 7-membered, monocyclic, saturated, carbocyclyl or heterocyclyl.

63. The method of claim 7, wherein the compound is of the formula:

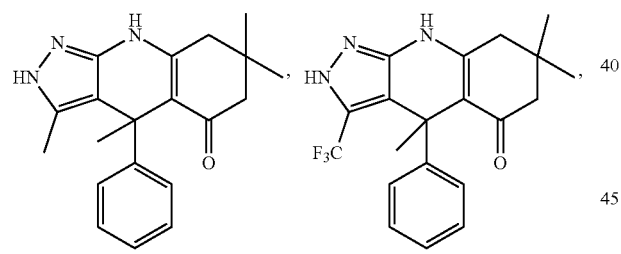

or a pharmaceutically acceptable salt thereof.

64. The method of claim 7, wherein the compound is of the formula:

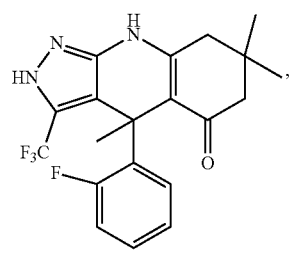

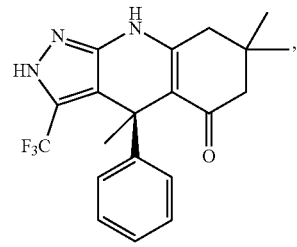

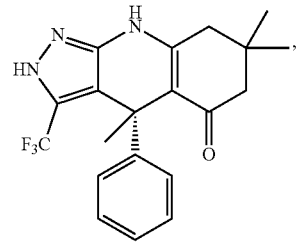

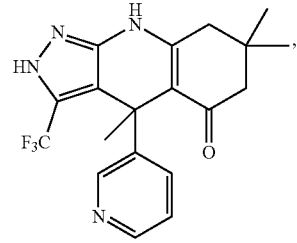

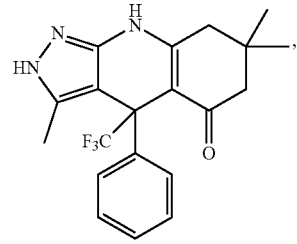

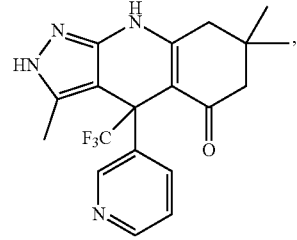

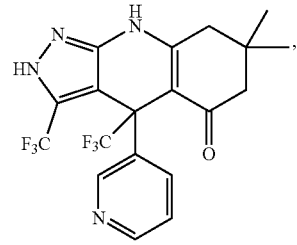

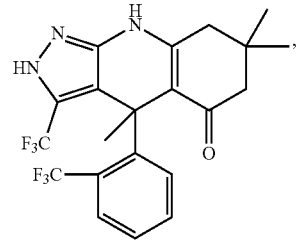

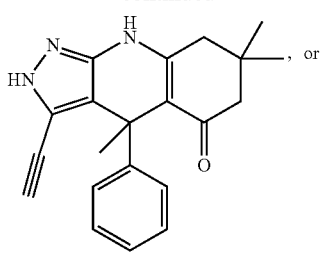
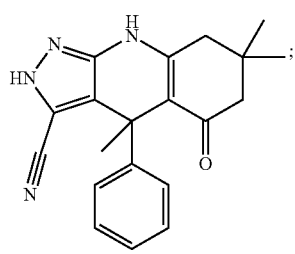
or a pharmaceutically acceptable salt thereof.
65. The method of claim 7, wherein the compound is of the formula:
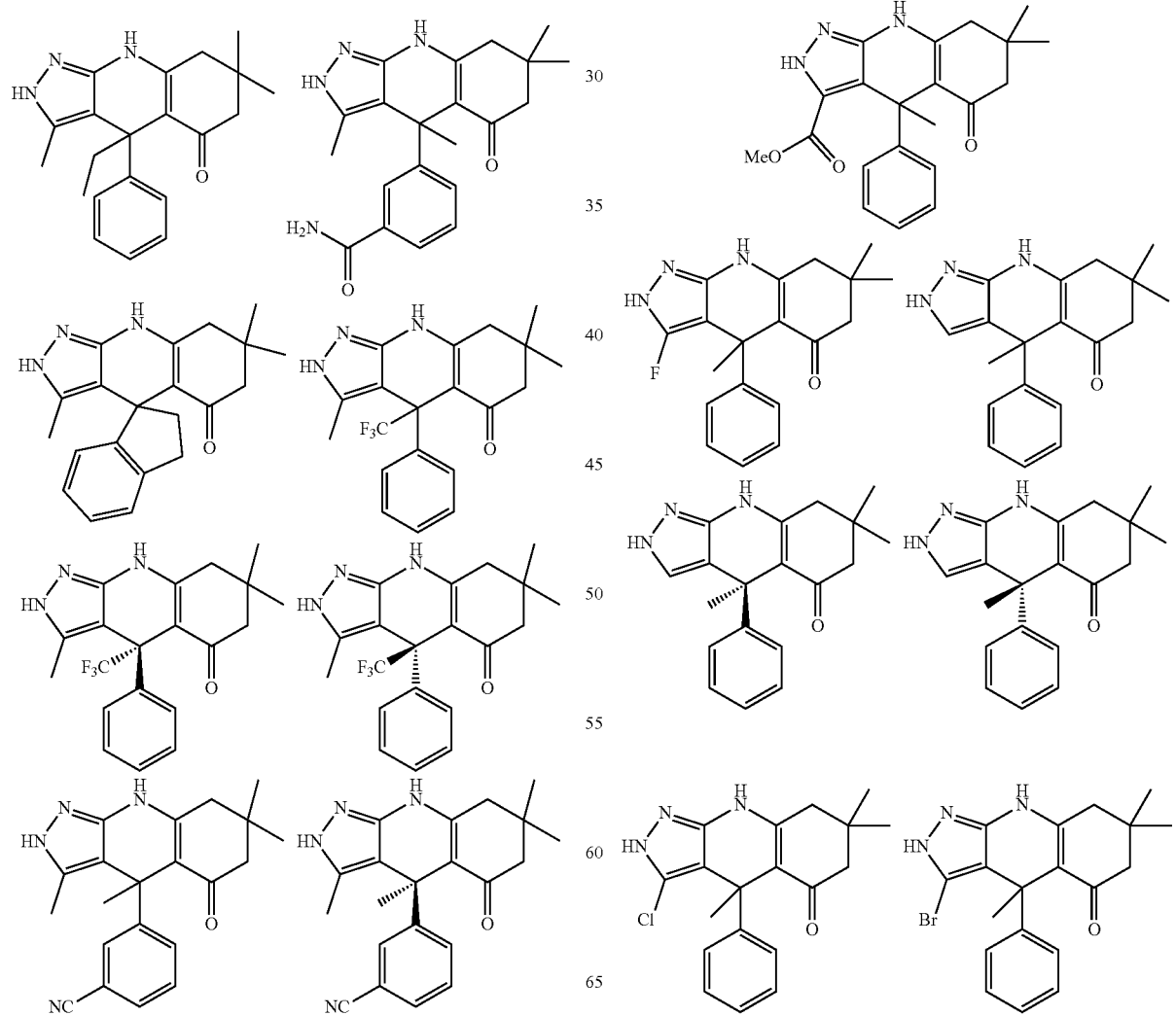

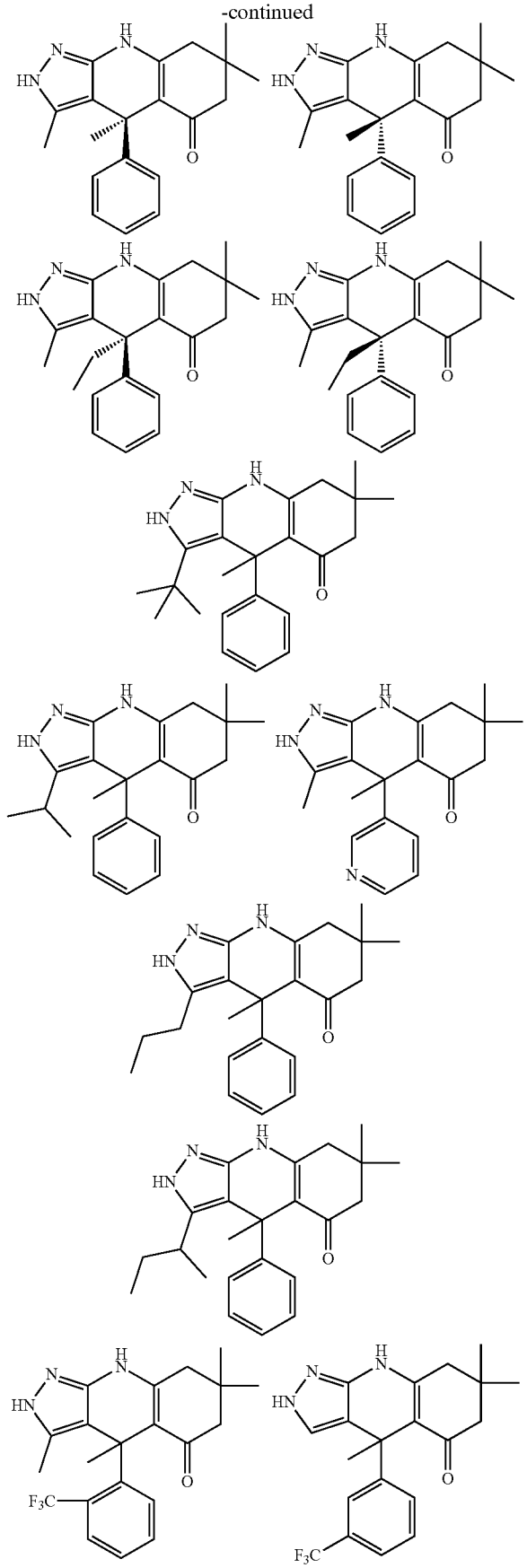
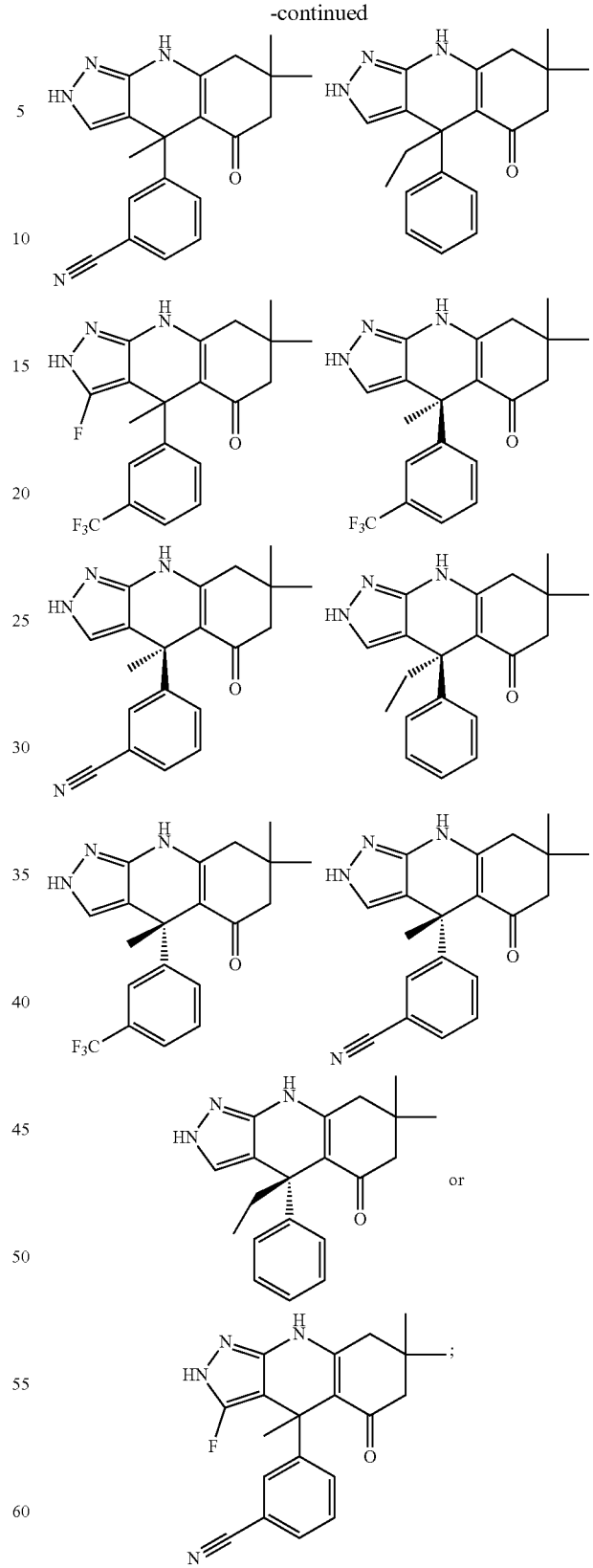
or a pharmaceutically acceptable salt thereof.
66. The method of claim 7, wherein the compound is of the formula:

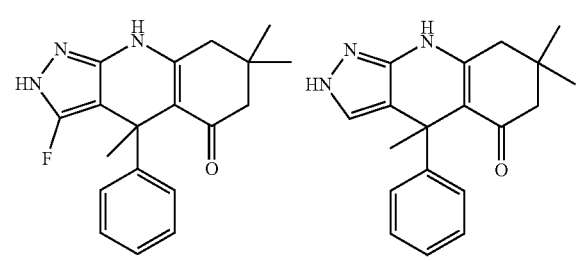
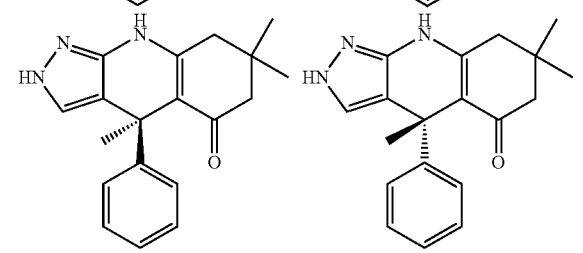
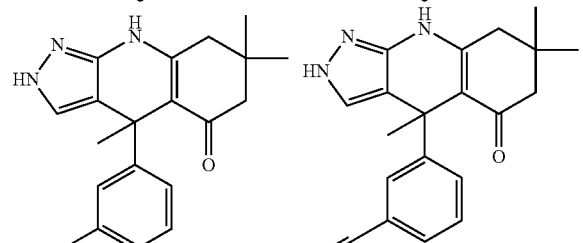
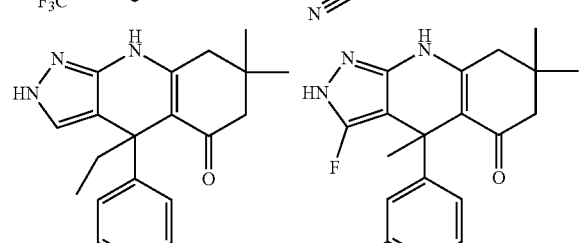
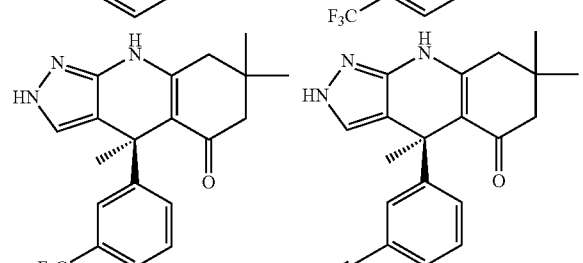
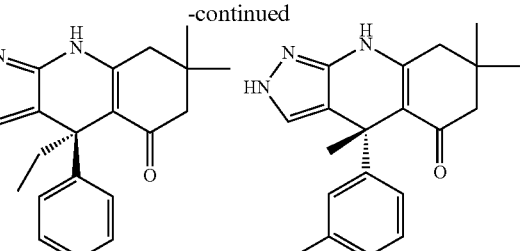
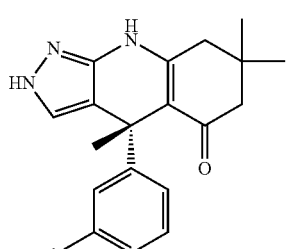
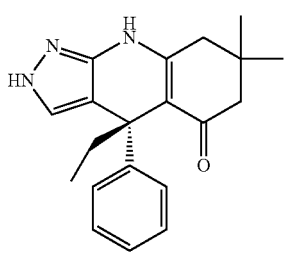
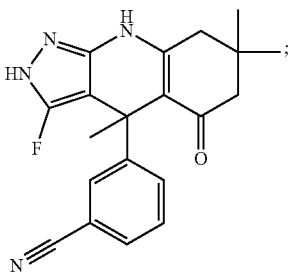
or a pharmaceutically acceptable salt thereof.
* * * * *

UNITED STATES PATENT AND TRADEMARK OFFICE
CERTIFICATE OF CORRECTION

PATENT NO. : 10,137,122 B2
APPLICATION NO. : 14/799281
DATED : November 27, 2018
INVENTOR(S) : Florence Fevrier Wagner et al.

Page 1 of 1

It is certified that error appears in the above-identified patent and that said Letters Patent is hereby corrected as shown below:

In the Claims

Claim 5, Column 232, Lines 47-48, "–$SO_2R$, –$SO_2OR$" should be replaced with: -- –$SO_2R^{cc}$, –$SO_2OR^{cc}$--.

Claim 7, Column 240, Line 17, "$C_{1-10}$ aryl" should be replaced with: --$C_{6-10}$ aryl--.

Claim 7, Column 240, Line 66, "–$OSi(C_{1-4}$ alkyl$)_3$" should be replaced with: -- –$OSi(C_{1-6}$ alkyl$)_3$,--.

Claim 7, Column 241, Lines 3-4, "–$OP(=)(OC_{1-6}alkyl)_2$" should be replaced with:
-- –$OP(=O)(OC_{1-6}alkyl)_2$--.

Claim 9, Column 241, Lines 20-25, the formula: " 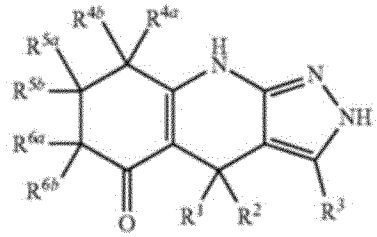 " should be replaced with the formula: -- 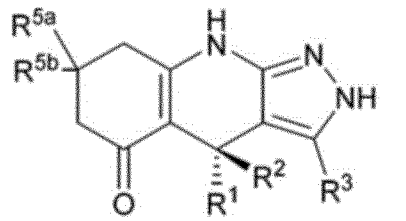 --.

Signed and Sealed this
Third Day of December, 2019

Andrei Iancu
*Director of the United States Patent and Trademark Office*